United States Patent
Shipovskov et al.

(10) Patent No.: US 11,453,871 B2
(45) Date of Patent: Sep. 27, 2022

(54) TRYPSIN-LIKE SERINE PROTEASES AND USES THEREOF

(71) Applicant: DANISCO US INC., Palo Alto, CA (US)

(72) Inventors: Stepan Shipovskov, Palo Alto, CA (US); Zhengzheng Zou, Palo Alto, CA (US); Shukun Yu, Palo Alto, CA (US); Xiaogang Gu, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 210 days.

(21) Appl. No.: 16/489,153

(22) PCT Filed: Mar. 8, 2018

(86) PCT No.: PCT/US2018/021440
§ 371 (c)(1),
(2) Date: Aug. 27, 2019

(87) PCT Pub. No.: WO2018/169750
PCT Pub. Date: Sep. 20, 2018

(65) Prior Publication Data
US 2020/0216827 A1    Jul. 9, 2020

(51) Int. Cl.
*C12N 9/54* (2006.01)
*C11D 3/386* (2006.01)
*C11D 11/00* (2006.01)

(52) U.S. Cl.
CPC .......... *C12N 9/54* (2013.01); *C11D 3/38636* (2013.01); *C11D 11/0017* (2013.01); *C11D 11/0023* (2013.01)

(58) Field of Classification Search
CPC ........... C11D 11/0017; C11D 3/38636; C11D 11/0023; C12N 9/52; C12N 9/54
See application file for complete search history.

(56) References Cited

U.S. PATENT DOCUMENTS

2013/0260438 A1* 10/2013 Alekseyev ............. C11D 3/386
435/221
2014/0228274 A1* 8/2014 Mikkelsen ......... C11D 3/38636
510/393

OTHER PUBLICATIONS

Page et al. Engineering the Primary Substrate Specificity of Streptomyces griseus Trypsin. Biochemistry (2003),42(30), 9060-9066. (Year: 2003).*
Venalainen et al. Evolutionary relationships of the prolyl oligopeptidase family enzymes. Eur J Biochem (2004), 271, 2705-2715. (Year: 2004).*
Perona and Craik. Structural basis of substrate specificity in the serine proteases. Protein Science (1995), 4, 337-360. (Year: 1995).*
Siezen et al. Subtilases: The superfamily of subtilisin-like serine proteases. Protein Science (1997), 6, 501-523. (Year: 1997).*
Hedstrom et al. An Overview of Serine Proteases. Current Protocols in Protein Science (2001), Suppl. 26, 21.10.1-21.10.8. (Year: 2001).*

* cited by examiner

*Primary Examiner* — Sean C. Barron

(57) ABSTRACT

Described herein is at least one novel trypsin-like serine protease polypeptide and uses thereof. Further described herein are cleaning compositions containing at least one polypeptide described herein, wherein said composition can be used to clean fabrics and hard surfaces. Even further described herein is at least one cleaning composition selected from a laundry detergent, a dishwashing detergent (e.g., automatic and hand dish), and a personal care composition. Even still further, at least one polypeptide having improved soil removal and/or stability compared to at least one reference polypeptide is described herein.

6 Claims, 14 Drawing Sheets

Figure 1:
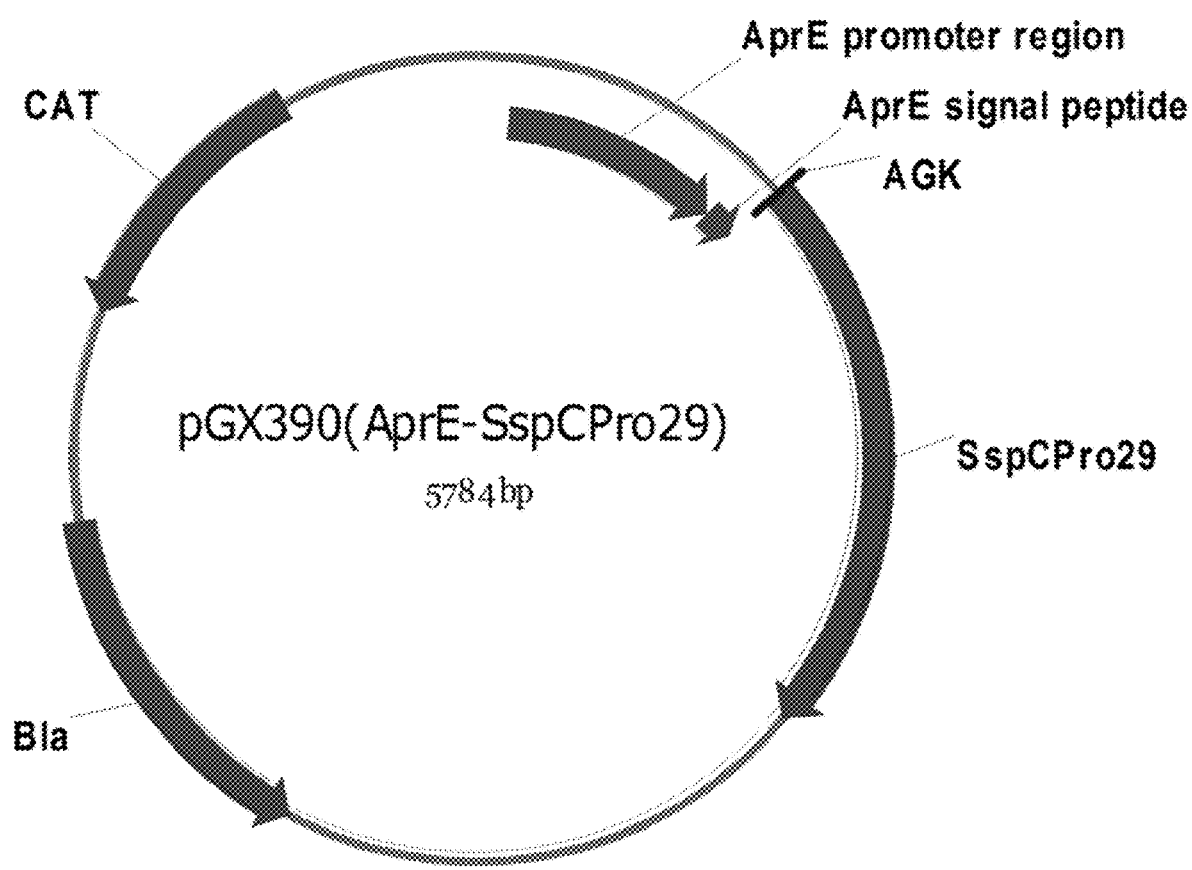

Specification includes a Sequence Listing.

```
                 1          10         20         30         40         50         60
                 |          |          |          |          |          |          |
SspCPro29        ----------APSDGHGPVA---APPPAARSAADALAVSAVQPDVLRAMQRDLGLTPAEARQRLAN
SspCPro33        -------------------AQPSP---GAAFGAQSAARALGAEAQPELLAAMGRDLGLTRAQAERRLVN
SspCPro23        -----------------------APDG------KPAAKTAARTLAATAAQPELLSAMQRDLGLTRPQALTRLAN
SspCPro59        --------------------AADAA---PPAP--PTAAATAGVDNASPGLLRAMQRDLGVTEAQARARLAN
WP_064069271     ------------------------AATPA-----PAARSAATTLAVSAVQPDVLRAMQRDLGLTGAEARVRLAN
WP_030548298     -----------------SAQQDGT-----PPGAVAHTAADTLAVSAAQPELLRAMQRDLGLTRAQAERRLVN
WP_005320871     ----------------SAQPA------GGAAPSAANTLAVSAAQPELLRAMQRDLGLTRAEAERRLVN
WP_024756173     ----------------TAAPDG-----NPAAKTAAQTLAAGAAQPELLSAMQRDLGLTRPQALTRLAN
WP_030313004     -----AAAPDGRDPHRAPTVRTAAQALGADSARPELLDAMRRDLGLTHSQARTRLAN
WP_030212164     -------------TAAPHDK------DRAFTVKTAADALGAASASAQPELLRAMQRDLGLTRAQAENRLAM
WP_031004112     -------------TAAPPSP-------GTAPAVQSAARALGAEARPELLAAMGRDLGLTRAQAERRLVN
WP_026277977     LASLQGYAAAQPSA---ASPGGGTSAAGTLAVSAAQPGLKRAMQRDLGLTRAQAERRLVN
WP_043225562     -------------TAAQFSP------GTGPGALSAARALGAEEARPELLAAMGRDLGLTRAQAERRLVN
WP_030749137     -------------TAAQPSP------GSAPSVRSAAHALGADEARPELLAAMGRDLGLTRFQAEHRLVN
WP_055639793     AGLQAGTATAAPDG----KPAAKTAARTLATAAAQPELLSAMQRDLGLTRPQALTRLAM
WO2015048332-44360   ---AAVFDAGEPHPAPTVRTAAQTLGADAAAPEVLDAMRRDLGLSHAQALTRLAN
WO2015048332-44127   ------GAATEAA---DPAAPQKSATATLRPGDAPABLLTALQRDLGLTPTQAKDRLAH

SspCPro29        EAEAGATAAARLRQRLAGSYAGAWVEGHASSVLTVATTPADDAAAIRASGAEADVVAHSLA
SspCPro33        EAEAGAAAAARILRDRIGGSFAGAWVEGAEBSGSLTVATTRAADLDAIRAAGATARLVRHDLS
SspCPro23        EAEAGATAAARLRQGLGGAFAGAWDGPESGTLTVATTRAADAAAIRATGADARLVSHSLT
SspCPro59        EAEAGATAAAVAGRLRTSLGGDFAGAWVHGPDSAKLSVATTDASDRAAIEAGGAHAVVVRHELP
WP_064069271     EAEAGATAALLRQRLGGSFAGAWVEGDVSSVLTVATTRAADAAAIRASGAEADVVTHGLA
WP_030548298     EAEAGATAAVLRQRLGGSFAGAWVEGADSGTLTVATTRAADAAAIRAAGAEBSRTVTHNLA
WP_005320871     EAEAGATAAVLRQRLGDSFAGAWVEGADSGTLTVATTRAADAAAIRAGGAEARTVTHTLA
WP_024756173     EAEAGATAAARLRQGIGGAFAGAWVEGAESGTLTVATTRAADAAVIRATGANARLVSHELT
WP_030313004     EAEAGARAAARAAARLPLDLGGAFAGAWDGPESGTLTVATTRAADTPAIRATGARARLVRHGLA
WP_030212164     EAEAGATAAARAAARLRDRLGGAFAGAWVEGAESGSLTVATTRAADLAAIRAADHAAVRABGAKPVAAGASLA
WP_031004112     EAEAGATAAARLQORLGASFAGAWVSGAESGTLTVATTRAADHAAVRABGAKPVAAGASLA
WP_026277977     EAEAGATAAARLRDRLGGSFAGAWVAGAESGSLTVATTRAADLAAIRAAGAEAALVRHGLP
WP_043225562     EAEAGATAAARLRQHLGGSFAGAWVAGAESGSLTVATTRAADLAAIRAAGAEAALVRHGLT
WP_030749137     EAEAGATAAGLRQSLAGAFAGAWVDGAESGTLTVATTRSADTAAIRATGANARLVPHSLT
WP_055639793     EAEAGATAAGLRQGLGGAFAGAWDGAESGTLTVATTRSSDAAAIRATGARARLVTHPLT
WO2015048332-44360   EAEAGATAARLRARLGAAFAGAWDGADSATLTVATTRAADAAAIRAAGAEAKLVSRSLA
WO2015048332-44127   EAEAGATAARLRARLGAAFAGAWDGADSATLTVATTRAADAAAIRAAGAEAKLVSRSLA
```

Figure 11A

| | | |
|---|---|---|
| SspCPro29 | ALDRTKAALDRAARTAADVGV-- | PVRYTVDVRTNSVVQAVDPGAAASLVGFVSEADFSRI |
| SspCPro33 | SLERAKAALDRAAGADA------ | PVRYVDVRANQLVVEEVRAGAGARLLAAATG-VPRELY |
| SspCPro23 | ALERAKRTIDGAATAEA------ | PVRYVDVRANVLVVEETRAGAGARLVRATG-VPRDLV |
| SspCPro59 | RLDGALAKILDEAASAAPSTAAEV | PVRYVDVTANKVTLQTVRPAAAKALVVAAG-VDPALV |
| WP_064069271 | QLDRTKAALDRAARTTATTGV-- | PVWYTVDVRTNSVVGAADRAAAAALVARVGEADRSRI |
| WP_030548298 | ELDRTKAALDRAAERNSSTDV-- | PVWYTVDVRTNSVVGAADRAAAAALVARVGEADRSRI |
| WP_005320871 | ELDRAKAALDRAAARDSSTDV-- | PVWYVDVRANAVVVRAVEKAAAQTLIEATA-ADRDRI |
| WP_024756173 | ALERAKRALDGAATAEA------ | PVRYVDVRANVLVVEETRPGAGARLVRATG-VPRDLV |
| WP_030313004 | ALERAKORLLRTAGTDA------ | PVRYVDVRANVLVVEEARAGAGARLVRATG-VPRELV |
| WP_030212164 | ALERAKEZALDRAATADV------ | PVRYVDVRANVLVVEEARAGAGARLVAATG-VPRDLV |
| WP_031041112 | ALERAKESLDRAAGADA------ | PVRYVDVRANVLVVEETRAGAGARLAAETG-VARELV |
| WP_026277977 | ELDRAKAALDRAAARAGSPAV-- | PVWYVDVRENTVVVGAENTARAEALIAASG-ADRDRI |
| WP_043225562 | ALERAKAALDRAATADA------ | PVRLYDIRANALVVEETRAGAGKRLVAATG-VPAELV |
| WP_030749137 | ALEFARTALDRAATADA------ | PVRYVDVRANVLVVEETRAGAGDRLVAATG-VPRELV |
| WP_055639793 | ALERAKRALDRGATAEA------ | PVRYVDVRANVLVVEETRAGAGARLVEAAG-VPRDLV |
| WO2015048332-44360 | ILERAKERILDRAATADA------ | PVRLYDVRANVLVVEETKAGAGARLLAATG-VPRELV |
| WO2015048332-44127 | DLDAVRAGLDRAATAET------ | PVRYVDPKTNTLVEETRPGAAAGLLAATG-TDPALA |

| | | |
|---|---|---|
| SspCPro29 | RVVPTR---ERPRPLYDIRGGDAYYMGGSGGRCSVGFPVTRGTQAGFATAGHCGRAGTTTTG |
| SspCPro33 | RVERST---EAPRPLYDLRGGDAYMGGSGGRCSVGFPVTRGTTQGFATAGHCGRAGQTTSG |
| SspCPro23 | RVVRTT---SAPRPLYDIRGGDAYMGGSGGRCSVGFPVTRGTTQGFATAGHCGRAGTTTSG |
| SspCPro59 | RVEKSA---EREPLYDLEGGDAYMNGSGGRCSVGFPVTKGTGGFATAGHCGRVGTTTTG |
| WP_064069271 | RVVPTR---ERPRPLYDIPGGDAYYMGGSGGHCSVGFAITRGTQAGFATAGHCGRAGTTTG |
| WP_030548298 | RVVPTG---EQPRPLYDIPGGDAYYMGGGDAYMGGGRCSVGFAVTRGTTQGFATAGHCGRAGTSTSG |
| WP_005320871 | RVVPTE---EQPRPLYDIPGGDAYMGGGDAYMGGGRCSVGFAVTRGTTQGFATAGHCGRAGTSTSG |
| WP_024756173 | RVVRTA---SAPRPLYDIRGGDAYMGGGDAYMGGGRCSVGFAVTBGTTQGFATAGHCGRAGTTTSG |
| WP_030313004 | RVVRTG---QAPRPLYDIRGGDAYYMGGSGGRCSVGFPFITKGTTQGFATAGHCGRAGTTTSG |
| WP_030212164 | RVVRTA---EAPRPLYDIRGGDLAYMGGGDAYMGGGRCSVGFAVTRGTTQGFATAGHCGRAGTTTSG |
| WP_031041112 | RVVRSA---EAPRPLYDIRGGDAYYMGGGDAYMGGGRCSVGFAVTRGTTQGFATAGHCGRAGTTTSG |
| WP_026277977 | RVAATG---ESPRPLYDIFGGDLRGGDAYYMGGGDAYMGGGRCSVGFPVTRGTQHGFATAGHCGRAGTATSG |
| WP_043225562 | RVVRSA---EAPRPLYDIRGGDLRGGDAYYMGGGDAYMGGGRCSVGFAVTRGATQGFATAGHCGRAGTTTSG |
| WP_030749137 | RVVRSA---QAPRPLYDIRGGDAYYMGGGDAYMGGGRCSVGFPVTRGTTQGFATAGHCGRAGQSTSG |
| WP_055639793 | RVVRTD---PAPRPLYDIPGGDLRGGDAYYMGGGDAYMGGGRCSVGFAVTRGATQGFATAGHCGRAGTTTSG |
| WO2015048332-44360 | RVVRSG---QAPRPLYDLEGGDAYYMGGGDAYMGGGRCSVGFPVTRGTTQGFATAGHCGRAGTTTSG |
| WO2015048332-44127 | TVVRTAAEGQAPRPLYDLEGGDAYYMNGQGRCSVGFPVTRGTTQGFATAGHCGRAGTTTSG |

Figure 11B

```
SspCPro29         YNRVAQGSFQASTFPGRDTAWVATNTNWTATPYVKGAGGANVRVAGSVQQPVGASVCRSG
SspCPro33         YNQVAQGSFQGSVFPGSIMAWVAANSSWTATPYVKGAGGANVQVTGSVLQPVGASVCRSG
SspCPro23         FNQVAQGSFQGSIFPGNDMAWVAANTNWTSTPYVKGSGGANVQVTGSVLQPVGASVCRSG
SspCPro59         YNQVAQGSFQASTFPGRDMAWVATNSNWTATPYVKGNSG-NVQVAGSTQAAVGASVCRSG
WP_064069271      YNQVAQGSFQASTFPGRDTAWVATSTNWTATPYVKGAGGANVQVTGSVQQPVGASVCRSG
WP_030548298      YNQVAQGTFQASTFPGRDTAWVATNGNWTSTPYVKGQGGQNIQVTGSVQQPVGASICRSG
WP_005320871      YNQVAQGTFQASTFPGRDTAWVATNGNWTAAANSNWTSTPYVKGQSGQNIQVTGSVQQPVGASICRSG
WP_024756173      FNQAAQGSFQGSIFPGNDMAWVAANSNWTSTPYVKGSGGANVQVTGSVLQPVGSSVCRSG
WP_030313004      FNQVAQGSFQGSVFPGSSDMAWVATNSNWTATPYVKGAGGANVQVTGSVLQPVGGSVCRSG
WP_030212164      YNQVAQGSFQGSIFPGNDMAWVAANTNWTATPYVEGAGGANVQVTGSVLQPVGASVCRSG
WP_031004112      FNQVAQGTFQASTFPGRDTAWVLTNSQWTATPYVKGAGGANVQVTGSVLQPVGASVCRSG
WP_026277977      YNQVAQGSFQASTFPGNDMAWVAANSNWTATPYVKGSGGANVQVTGSVLQPVGSSVCRSG
WP_043225562      FNQVAQGSFQGSIFPGNDMAWVAANGNWTAANGNWTAANTNWTATPYVKGSGGANVQVTGSVLQPVGASVCRSG
WP_030749137      YNQVAQGTFQASTFPGNDMAWVAANTNWTATPYVKGSGGANVQVTGSVLQPVGASVCRSG
WP_055639793      FNQVAQGSFQGSVFPGNDMAWVAANGWTATSWTATPYVKGSGGANVQVTGSVLQPVGASVCRSG
WO2015048332-44360 FNQVAQGSFQASTFPGNDMAWVAANTSWTATSWTATPYVKGSGGANVQVTGSVLQPVGASVCRSG
WO2015048332-44127 FNQVAQGSFQASVFPGNDMAWVAANTSWTATPYVKGSGGANVQVTGSVLQPVGASVCRSG

SspCPro29         STTGWHCGTIQQHNTSVTYPEGTITGVTRTSVCAEPGDSGGSYISGSQAQGVTSGGSGDC
SspCPro33         STTGWHCGTIQQHNTSVTYPEGTISGVTRTTVCAEPGDSGGSYISGSQAQGVTSGGSGNC
SspCPro23         STTGWHCGTIQQHNTSVTYPEGTISGVTRTTVCAEPGDSGGSYISGSQAQGVTSGGSGNC
SspCPro59         STTGWHCGTIQQHNTSVTYPEGTISGVTRTTVCAEPGDSGGSYISGSQAQGVTSGGSGNC
WP_064069271      STTGWHCGTIQQHNTSVTYPEGTISGVTRTSVCAEPGDSGGSYISGTQAQGVTSGGSGDC
WP_030548298      STTGWHCGTIQQHNTSVTYPEGTIIGVTRTTVCAEPGDSGGSYISGSQAQGVTSGGSGNC
WP_005320871      STTGWHCGTISQHNTSVTYPEGTIIGVTRTTVCAEPGDSGGSYISGSQAQGVTSGGSGDC
WP_024756173      STTGWHCGTISQHNTSVTYPEGTISGVTRTTVCAEPGDSGGSYISGSQAQGVTSGGSGNC
WP_030313004      STTGWHCGTIQQHNTSVTYPEGTISGVTRTTVCAEPGDSGGSYISGSQAQGVTSGGSGNC
WP_030212164      STTGWHCGTIQQHNTSVTYPEGTISGVTRTTVCAEPGDSGGSYISGSQAQGVTSGGSGNC
WP_031004112      STTGWHCGTIQQHNTSVTYPEGTISGVTRTTVCAEPGDSGGSYISGSQAQGVTSGGSGNC
WP_026277977      STTGWHCGTVQQHNTSVTYPEGTISGVTRTTVCAEPGDSGGSYISGSQAQGVTSGGSGNC
WP_043225562      STTGWHCGTIQQHNTSVTYPEGTISGVTRTTVCAEPGDSGGSYISGSQAQGVTSGGSGNC
WP_030749137      STTGWHCGTIQQHNTSVTYQEGTISGVTRTTVCAEPGDSGGSYISGSQAQGVTSGGSGNC
WP_055639793      STTGWHCGTIQQHNTSVTYPEGTISGVTRTTVCAEPGDSGGSYISGSQAQGVTSGGTGNC
WO2015048332-44360 STTGWHCGTVQQHNTSVTYPEGTISGVTRTTVCAEPGDSGGSYISGSQAQGVTSGGSGNC
WO2015048332-44127 STTGWHCGTVQQHNTSVTYPEGTISGVTRTTVCAEPGDSGGSYISGSQAQGVTSGGSGDC
```

Figure 11C

```
SspCPro29           RSGGTTYHQPINPLLQAYGLTLTLTTT-T----GPGDPGPGDPDEPGGTWAAGTVYRAGDQV
SspCPro33           SSGGTTYFQPLNPILSAYGLTLTLKTTGTDPGPGPG---PGEP-EPGGTWKAGTVYAAGATV
SspCPro23           SSGGTTFFQPLNPILQNYGLTLTLKTTGSD---PGPG---PGEP-QPGGTWAAGKVYAAGDTV
SspCPro59           RSGGTTYYQPINPILQNYGLTLKTT-SD---DPG---PGEPGEPGGTWAAGTVYAAGAQV
WP_064069271        RSGGTTYHQPINPLLQGYGLTLRTT-T----DPDD---PGDPGEPGGTWAAGTVYRAGDQV
WP_030548298        RSGGTTYHQPINPLLQGYGLTLKTT-VDEG-DPGD---EGDPGEPGGTWAAGTVYQAGAQV
WP_005320871        RSGGTTYHQPNPLLQGYGLTLTLKTT-T----DPGE--PGEPGEPGGTWAAGTVYQAGAQV
WP_024756173        SSGGTFFQPLNPLLQNYGLTLTLKTTGSD---PGPG---PGEP-QPGGTWAAGKVYAAGDVV
WP_030313004        SSGGTFFQPLNPLLQNYGLTLTLKTTGTD---PGPGPG---PGEP-EPGGTWAAGKVYAAGDTV
WP_030212164        SSGGTFFQPLNPLLQNYGLTLTLKTTGSD---PGPG--PG-EP-EPGGTWAAGKNYAAGDTV
WP_031004112        SSGGTFFQPLNPILSNYGLTLTLRTAGTD---PGPGPG---PGEP-EPGGTWKAGTVYAAGATV
WP_026777977        RTGGTTYHQPINPLLQAYGLTLTLRTT---TDPGPGPGE---P---PGEPGGTWKAGTVYATGAQV
WP_043225562        SSGGTTYFQPLNPLLSNYGLTLTLRTTGTD---PGPGPG----PGEP-EPGGTWKAGTVYAAGATV
WP_030749137        SSGGTTYFQPLNPLLSGYGLTLKTTGSDPGPGPG-----PGEP-QPGGTWTAGKVYAAGKVYAAGDTV
WP_055639793        SSGGTFFQPLNPLLQNYGLTLKTTGTD---PGPG--PGEP-QPGGTWAAGKVYAAGATV
WO2015048332-44360  SSGGTTFFQPLNPILSAYGLTLKTTGGD---PGPG---PGEP-EPGGSWAAGTVYKAGDVV
WO2015048332-44127  TSGGTTFFQPLNPILSAYGLTLKVTGSDPGPGPG------PG-P--QPGGTWKAGTVYAAGDTV

SspCPro29           TYGGATYRCLQGHQAQAGWEPPNVPALWQRG
SspCPro33           TYGGSTYRCLQGHQAQAGWEPPNVPALWQRV
SspCPro23           TYGGATYRCLQGHQAQAGWEPPNVPALWQRQ
SspCPro59           TYGGATYRCLQGHQAQAGWEPPNVPALWQRA
WP_064069271        TYGGATYRCLQGHQAQAGWEPPNVPALWQRG
WP_030548298        TYGGATYRCLQGHQAQAGWEPPNAPALWQRL
WP_005320871        TYGGVTYRCLQGHQAQAGWEPPNVPALWQRL
WP_024756173        TYGGSTYRCLQGHQAQTGWEPPNVPALWQRQ
WP_030313004        TYGGASYRCLQGHQAQAGWQPPNVPALWQRL
WP_030212164        TYGGSTYRCLQGHQAQTGWEPSNVPALWQRV
WP_031004112        TYGGSTYRCLQGHQAQAGWEPPNVPALWQRL
WP_026777977        TYGGSTYRCLQAHQAQAGWEPSNVPALWQRV
WP_043225562        TYGGSTYRCLQGHQAQTGWEPPNVPALWQPI
WP_030749137        TYGGATYRCLQGHQAQTGWEPPNVPALWQRQ
WP_055639793        TYGGASYRCLQGHQAQAGWQPPNVPALWQRL
WO2015048332-44360  TYGGAAYRCLQGHQAQTGWEPSVVPALWQKL
```

Figure 11D

Figure 12A

| | |
|---|---|
| SspCPro29 | TSVTYPEGTIIGVTRTSVTPTTVCAEPGDSGGSYISGSQAQGVTSGGSGDCRSGGTTYHQPINPL |
| SspCPro33 | TSVTYPEGTISGVTRTSVTPTTVCAEPGDSGGSYISGSQAQGVTSGGSGNCSSGGTTYFQPLNPI |
| SspCPro23 | TSVTYPEGTISGVTRTTVCAEPGDSGGSYISGSQAQGVTSGGSGNCSSGGTTFFQPLNPL |
| SspCPro59 | TSVTYPEGTIIGVTRTTVCAEPGDSGGSYISGTQAQGVTSGGSGNCRSGGTTYYQPINPL |
| WP_064069271 | TSVTYPEGTISGVTRTSVTPTTVCAEPGDSGGSYISGSQAQGVTSGGSGDCRSGGTTYHQPINPL |
| WP_026277977 | TSVTYPEGTIIGVTRTSVTPTTVCAEPGDSGGSYISGSQAQGVTSGGSGNCRTGGTTYHQPINPL |
| WP_030548298 | TSVTYPEGTISGVTRTTVCAEPGDSGGSYISGSQAQGVTSGGSGDCRSGGTTYHQPVNPL |
| WP_044383230 | TSVTYPEGTIIGVTRTSVTPTTVCAEPGDSGGSYISGSQAQGVTSGGSGDCRTGGTTYFQPINPL |
| WP_005320871 | TSVTYPEGTISGVTRTTVCAEPGDSGGSYISGSQAQGVTSGGSGDCRSGGTTFHQPINPL |
| WP_069630550 | TSVTYPEGTIIGVTRTSVTPTTVCAEPGDSGGSYISGSQAQGVTSGGSGNCSSGGTFYQPVNPL |
| WP_029386953 | TSVTYPEGTISGVTRTSVTPTTVCAEPGDSGGSYISGSQAQGVTSGGSGNCRTGGTTYFQPINPL |
| WP_055639793 | TSVTYPEGTISGVTRTTVCAEPGDSGGSYISGSQAQGVTSGGSGNCSSGGTTFFQPLNPL |
| WP_029386953 | TSVTYPEGTISGVTRTSVTPTTVCAEPGDSGGSYISGSQAQGVTSGGSGDCRTGGTTYFQPLNPL |
| WP_043225562 | TSVTYPEGTISGVTRTTVCAEPGDSGGSFISGSQAQGVTSGGSGNCSSGGTTYFQPINPL |
| WP_031135572 | TSVTYPQGTVSGVTRTSVTPTTVCAEPGDSGGSYISGSQAQGVTSGGSGDCFTGGTTYHQPLNPL |
| WP_053699044 | TSVTYPEGTIIGVTRTSVTPTTVCAEPGDSGGSYISGSQAQGVTSGGSGNCRSGGTTFFQPLNPL |
| WP_024756173 | TSVTYPEGTIISGVTRTTVCAEPGDSGGSYISGSQAQGVTSGGSGBCRSGGTTYHQPXNPL |
| Consensus | TSVTYPEGTISGVTRTTVCAEPGDSGGSYISGSQAQGVTSGGSGNCSSGGTTYFQPLNPL |

| | |
|---|---|
| SspCPro29 | LQAYGLTLTTT |
| SspCPro33 | LSAYGLTLRTT |
| SspCPro23 | LQNYGLTLKTT |
| SspCPro59 | LQNYGLTLKTT |
| WP_064069271 | LQAYGLTLRTT |
| WP_026277977 | LQNYGLTLRTT |
| WP_030548298 | LQGYGLTLRTT |
| WP_044383230 | LQTYGLTLPTN |
| WP_005320871 | LQGYGLTLKTT |
| WP_069630550 | LQAYALTLKTT |
| WP_029386953 | LQSYGLTLKTN |
| WP_055639793 | LQNYGLTLKTT |
| WP_043225562 | LSNYGLTLKTT |
| WP_031135572 | LQAYALTLTTT |
| WP_053699044 | LQGYGLTIKTG |
| WP_024756173 | LQNYGLTLKTT |
| Consensus | LQAYGLTLTTT |

Figure 12B

SEQUENCE LISTING

```
<160> NUMBER OF SEQ ID NOS: 54

<210> SEQ ID NO 1
<211> LENGTH: 1395
<212> TYPE: DNA
<213> ORGANISM: Streptomyces sp. C009

<400> SEQUENCE: 1
atgttccacc gacacgccag agccgcgtgc gtgggcgccg tgaccgtggg cgcgctggtc      60
ctgacggcac tgcaaggggc cgctgcggcg ccctcggacg gccacggccc ggtcgccgcg     120
cccccaccgg cggcccgttc ggcggccgac gccctcgccg tgtccgccgt acagccggac     180
gtgctgcgtg ccatgcaacg ggacctcggc ctcactccgg ccgaggcccg gcagcggctg     240
gcgaacgagg cggaggcggg cgcgaccgcc gcccgtctcc ggcagcggct ggccggctcg     300
tacgccggtg cctgggtcga ggggcacgcg tcgtccgtcc tgaccgtcgc caccacccgg     360
gccgatgacg cggcggcgat cagggcgagc ggcgccgagg ccgatgtcgt cgcgcacagt     420
ctggcggcgc tcgaccgcac caaggcggct ctggaccgtg cggcccgcac cgccgccgac     480
gtcggcgtcc ccgtctggta cgtcgacgtc cgcaccaact ccgtggtggt ccaggccgtg     540
gacccggggg cggcggcgtc gctggtcggc cgggtgagcg aggccgaccg gtcgcggata     600
cgggtcgtcc cgacgcggga acggccgcgc ccgctgtacg acatcagggg cggtgacgcg     660
tactacatgg gcggctccgg ccgctgctcg gtgggcttct cggtcacccg tgggacgcag     720
gcgggcttcg cgacggcggg gcactgcggc cgggccggca cgaccacgac cgggtacaac     780
cgggtggcgc agggctcgtt ccaggcctcg acgttcccgg gccgggacac ggcctgggtg     840
gcgacgaaca ccaactggac cgcgaccccg tacgtgaagg gcgcgggcgg cgcgaacgtc     900
cgggtggccg gttcggtcca gcagccggtc ggcgcctcgg tctgccgctc gggctccacc     960
```

```
acgggctggc actgcggcac catccagcag cacaacacca gcgtgacgta cccggagggc    1020
accatcaccg gggtgacgcg gacctcggtg tgcgccgaac ccggtgactc cggtgggtcg    1080
tacatctccg gcagccaggc gcagggcgtc acctccggcg gttcgggcga ctgccggagc    1140 ggggtacga cctaccacca gccgatcaac ccgctgctgc aggcgtacgg gctgacgctg     1200
acgacgacca ccggacccgg cgacccgggc ccggcgacc cggacgagcc gggcggcaca     1260
tgggcggccg gcaccgtcta ccgggcgggt gaccaggtca cgtacggcgg tgcgacctac    1320
cgctgcctgc agggccacca ggcgcaggcc gggtgggaac cgccgaacgt cccggcgctc    1380
tggcagcgcg gctga                                                     1395
```

<210> SEQ ID NO 2
<211> LENGTH: 29
<212> TYPE: PRT
<213> ORGANISM: Streptomyces sp. C009

<400> SEQUENCE: 2

```
Met Phe His Arg His Ala Arg Ala Ala Cys Val Gly Ala Val Thr Val
1               5                   10                  15

Gly Ala Leu Val Leu Thr Ala Leu Gln Gly Ala Ala Ala
            20                  25
```

<210> SEQ ID NO 3
<211> LENGTH: 464
<212> TYPE: PRT
<213> ORGANISM: Streptomyces sp. C009

<400> SEQUENCE: 3

```
Met Phe His Arg His Ala Arg Ala Ala Cys Val Gly Ala Val Thr Val
1               5                   10                  15

Gly Ala Leu Val Leu Thr Ala Leu Gln Gly Ala Ala Ala Pro Ser
            20                  25                  30

Asp Gly His Gly Pro Val Ala Ala Pro Pro Ala Ala Arg Ser Ala
        35                  40                  45

Ala Asp Ala Leu Ala Val Ser Ala Val Gln Pro Asp Val Leu Arg Ala
50                  55                  60

Met Gln Arg Asp Leu Gly Leu Thr Pro Ala Glu Ala Arg Gln Arg Leu
65                  70                  75                  80

Ala Asn Glu Ala Glu Ala Gly Ala Thr Ala Ala Arg Leu Arg Gln Arg
                85                  90                  95

Leu Ala Gly Ser Tyr Ala Gly Ala Trp Val Glu Gly His Ala Ser Ser
            100                 105                 110

Val Leu Thr Val Ala Thr Thr Arg Ala Asp Asp Ala Ala Ala Ile Arg
        115                 120                 125

Ala Ser Gly Ala Glu Ala Asp Val Val Ala His Ser Leu Ala Ala Leu
    130                 135                 140

Asp Arg Thr Lys Ala Ala Leu Asp Arg Ala Ala Arg Thr Ala Ala Asp
145                 150                 155                 160

Val Gly Val Pro Val Trp Tyr Val Asp Val Arg Thr Asn Ser Val Val
                165                 170                 175

Val Gln Ala Val Asp Pro Gly Ala Ala Ser Leu Val Gly Arg Val
            180                 185                 190

Ser Glu Ala Asp Arg Ser Arg Ile Arg Val Val Pro Thr Arg Glu Arg
        195                 200                 205

Pro Arg Pro Leu Tyr Asp Ile Arg Gly Gly Asp Ala Tyr Tyr Met Gly
    210                 215                 220
```

-continued

Gly Ser Gly Arg Cys Ser Val Gly Phe Ser Val Thr Arg Gly Thr Gln
225                 230                 235                 240

Ala Gly Phe Ala Thr Ala Gly His Cys Gly Arg Ala Gly Thr Thr Thr
            245                 250                 255

Thr Gly Tyr Asn Arg Val Ala Gln Gly Ser Phe Gln Ala Ser Thr Phe
        260                 265                 270

Pro Gly Arg Asp Thr Ala Trp Val Ala Thr Asn Thr Asn Trp Thr Ala
    275                 280                 285

Thr Pro Tyr Val Lys Gly Ala Gly Ala Asn Val Arg Val Ala Gly
    290                 295                 300

Ser Val Gln Gln Pro Val Gly Ala Ser Val Cys Arg Ser Gly Ser Thr
305                 310                 315                 320

Thr Gly Trp His Cys Gly Thr Ile Gln Gln His Asn Thr Ser Val Thr
                325                 330                 335

Tyr Pro Glu Gly Thr Ile Thr Gly Val Thr Arg Thr Ser Val Cys Ala
            340                 345                 350

Glu Pro Gly Asp Ser Gly Gly Ser Tyr Ile Ser Gly Ser Gln Ala Gln
        355                 360                 365

Gly Val Thr Ser Gly Gly Ser Gly Asp Cys Arg Ser Gly Gly Thr Thr
    370                 375                 380

Tyr His Gln Pro Ile Asn Pro Leu Leu Gln Ala Tyr Gly Leu Thr Leu
385                 390                 395                 400

Thr Thr Thr Thr Gly Pro Gly Asp Pro Gly Pro Gly Asp Pro Asp Glu
                405                 410                 415

Pro Gly Gly Thr Trp Ala Ala Gly Thr Val Tyr Arg Ala Gly Asp Gln
            420                 425                 430

Val Thr Tyr Gly Gly Ala Thr Tyr Arg Cys Leu Gln Gly His Gln Ala
        435                 440                 445

Gln Ala Gly Trp Glu Pro Pro Asn Val Pro Ala Leu Trp Gln Arg Gly
    450                 455                 460

<210> SEQ ID NO 4
<211> LENGTH: 1371
<212> TYPE: DNA
<213> ORGANISM: Streptomyces sp. C001

<400> SEQUENCE: 4
atgctccgac gacacgcccg tgcggcgtgt accgcgctgg ccgccgccgg gatggtgctg      60
gccgggcttc aggccgggtc cgccaccgcc gcgcagccct ccccggagc gcgcgcccggc     120 gcgcagagcg ccgctcgggc gctcggcgcc ggcgaggcgc agcccgaact gctcgccgcg    180
atgggccgcg acctgggcct gacccggggcc caggcagagc gccggctcgt caacgaggcc    240
gaggcgggcg ccgcggccgc ccggctccgc gaccggatcg gcggctcctt cgccggggcc    300
tgggtcgagg gggccgagtc cggctccctg accgtggcca ccacccgcgc cgccgacctc    360
gacgcgatcc gggcggccgg ggcgacggcc cggctcgtcc ggcacgacct gtcctcgctg    420
gagcgggcga aggccgccct cgaccgggcc gcgggcgccg acgcgccggt cggtacgtg     480 gacgtgcgcg ccaaccagtt ggtcgtcgag gaggtccggg ccgtgccgg ggcgcgcctg    540 gcggcggcca ccggggtgcc gcgggagctg gtgcgggtgg agcggagcac cgaggcgccg    600
cgcccgctgt acgacctccg gggcggcgac gcgtactaca tgggcggcgg cgggcgctgc    660
tcggtcggct cccgtgtgac ccggggcacc acgcagggct cgcgacggc cgggcactgc    720 ggccgcgccg gccagaccac cagcggctac aaccaggtcg cccagggcag cttccaggcc    780

```
tcggtcttcc ccggcagcga catggcgtgg gtcgcggcca acagcagctg gaccgccacc     840
ccgtacgtga agggcgcggg cggcgcgaac gtccaggtca ccggctccgt gctgcagccc     900
gtgggcgcct ccgtctgccg ctcgggctcc accaccggct ggcactgcgg caccatccag     960
cagcacaaca cgagcgtgac gtacccggag ggcacgatct ccggcgtgac ccggacgacg    1020
gtctgcgccg agcccggcga ctcgggcggc tcgtacatct ccggcagcca ggcgcagggc    1080
gtcacctcgg gcggctccgg caactgctcc agcggcggca ccacgtactt ccagccgctg    1140
aacccgatcc tgtcggccta cggcctgacc ctgaagacca ccggcaccga cccgggcccc    1200
ggcccgggcc cggcgagcc ggagccgggc ggcacgtgga aggcgggcac ggtgtacgcg    1260
gccggcgcca ccgtcacgta cggcggttcc acctaccgct gcctccaggg ccaccaggcg    1320
cagaccggct gggagccgcc gaacgtaccg gcgctctggc agcgggtctg a             1371
```

<210> SEQ ID NO 5
<211> LENGTH: 30
<212> TYPE: PRT
<213> ORGANISM: Streptomyces sp. C001

<400> SEQUENCE: 5

```
Met Leu Arg Arg His Ala Arg Ala Ala Cys Thr Ala Leu Ala Ala Ala
1               5                   10                  15

Gly Met Val Leu Ala Gly Leu Gln Ala Gly Ser Ala Thr Ala
            20                  25                  30
```

<210> SEQ ID NO 6
<211> LENGTH: 456
<212> TYPE: PRT
<213> ORGANISM: Streptomyces sp. C001

<400> SEQUENCE: 6

```
Met Leu Arg Arg His Ala Arg Ala Ala Cys Thr Ala Leu Ala Ala Ala
1               5                   10                  15

Gly Met Val Leu Ala Gly Leu Gln Ala Gly Ser Ala Thr Ala Ala Gln
            20                  25                  30

Pro Ser Pro Gly Ala Ala Pro Gly Ala Gln Ser Ala Ala Arg Ala Leu
        35                  40                  45

Gly Ala Ala Glu Ala Gln Pro Glu Leu Leu Ala Ala Met Gly Arg Asp
    50                  55                  60

Leu Gly Leu Thr Arg Ala Gln Ala Glu Arg Arg Leu Val Asn Glu Ala
65              70                  75                  80

Glu Ala Gly Ala Ala Ala Arg Leu Arg Asp Arg Ile Gly Gly Ser
            85                  90                  95

Phe Ala Gly Ala Trp Val Glu Gly Ala Glu Ser Gly Ser Leu Thr Val
        100                 105                 110

Ala Thr Thr Arg Ala Ala Asp Leu Asp Ala Ile Arg Ala Ala Gly Ala
    115                 120                 125

Thr Ala Arg Leu Val Arg His Asp Leu Ser Ser Leu Glu Arg Ala Lys
130                 135                 140

Ala Ala Leu Asp Arg Ala Ala Gly Ala Asp Ala Pro Val Arg Tyr Val
145                 150                 155                 160

Asp Val Arg Ala Asn Gln Leu Val Val Glu Glu Val Arg Ala Gly Ala
                165                 170                 175

Gly Ala Arg Leu Ala Ala Ala Thr Gly Val Pro Arg Glu Leu Val Arg
            180                 185                 190
```

Val Glu Arg Ser Thr Glu Ala Pro Arg Pro Leu Tyr Asp Leu Arg Gly
            195                 200                 205

Gly Asp Ala Tyr Tyr Met Gly Gly Gly Arg Cys Ser Val Gly Phe
210                 215                 220

Pro Val Thr Arg Gly Thr Thr Gln Gly Phe Ala Thr Ala Gly His Cys
225                 230                 235                 240

Gly Arg Ala Gly Gln Thr Thr Ser Gly Tyr Asn Gln Val Ala Gln Gly
                245                 250                 255

Ser Phe Gln Gly Ser Val Phe Pro Gly Ser Asp Met Ala Trp Val Ala
                260                 265                 270

Ala Asn Ser Ser Trp Thr Ala Thr Pro Tyr Val Lys Gly Ala Gly Gly
            275                 280                 285

Ala Asn Val Gln Val Thr Gly Ser Val Leu Gln Pro Val Gly Ala Ser
            290                 295                 300

Val Cys Arg Ser Gly Ser Thr Thr Gly Trp His Cys Gly Thr Ile Gln
305                 310                 315                 320

Gln His Asn Thr Ser Val Thr Tyr Pro Glu Gly Thr Ile Ser Gly Val
                325                 330                 335

Thr Arg Thr Thr Val Cys Ala Glu Pro Gly Asp Ser Gly Gly Ser Tyr
            340                 345                 350

Ile Ser Gly Ser Gln Ala Gln Gly Val Thr Ser Gly Ser Gly Asn
            355                 360                 365

Cys Ser Ser Gly Gly Thr Thr Tyr Phe Gln Pro Leu Asn Pro Ile Leu
370                 375                 380

Ser Ala Tyr Gly Leu Thr Leu Lys Thr Thr Gly Thr Asp Pro Gly Pro
385                 390                 395                 400

Gly Pro Gly Pro Gly Glu Pro Glu Pro Gly Gly Thr Trp Lys Ala Gly
                405                 410                 415

Thr Val Tyr Ala Ala Gly Ala Thr Val Thr Tyr Gly Gly Ser Thr Tyr
            420                 425                 430

Arg Cys Leu Gln Gly His Gln Ala Gln Thr Gly Trp Glu Pro Pro Asn
            435                 440                 445

Val Pro Ala Leu Trp Gln Arg Val
450                 455

<210> SEQ ID NO 7
<211> LENGTH: 1356
<212> TYPE: DNA
<213> ORGANISM: Streptomyces sp. C003

<400> SEQUENCE: 7

| | |
|---|---|
| atgctccgac gacacgcccg cgcggcgtgt accgcgctgg tcgccgccgg gatggcgctg | 60 |
| gccggcctcc aggccggcac cgccaccgcg gcaccggacg ggaaaccggc agcgaagacc | 120 |
| gccgctcgga ccctcgccgc caccgccgcc cagcccgaac tcctctccgc catgcagcgc | 180 |
| gacctgggac tcacccgccc ccaggcactg accggctcg ccaacgaggc cgaggccggc | 240 |
| gccaccgccg cccggctccg ccagggcctc ggcggcgcct tcgccggagc ctgggtcgac | 300 |
| gggcccgagt ccggcaccct gaccgtggcc accaccccgcg ccgccgacgc ggccgcgata | 360 |
| cgcgccaccg cgccgacgc ccggctcgtc tcccacagcc tgaccgccct ggagcgggcc | 420 |
| aagcggaccc tggacggggc cgccaccgcc gaggcacccg tccgctacgt cgacgtccgc | 480 |
| gccaacgtcc tcgtcgtcga ggagacgcgg gccggcgccg gggcacggct cgtccgggcg | 540 |
| accggggtcc cgcgcgacct ggtgcgcgtg gtcaggacca catccgcacc gcgcccgctg | 600 |

```
tacgacatcc ggggcggcga cgcgtactac atgggcggcg cggccgctg     660
ctccgtcggt ttcgcggtga cccgcggcac gacgcagggc ttcgccactg cgggccactg    720
cggccgcgcc ggcacgacga ccagcggctt caaccaggtc gcccagggca gcttccaggg    780
ctcgatcttc cccggcaacg acatggcctg ggtcgccgcc aacaccaact ggacctccac    840
cccgtacgtc aagggctccg gcggcgcgaa cgtccaggtg accgggtccg tcctccagcc    900
cgtcggcgcg tccgtctgcc gctcaggctc gaccaccggc tggcactgcg gcacgatcca    960
gcagcacaac accagcgtca cctaccccga gggcaccatc tccggagtga cccgcacgac    1020
ggtctgcgcc gaacccggcg actccggcgg ctcgtacatc tccggcagcc aggcccaggg    1080
cgtgacctcg ggcggctcgg gcaactgctc cagcggcggc acgaccttct tccagccgct    1140
caacccgctg ctgcagaact acggcctgac cctgaagacc accggcagcg atccggggcc    1200
cgggcccggc gagccgcagc ccggcggcac ctgggcggcg ggcaaggtct acgcggccgg    1260
tgacacggtc acctacggcg gcgcgaccta ccgctgcctc cagggccacc aggcccagac    1320
cggctgggag ccgccgaacg tcccggccct ctggcagcgc cagtga                   1356
```

<210> SEQ ID NO 8
<211> LENGTH: 30
<212> TYPE: PRT
<213> ORGANISM: Streptomyces sp. C003

<400> SEQUENCE: 8

```
Met Leu Arg Arg His Ala Arg Ala Ala Cys Thr Ala Leu Val Ala Ala
1               5                   10                  15

Gly Met Ala Leu Ala Gly Leu Gln Ala Gly Thr Ala Thr Ala
            20                  25                  30
```

<210> SEQ ID NO 9
<211> LENGTH: 451
<212> TYPE: PRT
<213> ORGANISM: Streptomyces sp. C003

<400> SEQUENCE: 9

```
Met Leu Arg Arg His Ala Arg Ala Ala Cys Thr Ala Leu Val Ala Ala
1               5                   10                  15

Gly Met Ala Leu Ala Gly Leu Gln Ala Gly Thr Ala Thr Ala Pro
            20                  25                  30

Asp Gly Lys Pro Ala Ala Lys Thr Ala Ala Arg Thr Leu Ala Ala Thr
        35                  40                  45

Ala Ala Gln Pro Glu Leu Leu Ser Ala Met Gln Arg Asp Leu Gly Leu
50                  55                  60

Thr Arg Pro Gln Ala Leu Thr Arg Leu Ala Asn Glu Ala Glu Ala Gly
65                  70                  75                  80

Ala Thr Ala Ala Arg Leu Arg Gln Gly Leu Gly Ala Phe Ala Gly
            85                  90                  95

Ala Trp Val Asp Gly Pro Glu Ser Gly Thr Leu Thr Val Ala Thr Thr
                100                 105                 110

Arg Ala Ala Asp Ala Ala Ala Ile Arg Ala Thr Gly Ala Asp Ala Arg
        115                 120                 125

Leu Val Ser His Ser Leu Thr Ala Leu Glu Arg Ala Lys Arg Thr Leu
            130                 135                 140

Asp Gly Ala Ala Thr Ala Glu Ala Pro Val Arg Tyr Val Asp Val Arg
145                 150                 155                 160

Ala Asn Val Leu Val Val Glu Glu Thr Arg Ala Gly Ala Gly Ala Arg
```

```
                165                 170                 175
Leu Val Arg Ala Thr Gly Val Pro Arg Asp Leu Val Arg Val Arg
            180                 185                 190

Thr Thr Ser Ala Pro Arg Pro Leu Tyr Asp Ile Arg Gly Gly Asp Ala
            195                 200                 205

Tyr Tyr Met Gly Gly Gly Arg Cys Ser Val Gly Phe Ala Val Thr
210                 215                 220

Arg Gly Thr Thr Gln Gly Phe Ala Thr Ala Gly His Cys Gly Arg Ala
225                 230                 235                 240

Gly Thr Thr Thr Ser Gly Phe Asn Gln Val Ala Gln Gly Ser Phe Gln
                245                 250                 255

Gly Ser Ile Phe Pro Gly Asn Asp Met Ala Trp Val Ala Ala Asn Thr
            260                 265                 270

Asn Trp Thr Ser Thr Pro Tyr Val Lys Gly Ser Gly Ala Asn Val
            275                 280                 285

Gln Val Thr Gly Ser Val Leu Gln Pro Val Gly Ala Ser Val Cys Arg
            290                 295                 300

Ser Gly Ser Thr Thr Gly Trp His Cys Gly Thr Ile Gln Gln His Asn
305                 310                 315                 320

Thr Ser Val Thr Tyr Pro Glu Gly Thr Ile Ser Gly Val Thr Arg Thr
                325                 330                 335

Thr Val Cys Ala Glu Pro Gly Asp Ser Gly Ser Tyr Ile Ser Gly
            340                 345                 350

Ser Gln Ala Gln Gly Val Thr Ser Gly Gly Ser Gly Asn Cys Ser Ser
            355                 360                 365

Gly Gly Thr Thr Phe Phe Gln Pro Leu Asn Pro Leu Leu Gln Asn Tyr
            370                 375                 380

Gly Leu Thr Leu Lys Thr Thr Gly Ser Asp Pro Gly Pro Gly Pro Gly
385                 390                 395                 400

Glu Pro Gln Pro Gly Gly Thr Trp Ala Ala Gly Lys Val Tyr Ala Ala
                405                 410                 415

Gly Asp Thr Val Thr Tyr Gly Gly Ala Thr Tyr Arg Cys Leu Gln Gly
            420                 425                 430

His Gln Ala Gln Thr Gly Trp Glu Pro Pro Asn Val Pro Ala Leu Trp
            435                 440                 445

Gln Arg Gln
    450

<210> SEQ ID NO 10
<211> LENGTH: 1365
<212> TYPE: DNA
<213> ORGANISM: Streptomyces sp. S055

<400> SEQUENCE: 10
atgctccaca gacatgccaa agcgtcctgt gccgcgttcg cggccgtcgg cgcgctggtg      60
ctggcagggc tgcccgcaac ggccgccgcg gacgcggccc cacccgcacc gcccaccgcg     120
gccgcgacgg cgggcgtcga caacgcctcg ccagggctgc tgcgggccat gcagcgcgac     180
ctcggagtga ccgaggcgca ggcaagggcg cggctggcga atgaggccga ggccggtgcg     240
gtcgccggac ggctgcggat atcgctcggc ggcgacttcg ccggtgcctg ggtgcacggc     300
cccgactccg ccaaactgag cgtggccacc acggacgcct cggacagggc gcgatcgag     360 gccgggggcg cgcacgccgt cgtcgtacgg cacaccctgc cccggctgga cggagcgctg     420
gcgaagctgg acgaggcggc gtccgccgct ccgtccacgg ccgccgaggt acccgtccgg     480
```

```
tacgtggacg tcacggcgaa ccgcgtgacg ctgcaaaccg tacggccggc cgccgcgaag    540
gcgctcgtcg tggccgcggg ggtcgacccc gcgctcgtcc gcgtggagaa gtcggcggag    600
cgtccgcgtc cgctgtacga cctgcggggc ggcgacgcgt actacatgaa cggcagcggc    660
cgctgttccg tcggatttcc ggtcaccaag ggaacgcagc agggcttcgc caccgccgga    720
cactgcgggc gcgtcggcac gacgaccacc ggctacaacc aggtcgccca ggggtccttc    780
caggcctcca ccttccccgg ccgtgacatg gcctgggtgg ccaccaacag caactggacc    840
gccaccccct acgtcaaggg caacagcgga aacgtccagg tcgccggctc gacacaggcc    900
gccgtcggcg cgtcggtctg ccgttcgggg tccaccaccg gctggcactg cggcaccatc    960
cagcagcaca acaccagcgt cacctacccc gaaggcacca tcagtggtgt gacccgcacc   1020
acggtctgtg ccgagcccgg cgactcaggc ggctcctaca tctccggcag ccaggcccag   1080
ggcgtcacct ccggcgggtc gggcaactgc cgctccggcg gcaccaccta ctaccagccg   1140
atcaacccgc tgctccagaa ctacgggctg accctcaaga ccacctcgga cgaccccggc   1200
ccgggtgagc cgggggagcc cggcggcacc tgggccgcgg gaaccgtcta cgcggcggga   1260
gcccaggtga cgtacggcgg ggccacctac cggtgcctcc agggacacca ggcccaggcc   1320
ggctgggagc ccccgaacgt gcccgccctg tggcagcggg cgtga                   1365
```

<210> SEQ ID NO 11
<211> LENGTH: 28
<212> TYPE: PRT
<213> ORGANISM: Streptomyces sp. S055

<400> SEQUENCE: 11

Met Leu His Arg His Ala Lys Ala Ser Cys Ala Ala Phe Ala Ala Val
1               5                   10                  15

Gly Ala Leu Val Leu Ala Gly Leu Pro Ala Thr Ala
            20                  25

<210> SEQ ID NO 12
<211> LENGTH: 454
<212> TYPE: PRT
<213> ORGANISM: Streptomyces sp. S055

<400> SEQUENCE: 12

Met Leu His Arg His Ala Lys Ala Ser Cys Ala Ala Phe Ala Ala Val
1               5                   10                  15

Gly Ala Leu Val Leu Ala Gly Leu Pro Ala Thr Ala Ala Ala Asp Ala
            20                  25                  30

Ala Pro Pro Ala Pro Pro Thr Ala Ala Ala Thr Ala Gly Val Asp Asn
        35                  40                  45

Ala Ser Pro Gly Leu Leu Arg Ala Met Gln Arg Asp Leu Gly Val Thr
    50                  55                  60

Glu Ala Gln Ala Arg Ala Arg Leu Ala Asn Glu Ala Glu Ala Gly Ala
65                  70                  75                  80

Val Ala Gly Arg Leu Arg Ile Ser Leu Gly Gly Asp Phe Ala Gly Ala
                85                  90                  95

Trp Val His Gly Pro Asp Ser Ala Lys Leu Ser Val Ala Thr Thr Asp
            100                 105                 110

Ala Ser Asp Arg Ala Ala Ile Glu Ala Gly Gly Ala His Ala Val Val
        115                 120                 125

Val Arg His Thr Leu Pro Arg Leu Asp Gly Ala Leu Ala Lys Leu Asp
    130                 135                 140

Glu Ala Ala Ser Ala Ala Pro Ser Thr Ala Ala Glu Val Pro Val Arg
145                 150                 155                 160

Tyr Val Asp Val Thr Ala Asn Arg Val Thr Leu Gln Thr Val Arg Pro
                165                 170                 175

Ala Ala Ala Lys Ala Leu Val Val Ala Ala Gly Val Asp Pro Ala Leu
            180                 185                 190

Val Arg Val Glu Lys Ser Ala Glu Arg Pro Arg Pro Leu Tyr Asp Leu
        195                 200                 205

Arg Gly Gly Asp Ala Tyr Tyr Met Asn Gly Ser Gly Arg Cys Ser Val
    210                 215                 220

Gly Phe Pro Val Thr Lys Gly Thr Gln Gln Gly Phe Ala Thr Ala Gly
225                 230                 235                 240

His Cys Gly Arg Val Gly Thr Thr Thr Gly Tyr Asn Gln Val Ala
                245                 250                 255

Gln Gly Ser Phe Gln Ala Ser Thr Phe Pro Gly Arg Asp Met Ala Trp
                260                 265                 270

Val Ala Thr Asn Ser Asn Trp Thr Ala Thr Pro Tyr Val Lys Gly Asn
                275                 280                 285

Ser Gly Asn Val Gln Val Ala Gly Ser Thr Gln Ala Ala Val Gly Ala
    290                 295                 300

Ser Val Cys Arg Ser Gly Ser Thr Thr Gly Trp His Cys Gly Thr Ile
305                 310                 315                 320

Gln Gln His Asn Thr Ser Val Thr Tyr Pro Glu Gly Thr Ile Ser Gly
                325                 330                 335

Val Thr Arg Thr Thr Val Cys Ala Glu Pro Gly Asp Ser Gly Gly Ser
            340                 345                 350

Tyr Ile Ser Gly Ser Gln Ala Gln Gly Val Thr Ser Gly Ser Gly
            355                 360                 365

Asn Cys Arg Ser Gly Gly Thr Thr Tyr Gln Pro Ile Asn Pro Leu
            370                 375                 380

Leu Gln Asn Tyr Gly Leu Thr Leu Lys Thr Thr Ser Asp Asp Pro Gly
385                 390                 395                 400

Pro Gly Glu Pro Gly Glu Pro Gly Gly Thr Trp Ala Ala Gly Thr Val
                405                 410                 415

Tyr Ala Ala Gly Ala Gln Val Thr Tyr Gly Gly Ala Thr Tyr Arg Cys
            420                 425                 430

Leu Gln Gly His Gln Ala Gln Ala Gly Trp Glu Pro Pro Asn Val Pro
            435                 440                 445

Ala Leu Trp Gln Arg Ala
    450

<210> SEQ ID NO 13
<211> LENGTH: 1362
<212> TYPE: DNA
<213> ORGANISM: artificial sequence
<220> FEATURE:
<223> OTHER INFORMATION: synthesized gene

<400> SEQUENCE: 13
gtgagaagca aaaaattgtg gatcagcttg ttgtttgcgt taacgttaat ctttacgatg    60
gcgttcagca acatgagcgc gcaggctgct ggaaaagcac cggatggcaa accggcagca   120
aaaacagcag caagaacact ggcagcaaca gcagcgcaac cggaactgct gtcagcaatg   180
caaagagatc tgggcctgac aagaccgcaa gcacttacaa gactggcaaa tgaagcagaa   240

| | |
|---|---|
| gcaggcgcaa cagcggcaag actgagacaa ggcctgggag gcgcatttgc aggcgcatgg | 300 |
| gttgatggac cggaatcagg cacactgaca gttgcaacaa caagagcagc agatgcagca | 360 |
| gcaattagag caacaggcgc agatgcaaga ctggtttcac attcactgac agcactggaa | 420 |
| agagcaaaaa gaacacttga tggcgcagcg acagcggaag caccggttag atatgttgat | 480 |
| gttagagcaa atgttctggt cgttgaagaa acaagagctg gcgcaggcgc tagactggtc | 540 |
| agagcgacag gcgttccgag agatcttgtt agagttgtta gaacaacatc agcaccgcgt | 600 |
| ccgctgtatg atattagagg cggagatgcg tattatatgg gaggcggagg cagatgctca | 660 |
| gttggctttg cagttacaag aggcacaaca caaggctttg cgacagcagg ccattgcggc | 720 |
| agagctggca caacaacatc tggctttaat caagttgcac aaggctcatt tcaaggctca | 780 |
| attttccgg gaaatgatat ggcatgggtc gcagcaaata caaattggac atcaacaccg | 840 |
| tatgttaaag gctcaggcgg agcgaatgtt caagttacag gctcagttct gcagccggtt | 900 |
| ggcgcatcag tttgcagatc aggctcaaca acaggctggc attgcggaac aattcaacaa | 960 |
| cataatacaa gcgtcacata tccggaaggc acaatttcag gcgttacaag aacaacagtt | 1020 |
| tgcgcagaac ctggcgattc aggcggatca tatatttcag gcagccaagc acaaggcgtg | 1080 |
| acatcaggcg gaagcggcaa ttgctcatct ggcggaacaa cattttttca accgctgaat | 1140 |
| ccgctgctgc aaaattatgg cctgacactg aaaacaacag gatcagatcc gggaccggga | 1200 |
| cctggcgaac cgcaaccggg tggaacatgg gcagcaggca agtttatgc agcaggcgat | 1260 |
| acagttacat atggcggagc tacatataga tgcctgcaag ccatcaagc acaaacagga | 1320 |
| tgggaaccgc ctaatgttcc ggcactgtgg caaagacaat aa | 1362 |

<210> SEQ ID NO 14
<211> LENGTH: 1404
<212> TYPE: DNA
<213> ORGANISM: artificial sequence
<220> FEATURE:
<223> OTHER INFORMATION: synthesized gene

<400> SEQUENCE: 14

| | |
|---|---|
| gtgagaagca aaaaattgtg gatcagcttg ttgtttgcgt taacgttaat ctttacgatg | 60 |
| gcgttcagca acatgagcgc gcaggctgct ggaaaagcac cgtcagatgg ccatggaccg | 120 |
| gttgcagcac cgcctccggc agcaagatca gcagcagatg cactggcagt ttcagcagtt | 180 |
| caaccggatg ttctgagagc aatgcaaaga gatctgggcc tgacaccggc agaagcaaga | 240 |
| caaagactgg caaatgaagc agaagcaggc gcaacagcag caagactgag acagagactt | 300 |
| gcaggctcat atgcaggcgc atgggttgaa ggccatgcat catcagttct gacagttgca | 360 |
| acaacaagag cagatgatgc agcagcaatt agagcatcag cgctgaagc agatgttgtt | 420 |
| gcgcattcac tggcagcact ggatagaaca aaagcagcgc ttgatagagc agcgagaaca | 480 |
| gcggctgatg ttggcgttcc ggtttggtat gttgatgtta gaacaaatag cgttgttgtc | 540 |
| caagcagttg atcctggcgc agcagcatca ctggttggca gagtttcaga agcagataga | 600 |
| tcaagaatta gagttgtccc gacaagagaa agaccgcgtc cgctgtatga tattagaggc | 660 |
| ggagatgcgt attatatggg aggctcaggc agatgctcag ttggcttttc agttacaaga | 720 |
| ggcacacaag caggctttgc gacagcaggc cattgcggca gagctggcac aacaacaaca | 780 |
| ggctataata gagttgcaca aggctcattt caagcgtcaa catttccggg aagagataca | 840 |
| gcatgggtcg caacaaatac aaattggaca gcaacaccgt atgttaaagg cgcaggcgga | 900 |
| gcaaatgtta gagtcgcagg ctcagttcaa cagccggttg gcgcatcagt ttgcagatca | 960 |

```
ggcagcacaa caggatggca ttgcggaaca attcaacaac ataatacaag cgtgacatat    1020
ccggaaggca caattacagg cgttacaaga acaagcgttt gcgcagaacc tggcgattca    1080
ggcggatcat atatttcagg ctcacaagca caaggcgtca catctggcgg atcaggcgat    1140
tgcagaagcg gaggcacaac atatcatcaa ccgattaatc cgctgctgca agcatatggc    1200
cttacactga caacgacgac aggccctggc gatccgggac cgggtgatcc ggatgaaccg    1260
ggtggcacat gggcagcagg cacagtttat agagcaggcg atcaagttac atatggcgga    1320
gcgacatata gatgccttca aggccatcaa gcacaggcag gctgggaacc gcctaatgtt    1380
ccggcactgt ggcaaagagg ctaa                                           1404

<210> SEQ ID NO 15
<211> LENGTH: 1377
<212> TYPE: DNA
<213> ORGANISM: artificial sequence
<220> FEATURE:
<223> OTHER INFORMATION: synthesized gene

<400> SEQUENCE: 15
gtgagaagca aaaaattgtg gatcagcttg ttgtttgcgt taacgttaat ctttacgatg      60
gcgttcagca acatgagcgc gcaggctgct ggaaaagcac aaccgtcacc tggcgcagcg     120
cctggcgcac aatcagcagc aagagcactt ggcgcagcag aagcacaacc ggaactgctg     180
gcagcaatgg gcagagatct gggcctgaca agagcacaag cagaaagacg cctggttaat     240
gaagcggaag caggcgcagc ggcagcaaga ctgagagata gaattggcgg atcatttgca     300
ggcgcatggg ttgaaggcgc agaatcaggc tcactgacag ttgcaacaac aagagcagca     360
gatctggatg caattagagc ggcaggcgca acagcgagac tggttagaca tgatctgtca     420
tcactggaaa gagcaaaagc ggcacttgat agagcagctg gcgcagatgc accggttaga     480
tatgttgatg ttagagcaaa tcaactggtc gtcgaagaag ttagagcagg cgctggcgca     540
agactggcag cagcaacagg cgttccgaga gaacttgtta gagttgaaag atcaacagaa     600
gcaccgcgtc cgctgtatga tctgagaggc ggagatgcgt attatatggg aggcggaggc     660
agatgctcag ttggctttcc ggttacaaga ggcacaacac aaggctttgc aacagcaggc     720
cattgcggca gcagggcca aacaacatca ggctataatc aagttgcaca aggctcattt     780
caaggctcag ttttttccggg atcagatatg gcatgggtcg cagcaaattc atcatggaca     840
gcaacaccgt atgttaaagg cgcaggcgga gcgaatgttc aagttacagg cagcgttctg     900
cagccggttg gcgcaagcgt ttgcagatca ggatcaacaa caggctggca ttgcggaaca     960
attcaacaac ataatacaag cgtcacatat ccggaaggca caatttcagg cgttacaaga    1020
acaacagttt gcgcagaacc tggcgatagc ggaggctcat atatttcagg cagccaagca    1080
caaggcgtga catcaggcgg atcaggcaat tgctcatctg gcggaacaac atatttcaa     1140 ccgctgaatc cgattctgtc agcatatggc ctgacactga aaacaacggg cacagatccg    1200
ggaccgggtc cgggacctgg cgaacctgaa ccgggtggca catggaaagc aggcacagtt    1260
tatgctgcag gcgctacagt tacatatggc ggaagcacat atagatgcct gcaaggccat    1320
caagcacaaa caggatggga accgcctaat gttccggcac tgtggcaaag agtttaa      1377

<210> SEQ ID NO 16
<211> LENGTH: 1374
<212> TYPE: DNA
<213> ORGANISM: artificial sequence
<220> FEATURE:
```

<223> OTHER INFORMATION: synthesized gene

<400> SEQUENCE: 16

```
gtgagaagca aaaaattgtg atcagcttg ttgtttgcgt taacgttaat ctttacgatg      60
gcgttcagca acatgagcgc gcaggctgct ggaaaagcag cagatgcagc acctccggca    120
cctcctacgg cagcagcaac ggcaggcgtt gataatgcat caccgggact tttaagagca    180
atgcaaagag atcttggagt tacagaagca caagcacgcg cacgccttgc aaacgaagca    240
gaagcaggcg cagttgcagg acgccttaga attagcctcg ggggcgattt tgcaggcgca    300
tgggttcatg gccctgatag cgcaaaactg agcgttgcaa cgacagatgc atcagatcgc    360
gcagcaatcg aagctggcgg cgcacatgca gttgttgttc gccatacact gcctagactt    420
gatggcgcac tggcaaaact tgatgaagca gcatctgcag caccgtctac ggcagcagaa    480
gttccggttc gctatgttga tgttacggca aatagagtta cacttcaaac ggttcgccct    540
gcagcagcaa aagcactggt tgttgcagca ggcgttgatc ctgcattagt tcgcgttgaa    600
aaatctgcag aaagacctag accgctgtat gacttgcgag gcggagatgc atattatatg    660
aatggctctg ccgctgctc agttggcttt cctgttacga aggaacaca acaaggattt      720
gcaacggcag gccattgtgg tcgtgttgga acgacgacga caggctataa tcaagttgca    780
caaggctcat ttcaagcatc tacatttccg ggccgcgata tggcatgggt tgcaacaaat    840
tctaattgga cggcaacacc ttatgttaaa ggaaatagcg gaaatgttca agttgcaggc    900
tctacacaag cagcagttgg cgcatctgtt tgccgctctg gatctacgac gggctggcat    960
tgcggaacaa tccaacaaca taatacgtca gttacgtatc ctgaaggaac gatttctgga   1020
gttacacgca cgacggtttg cgcagaaccg ggagatagcg gaggatcata tattagcgga   1080
tctcaagcac aaggcgttac gagcggagga tctggaaatt gccgctctgg cggaacgaca   1140
tattatcaac ctattaatcc tcttcttcaa aattatggac tgacacttaa aacgacgtca   1200
gatgatccgg gaccgggcga accgggagaa ccgggcggaa catgggcagc aggaacagtt   1260
tatgcagcag gcgcacaagt tacgtatgga ggcgcaacgt atcgctgctt acaaggccat   1320
caagcacaag caggctggga acctccgaat gttccggcac tgtggcaacg cgca         1374
```

<210> SEQ ID NO 17
<211> LENGTH: 29
<212> TYPE: PRT
<213> ORGANISM: Bacillus subtilis

<400> SEQUENCE: 17

```
Met Arg Ser Lys Lys Leu Trp Ile Ser Leu Leu Phe Ala Leu Thr Leu
1               5                   10                  15
Ile Phe Thr Met Ala Phe Ser Asn Met Ser Ala Gln Ala
            20                  25
```

<210> SEQ ID NO 18
<211> LENGTH: 191
<212> TYPE: PRT
<213> ORGANISM: Streptomyces sp. C009

<400> SEQUENCE: 18

```
Tyr Asp Ile Arg Gly Gly Asp Ala Tyr Tyr Met Gly Gly Ser Gly Arg
1               5                   10                  15
Cys Ser Val Gly Phe Ser Val Thr Arg Gly Thr Gln Ala Gly Phe Ala
            20                  25                  30
Thr Ala Gly His Cys Gly Arg Ala Gly Thr Thr Thr Thr Gly Tyr Asn
```

```
                35                  40                  45
Arg Val Ala Gln Gly Ser Phe Gln Ala Ser Thr Phe Pro Gly Arg Asp
 50                  55                  60

Thr Ala Trp Val Ala Thr Asn Thr Asn Trp Thr Ala Thr Pro Tyr Val
 65                  70                  75                  80

Lys Gly Ala Gly Gly Ala Asn Val Arg Val Ala Gly Ser Val Gln Gln
                 85                  90                  95

Pro Val Gly Ala Ser Val Cys Arg Ser Gly Ser Thr Thr Gly Trp His
                100                 105                 110

Cys Gly Thr Ile Gln Gln His Asn Thr Ser Val Thr Tyr Pro Glu Gly
                115                 120                 125

Thr Ile Thr Gly Val Thr Arg Thr Ser Val Cys Ala Glu Pro Gly Asp
            130                 135                 140

Ser Gly Gly Ser Tyr Ile Ser Gly Ser Gln Ala Gln Gly Val Thr Ser
145                 150                 155                 160

Gly Gly Ser Gly Asp Cys Arg Ser Gly Gly Thr Thr Tyr His Gln Pro
                165                 170                 175

Ile Asn Pro Leu Leu Gln Ala Tyr Gly Leu Thr Leu Thr Thr Thr
            180                 185                 190

<210> SEQ ID NO 19
<211> LENGTH: 191
<212> TYPE: PRT
<213> ORGANISM: Streptomyces sp. C001

<400> SEQUENCE: 19

Tyr Asp Leu Arg Gly Gly Asp Ala Tyr Tyr Met Gly Gly Gly Gly Arg
 1               5                  10                  15

Cys Ser Val Gly Phe Pro Val Thr Arg Gly Thr Thr Gln Gly Phe Ala
                 20                  25                  30

Thr Ala Gly His Cys Gly Arg Ala Gly Gln Thr Thr Ser Gly Tyr Asn
                 35                  40                  45

Gln Val Ala Gln Gly Ser Phe Gln Gly Ser Val Phe Pro Gly Ser Asp
 50                  55                  60

Met Ala Trp Val Ala Ala Asn Ser Ser Trp Thr Ala Thr Pro Tyr Val
 65                  70                  75                  80

Lys Gly Ala Gly Gly Ala Asn Val Gln Val Thr Gly Ser Val Leu Gln
                 85                  90                  95

Pro Val Gly Ala Ser Val Cys Arg Ser Gly Ser Thr Thr Gly Trp His
                100                 105                 110

Cys Gly Thr Ile Gln Gln His Asn Thr Ser Val Thr Tyr Pro Glu Gly
                115                 120                 125

Thr Ile Ser Gly Val Thr Arg Thr Thr Val Cys Ala Glu Pro Gly Asp
            130                 135                 140

Ser Gly Gly Ser Tyr Ile Ser Gly Ser Gln Ala Gln Gly Val Thr Ser
145                 150                 155                 160

Gly Gly Ser Gly Asn Cys Ser Ser Gly Gly Thr Thr Tyr Phe Gln Pro
                165                 170                 175

Leu Asn Pro Ile Leu Ser Ala Tyr Gly Leu Thr Leu Lys Thr Thr
            180                 185                 190

<210> SEQ ID NO 20
<211> LENGTH: 191
<212> TYPE: PRT
<213> ORGANISM: Streptomyces sp. C003
```

```
<400> SEQUENCE: 20

Tyr Asp Ile Arg Gly Gly Asp Ala Tyr Tyr Met Gly Gly Gly Arg
1               5                   10                  15

Cys Ser Val Gly Phe Ala Val Thr Arg Gly Thr Thr Gln Gly Phe Ala
            20                  25                  30

Thr Ala Gly His Cys Gly Arg Ala Gly Thr Thr Thr Ser Gly Phe Asn
        35                  40                  45

Gln Val Ala Gln Gly Ser Phe Gln Gly Ser Ile Phe Pro Gly Asn Asp
    50                  55                  60

Met Ala Trp Val Ala Ala Asn Thr Asn Trp Thr Ser Thr Pro Tyr Val
65                  70                  75                  80

Lys Gly Ser Gly Gly Ala Asn Val Gln Val Thr Gly Ser Val Leu Gln
                85                  90                  95

Pro Val Gly Ala Ser Val Cys Arg Ser Gly Ser Thr Thr Gly Trp His
            100                 105                 110

Cys Gly Thr Ile Gln Gln His Asn Thr Ser Val Thr Tyr Pro Glu Gly
        115                 120                 125

Thr Ile Ser Gly Val Thr Arg Thr Thr Val Cys Ala Glu Pro Gly Asp
    130                 135                 140

Ser Gly Gly Ser Tyr Ile Ser Gly Ser Gln Ala Gln Gly Val Thr Ser
145                 150                 155                 160

Gly Gly Ser Gly Asn Cys Ser Ser Gly Gly Thr Thr Phe Phe Gln Pro
                165                 170                 175

Leu Asn Pro Leu Leu Gln Asn Tyr Gly Leu Thr Leu Lys Thr Thr
            180                 185                 190

<210> SEQ ID NO 21
<211> LENGTH: 190
<212> TYPE: PRT
<213> ORGANISM: Streptomyces sp. S055

<400> SEQUENCE: 21

Tyr Asp Leu Arg Gly Gly Asp Ala Tyr Tyr Met Asn Gly Ser Gly Arg
1               5                   10                  15

Cys Ser Val Gly Phe Pro Val Thr Lys Gly Thr Gln Gln Gly Phe Ala
            20                  25                  30

Thr Ala Gly His Cys Gly Arg Val Gly Thr Thr Thr Gly Tyr Asn
        35                  40                  45

Gln Val Ala Gln Gly Ser Phe Gln Ala Ser Thr Phe Pro Gly Arg Asp
    50                  55                  60

Met Ala Trp Val Ala Thr Asn Ser Asn Trp Thr Ala Thr Pro Tyr Val
65                  70                  75                  80

Lys Gly Asn Ser Gly Asn Val Gln Val Ala Gly Ser Thr Gln Ala Ala
                85                  90                  95

Val Gly Ala Ser Val Cys Arg Ser Gly Ser Thr Thr Gly Trp His Cys
            100                 105                 110

Gly Thr Ile Gln Gln His Asn Thr Ser Val Thr Tyr Pro Glu Gly Thr
        115                 120                 125

Ile Ser Gly Val Thr Arg Thr Thr Val Cys Ala Glu Pro Gly Asp Ser
    130                 135                 140

Gly Gly Ser Tyr Ile Ser Gly Ser Gln Ala Gln Gly Val Thr Ser Gly
145                 150                 155                 160

Gly Ser Gly Asn Cys Arg Ser Gly Gly Thr Thr Tyr Tyr Gln Pro Ile
                165                 170                 175
```

```
Asn Pro Leu Leu Gln Asn Tyr Gly Leu Thr Leu Lys Thr Thr
            180                 185                 190

<210> SEQ ID NO 22
<211> LENGTH: 435
<212> TYPE: PRT
<213> ORGANISM: Streptomyces sp. C009

<400> SEQUENCE: 22

Ala Pro Ser Asp Gly His Gly Pro Val Ala Pro Pro Ala Ala
1               5                   10                  15

Arg Ser Ala Ala Asp Ala Leu Ala Val Ser Ala Val Gln Pro Asp Val
                20                  25                  30

Leu Arg Ala Met Gln Arg Asp Leu Gly Leu Thr Pro Ala Glu Ala Arg
            35                  40                  45

Gln Arg Leu Ala Asn Glu Ala Glu Ala Gly Ala Thr Ala Ala Arg Leu
        50                  55                  60

Arg Gln Arg Leu Ala Gly Ser Tyr Ala Gly Ala Trp Val Glu Gly His
65                  70                  75                  80

Ala Ser Ser Val Leu Thr Val Ala Thr Thr Arg Ala Asp Asp Ala Ala
                85                  90                  95

Ala Ile Arg Ala Ser Gly Ala Glu Ala Asp Val Val Ala His Ser Leu
            100                 105                 110

Ala Ala Leu Asp Arg Thr Lys Ala Ala Leu Asp Arg Ala Ala Arg Thr
        115                 120                 125

Ala Ala Asp Val Gly Val Pro Val Trp Tyr Val Asp Val Arg Thr Asn
    130                 135                 140

Ser Val Val Gln Ala Val Asp Pro Gly Ala Ala Ala Ser Leu Val
145                 150                 155                 160

Gly Arg Val Ser Glu Ala Asp Arg Ser Arg Ile Arg Val Val Pro Thr
                165                 170                 175

Arg Glu Arg Pro Arg Pro Leu Tyr Asp Ile Arg Gly Gly Asp Ala Tyr
            180                 185                 190

Tyr Met Gly Gly Ser Gly Arg Cys Ser Val Gly Phe Ser Val Thr Arg
        195                 200                 205

Gly Thr Gln Ala Gly Phe Ala Thr Ala Gly His Cys Gly Arg Ala Gly
    210                 215                 220

Thr Thr Thr Thr Gly Tyr Asn Arg Val Ala Gln Gly Ser Phe Gln Ala
225                 230                 235                 240

Ser Thr Phe Pro Gly Arg Asp Thr Ala Trp Val Ala Thr Asn Thr Asn
                245                 250                 255

Trp Thr Ala Thr Pro Tyr Val Lys Gly Ala Gly Gly Ala Asn Val Arg
            260                 265                 270

Val Ala Gly Ser Val Gln Gln Pro Val Gly Ala Ser Val Cys Arg Ser
        275                 280                 285

Gly Ser Thr Thr Gly Trp His Cys Gly Thr Ile Gln Gln His Asn Thr
    290                 295                 300

Ser Val Thr Tyr Pro Glu Gly Thr Ile Thr Gly Val Thr Arg Thr Ser
305                 310                 315                 320

Val Cys Ala Glu Pro Gly Asp Ser Gly Gly Ser Tyr Ile Ser Gly Ser
                325                 330                 335

Gln Ala Gln Gly Val Thr Ser Gly Gly Ser Gly Asp Cys Arg Ser Gly
            340                 345                 350

Gly Thr Thr Tyr His Gln Pro Ile Asn Pro Leu Leu Gln Ala Tyr Gly
        355                 360                 365
```

Leu Thr Leu Thr Thr Thr Thr Gly Pro Gly Asp Pro Gly Pro Gly Asp
    370                 375                 380

Pro Asp Glu Pro Gly Gly Thr Trp Ala Ala Gly Thr Val Tyr Arg Ala
385                 390                 395                 400

Gly Asp Gln Val Thr Tyr Gly Gly Ala Thr Tyr Arg Cys Leu Gln Gly
                405                 410                 415

His Gln Ala Gln Ala Gly Trp Glu Pro Pro Asn Val Pro Ala Leu Trp
            420                 425                 430

Gln Arg Gly
        435

<210> SEQ ID NO 23
<211> LENGTH: 426
<212> TYPE: PRT
<213> ORGANISM: Streptomyces sp. C001

<400> SEQUENCE: 23

Ala Gln Pro Ser Pro Gly Ala Ala Pro Gly Ala Gln Ser Ala Ala Arg
1               5                   10                  15

Ala Leu Gly Ala Ala Glu Ala Gln Pro Glu Leu Leu Ala Ala Met Gly
            20                  25                  30

Arg Asp Leu Gly Leu Thr Arg Ala Gln Ala Glu Arg Arg Leu Val Asn
        35                  40                  45

Glu Ala Glu Ala Gly Ala Ala Ala Arg Leu Arg Asp Arg Ile Gly
    50                  55                  60

Gly Ser Phe Ala Gly Ala Trp Val Glu Gly Ala Glu Ser Gly Ser Leu
65              70                  75                  80

Thr Val Ala Thr Thr Arg Ala Ala Asp Leu Asp Ala Ile Arg Ala Ala
                85                  90                  95

Gly Ala Thr Ala Arg Leu Val Arg His Asp Leu Ser Ser Leu Glu Arg
            100                 105                 110

Ala Lys Ala Ala Leu Asp Arg Ala Ala Gly Ala Asp Ala Pro Val Arg
        115                 120                 125

Tyr Val Asp Val Arg Ala Asn Gln Leu Val Val Glu Glu Val Arg Ala
    130                 135                 140

Gly Ala Gly Ala Arg Leu Ala Ala Ala Thr Gly Val Pro Arg Glu Leu
145                 150                 155                 160

Val Arg Val Glu Arg Ser Thr Glu Ala Pro Arg Pro Leu Tyr Asp Leu
                165                 170                 175

Arg Gly Gly Asp Ala Tyr Tyr Met Gly Gly Gly Arg Cys Ser Val
            180                 185                 190

Gly Phe Pro Val Thr Arg Gly Thr Thr Gln Gly Phe Ala Thr Ala Gly
        195                 200                 205

His Cys Gly Arg Ala Gly Gln Thr Thr Ser Gly Tyr Asn Gln Val Ala
    210                 215                 220

Gln Gly Ser Phe Gln Gly Ser Val Phe Pro Gly Ser Asp Met Ala Trp
225                 230                 235                 240

Val Ala Ala Asn Ser Ser Trp Thr Ala Thr Pro Tyr Val Lys Gly Ala
                245                 250                 255

Gly Gly Ala Asn Val Gln Val Thr Gly Ser Val Leu Gln Pro Val Gly
            260                 265                 270

Ala Ser Val Cys Arg Ser Gly Ser Thr Thr Gly Trp His Cys Gly Thr
        275                 280                 285

Ile Gln Gln His Asn Thr Ser Val Thr Tyr Pro Glu Gly Thr Ile Ser

```
               290                 295                 300
Gly Val Thr Arg Thr Val Cys Ala Glu Pro Gly Asp Ser Gly Gly
305                 310                 315                 320

Ser Tyr Ile Ser Gly Ser Gln Ala Gln Gly Val Thr Ser Gly Gly Ser
                325                 330                 335

Gly Asn Cys Ser Ser Gly Gly Thr Thr Tyr Phe Gln Pro Leu Asn Pro
                340                 345                 350

Ile Leu Ser Ala Tyr Gly Leu Thr Leu Lys Thr Thr Gly Thr Asp Pro
                355                 360                 365

Gly Pro Gly Pro Gly Pro Gly Glu Pro Glu Pro Gly Gly Thr Trp Lys
370                 375                 380

Ala Gly Thr Val Tyr Ala Ala Gly Ala Thr Val Thr Tyr Gly Gly Ser
385                 390                 395                 400

Thr Tyr Arg Cys Leu Gln Gly His Gln Ala Gln Thr Gly Trp Glu Pro
                405                 410                 415

Pro Asn Val Pro Ala Leu Trp Gln Arg Val
                420                 425

<210> SEQ ID NO 24
<211> LENGTH: 421
<212> TYPE: PRT
<213> ORGANISM: Streptomyces sp. C003

<400> SEQUENCE: 24

Ala Pro Asp Gly Lys Pro Ala Ala Lys Thr Ala Ala Arg Thr Leu Ala
1               5                   10                  15

Ala Thr Ala Ala Gln Pro Glu Leu Leu Ser Ala Met Gln Arg Asp Leu
                20                  25                  30

Gly Leu Thr Arg Pro Gln Ala Leu Thr Arg Leu Ala Asn Glu Ala Glu
            35                  40                  45

Ala Gly Ala Thr Ala Ala Arg Leu Arg Gln Gly Leu Gly Gly Ala Phe
    50                  55                  60

Ala Gly Ala Trp Val Asp Gly Pro Glu Ser Gly Thr Leu Thr Val Ala
65                  70                  75                  80

Thr Thr Arg Ala Ala Asp Ala Ala Ile Arg Ala Thr Gly Ala Asp
                85                  90                  95

Ala Arg Leu Val Ser His Ser Leu Thr Ala Leu Glu Arg Ala Lys Arg
                100                 105                 110

Thr Leu Asp Gly Ala Ala Thr Ala Glu Ala Pro Val Arg Tyr Val Asp
            115                 120                 125

Val Arg Ala Asn Val Leu Val Glu Glu Thr Arg Ala Gly Ala Gly
    130                 135                 140

Ala Arg Leu Val Arg Ala Thr Gly Val Pro Arg Asp Leu Val Arg Val
145                 150                 155                 160

Val Arg Thr Thr Ser Ala Pro Arg Pro Leu Tyr Asp Ile Arg Gly Gly
                165                 170                 175

Asp Ala Tyr Tyr Met Gly Gly Gly Arg Cys Ser Val Gly Phe Ala
                180                 185                 190

Val Thr Arg Gly Thr Thr Gln Gly Phe Ala Thr Ala Gly His Cys Gly
            195                 200                 205

Arg Ala Gly Thr Thr Thr Ser Gly Phe Asn Gln Val Ala Gln Gly Ser
    210                 215                 220

Phe Gln Gly Ser Ile Phe Pro Gly Asn Asp Met Ala Trp Val Ala Ala
225                 230                 235                 240
```

-continued

```
Asn Thr Asn Trp Thr Ser Thr Pro Tyr Val Lys Gly Ser Gly Gly Ala
            245                 250                 255

Asn Val Gln Val Thr Gly Ser Val Leu Gln Pro Val Gly Ala Ser Val
        260                 265                 270

Cys Arg Ser Gly Ser Thr Thr Gly Trp His Cys Gly Thr Ile Gln Gln
    275                 280                 285

His Asn Thr Ser Val Thr Tyr Pro Glu Gly Thr Ile Ser Gly Val Thr
290                 295                 300

Arg Thr Thr Val Cys Ala Glu Pro Gly Asp Ser Gly Ser Gly Ser Tyr Ile
305                 310                 315                 320

Ser Gly Ser Gln Ala Gln Gly Val Thr Ser Gly Gly Ser Gly Asn Cys
            325                 330                 335

Ser Ser Gly Gly Thr Thr Phe Phe Gln Pro Leu Asn Pro Leu Leu Gln
        340                 345                 350

Asn Tyr Gly Leu Thr Leu Lys Thr Thr Gly Ser Asp Pro Gly Pro Gly
    355                 360                 365

Pro Gly Glu Pro Gln Pro Gly Thr Trp Ala Ala Gly Lys Val Tyr
370                 375                 380

Ala Ala Gly Asp Thr Val Thr Tyr Gly Gly Ala Thr Tyr Arg Cys Leu
385                 390                 395                 400

Gln Gly His Gln Ala Gln Thr Gly Trp Glu Pro Pro Asn Val Pro Ala
            405                 410                 415

Leu Trp Gln Arg Gln
            420

<210> SEQ ID NO 25
<211> LENGTH: 426
<212> TYPE: PRT
<213> ORGANISM: Streptomyces sp. S055

<400> SEQUENCE: 25

Ala Ala Asp Ala Ala Pro Pro Ala Pro Pro Thr Ala Ala Thr Ala
1               5                   10                  15

Gly Val Asp Asn Ala Ser Pro Gly Leu Leu Arg Ala Met Gln Arg Asp
            20                  25                  30

Leu Gly Val Thr Glu Ala Gln Ala Arg Ala Arg Leu Ala Asn Glu Ala
        35                  40                  45

Glu Ala Gly Ala Val Ala Gly Arg Leu Arg Ile Ser Leu Gly Gly Asp
    50                  55                  60

Phe Ala Gly Ala Trp Val His Gly Pro Asp Ser Ala Lys Leu Ser Val
65                  70                  75                  80

Ala Thr Thr Asp Ala Ser Asp Arg Ala Ala Ile Glu Ala Gly Ala
            85                  90                  95

His Ala Val Val Val Arg His Thr Leu Pro Arg Leu Asp Gly Ala Leu
            100                 105                 110

Ala Lys Leu Asp Glu Ala Ala Ser Ala Ala Pro Ser Thr Ala Ala Glu
        115                 120                 125

Val Pro Val Arg Tyr Val Asp Val Thr Ala Asn Arg Val Thr Leu Gln
    130                 135                 140

Thr Val Arg Pro Ala Ala Ala Lys Ala Leu Val Val Ala Ala Gly Val
145                 150                 155                 160

Asp Pro Ala Leu Val Arg Val Glu Lys Ser Ala Glu Arg Pro Arg Pro
            165                 170                 175

Leu Tyr Asp Leu Arg Gly Gly Asp Ala Tyr Tyr Met Asn Gly Ser Gly
            180                 185                 190
```

```
Arg Cys Ser Val Gly Phe Pro Val Thr Lys Gly Thr Gln Gln Gly Phe
        195                 200                 205

Ala Thr Ala Gly His Cys Gly Arg Val Gly Thr Thr Thr Thr Gly Tyr
        210                 215                 220

Asn Gln Val Ala Gln Gly Ser Phe Gln Ala Ser Thr Phe Pro Gly Arg
225                 230                 235                 240

Asp Met Ala Trp Val Ala Thr Asn Ser Asn Trp Thr Ala Thr Pro Tyr
                245                 250                 255

Val Lys Gly Asn Ser Gly Asn Val Gln Val Ala Gly Ser Thr Gln Ala
            260                 265                 270

Ala Val Gly Ala Ser Val Cys Arg Ser Gly Ser Thr Thr Gly Trp His
            275                 280                 285

Cys Gly Thr Ile Gln Gln His Asn Thr Ser Val Thr Tyr Pro Glu Gly
            290                 295                 300

Thr Ile Ser Gly Val Thr Arg Thr Val Cys Ala Glu Pro Gly Asp
305                 310                 315                 320

Ser Gly Gly Ser Tyr Ile Ser Gly Ser Gln Ala Gln Gly Val Thr Ser
                325                 330                 335

Gly Gly Ser Gly Asn Cys Arg Ser Gly Gly Thr Thr Tyr Tyr Gln Pro
            340                 345                 350

Ile Asn Pro Leu Leu Gln Asn Tyr Gly Leu Thr Leu Lys Thr Thr Ser
            355                 360                 365

Asp Asp Pro Gly Pro Gly Glu Pro Gly Glu Pro Gly Gly Thr Trp Ala
        370                 375                 380

Ala Gly Thr Val Tyr Ala Ala Gly Ala Gln Val Thr Tyr Gly Gly Ala
385                 390                 395                 400

Thr Tyr Arg Cys Leu Gln Gly His Gln Ala Gln Ala Gly Trp Glu Pro
                405                 410                 415

Pro Asn Val Pro Ala Leu Trp Gln Arg Ala
            420                 425

<210> SEQ ID NO 26
<211> LENGTH: 453
<212> TYPE: PRT
<213> ORGANISM: Streptomyces albulus

<400> SEQUENCE: 26

Met Phe His Arg His Ala Arg Ala Ala Cys Val Gly Ala Val Thr Val
1               5                   10                  15

Gly Ala Leu Val Leu Thr Ala Leu Gln Gly Ala Ser Ala Ala Thr Pro
            20                  25                  30

Ala Pro Ala Ala Arg Ser Ala Ala Thr Thr Leu Ala Val Ser Ala Val
        35                  40                  45

Gln Pro Asp Val Leu Arg Ala Met Gln Arg Asp Leu Gly Leu Thr Gly
    50                  55                  60

Ala Glu Ala Arg Val Arg Leu Ala Asn Glu Ala Glu Ala Gly Ala Thr
65                  70                  75                  80

Ala Ala Leu Leu Arg Gln Arg Leu Gly Gly Ser Phe Ala Gly Ala Trp
                85                  90                  95

Val Glu Gly Asp Val Ser Ser Val Leu Thr Val Ala Thr Thr Arg Ala
            100                 105                 110

Ala Asp Ala Ala Ala Ile Arg Ala Ser Gly Ala Glu Ala Asp Val Val
        115                 120                 125

Thr His Gly Leu Ala Gln Leu Asp Arg Thr Lys Ala Ala Leu Asp Arg
```

130                 135                 140
Ala Ala Arg Thr Thr Ala Thr Thr Gly Val Pro Val Trp Tyr Val Asp
145                 150                 155                 160

Val Arg Thr Asn Ser Val Val Gly Ala Ala Asp Arg Ala Ala Ala
                165                 170                 175

Ala Ala Leu Val Ala Arg Val Gly Glu Ala Asp Arg Ser Arg Ile Arg
            180                 185                 190

Val Val Pro Thr Arg Glu Arg Pro Arg Pro Leu Tyr Asp Ile Arg Gly
                195                 200                 205

Gly Asp Ala Tyr Tyr Met Gly Gly Ser Gly Arg Cys Ser Val Gly Phe
            210                 215                 220

Ala Ile Thr Arg Gly Thr Gln Ala Gly Phe Ala Thr Ala Gly His Cys
225                 230                 235                 240

Gly Arg Ala Gly Thr Thr Thr Gly Tyr Asn Gln Val Ala Gln Gly
                245                 250                 255

Ser Phe Gln Ala Ser Thr Phe Pro Gly Arg Asp Thr Ala Trp Val Ala
            260                 265                 270

Thr Ser Thr Asn Trp Thr Ala Thr Pro Tyr Val Lys Gly Ala Gly Gly
                275                 280                 285

Ala Asn Val Gln Val Thr Gly Ser Val Gln Gln Pro Val Gly Ala Ser
        290                 295                 300

Val Cys Arg Ser Gly Ser Thr Thr Gly Trp His Cys Gly Thr Ile Gln
305                 310                 315                 320

Gln His Asn Thr Ser Val Thr Tyr Pro Glu Gly Thr Ile Ser Gly Val
                325                 330                 335

Thr Arg Thr Ser Val Cys Ala Glu Pro Gly Asp Ser Gly Ser Tyr
            340                 345                 350

Ile Ser Gly Thr Gln Ala Gln Gly Val Thr Ser Gly Ser Gly Asp
                355                 360                 365

Cys Arg Ser Gly Gly Thr Thr Tyr His Gln Pro Ile Asn Pro Leu Leu
370                 375                 380

Gln Ala Tyr Gly Leu Thr Leu Arg Thr Thr Thr Asp Pro Asp Asp Pro
385                 390                 395                 400

Gly Asp Pro Gly Glu Pro Gly Gly Thr Trp Ala Ala Gly Thr Val Tyr
                405                 410                 415

Arg Ala Gly Asp Gln Val Thr Tyr Gly Gly Ala Thr Tyr Arg Cys Leu
            420                 425                 430

Gln Gly His Gln Ala Gln Ala Gly Trp Glu Pro Pro Asn Val Pro Ala
                435                 440                 445

Leu Trp Gln Arg Gly
        450

<210> SEQ ID NO 27
<211> LENGTH: 456
<212> TYPE: PRT
<213> ORGANISM: Streptomyces sp. NRRL F-5193

<400> SEQUENCE: 27

Met Leu Arg Arg His Ala Arg Ala Ala Cys Thr Ala Leu Ala Ala Ala
1               5                   10                  15

Gly Met Val Leu Ala Gly Leu Gln Ala Gly Ser Ala Thr Ala Ala Gln
            20                  25                  30

Pro Ser Pro Gly Thr Gly Pro Gly Ala Leu Ser Ala Ala Arg Ala Leu
        35                  40                  45

```
Gly Ala Ala Glu Ala Arg Pro Glu Leu Leu Ala Ala Met Gly Arg Asp
 50                  55                  60

Leu Gly Leu Thr Arg Ala Gln Ala Glu Arg Leu Val Asn Glu Ala
 65                  70                  75                  80

Glu Ala Gly Ala Ala Ala Arg Leu Arg Asp Arg Leu Gly Gly Ser
                 85                  90                  95

Phe Ala Gly Ala Trp Val Ala Gly Ala Glu Ser Gly Ser Leu Thr Val
                100                 105                 110

Ala Thr Thr Arg Ala Ala Asp Leu Ala Ala Ile Arg Ala Ala Gly Ala
                115                 120                 125

Glu Ala Ala Leu Val Arg His Gly Leu Pro Ala Leu Glu Arg Ala Lys
130                 135                 140

Ala Ala Leu Asp Arg Ala Ala Thr Ala Asp Ala Pro Val Arg Tyr Val
145                 150                 155                 160

Asp Ile Arg Ala Asn Ala Leu Val Val Glu Glu Thr Arg Ala Gly Ala
                165                 170                 175

Gly Lys Arg Leu Val Ala Ala Thr Gly Val Pro Ala Glu Leu Val Arg
                180                 185                 190

Val Val Arg Ser Ala Glu Ala Pro Arg Pro Leu Tyr Asp Leu Arg Gly
                195                 200                 205

Gly Asp Ala Tyr Tyr Met Gly Gly Gly Arg Cys Ser Val Gly Phe
210                 215                 220

Pro Val Thr Arg Gly Thr Thr Gln Gly Phe Ala Thr Ala Gly His Cys
225                 230                 235                 240

Gly Arg Ala Gly Gln Thr Thr Ser Gly Tyr Asn Gln Val Ala Gln Gly
                245                 250                 255

Ser Phe Gln Ala Ser Ile Phe Pro Gly Asn Asp Met Ala Trp Val Ala
                260                 265                 270

Ala Asn Ser Asn Trp Thr Ala Thr Pro Tyr Val Lys Gly Ala Gly Gly
                275                 280                 285

Ala Asn Val Gln Val Thr Gly Ser Val Leu Gln Pro Val Gly Ala Ser
                290                 295                 300

Val Cys Arg Ser Gly Ser Thr Thr Gly Trp His Cys Gly Thr Ile Gln
305                 310                 315                 320

Gln His Asn Thr Ser Val Thr Tyr Pro Glu Gly Thr Ile Ser Gly Val
                325                 330                 335

Thr Arg Thr Thr Val Cys Ala Glu Pro Gly Asp Ser Gly Ser Tyr
                340                 345                 350

Ile Ser Gly Ser Gln Ala Gln Gly Val Thr Ser Gly Gly Ser Gly Asn
                355                 360                 365

Cys Ser Ser Gly Gly Thr Thr Tyr Phe Gln Pro Leu Asn Pro Ile Leu
370                 375                 380

Ser Asn Tyr Gly Leu Thr Leu Lys Thr Thr Gly Thr Asp Pro Gly Pro
385                 390                 395                 400

Gly Pro Gly Pro Gly Glu Pro Glu Pro Gly Gly Thr Trp Lys Ala Gly
                405                 410                 415

Thr Val Tyr Ala Ala Gly Ala Thr Val Thr Tyr Gly Gly Ser Thr Tyr
                420                 425                 430

Arg Cys Leu Gln Gly His Gln Ala Gln Ala Gly Trp Glu Pro Pro Asn
                435                 440                 445

Val Pro Ala Leu Trp Gln Arg Val
450                 455
```

<210> SEQ ID NO 28
<211> LENGTH: 451
<212> TYPE: PRT
<213> ORGANISM: Streptomyces exfoliatus

<400> SEQUENCE: 28

```
Met Leu Arg Arg His Thr Arg Ala Ala Cys Thr Ala Leu Val Ala Ala
1               5                   10                  15

Gly Met Ala Leu Ala Gly Leu Gln Ala Gly Thr Ala Thr Ala Ala Pro
            20                  25                  30

Asp Gly Asn Pro Ala Ala Lys Thr Ala Ala Gln Thr Leu Ala Ala Gly
        35                  40                  45

Ala Ala Gln Pro Glu Leu Leu Ser Ala Met Gln Arg Asp Leu Gly Leu
    50                  55                  60

Thr Arg Pro Gln Ala Leu Thr Arg Leu Ala Asn Glu Ala Glu Ala Gly
65                  70                  75                  80

Ala Thr Ala Ala Arg Leu Arg Gln Gly Leu Gly Gly Ala Phe Ala Gly
                85                  90                  95

Ala Trp Val Asp Gly Pro Glu Ser Gly Thr Leu Thr Val Ala Thr Thr
            100                 105                 110

Arg Ala Ala Asp Ala Ala Val Ile Arg Ala Thr Gly Ala Asn Ala Arg
        115                 120                 125

Leu Val Ser His Thr Leu Thr Ala Leu Glu Arg Ala Lys Arg Ala Leu
    130                 135                 140

Asp Gly Ala Ala Thr Ala Glu Ala Pro Val Arg Tyr Val Asp Val Arg
145                 150                 155                 160

Ala Asn Val Leu Val Glu Glu Thr Arg Pro Gly Ala Gly Ala Arg
                165                 170                 175

Leu Val Arg Ala Thr Gly Val Pro Arg Asp Leu Val Arg Val Val Arg
            180                 185                 190

Thr Ala Ser Ala Pro Arg Pro Leu Tyr Asp Ile Arg Gly Gly Asp Ala
        195                 200                 205

Tyr Tyr Met Gly Gly Gly Arg Cys Ser Val Gly Phe Ala Val Thr
    210                 215                 220

Arg Gly Thr Thr Gln Gly Phe Ala Thr Ala Gly His Cys Gly Arg Ala
225                 230                 235                 240

Gly Thr Thr Thr Ser Gly Phe Asn Gln Ala Ala Gln Gly Ser Phe Gln
                245                 250                 255

Gly Ser Ile Phe Pro Gly Asn Asp Met Ala Trp Val Ala Ala Asn Thr
            260                 265                 270

Asn Trp Thr Ser Thr Pro Tyr Val Lys Gly Ser Gly Ala Asn Val
        275                 280                 285

Gln Val Thr Gly Ser Val Leu Gln Pro Val Gly Ala Ser Val Cys Arg
    290                 295                 300

Ser Gly Ser Thr Thr Gly Trp His Cys Gly Thr Ile Gln Gln His Asn
305                 310                 315                 320

Thr Ser Val Thr Tyr Pro Glu Gly Ile Ile Ser Gly Val Thr Arg Thr
                325                 330                 335

Thr Val Cys Ala Glu Pro Gly Asp Ser Gly Ser Tyr Ile Ser Gly
            340                 345                 350

Ser Gln Ala Gln Gly Val Thr Ser Gly Ser Gly Asn Cys Ser Ser
        355                 360                 365

Gly Gly Thr Thr Phe Phe Gln Pro Leu Asn Pro Leu Leu Gln Asn Tyr
    370                 375                 380
```

Gly Leu Thr Leu Lys Thr Thr Gly Ser Asp Pro Gly Pro Gly Pro Gly
385                 390                 395                 400

Glu Pro Gln Pro Gly Gly Thr Trp Ala Ala Gly Lys Val Tyr Ala Ala
                405                 410                 415

Gly Asp Thr Val Thr Tyr Gly Gly Thr Tyr Arg Cys Leu Gln Gly
            420                 425                 430

His Gln Ala Gln Thr Gly Trp Glu Pro Pro Asn Val Pro Ala Leu Trp
            435                 440                 445

Gln Arg Gln
    450

<210> SEQ ID NO 29
<211> LENGTH: 459
<212> TYPE: PRT
<213> ORGANISM: Streptomyces albus

<400> SEQUENCE: 29

Met Leu His Arg His Ala Lys Ala Ala Gly Val Gly Ala Ala Ala Ala
1               5                   10                  15

Ala Leu Val Leu Thr Thr Leu Gln Gly Ala Ala Ser Ala Gln Gln Asp
            20                  25                  30

Gly Thr Pro Pro Gly Ala Val Ala His Thr Ala Ala Asp Thr Leu Ala
        35                  40                  45

Val Ser Ala Ala Gln Pro Glu Leu Leu Arg Ala Met Gln Arg Asp Leu
50                  55                  60

Gly Leu Thr Arg Ala Gln Ala Glu Arg Arg Leu Val Asn Glu Ala Glu
65                  70                  75                  80

Ala Gly Ala Thr Ala Ala Val Leu Arg Gln Arg Leu Gly Gly Ser Phe
                85                  90                  95

Ala Gly Ala Trp Val Glu Gly Ala Asp Ser Gly Thr Leu Thr Val Ala
            100                 105                 110

Thr Thr Arg Ala Ala Asp Ala Ala Ala Ile Arg Ala Ala Gly Ala Glu
        115                 120                 125

Ser Arg Thr Val Thr His Asn Leu Ala Glu Leu Asp Arg Thr Lys Ala
130                 135                 140

Ala Leu Asp Arg Ala Ala Glu Arg Asn Ser Ser Thr Asp Val Pro Val
145                 150                 155                 160

Trp Tyr Val Asp Val Arg Ala Asn Ala Val Val Arg Ala Val Glu
                165                 170                 175

Lys Ala Ala Ala Gln Thr Leu Ile Glu Ala Thr Ala Ala Asp Arg Asp
            180                 185                 190

Arg Ile Arg Val Val Pro Thr Gly Glu Gln Pro Arg Pro Leu Tyr Asp
        195                 200                 205

Ile Arg Gly Gly Asp Ala Tyr Tyr Met Gly Gly Gly Arg Cys Ser
210                 215                 220

Val Gly Phe Ala Val Thr Arg Gly Thr Thr Gln Gly Phe Ala Thr Ala
225                 230                 235                 240

Gly His Cys Gly Arg Ala Gly Thr Ala Thr Ser Gly Tyr Asn Gln Val
                245                 250                 255

Ala Gln Gly Thr Phe Gln Ala Ser Thr Phe Pro Gly Arg Asp Thr Ala
            260                 265                 270

Trp Val Ala Thr Asn Gly Asn Trp Thr Ser Thr Pro Tyr Val Lys Gly
        275                 280                 285

Gln Gly Gly Gln Asn Ile Gln Val Thr Gly Ser Val Gln Gln Pro Val
290                 295                 300

```
Gly Ala Ser Ile Cys Arg Ser Gly Ser Thr Thr Gly Trp His Cys Gly
305                 310                 315                 320

Thr Ile Ser Gln His Asn Thr Ser Val Thr Tyr Pro Glu Gly Thr Ile
                325                 330                 335

Ser Gly Val Thr Arg Thr Thr Val Cys Ala Glu Pro Gly Asp Ser Gly
            340                 345                 350

Gly Ser Tyr Ile Ser Gly Ser Gln Ala Gln Gly Val Thr Ser Gly Gly
        355                 360                 365

Ser Gly Asp Cys Arg Ser Gly Gly Thr Thr Tyr His Gln Pro Val Asn
370                 375                 380

Pro Leu Leu Gln Gly Tyr Gly Leu Thr Leu Lys Thr Thr Val Asp Pro
385                 390                 395                 400

Gly Asp Pro Gly Asp Pro Gly Asp Pro Gly Glu Pro Gly Gly Thr Trp
                405                 410                 415

Ala Ala Gly Thr Val Tyr Gln Ala Gly Ala Gln Val Thr Tyr Gly Gly
                420                 425                 430

Ala Thr Tyr Arg Cys Leu Gln Gly His Gln Ala Gln Ala Gly Trp Glu
                435                 440                 445

Pro Pro Asn Ala Pro Ala Leu Trp Gln Arg Leu
    450                 455
```

<210> SEQ ID NO 30
<211> LENGTH: 453
<212> TYPE: PRT
<213> ORGANISM: Streptomyces pristinaespiralis

<400> SEQUENCE: 30

```
Met Leu His Arg His Ala Lys Ala Ala Cys Val Gly Ala Ala Ala Ala
1               5                   10                  15

Ala Ala Leu Val Leu Thr Ser Leu Gln Gly Ala Ala Ser Ala Gln Pro
                20                  25                  30

Ala Gly Gly Ala Ala Pro Ser Ala Ala Asn Thr Leu Ala Val Ser Ala
            35                  40                  45

Ala Gln Pro Glu Leu Leu Arg Ala Met Gln Arg Asp Leu Gly Leu Thr
50                  55                  60

Arg Ala Glu Ala Glu Arg Arg Leu Val Asn Glu Ala Glu Ala Gly Ala
65                  70                  75                  80

Thr Ala Ala Val Leu Arg Gln Arg Leu Gly Asp Ser Phe Ala Gly Ala
                85                  90                  95

Trp Val Glu Gly Ala Asp Ser Gly Thr Leu Thr Val Ala Thr Thr Arg
                100                 105                 110

Ala Ala Asp Ala Ala Ala Ile Arg Ala Gly Gly Ala Glu Ala Arg Thr
            115                 120                 125

Val Thr His Thr Leu Ala Glu Leu Asp Arg Ala Lys Ala Ala Leu Asp
        130                 135                 140

Arg Ala Ala Arg Asp Ser Ser Thr Asp Val Pro Val Trp Tyr Val
145                 150                 155                 160

Asp Val Arg Ala Asn Ala Val Val Arg Ala Val Glu Arg Ser Ala
                165                 170                 175

Ala Gln Thr Leu Ile Gly Ala Ser Gly Ala Glu Arg Asp Leu Ile Arg
                180                 185                 190

Val Val Pro Thr Glu Glu Gln Pro Arg Pro Leu Tyr Asp Ile Arg Gly
            195                 200                 205

Gly Asp Ala Tyr Tyr Met Gly Gly Gly Gly Arg Cys Ser Val Gly Phe
```

-continued

```
                210                 215                 220
Ala Val Thr Arg Gly Thr Thr Gln Gly Phe Ala Thr Ala Gly His Cys
225                 230                 235                 240

Gly Arg Ala Gly Thr Ser Thr Ser Gly Tyr Asn Gln Val Ala Gln Gly
                245                 250                 255

Thr Phe Gln Ala Ser Thr Phe Pro Gly Arg Asp Thr Ala Trp Val Ala
                260                 265                 270

Ala Asn Ser Asn Trp Thr Ser Thr Pro Tyr Val Lys Gly Gln Ser Gly
                275                 280                 285

Gln Asn Ile Gln Val Thr Gly Ser Val Gln Gln Pro Val Gly Ala Ser
                290                 295                 300

Ile Cys Arg Ser Gly Ser Thr Thr Gly Trp His Cys Gly Thr Ile Ser
305                 310                 315                 320

Gln His Asn Thr Ser Val Thr Tyr Pro Glu Gly Thr Ile Thr Gly Val
                325                 330                 335

Thr Arg Thr Thr Val Cys Ala Glu Pro Gly Asp Ser Gly Gly Ser Tyr
                340                 345                 350

Ile Ser Gly Ser Gln Ala Gln Gly Val Thr Ser Gly Gly Ser Gly Asp
                355                 360                 365

Cys Arg Ser Gly Gly Thr Thr Phe His Gln Pro Ile Asn Pro Leu Leu
                370                 375                 380

Gln Gly Tyr Gly Leu Thr Leu Lys Thr Thr Thr Asp Pro Gly Glu Pro
385                 390                 395                 400

Gly Glu Pro Gly Glu Pro Gly Gly Thr Trp Ala Ala Gly Thr Val Tyr
                405                 410                 415

Gln Ala Gly Ala Gln Val Thr Tyr Gly Gly Val Thr Tyr Arg Cys Leu
                420                 425                 430

Gln Gly His Gln Ala Gln Ala Gly Trp Glu Pro Pro Asn Val Pro Ala
                435                 440                 445

Leu Trp Gln Arg Leu
                450

<210> SEQ ID NO 31
<211> LENGTH: 451
<212> TYPE: PRT
<213> ORGANISM: Streptomyces venezuelae

<400> SEQUENCE: 31

Met Leu Arg Arg His Ala Arg Ala Ala Cys Thr Ala Leu Val Ala Ala
1                   5                   10                  15

Gly Met Ala Leu Ala Gly Leu Gln Ala Gly Thr Ala Thr Ala Ala Pro
                20                  25                  30

Asp Gly Lys Pro Ala Ala Lys Thr Ala Ala Arg Thr Leu Ala Thr Ala
                35                  40                  45

Ala Ala Gln Pro Glu Leu Leu Ser Ala Met Gln Arg Asp Leu Gly Leu
                50                  55                  60

Thr Arg Pro Gln Ala Leu Thr Arg Leu Ala Asn Glu Ala Glu Ala Gly
65                  70                  75                  80

Ala Thr Ala Ala Gly Leu Arg Gln Ser Leu Ala Gly Ala Phe Ala Gly
                85                  90                  95

Ala Trp Val Asp Gly Ala Glu Ser Gly Thr Leu Thr Val Ala Thr Thr
                100                 105                 110

Arg Ser Ala Asp Thr Ala Ala Ile Arg Ala Thr Gly Ala Asn Ala Arg
                115                 120                 125
```

```
Leu Val Pro His Ser Leu Thr Ala Leu Glu Arg Ala Lys Arg Ala Leu
        130                 135                 140
Asp Arg Gly Ala Thr Ala Glu Ala Pro Val Arg Tyr Val Asp Val Arg
145                 150                 155                 160
Ala Asn Val Leu Val Glu Glu Thr Arg Ala Gly Ala Gly Ala Arg
                165                 170                 175
Leu Val Glu Ala Ala Gly Val Pro Arg Asp Leu Val Arg Val Val Arg
                180                 185                 190
Thr Asp Arg Ala Pro Arg Pro Leu Tyr Asp Ile Arg Gly Gly Asp Ala
                195                 200                 205
Tyr Tyr Met Gly Gly Gly Arg Cys Ser Val Gly Phe Ala Val Thr
        210                 215                 220
Arg Gly Ala Thr Gln Gly Phe Ala Thr Ala Gly His Cys Gly Arg Ala
225                 230                 235                 240
Gly Thr Thr Thr Ser Gly Phe Asn Gln Val Ala Gln Gly Ser Phe Gln
                245                 250                 255
Ala Ser Thr Phe Pro Gly Asn Asp Met Ala Trp Val Ala Ala Asn Thr
                260                 265                 270
Asn Trp Thr Ser Thr Pro Tyr Val Lys Gly Ser Gly Gly Ala Asn Val
        275                 280                 285
Gln Val Thr Gly Ser Val Leu Gln Pro Val Gly Ala Ser Val Cys Arg
    290                 295                 300
Ser Gly Ser Thr Thr Gly Trp His Cys Gly Thr Ile Gln Gln His Asn
305                 310                 315                 320
Thr Ser Val Thr Tyr Pro Glu Gly Thr Ile Ser Gly Val Thr Arg Thr
                325                 330                 335
Thr Val Cys Ala Glu Pro Gly Asp Ser Gly Gly Ser Tyr Ile Ser Gly
                340                 345                 350
Ser Gln Ala Gln Gly Val Thr Ser Gly Gly Ser Gly Asn Cys Ser Ser
        355                 360                 365
Gly Gly Thr Thr Phe Phe Gln Pro Leu Asn Pro Leu Gln Asn Tyr
    370                 375                 380
Gly Leu Thr Leu Lys Thr Thr Gly Thr Asp Pro Gly Pro Gly Pro Gly
385                 390                 395                 400
Glu Pro Gln Pro Gly Gly Thr Trp Ala Ala Gly Lys Val Tyr Ala Ala
                405                 410                 415
Gly Ala Thr Val Thr Tyr Gly Gly Ala Thr Tyr Arg Cys Leu Gln Gly
                420                 425                 430
His Gln Ala Gln Thr Gly Trp Glu Pro Pro Asn Val Pro Ala Leu Trp
        435                 440                 445
Gln Arg Gln
    450

<210> SEQ ID NO 32
<211> LENGTH: 456
<212> TYPE: PRT
<213> ORGANISM: Streptomyces venezuelae

<400> SEQUENCE: 32

Met Leu Arg Arg His Ala Arg Ala Ala Cys Thr Ala Leu Val Ala Ala
1               5                   10                  15
Gly Leu Ala Leu Ala Gly Leu Gln Ala Gly Thr Ala Ala Ala Val Pro
            20                  25                  30
Asp Ala Gly Glu Pro His Pro Ala Pro Thr Val Arg Thr Ala Ala Gln
        35                  40                  45
```

-continued

Thr Leu Gly Ala Asp Ala Ala Pro Glu Val Leu Asp Ala Met Arg
    50                  55                  60

Arg Asp Leu Gly Leu Ser His Ala Gln Ala Leu Thr Arg Leu Ala Asn
65                  70                  75                  80

Glu Ala Glu Ala Gly Ala Thr Ala Ala Arg Leu Arg Gln Gly Leu Gly
                85                  90                  95

Gly Ala Phe Ala Gly Ala Trp Val Asp Gly Ala Glu Ser Gly Thr Leu
                100                 105                 110

Thr Val Ala Thr Thr Arg Ser Ser Asp Ala Ala Ala Ile Arg Ala Thr
            115                 120                 125

Gly Ala Arg Ala Arg Leu Val Thr His Pro Leu Thr Ile Leu Glu Arg
            130                 135                 140

Ala Lys Glu Arg Leu Asp Arg Ala Ala Thr Ala Asp Ala Pro Val Arg
145                 150                 155                 160

Tyr Val Asp Val Arg Ala Asn Val Leu Val Glu Glu Thr Lys Ala
                165                 170                 175

Gly Ala Gly Ala Arg Leu Leu Ala Ala Thr Gly Val Pro Arg Glu Leu
                180                 185                 190

Val Arg Val Arg Ser Gly Gln Ala Pro Arg Pro Leu Tyr Asp Leu
        195                 200                 205

Arg Gly Gly Asp Ala Tyr Tyr Met Gly Gly Gly Arg Cys Ser Val
    210                 215                 220

Gly Phe Pro Val Thr Arg Gly Thr Thr Gln Gly Phe Ala Thr Ala Gly
225                 230                 235                 240

His Cys Gly Arg Ala Gly Thr Thr Thr Ser Gly Phe Asn Gln Val Ala
                245                 250                 255

Gln Gly Ser Phe Gln Gly Ser Ile Phe Pro Gly Asn Asp Met Ala Trp
                260                 265                 270

Val Ala Ala Asn Gly Asn Trp Thr Ala Thr Pro Tyr Val Lys Gly Ser
            275                 280                 285

Gly Gly Ala Asn Val Gln Val Thr Gly Ser Val Leu Gln Pro Val Gly
        290                 295                 300

Ser Ser Val Cys Arg Ser Gly Ser Thr Thr Gly Trp His Cys Gly Thr
305                 310                 315                 320

Val Gln Gln His Asn Thr Ser Val Thr Tyr Pro Glu Gly Thr Ile Ser
            325                 330                 335

Gly Val Thr Arg Thr Thr Val Cys Ala Glu Pro Gly Asp Ser Gly Gly
            340                 345                 350

Ser Tyr Ile Ser Gly Ser Gln Ala Gln Gly Val Thr Ser Gly Gly Ser
        355                 360                 365

Gly Asn Cys Ser Ser Gly Gly Thr Thr Phe Phe Gln Pro Leu Asn Pro
    370                 375                 380

Leu Leu Gln Asn Tyr Gly Leu Thr Leu Lys Thr Thr Gly Gly Asp Pro
385                 390                 395                 400

Gly Pro Gly Pro Gly Glu Pro Glu Pro Gly Ser Trp Ala Ala Gly
                405                 410                 415

Thr Val Tyr Lys Ala Gly Asp Val Val Thr Tyr Gly Gly Ala Ser Tyr
            420                 425                 430

Arg Cys Leu Gln Gly His Gln Ala Gln Ala Gly Trp Gln Pro Pro Asn
        435                 440                 445

Val Pro Ala Leu Trp Gln Arg Leu
    450                 455

-continued

```
<210> SEQ ID NO 33
<211> LENGTH: 455
<212> TYPE: PRT
<213> ORGANISM: unknown
<220> FEATURE:
<223> OTHER INFORMATION: Streptomyces sp.

<400> SEQUENCE: 33

Met Leu Lys Arg His Ala Arg Ala Ala Cys Thr Ala Leu Ala Ala Ala
1               5                   10                  15

Gly Leu Leu Ala Gly Thr Thr Ala Ala Gly Ala Ala Thr Pro Ala
            20                  25                  30

Ala Asp Pro Ala Ala Pro Gln Lys Ser Ala Thr Ala Thr Leu Arg Pro
            35                  40                  45

Gly Asp Ala Pro Ala Glu Leu Leu Thr Ala Leu Gln Arg Asp Leu Gly
        50                  55                  60

Leu Thr Pro Thr Gln Ala Lys Asp Arg Leu Ala His Glu Ala Glu Ala
65                  70                  75                  80

Gly Ala Thr Ala Ala Arg Leu Arg Ala Arg Leu Gly Ala Ala Phe Ala
                85                  90                  95

Gly Ala Trp Val Asp Gly Ala Asp Ser Ala Thr Leu Thr Val Ala Thr
            100                 105                 110

Thr Arg Ala Ala Asp Ala Ala Ala Ile Arg Ala Ala Gly Ala Glu Ala
        115                 120                 125

Lys Leu Val Ser Arg Ser Leu Ala Asp Leu Asp Ala Val Arg Ala Gly
130                 135                 140

Leu Asp Arg Ala Ala Thr Ala Glu Thr Pro Val Arg Tyr Val Asp Pro
145                 150                 155                 160

Arg Thr Asn Thr Leu Val Val Glu Glu Thr Arg Pro Gly Ala Ala Ala
                165                 170                 175

Gly Leu Leu Ala Ala Thr Gly Thr Asp Pro Ala Leu Ala Thr Val Val
            180                 185                 190

Arg Thr Ala Ala Glu Gln Ala Pro Arg Pro Leu Tyr Asp Leu Arg Gly
        195                 200                 205

Gly Asp Ala Tyr Tyr Met Asn Gly Gln Gly Arg Cys Ser Val Gly Phe
    210                 215                 220

Pro Val Thr Arg Gly Thr Thr Gln Gly Phe Ala Thr Ala Gly His Cys
225                 230                 235                 240

Gly Arg Ala Gly Thr Thr Thr Ser Gly Phe Asn Gln Val Ala Gln Gly
                245                 250                 255

Ser Phe Gln Ala Ser Val Phe Pro Gly Asn Asp Met Ala Trp Val Ala
            260                 265                 270

Ala Asn Thr Ser Trp Thr Ala Thr Pro Tyr Val Lys Gly Ser Gly Gly
        275                 280                 285

Ala Asn Val Gln Val Thr Gly Ser Val Leu Gln Pro Val Gly Ser Ser
    290                 295                 300

Val Cys Arg Ser Gly Ser Thr Thr Gly Trp His Cys Gly Thr Val Gln
305                 310                 315                 320

Gln His Asn Thr Ser Val Thr Tyr Pro Glu Gly Thr Ile Ser Gly Val
                325                 330                 335

Thr Arg Thr Thr Val Cys Ala Glu Pro Gly Asp Ser Gly Gly Ser Tyr
            340                 345                 350

Ile Ser Gly Ser Gln Ala Gln Gly Val Thr Ser Gly Gly Ser Gly Asp
        355                 360                 365
```

```
Cys Thr Ser Gly Gly Thr Thr Phe Phe Gln Pro Leu Asn Pro Ile Leu
    370                 375                 380

Ser Ala Tyr Gly Leu Thr Leu Lys Val Thr Gly Ser Asp Pro Gly Pro
385                 390                 395                 400

Gly Pro Gly Pro Gly Pro Gln Pro Gly Gly Thr Trp Lys Ala Gly Thr
                405                 410                 415

Val Tyr Ala Ala Gly Asp Thr Val Thr Tyr Gly Gly Ala Ala Tyr Arg
            420                 425                 430

Cys Leu Gln Gly His Gln Ala Gln Thr Gly Trp Glu Pro Ser Val Val
        435                 440                 445

Pro Ala Leu Trp Gln Lys Leu
    450                 455

<210> SEQ ID NO 34
<211> LENGTH: 456
<212> TYPE: PRT
<213> ORGANISM: Streptomyces flavochromogenes

<400> SEQUENCE: 34

Met Leu Arg Arg His Ala Arg Ala Ala Cys Thr Ser Leu Val Ala Ala
1               5                   10                  15

Gly Met Ala Leu Ala Gly Leu Gln Ala Gly Ser Ala Ala Ala Ala Pro
            20                  25                  30

Asp Gly Arg Asp Pro His Arg Ala Pro Thr Val Arg Thr Ala Ala Gln
        35                  40                  45

Ala Leu Gly Ala Asp Ser Ala Arg Pro Glu Leu Leu Asp Ala Met Arg
    50                  55                  60

Arg Asp Leu Gly Leu Thr His Ser Gln Ala Arg Thr Arg Leu Ala Asn
65                  70                  75                  80

Glu Ala Glu Ala Gly Ala Thr Ala Ala Arg Leu Arg Gln Gly Leu Gly
                85                  90                  95

Gly Ala Phe Ala Gly Ala Trp Val Asp Gly Ala Glu Ala Gly Thr Leu
            100                 105                 110

Thr Val Ala Thr Thr Arg Ala Ala Asp Thr Pro Ala Ile Arg Ala Thr
        115                 120                 125

Gly Ala Arg Ala Arg Leu Val Thr His Ser Leu Thr Ala Leu Glu Arg
    130                 135                 140

Ala Lys Gln Arg Leu Asp Arg Thr Ala Gly Thr Asp Ala Pro Val Arg
145                 150                 155                 160

Tyr Val Asp Val Arg Ala Asn Val Leu Val Glu Glu Thr Arg Ala
                165                 170                 175

Gly Ala Gly Ala Arg Leu Val Arg Ala Thr Gly Val Pro Arg Glu Leu
            180                 185                 190

Val Arg Val Arg Thr Gly Gln Ala Pro Arg Pro Leu Tyr Asp Ile
        195                 200                 205

Arg Gly Gly Asp Ala Tyr Tyr Met Gly Gly Gly Arg Cys Ser Val
    210                 215                 220

Gly Phe Ala Val Thr Arg Gly Thr Thr Gln Gly Phe Ala Thr Ala Gly
225                 230                 235                 240

His Cys Gly Arg Ala Gly Thr Thr Thr Ser Gly Phe Asn Gln Val Ala
                245                 250                 255

Gln Gly Ser Phe Gln Gly Ser Val Phe Pro Gly Asn Asp Met Ala Trp
            260                 265                 270

Val Ala Ala Asn Thr Asn Trp Thr Ser Thr Pro Tyr Val Lys Gly Ser
        275                 280                 285
```

```
Gly Gly Ala Asn Val Gln Val Thr Gly Ser Val Leu Gln Pro Val Gly
            290                 295                 300

Ser Ser Val Cys Arg Ser Gly Ser Thr Thr Gly Trp His Cys Gly Thr
305                 310                 315                 320

Val Gln Gln His Asn Thr Ser Val Thr Tyr Pro Glu Gly Thr Ile Ser
                325                 330                 335

Gly Val Thr Arg Thr Thr Val Cys Ala Glu Pro Gly Asp Ser Gly Gly
                340                 345                 350

Ser Tyr Ile Ser Gly Ser Gln Ala Gln Gly Val Thr Ser Gly Gly Ser
                355                 360                 365

Gly Asn Cys Ser Ser Gly Gly Thr Thr Phe Phe Gln Pro Leu Asn Pro
            370                 375                 380

Leu Leu Gln Asn Tyr Gly Leu Thr Leu Lys Thr Thr Gly Thr Asp Pro
385                 390                 395                 400

Gly Pro Gly Pro Gly Glu Pro Glu Pro Gly Gly Thr Trp Ala Ala Gly
                405                 410                 415

Lys Val Tyr Ala Ala Gly Asp Val Val Thr Tyr Gly Gly Ala Ser Tyr
                420                 425                 430

Arg Cys Leu Gln Gly His Gln Ala Gln Ala Gly Trp Gln Pro Pro Asn
            435                 440                 445

Val Pro Ala Leu Trp Gln Arg Leu
            450                 455

<210> SEQ ID NO 35
<211> LENGTH: 454
<212> TYPE: PRT
<213> ORGANISM: Streptomyces bikiniensis

<400> SEQUENCE: 35

Met Leu Arg Arg His Ala Arg Thr Ala Cys Thr Val Leu Ala Ala Ala
1               5                   10                  15

Gly Leu Ala Leu Ala Gly Leu Gln Ala Gly Ser Ala Thr Ala Ala Pro
            20                  25                  30

His Asp Lys Asp Arg Ala Pro Thr Val Arg Thr Ala Ala Asp Ala Leu
        35                  40                  45

Gly Ala Ala Ser Ala Gln Pro Glu Leu Leu Arg Ala Met Gln Arg Asp
    50                  55                  60

Leu Gly Leu Thr Arg Ala Gln Ala Glu Asn Arg Leu Ala Asn Glu Ala
65                  70                  75                  80

Glu Ala Gly Ala Arg Ala Ala Gly Leu Arg Leu Asp Leu Gly Gly Ala
                85                  90                  95

Phe Ala Gly Ala Trp Val Asp Gly Ala Glu Ser Gly Thr Leu Thr Val
            100                 105                 110

Ala Thr Thr Arg Ala Ala Asp Ala Ala Ala Ile Arg Ala Ala Gly Ala
            115                 120                 125

His Ala Glu Val Val Thr His Gly Leu Ser Ala Leu Glu Arg Ala Lys
        130                 135                 140

Glu Ala Leu Asp Arg Ala Ala Thr Ala Asp Val Pro Val Arg Tyr Val
145                 150                 155                 160

Asp Val Arg Ala Asn Val Leu Val Glu Glu Ala Arg Ala Gly Ala
                165                 170                 175

Gly Ala Arg Leu Val Ala Thr Gly Val Pro Arg Asp Leu Val Lys
            180                 185                 190

Val Val Arg Thr Ala Glu Ala Pro Arg Pro Leu Tyr Asp Leu Arg Gly
```

```
                195                 200                 205
Gly Asp Ala Tyr Tyr Met Asn Gly Ser Gly Arg Cys Ser Val Gly Phe
210                 215                 220

Pro Ile Thr Lys Gly Thr Thr Gln Gly Phe Ala Thr Ala Gly His Cys
225                 230                 235                 240

Gly Arg Ala Gly Thr Ser Ser Gly Tyr Asn Gln Val Ala Gln Gly
                245                 250                 255

Ser Phe Gln Ala Ser Val Phe Pro Gly Ser Asp Met Ala Trp Val Ala
            260                 265                 270

Thr Asn Ser Asn Trp Thr Ala Thr Pro Tyr Val Lys Gly Ala Gly Gly
        275                 280                 285

Ala Asn Val Gln Val Thr Gly Ser Val Leu Gln Pro Val Gly Ser Ser
    290                 295                 300

Val Cys Arg Ser Gly Ser Thr Thr Gly Trp His Cys Gly Thr Val Gln
305                 310                 315                 320

Gln His Asn Thr Ser Val Thr Tyr Pro Glu Gly Thr Ile Ser Gly Val
                325                 330                 335

Thr Arg Thr Thr Val Cys Ala Glu Pro Gly Asp Ser Gly Gly Ser Tyr
            340                 345                 350

Ile Ser Gly Ser Gln Ala Gln Gly Val Thr Ser Gly Gly Ser Gly Asn
        355                 360                 365

Cys Ser Ser Gly Gly Thr Thr Phe Phe Gln Pro Leu Asn Pro Ile Leu
    370                 375                 380

Gln Asn Tyr Gly Leu Thr Leu Lys Thr Thr Asp Pro Gly Pro Gly
385                 390                 395                 400

Pro Gly Pro Glu Pro Glu Pro Gly Gly Thr Trp Ala Ala Gly Lys Val
                405                 410                 415

Tyr Lys Ala Gly Asp Thr Val Thr Tyr Gly Gly Ser Thr Tyr Arg Cys
            420                 425                 430

Leu Gln Gly His Gln Ala Gln Thr Gly Trp Glu Pro Ser Asn Val Pro
        435                 440                 445

Ala Leu Trp Gln Arg Val
    450

<210> SEQ ID NO 36
<211> LENGTH: 456
<212> TYPE: PRT
<213> ORGANISM: Streptomyces griseus

<400> SEQUENCE: 36

Met Leu Arg Arg His Ala Arg Ala Ala Cys Thr Ala Leu Ala Ala Ala
1               5                   10                  15

Gly Met Ala Leu Ala Gly Leu Gln Ala Gly Ser Ala Thr Ala Ala Gln
            20                  25                  30

Pro Ser Pro Gly Ser Ala Pro Ser Val Arg Ser Ala Ala His Ala Leu
        35                  40                  45

Gly Ala Asp Glu Ala Arg Pro Glu Leu Leu Ala Ala Met Gly Arg Asp
    50                  55                  60

Leu Gly Leu Thr Arg Thr Gln Ala Glu His Arg Leu Val Asn Glu Ala
65                  70                  75                  80

Glu Ala Gly Ala Thr Ala Ala Arg Leu Arg Gln His Leu Gly Gly Ser
                85                  90                  95

Phe Ala Gly Ala Trp Val Ala Gly Ala Glu Ser Gly Ser Leu Thr Val
            100                 105                 110
```

```
Ala Thr Thr Arg Ala Ala Asp Leu Ala Ala Ile Arg Ala Ala Gly Ala
            115                 120                 125

Glu Ala Ala Leu Val Arg His Gly Leu Thr Ala Leu Glu Arg Ala Arg
        130                 135                 140

Thr Ala Leu Asp Arg Ala Ala Thr Ala Asp Ala Pro Val Arg Tyr Val
145                 150                 155                 160

Asp Val Arg Ala Asn Val Leu Val Glu Glu Thr Arg Ala Gly Ala
                165                 170                 175

Gly Asp Arg Leu Val Ala Ala Thr Gly Val Pro Arg Glu Leu Val Arg
            180                 185                 190

Val Val Arg Ser Ala Gly Ala Pro Arg Pro Leu Tyr Asp Ile Arg Gly
            195                 200                 205

Gly Asp Ala Tyr Tyr Met Gly Gly Gly Arg Cys Ser Val Gly Phe
            210                 215                 220

Pro Val Thr Arg Gly Thr Thr Gln Gly Phe Ala Thr Ala Gly His Cys
225                 230                 235                 240

Gly Arg Ala Gly Gln Ser Thr Ser Gly Phe Asn Gln Val Ala Gln Gly
                245                 250                 255

Thr Phe Gln Ala Ser Val Phe Pro Gly Asn Asp Met Ala Trp Val Ala
            260                 265                 270

Ala His Thr Asn Trp Thr Ser Thr Pro Tyr Val Lys Gly Ala Gly Gly
            275                 280                 285

Ala Asn Val Gln Val Thr Gly Ser Val Leu Gln Pro Val Gly Ser Ser
            290                 295                 300

Val Cys Arg Ser Gly Ser Thr Thr Gly Trp His Cys Gly Thr Ile Gln
305                 310                 315                 320

Gln His Asn Thr Ser Val Thr Tyr Gln Glu Gly Thr Val Ser Gly Val
                325                 330                 335

Thr Arg Thr Thr Val Cys Ala Glu Pro Gly Asp Ser Gly Gly Ser Tyr
            340                 345                 350

Ile Ser Gly Ser Gln Ala Gln Gly Val Thr Ser Gly Thr Gly Asn
            355                 360                 365

Cys Ser Ser Gly Gly Thr Thr Tyr Phe Gln Pro Leu Asn Pro Ile Leu
            370                 375                 380

Ser Gly Tyr Gly Leu Thr Leu Lys Thr Thr Gly Ser Asp Pro Gly Pro
385                 390                 395                 400

Gly Pro Gly Pro Gly Glu Pro Gln Pro Gly Gly Thr Trp Thr Ala Gly
                405                 410                 415

Lys Val Tyr Ala Ala Gly Asp Thr Val Thr Tyr Gly Ser Thr Tyr
            420                 425                 430

Arg Cys Leu Gln Ala His Gln Ala Gln Ala Gly Trp Glu Pro Ser Asn
            435                 440                 445

Val Pro Ala Leu Trp Gln Arg Ile
            450                 455

<210> SEQ ID NO 37
<211> LENGTH: 454
<212> TYPE: PRT
<213> ORGANISM: Streptomyces sp. NRRL_F-5727

<400> SEQUENCE: 37

Met Leu Arg Arg His Ala Arg Ala Ala Cys Thr Val Leu Ala Ala Ala
1               5                   10                  15

Gly Met Val Leu Ala Gly Leu Gln Ala Gly Ser Ala Thr Ala Ala Pro
            20                  25                  30
```

```
Pro Ser Pro Gly Thr Ala Pro Ala Val Gln Ser Ala Ala Arg Ala Leu
        35                  40                  45

Gly Ala Gly Glu Ala Arg Pro Glu Leu Leu Ala Ala Met Gly Arg Asp
 50                  55                  60

Leu Gly Leu Thr Arg Ala Gln Ala Glu Arg Arg Leu Val Asn Glu Ala
 65                  70                  75                  80

Glu Ala Gly Ala Thr Ala Ala Arg Leu Arg Asp Arg Leu Gly Gly Ala
                 85                  90                  95

Phe Ala Gly Ala Trp Val Gly Ala Glu Ser Gly Ser Leu Thr Val
                100                 105                 110

Ala Thr Thr Arg Ala Ala Asp Leu Ala Ala Ile Arg Ala Ala Gly Ala
                115                 120                 125

Thr Ala Arg Leu Val Arg His Asp Leu Ala Ala Leu Glu Arg Ala Lys
        130                 135                 140

Glu Ser Leu Asp Arg Ala Ala Gly Ala Asp Ala Pro Val Arg Tyr Val
145                 150                 155                 160

Asp Val Arg Ala Asn Val Leu Val Val Glu Glu Thr Arg Ala Gly Ala
                    165                 170                 175

Gly Ala Arg Leu Ala Ala Glu Thr Gly Val Ala Arg Glu Leu Val Arg
                180                 185                 190

Val Val Arg Ser Ala Glu Ala Pro Arg Pro Leu Tyr Asp Leu Arg Gly
        195                 200                 205

Gly Asp Ala Tyr Tyr Met Gly Gly Gly Arg Cys Ser Val Gly Phe
210                 215                 220

Pro Val Thr Arg Gly Thr Thr Gln Gly Phe Ala Thr Ala Gly His Cys
225                 230                 235                 240

Gly Arg Ala Gly Gln Ser Thr Ser Gly Tyr Asn Gln Val Ala Gln Gly
                    245                 250                 255

Thr Phe Gln Ala Ser Val Phe Pro Gly Asn Asp Met Ala Trp Val Ala
        260                 265                 270

Ala Asn Ser Ser Trp Thr Ala Thr Pro Tyr Val Lys Gly Ala Gly Gly
        275                 280                 285

Ala Asn Val Gln Val Thr Gly Ser Val Leu Gln Pro Val Gly Ala Ser
        290                 295                 300

Val Cys Arg Ser Gly Ser Thr Thr Gly Trp His Cys Gly Thr Ile Gln
305                 310                 315                 320

Gln His Asn Thr Ser Val Thr Tyr Pro Glu Gly Thr Ile Ser Gly Val
                    325                 330                 335

Thr Arg Thr Thr Val Cys Ala Glu Pro Gly Asp Ser Gly Gly Ser Tyr
                340                 345                 350

Ile Ser Gly Ser Gln Ala Gln Gly Val Thr Ser Gly Gly Ser Gly Asn
                355                 360                 365

Cys Ser Ser Gly Gly Thr Thr Phe Phe Gln Pro Leu Asn Pro Ile Leu
        370                 375                 380

Ser Asn Tyr Gly Leu Thr Leu Arg Thr Ala Gly Thr Asp Pro Gly Pro
385                 390                 395                 400

Gly Pro Gly Glu Pro Glu Pro Gly Gly Thr Trp Lys Ala Gly Thr Val
                405                 410                 415

Tyr Ala Ala Gly Ala Thr Val Thr Tyr Gly Gly Ser Thr Tyr Arg Cys
                420                 425                 430

Leu Gln Gly His Gln Ala Gln Ala Gly Trp Glu Pro Pro Asn Val Pro
        435                 440                 445
```

```
Ala Leu Trp Gln Arg Val
        450

<210> SEQ ID NO 38
<211> LENGTH: 458
<212> TYPE: PRT
<213> ORGANISM: Streptomyces sp. CNT372

<400> SEQUENCE: 38

Met Phe His Arg Pro Val Arg Ala Ala Cys Ala Ala Val Ala Ala
1               5                   10                  15

Gly Ala Leu Val Leu Ala Ser Leu Gln Gly Tyr Ala Ala Gln Pro
            20                  25                  30

Ser Ala Ala Ser Pro Gly Gly Thr Ser Ala Ala Gly Thr Leu Ala
            35                  40                  45

Val Ser Ala Ala Gln Pro Gly Leu Lys Arg Ala Met Gln Arg Asp Leu
    50                  55                  60

Gly Leu Thr Ala Ala Gln Ala Glu Arg Arg Leu Val Asn Glu Ala Glu
65                  70                  75                  80

Ala Gly Ala Ala Ala Ala Arg Leu Gln Gln Arg Leu Gly Ala Ser Phe
                85                  90                  95

Ala Gly Ala Trp Val Ser Gly Ala Glu Ser Gly Thr Leu Thr Val Ala
            100                 105                 110

Thr Thr Arg Ala Ala Asp His Ala Ala Val Arg Ala Glu Gly Ala Lys
            115                 120                 125

Pro Val Ala Ala Gly Ala Ser Leu Ala Glu Leu Asp Arg Ala Lys Ala
            130                 135                 140

Ala Leu Asp Arg Ala Ala Arg Ala Gly Ser Pro Ala Val Pro Val
145                 150                 155                 160

Trp Tyr Val Asp Val Arg Glu Asn Thr Val Val Gly Ala Arg Asn
                165                 170                 175

Thr Ala Ala Ala Glu Ala Leu Ile Ala Ala Ser Gly Ala Asp Arg Asp
            180                 185                 190

Arg Ile Arg Val Ala Ala Thr Gly Glu Ser Pro Arg Pro Leu Tyr Asp
    195                 200                 205

Ile Arg Gly Gly Asp Ala Tyr Tyr Met Gly Gly Gly Arg Cys Ser
        210                 215                 220

Val Gly Phe Ala Val Thr Arg Gly Thr Gln His Gly Phe Ala Thr Ala
225                 230                 235                 240

Gly His Cys Gly Arg Ala Gly Thr Ala Thr Ser Gly Phe Asn Gln Val
                245                 250                 255

Ala Gln Gly Thr Phe Gln Ala Ser Thr Phe Pro Gly Arg Asp Thr Ala
            260                 265                 270

Trp Val Leu Thr Asn Ser Gln Trp Thr Ala Thr Pro Tyr Val Lys Gly
            275                 280                 285

Ala Gly Gly Gln Asn Val Gln Val Ala Gly Ser Val Gln Gln Pro Val
            290                 295                 300

Gly Ala Ser Val Cys Arg Ser Gly Ser Thr Thr Gly Trp His Cys Gly
305                 310                 315                 320

Thr Ile Gln Gln His Asn Thr Ser Val Thr Tyr Pro Glu Gly Thr Ile
                325                 330                 335

Thr Gly Val Thr Arg Thr Ser Val Cys Ala Glu Pro Gly Asp Ser Gly
            340                 345                 350

Gly Ser Tyr Ile Ser Gly Ser Gln Ala Gln Gly Val Thr Ser Gly Gly
            355                 360                 365
```

```
Ser Gly Asn Cys Arg Thr Gly Thr Thr Tyr His Gln Pro Ile Asn
        370                 375                 380

Pro Leu Leu Gln Ala Tyr Gly Leu Thr Leu Arg Thr Thr Asp Pro
385                 390                 395                 400

Gly Pro Gly Pro Gly Glu Pro Gly Glu Pro Gly Gly Thr Trp Ala
                405                 410                 415

Ala Gly Thr Val Tyr Ala Thr Gly Ala Gln Val Thr Tyr Gly Gly Ala
                420                 425                 430

Thr Tyr Arg Cys Leu Gln Gly His Gln Ala Gln Thr Gly Trp Glu Pro
                435                 440                 445

Pro Asn Val Pro Ala Leu Trp Gln Arg Leu
            450                 455

<210> SEQ ID NO 39
<211> LENGTH: 191
<212> TYPE: PRT
<213> ORGANISM: Streptomyces griseus

<400> SEQUENCE: 39

Ala Asp Ile Arg Gly Gly Asp Ala Tyr Tyr Met Asn Gly Ser Gly Arg
1               5                   10                  15

Cys Ser Val Gly Phe Ser Val Thr Arg Gly Thr Gln Asn Gly Phe Ala
                20                  25                  30

Thr Ala Gly His Cys Gly Arg Val Gly Thr Thr Thr Asn Gly Val Asn
            35                  40                  45

Gln Gln Ala Gln Gly Thr Phe Gln Gly Ser Thr Phe Pro Gly Arg Asp
        50                  55                  60

Ile Ala Trp Val Ala Thr Asn Ala Asn Trp Thr Pro Arg Pro Leu Val
65                  70                  75                  80

Asn Gly Tyr Gly Arg Gly Asp Val Thr Val Ala Gly Ser Thr Ala Ser
                85                  90                  95

Val Val Gly Ala Ser Val Cys Arg Ser Gly Ser Thr Thr Gly Trp His
                100                 105                 110

Cys Gly Thr Ile Gln Gln Leu Asn Thr Ser Val Thr Tyr Pro Glu Gly
            115                 120                 125

Thr Ile Ser Gly Val Thr Arg Thr Ser Val Cys Ala Glu Pro Gly Asp
        130                 135                 140

Ser Gly Gly Ser Tyr Ile Ser Gly Ser Gln Ala Gln Gly Val Thr Ser
145                 150                 155                 160

Gly Gly Ser Gly Asn Cys Ser Ser Gly Gly Thr Thr Tyr Phe Gln Pro
                165                 170                 175

Ile Asn Pro Leu Leu Gln Ala Tyr Gly Leu Thr Leu Val Thr Ser
            180                 185                 190

<210> SEQ ID NO 40
<211> LENGTH: 275
<212> TYPE: PRT
<213> ORGANISM: Bacillus amyloliquefaciens

<400> SEQUENCE: 40

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45
```

```
Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 41
<211> LENGTH: 269
<212> TYPE: PRT
<213> ORGANISM: Bacillus lentus

<400> SEQUENCE: 41

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
```

```
                130                 135                 140
Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 42
<211> LENGTH: 191
<212> TYPE: PRT
<213> ORGANISM: Streptomyces albulus

<400> SEQUENCE: 42

Tyr Asp Ile Arg Gly Gly Asp Ala Tyr Tyr Met Gly Gly Ser Gly Arg
1               5                   10                  15

Cys Ser Val Gly Phe Ala Ile Thr Arg Gly Thr Gln Ala Gly Phe Ala
            20                  25                  30

Thr Ala Gly His Cys Gly Arg Ala Gly Thr Thr Thr Gly Tyr Asn
        35                  40                  45

Gln Val Ala Gln Gly Ser Phe Gln Ala Ser Thr Phe Pro Gly Arg Asp
    50                  55                  60

Thr Ala Trp Val Ala Thr Ser Thr Asn Trp Thr Ala Thr Pro Tyr Val
65                  70                  75                  80

Lys Gly Ala Gly Ala Asn Val Gln Val Thr Gly Ser Val Gln Gln
                85                  90                  95

Pro Val Gly Ala Ser Val Cys Arg Ser Gly Ser Thr Thr Gly Trp His
            100                 105                 110

Cys Gly Thr Ile Gln Gln His Asn Thr Ser Val Thr Tyr Pro Glu Gly
        115                 120                 125

Thr Ile Ser Gly Val Thr Arg Thr Ser Val Cys Ala Glu Pro Gly Asp
    130                 135                 140

Ser Gly Gly Ser Tyr Ile Ser Gly Thr Gln Ala Gln Gly Val Thr Ser
145                 150                 155                 160

Gly Gly Ser Gly Asp Cys Arg Ser Gly Thr Thr Tyr His Gln Pro
                165                 170                 175

Ile Asn Pro Leu Leu Gln Ala Tyr Gly Leu Thr Leu Arg Thr Thr
            180                 185                 190

<210> SEQ ID NO 43
<211> LENGTH: 191
<212> TYPE: PRT
<213> ORGANISM: Streptomyces sp. NRRL F-5193

<400> SEQUENCE: 43

Tyr Asp Leu Arg Gly Gly Asp Ala Tyr Tyr Met Gly Gly Gly Gly Arg
```

```
1               5                   10                  15
Cys Ser Val Gly Phe Pro Val Thr Arg Gly Thr Thr Gln Gly Phe Ala
                20                  25                  30
Thr Ala Gly His Cys Gly Arg Ala Gly Gln Thr Thr Ser Gly Tyr Asn
                35                  40                  45
Gln Val Ala Gln Gly Ser Phe Gln Ala Ser Ile Phe Pro Gly Asn Asp
        50                  55                  60
Met Ala Trp Val Ala Ala Asn Ser Asn Trp Thr Ala Thr Pro Tyr Val
65                  70                  75                  80
Lys Gly Ala Gly Ala Asn Val Gln Val Thr Gly Ser Val Leu Gln
                85                  90                  95
Pro Val Gly Ala Ser Val Cys Arg Ser Gly Ser Thr Thr Gly Trp His
                100                 105                 110
Cys Gly Thr Ile Gln Gln His Asn Thr Ser Val Thr Tyr Pro Glu Gly
                115                 120                 125
Thr Ile Ser Gly Val Thr Arg Thr Thr Val Cys Ala Glu Pro Gly Asp
        130                 135                 140
Ser Gly Gly Ser Tyr Ile Ser Gly Ser Gln Ala Gln Gly Val Thr Ser
145                 150                 155                 160
Gly Gly Ser Gly Asn Cys Ser Ser Gly Thr Thr Tyr Phe Gln Pro
                165                 170                 175
Leu Asn Pro Ile Leu Ser Asn Tyr Gly Leu Thr Leu Lys Thr Thr
                180                 185                 190
```

<210> SEQ ID NO 44
<211> LENGTH: 191
<212> TYPE: PRT
<213> ORGANISM: Streptomyces exfoliatus

<400> SEQUENCE: 44

```
Tyr Asp Ile Arg Gly Gly Asp Ala Tyr Tyr Met Gly Gly Gly Arg
1               5                   10                  15
Cys Ser Val Gly Phe Ala Val Thr Arg Gly Thr Thr Gln Gly Phe Ala
                20                  25                  30
Thr Ala Gly His Cys Gly Arg Ala Gly Thr Thr Thr Ser Gly Phe Asn
                35                  40                  45
Gln Ala Ala Gln Gly Ser Phe Gln Gly Ser Ile Phe Pro Gly Asn Asp
        50                  55                  60
Met Ala Trp Val Ala Ala Asn Thr Asn Trp Thr Ser Thr Pro Tyr Val
65                  70                  75                  80
Lys Gly Ser Gly Gly Ala Asn Val Gln Val Thr Gly Ser Val Leu Gln
                85                  90                  95
Pro Val Gly Ala Ser Val Cys Arg Ser Gly Ser Thr Thr Gly Trp His
                100                 105                 110
Cys Gly Thr Ile Gln Gln His Asn Thr Ser Val Thr Tyr Pro Glu Gly
                115                 120                 125
Ile Ile Ser Gly Val Thr Arg Thr Thr Val Cys Ala Glu Pro Gly Asp
        130                 135                 140
Ser Gly Gly Ser Tyr Ile Ser Gly Ser Gln Ala Gln Gly Val Thr Ser
145                 150                 155                 160
Gly Gly Ser Gly Asn Cys Ser Ser Gly Thr Thr Phe Phe Gln Pro
                165                 170                 175
Leu Asn Pro Leu Leu Gln Asn Tyr Gly Leu Thr Leu Lys Thr Thr
                180                 185                 190
```

<210> SEQ ID NO 45
<211> LENGTH: 191
<212> TYPE: PRT
<213> ORGANISM: Streptomyces albus

<400> SEQUENCE: 45

```
Tyr Asp Ile Arg Gly Gly Asp Ala Tyr Tyr Met Gly Gly Gly Gly Arg
1               5                   10                  15

Cys Ser Val Gly Phe Ala Val Thr Arg Gly Thr Thr Gln Gly Phe Ala
            20                  25                  30

Thr Ala Gly His Cys Gly Arg Ala Gly Thr Ala Thr Ser Gly Tyr Asn
        35                  40                  45

Gln Val Ala Gln Gly Thr Phe Gln Ala Ser Thr Phe Pro Gly Arg Asp
    50                  55                  60

Thr Ala Trp Val Ala Thr Asn Gly Asn Trp Thr Ser Thr Pro Tyr Val
65                  70                  75                  80

Lys Gly Gln Gly Gly Gln Asn Ile Gln Val Thr Gly Ser Val Gln Gln
                85                  90                  95

Pro Val Gly Ala Ser Ile Cys Arg Ser Gly Ser Thr Thr Gly Trp His
            100                 105                 110

Cys Gly Thr Ile Ser Gln His Asn Thr Ser Val Thr Tyr Pro Glu Gly
        115                 120                 125

Thr Ile Ser Gly Val Thr Arg Thr Thr Val Cys Ala Glu Pro Gly Asp
    130                 135                 140

Ser Gly Gly Ser Tyr Ile Ser Gly Ser Gln Ala Gln Gly Val Thr Ser
145                 150                 155                 160

Gly Gly Ser Gly Asp Cys Arg Ser Gly Thr Thr Tyr His Gln Pro
                165                 170                 175

Val Asn Pro Leu Leu Gln Gly Tyr Gly Leu Thr Leu Lys Thr Thr
            180                 185                 190
```

<210> SEQ ID NO 46
<211> LENGTH: 191
<212> TYPE: PRT
<213> ORGANISM: Streptomyces pristinaespiralis

<400> SEQUENCE: 46

```
Tyr Asp Ile Arg Gly Gly Asp Ala Tyr Tyr Met Gly Gly Gly Gly Arg
1               5                   10                  15

Cys Ser Val Gly Phe Ala Val Thr Arg Gly Thr Thr Gln Gly Phe Ala
            20                  25                  30

Thr Ala Gly His Cys Gly Arg Ala Gly Thr Ser Thr Ser Gly Tyr Asn
        35                  40                  45

Gln Val Ala Gln Gly Thr Phe Gln Ala Ser Thr Phe Pro Gly Arg Asp
    50                  55                  60

Thr Ala Trp Val Ala Ala Asn Ser Asn Trp Thr Ser Thr Pro Tyr Val
65                  70                  75                  80

Lys Gly Gln Ser Gly Gln Asn Ile Gln Val Thr Gly Ser Val Gln Gln
                85                  90                  95

Pro Val Gly Ala Ser Ile Cys Arg Ser Gly Ser Thr Thr Gly Trp His
            100                 105                 110

Cys Gly Thr Ile Ser Gln His Asn Thr Ser Val Thr Tyr Pro Glu Gly
        115                 120                 125

Thr Ile Thr Gly Val Thr Arg Thr Thr Val Cys Ala Glu Pro Gly Asp
    130                 135                 140
```

Ser Gly Gly Ser Tyr Ile Ser Gly Ser Gln Ala Gln Gly Val Thr Ser
145                 150                 155                 160

Gly Gly Ser Gly Asp Cys Arg Ser Gly Gly Thr Thr Phe His Gln Pro
                165                 170                 175

Ile Asn Pro Leu Leu Gln Gly Tyr Gly Leu Thr Leu Lys Thr Thr
            180                 185                 190

<210> SEQ ID NO 47
<211> LENGTH: 191
<212> TYPE: PRT
<213> ORGANISM: Streptomyces leeuwenhoekii

<400> SEQUENCE: 47

Tyr Asp Leu Arg Gly Gly Asp Ala Tyr Tyr Met Asn Gly Ser Gly Arg
1               5                   10                  15

Cys Ser Val Gly Phe Pro Val Thr Arg Gly Thr Gln Gln Gly Phe Ala
            20                  25                  30

Thr Ala Gly His Cys Gly Arg Ala Gly Thr Ser Thr Gly Tyr Asn
        35                  40                  45

Gln Ala Ala Gln Gly Thr Phe Gln Ala Ser Thr Phe Pro Gly Arg Asp
    50                  55                  60

Met Ala Trp Val Ala Thr Asn Ser Asn Trp Thr Ala Thr Pro Tyr Val
65                  70                  75                  80

Lys Gly Ala Gly Gly Gln Asn Val Gln Val Thr Gly Ser Thr Gln Ala
                85                  90                  95

Pro Val Gly Ser Ser Val Cys Arg Ser Gly Ser Thr Thr Gly Trp His
            100                 105                 110

Cys Gly Thr Ile Gln Gln Leu Asn Thr Ser Val Thr Tyr Pro Glu Gly
        115                 120                 125

Thr Ile Thr Gly Val Thr Arg Thr Ser Val Cys Ala Glu Pro Gly Asp
    130                 135                 140

Ser Gly Gly Ser Tyr Ile Ser Gly Ser Gln Ala Gln Gly Val Thr Ser
145                 150                 155                 160

Gly Gly Ser Gly Asn Cys Arg Thr Gly Gly Thr Thr Tyr Phe Gln Pro
                165                 170                 175

Leu Asn Pro Leu Leu Gln Ser Tyr Gly Leu Thr Leu Lys Thr Asn
            180                 185                 190

<210> SEQ ID NO 48
<211> LENGTH: 191
<212> TYPE: PRT
<213> ORGANISM: Streptomyces sp. CNT372

<400> SEQUENCE: 48

Tyr Asp Ile Arg Gly Gly Asp Ala Tyr Tyr Met Gly Gly Gly Gly Arg
1               5                   10                  15

Cys Ser Val Gly Phe Ala Val Thr Arg Gly Thr Gln His Gly Phe Ala
            20                  25                  30

Thr Ala Gly His Cys Gly Arg Ala Gly Thr Ala Thr Ser Gly Phe Asn
        35                  40                  45

Gln Val Ala Gln Gly Thr Phe Gln Ala Ser Thr Phe Pro Gly Arg Asp
    50                  55                  60

Thr Ala Trp Val Leu Thr Asn Ser Gln Trp Thr Ala Thr Pro Tyr Val
65                  70                  75                  80

Lys Gly Ala Gly Gly Gln Asn Val Gln Val Ala Gly Ser Val Gln Gln
                85                  90                  95

```
Pro Val Gly Ala Ser Val Cys Arg Ser Gly Ser Thr Thr Gly Trp His
            100                 105                 110

Cys Gly Thr Ile Gln Gln His Asn Thr Ser Val Thr Tyr Pro Glu Gly
        115                 120                 125

Thr Ile Thr Gly Val Thr Arg Thr Ser Val Cys Ala Glu Pro Gly Asp
    130                 135                 140

Ser Gly Gly Ser Tyr Ile Ser Gly Ser Gln Ala Gln Gly Val Thr Ser
145                 150                 155                 160

Gly Gly Ser Gly Asn Cys Arg Thr Gly Thr Thr Tyr His Gln Pro
                165                 170                 175

Ile Asn Pro Leu Leu Gln Ala Tyr Gly Leu Thr Leu Arg Thr Thr
            180                 185                 190

<210> SEQ ID NO 49
<211> LENGTH: 191
<212> TYPE: PRT
<213> ORGANISM: Streptomyces cyaneogriseus

<400> SEQUENCE: 49

Tyr Asp Leu Arg Gly Gly Asp Ala Tyr Tyr Met Asn Gly Ser Gly Arg
1               5                   10                  15

Cys Ser Val Gly Phe Pro Ile Thr Arg Gly Thr Gln Gln Gly Phe Ala
            20                  25                  30

Thr Ala Gly His Cys Gly Arg Ala Gly Thr Ser Thr Gly Tyr Asn
        35                  40                  45

Gln Ala Ala Gln Gly Thr Phe Gln Ala Ser Phe Pro Gly Arg Asp
    50                  55                  60

Met Ala Trp Val Ala Thr Asn Ser Asn Trp Thr Ala Thr Pro Tyr Val
65                  70                  75                  80

Lys Gly Ala Gly Gly Gln Asn Val Gln Val Ala Gly Ser Thr Gln Ala
                85                  90                  95

Pro Val Gly Ser Ser Val Cys Arg Ser Gly Ser Thr Gly Trp His
            100                 105                 110

Cys Gly Thr Val Gln Gln Leu Asn Thr Ser Val Thr Tyr Pro Glu Gly
        115                 120                 125

Thr Ile Thr Gly Val Thr Arg Thr Ser Val Cys Ala Glu Pro Gly Asp
    130                 135                 140

Ser Gly Gly Ser Tyr Ile Ser Gly Ser Gln Ala Gln Gly Val Thr Ser
145                 150                 155                 160

Gly Gly Ser Gly Asp Cys Arg Thr Gly Thr Thr Tyr Phe Gln Pro
                165                 170                 175

Ile Asn Pro Leu Leu Gln Thr Tyr Gly Leu Thr Leu Arg Thr Asn
            180                 185                 190

<210> SEQ ID NO 50
<211> LENGTH: 191
<212> TYPE: PRT
<213> ORGANISM: Streptomyces niveus

<400> SEQUENCE: 50

Tyr Asp Ile Arg Gly Gly Asp Ala Tyr Tyr Met Asn Gly Ser Gly Arg
1               5                   10                  15

Cys Ser Val Gly Phe Ala Val Thr Lys Gly Thr Gln Gln Gly Phe Ala
            20                  25                  30

Thr Ala Gly His Cys Gly Arg Pro Gly Thr Thr Thr Ser Gly Tyr Asn
        35                  40                  45
```

```
Gln Val Ala Gln Gly Ser Phe Gln Ala Ser Thr Phe Pro Gly Arg Asp
     50                  55                  60

Thr Ala Trp Val Ala Thr Asn Thr Asn Trp Thr Ser Thr Pro Tyr Val
 65                  70                  75                  80

Lys Gly Gln Gly Ala Ala Asn Val Gln Val Thr Gly Ser Thr Gln Ser
                 85                  90                  95

Pro Val Gly Ala Ser Val Cys Arg Ser Gly Ser Thr Thr Gly Trp His
                100                 105                 110

Cys Gly Val Ile Gln Gln His Asn Thr Ser Val Thr Tyr Pro Glu Gly
            115                 120                 125

Thr Ile Ser Gly Val Thr Arg Thr Thr Val Cys Ala Glu Pro Gly Asp
        130                 135                 140

Ser Gly Gly Ser Tyr Ile Ser Gly Ser Gln Ala Gln Gly Val Thr Ser
145                 150                 155                 160

Gly Gly Ser Gly Asn Cys Ser Ser Gly Gly Thr Thr Phe Tyr Gln Pro
                165                 170                 175

Val Asn Pro Leu Leu Gln Ala Tyr Ala Leu Thr Leu Lys Thr Thr
            180                 185                 190
```

<210> SEQ ID NO 51
<211> LENGTH: 191
<212> TYPE: PRT
<213> ORGANISM: Streptomyces venezuelae

<400> SEQUENCE: 51

```
Tyr Asp Ile Arg Gly Gly Asp Ala Tyr Met Gly Gly Gly Gly Arg
 1               5                   10                  15

Cys Ser Val Gly Phe Ala Val Thr Arg Gly Ala Thr Gln Gly Phe Ala
                 20                  25                  30

Thr Ala Gly His Cys Gly Arg Ala Gly Thr Thr Thr Ser Gly Phe Asn
             35                  40                  45

Gln Val Ala Gln Gly Ser Phe Gln Ala Ser Thr Phe Pro Gly Asn Asp
     50                  55                  60

Met Ala Trp Val Ala Ala Asn Thr Asn Trp Thr Ser Thr Pro Tyr Val
 65                  70                  75                  80

Lys Gly Ser Gly Gly Ala Asn Val Gln Val Thr Gly Ser Val Leu Gln
                 85                  90                  95

Pro Val Gly Ala Ser Val Cys Arg Ser Gly Ser Thr Thr Gly Trp His
                100                 105                 110

Cys Gly Thr Ile Gln Gln His Asn Thr Ser Val Thr Tyr Pro Glu Gly
            115                 120                 125

Thr Ile Ser Gly Val Thr Arg Thr Thr Val Cys Ala Glu Pro Gly Asp
        130                 135                 140

Ser Gly Gly Ser Tyr Ile Ser Gly Ser Gln Ala Gln Gly Val Thr Ser
145                 150                 155                 160

Gly Gly Ser Gly Asn Cys Ser Ser Gly Gly Thr Thr Phe Phe Gln Pro
                165                 170                 175

Leu Asn Pro Leu Leu Gln Asn Tyr Gly Leu Thr Leu Lys Thr Thr
            180                 185                 190
```

<210> SEQ ID NO 52
<211> LENGTH: 190
<212> TYPE: PRT
<213> ORGANISM: Streptomyces sp. NRRL F-5755

<400> SEQUENCE: 52

Tyr Asp Ile Arg Gly Gly Asp Ala Tyr Tyr Met Gly Gly Gly Arg Cys
1               5                   10                  15

Ser Val Gly Phe Ala Ile Thr Arg Gly Ser Gln Gln Gly Phe Ala Thr
            20                  25                  30

Ala Gly His Cys Gly Arg Ala Gly Thr Ser Thr Gly Tyr Asn Gln
        35                  40                  45

Val Ala Gln Gly Ser Phe Gln Ala Ser Thr Phe Pro Gly Arg Asp Thr
50                  55                  60

Ala Trp Val Ala Ala Asn Ser Asn Trp Thr Ser Thr Pro Tyr Val Lys
65                  70                  75                  80

Gly Gln Gly Gln Asn Val Arg Val Ala Gly Ser Thr Gln Ala Ala
            85                  90                  95

Val Gly Ala Ser Ile Cys Arg Ser Gly Ser Thr Thr Gly Trp His Cys
            100                 105                 110

Gly Thr Ile Gln Gln His Asn Thr Ser Val Thr Tyr Pro Gln Gly Thr
            115                 120                 125

Val Ser Gly Val Thr Arg Thr Ser Val Cys Ala Glu Pro Gly Asp Ser
130                 135                 140

Gly Gly Ser Phe Ile Ser Gly Ser Gln Ala Gln Gly Val Thr Ser Gly
145                 150                 155                 160

Gly Ser Gly Asn Cys Arg Ser Gly Gly Thr Thr Phe Tyr Gln Pro Ile
                165                 170                 175

Asn Pro Leu Leu Gln Gly Tyr Gly Leu Thr Leu Lys Thr Gly
            180                 185                 190

<210> SEQ ID NO 53
<211> LENGTH: 191
<212> TYPE: PRT
<213> ORGANISM: Streptomyces fradiae

<400> SEQUENCE: 53

Tyr Asp Ile Arg Gly Gly Asp Ala Tyr His Met Gly Gly Gly Arg
1               5                   10                  15

Cys Ser Val Gly Phe Ala Val Thr Lys Gly Thr Gln His Gly Phe Ala
            20                  25                  30

Thr Ala Gly His Cys Gly Arg Val Gly Thr Ser Thr Ser Gly Tyr Asn
            35                  40                  45

Gln Val Ala Gln Gly Thr Phe Gln Gly Ser Thr Phe Pro Gly Arg Asp
    50                  55                  60

Met Ala Trp Val Ala Ala Asn Thr Asn Trp Arg Ser Thr Pro Tyr Val
65                  70                  75                  80

Lys Gly Ala Gly Gly Gln Asn Val Gln Val Thr Gly Ser Thr Gln Ala
                85                  90                  95

Val Val Gly Ala Ser Val Cys Arg Ser Gly Ser Thr Thr Gly Trp His
            100                 105                 110

Cys Gly Thr Ile Gln Gln His Asn Thr Ser Val Thr Tyr Pro Glu Gly
            115                 120                 125

Thr Ile Ser Gly Val Thr Arg Thr Thr Val Cys Ala Glu Pro Gly Asp
130                 135                 140

Ser Gly Gly Ser Tyr Ile Ser Gly Ser Gln Ala Gln Gly Val Thr Ser
145                 150                 155                 160

Gly Gly Ser Gly Asp Cys Arg Thr Gly Gly Thr Thr Tyr His Gln Pro
                165                 170                 175

Leu Asn Pro Leu Leu Gln Ala Tyr Ala Leu Thr Leu Thr Thr Thr
            180                 185                 190

```
<210> SEQ ID NO 54
<211> LENGTH: 191
<212> TYPE: PRT
<213> ORGANISM: artificial sequence
<220> FEATURE:
<223> OTHER INFORMATION: predicted catalytic domain consensus sequence
<220> FEATURE:
<221> NAME/KEY: MISC_FEATURE
<222> LOCATION: (3)..(3)
<223> OTHER INFORMATION: X = I or L
<220> FEATURE:
<221> NAME/KEY: MISC_FEATURE
<222> LOCATION: (165)..(165)
<223> OTHER INFORMATION: B is D or N
<220> FEATURE:
<221> NAME/KEY: MISC_FEATURE
<222> LOCATION: (177)..(177)
<223> OTHER INFORMATION: X= I or L

<400> SEQUENCE: 54

Tyr Asp Xaa Arg Gly Gly Asp Ala Tyr Tyr Met Gly Gly Gly Arg
 1               5                  10                  15

Cys Ser Val Gly Phe Ala Val Thr Arg Gly Thr Gln Gln Gly Phe Ala
            20                  25                  30

Thr Ala Gly His Cys Gly Arg Ala Gly Thr Thr Thr Thr Gly Tyr Asn
        35                  40                  45

Gln Val Ala Gln Gly Ser Phe Gln Ala Ser Thr Phe Pro Gly Arg Asp
    50                  55                  60

Thr Ala Trp Val Ala Thr Asn Thr Asn Trp Thr Ala Thr Pro Tyr Val
65                  70                  75                  80

Lys Gly Ala Gly Gly Ala Asn Val Gln Val Ala Gly Ser Val Gln Gln
                85                  90                  95

Pro Val Gly Ala Ser Val Cys Arg Ser Gly Ser Thr Thr Gly Trp His
            100                 105                 110

Cys Gly Thr Ile Gln Gln His Asn Thr Ser Val Thr Tyr Pro Glu Gly
        115                 120                 125

Thr Ile Ser Gly Val Thr Arg Thr Thr Val Cys Ala Glu Pro Gly Asp
    130                 135                 140

Ser Gly Gly Ser Tyr Ile Ser Gly Ser Gln Ala Gln Gly Val Thr Ser
145                 150                 155                 160

Gly Gly Ser Gly Asx Cys Arg Ser Gly Gly Thr Thr Tyr His Gln Pro
                165                 170                 175

Xaa Asn Pro Leu Leu Gln Ala Tyr Gly Leu Thr Leu Thr Thr Thr
            180                 185                 190
```

TRYPSIN-LIKE SERINE PROTEASES AND USES THEREOF

INCORPORATION BY REFERENCE OF THE SEQUENCE LISTING

The sequence listing provided in the file named "20180301_NB41242WOPCT_SequenceListing.txt" with a size of 129 KB that was created on Mar. 1, 2018 and is filed herewith, is incorporated herein by reference in its entirety.

FIELD

Described herein is at least one novel trypsin-like serine protease polypeptide and uses thereof. Further described herein are cleaning compositions containing at least one polypeptide having serine protease activity described herein, wherein said composition can be used to clean fabrics and hard surfaces. Even further described herein is at least one cleaning composition selected from a laundry detergent, a dishwashing detergent (e.g., automatic and hand dish), and a personal care composition. Even still further, at least one polypeptide having serine protease activity and improved soil removal and/or stability compared to at least one reference polypeptide having serine protease activity is described herein.

BACKGROUND

Proteases (also called peptidases or proteinases) are enzymes capable of cleaving peptide bonds. Proteases have evolved multiple times, and different classes of proteases can perform the same reaction by completely different catalytic mechanisms. Proteases can be found in animals, plants, fungi, bacteria, archaea and viruses.

Proteolysis can be achieved by enzymes currently classified into six broad groups: aspartyl proteases, cysteine proteases, serine proteases (such as, e.g., subtilisins or trypsin-like proteases), threonine proteases, glutamic proteases, and metalloproteases.

Serine proteases are a subgroup of carbonyl hydrolases comprising a diverse class of enzymes having a wide range of specificities and biological functions. Notwithstanding this functional diversity, the catalytic machinery of serine proteases has been approached by at least two genetically distinct families of enzymes: 1) the subtilisins; and 2) trypsin-like serine proteases (also known as chymotrypsin-related). These two families of serine proteases or serine endopeptidases have very similar catalytic mechanisms. The tertiary structure of these two enzyme families brings together a conserved catalytic triad of amino acids consisting of serine, histidine and aspartate.

Much research has been conducted on the serine proteases, in particular, subtilisins, due largely to their useful industrial applications. Additional work has been focused on adverse environmental conditions (e.g., exposure to oxidative agents, chelating agents, extremes of temperature and/or pH) which can adversely impact the functionality of these enzymes in a variety of applications.

Thus, there is a continuing need to find new serine proteases such as trypsin-like proteases of prokaryotic origins which can be used under adverse conditions and retain or have improved proteolytic activity and/or stability.

SUMMARY

In a first embodiment, there is described at least one isolated polypeptide having serine protease activity, selected from: a) a polypeptide having an amino acid sequence of at least 91% identity with the amino acid sequence of SEQ ID NO:22; b) a polypeptide having an amino acid sequence of at least 94% identity with the amino acid sequence of SEQ ID NO:23; c) a polypeptide having an amino acid sequence of at least 98% identity with the amino acid sequence of SEQ ID NO:24; and d) a polypeptide having an amino acid sequence of at least 80% identity with the amino acid sequence of SEQ ID NO:25.

In a second embodiment, there is described at least one isolated polypeptide having serine protease activity and comprising a predicted precursor amino acid sequence selected from: SEQ ID NO:3; SEQ ID NO:6; SEQ ID NO:9; and SEQ ID NO:12.

In a third embodiment, there is described at least one isolated polypeptide having serine protease activity and comprising a protease catalytic region selected from: a) an amino acid sequence with at least 96% identity with the amino acid sequence of SEQ ID NO:18; b) an amino acid sequence with at least 98% identity with the amino acid sequence of SEQ ID NO:19; c) an amino acid sequence of SEQ ID NO:20; and d) an amino acid sequence with at least 91% identity with the amino acid sequence of SEQ ID NO:21.

In a fourth embodiment, there is described a recombinant construct comprising a regulatory sequence functional in a production host operably linked to a nucleotide sequence encoding at least one polypeptide having serine protease described herein selected from: a) a polypeptide comprising an amino acid sequence with at least 91% identity with the amino acid sequence of SEQ ID NO:22; b) a polypeptide comprising an amino acid sequence with at least 94% identity with the amino acid sequence of SEQ ID NO:23; c) a polypeptide comprising an amino acid sequence with at least 98% identity with the amino acid sequence of SEQ ID NO:24; and d) a polypeptide comprising an amino acid sequence with at least 80% identity with the amino acid sequence of SEQ ID NO:25. In one embodiment, the production host is selected from the group consisting of fungi, bacteria, and algae.

In a fifth embodiment, there is described a method for producing at least one polypeptide having serine protease activity described herein, comprising: (a) transforming a production host with a recombinant construct described herein; and (b) culturing the production host of step (a) under conditions whereby at least one polypeptide having serine protease activity described herein is produced. According to this method, at least one polypeptide having serine protease activity described herein is optionally recovered from the production host. In another aspect, a serine protease-containing culture supernatant is obtained by using any of the methods described herein.

In a still another aspect, the recombinant microbial production host for expressing at least one polypeptide having serine protease activity described herein, comprises a recombinant construct described herein. Furthermore, the production host is selected from the group consisting of bacteria, fungi and algae.

In a sixth embodiment, there is described animal feed comprising at least one one polypeptide having serine protease activity described herein wherein the polypeptideis present in an amount from 1-20 g/ton feed. Furthermore, this animal feed can comprise at least one direct fed microbial. In still another aspect, this animal feed comprises at least one other enzyme. In a still further aspect, this animal feed comprises at least one direct fed microbial and at least one other enzyme.

In a seventh embodiment, there is described a feed, feedstuff, a feed additive composition or premix comprising at least one polypeptide having serine protease activity described herein. In a further embodiment, the feed, feedstuff, feed additive composition or premix described herein comprises at least one direct fed microbial, at least one other enzyme, or a combination of at least direct fed microbial and at least one other enzyme.

In a seventh embodiment, the feed additive composition described herein further comprises at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben, and propyl paraben.

In an eighth embodiment, there is described a granulated feed additive composition for use in animal feed comprising at least one polypeptide having serine protease activity described herein, wherein the granulated feed additive composition comprises particles produced by a process selected from the group consisting of high shear granulation, drum granulation, extrusion, spheronization, fluidized bed agglomeration, fluidized bed spray coating, spray drying, freeze drying, prilling, spray chilling, spinning disk atomization, coacervation, tableting, and a combination thereof. In another emobidment, the particles of this granulated feed additive composition comprises a mean diameter of greater than 50 microns and less than 2000 microns. In another aspect, this feed additive composition is in a liquid form and, furthermore, is in a liquid form suitable for spray-drying on a feed pellet.

A ninth embodiment is directed to a cleaning or detergent composition comprising at least one polypeptide having serine protease activity described herein. In a further embodiment, the composition described herein comprises at least one polypeptide having serine protease activity, wherein said polypeptide comprises a protease catalytic region comprising an amino acid sequence with at least 96% identity with the amino acid sequence of SEQ ID NO:18, or an amino acid sequence of SEQ ID NO:20. In an even further embodiment, the composition described herein comprises at least one polypeptide having serine protease activity, wherein said polypeptide comprises an amino acid sequence with at least 91% identity with the amino acid sequence of SEQ ID NO:22, or at least 94% identity with the amino acid sequence of SEQ ID NO:23. In a still further embodiment, the composition described herein comprises at least one polypeptide having serine protease activity, wherein said polypeptide comprises (i) an amino acid sequence with at least 91% identity with the amino acid sequence of SEQ ID NO:22, or (ii) a protease catalytic region comprising an amino acid sequence with at least 96% identity with the amino acid sequence of SEQ ID NO:18. In an even still further embodiment, the composition described herein comprises at least one polypeptide having serine protease activity, wherein said polypeptide comprises (i) an amino acid sequence with at least 94% identity with the amino acid sequence of SEQ ID NO:23, or (ii) a protease catalytic region comprising an amino acid sequence of SEQ ID NO:20. In some embodiments, the composition described herein further comprises one or more surfactant. In yet other embodiments, the at least one polypeptide having serine protease activity described herein has cleaning activity in one or more composition described herein. In still other embodiments, the at least one polypeptide having serine protease activity described herein has cleaning activity at about 16° C. and/or about 32° C. in one or more composition described herein. In still other embodiments, the composition described herein is selected from a laundry detergent, a fabric softening detergent, a dishwashing detergent, and a hard-surface cleaning detergent.

A tenth embodiment is directed to a method of cleaning comprising contacting a surface or an item in need of cleaning with an effective amount of at least one polypeptide having serine protease activity described herein or at least one composition described herein; and optionally further comprising the step of rinsing said surface or item after contacting said surface or item with said polypeptide or composition. A further embodiment is directed to a method of cleaning comprising contacting a surface or an item in need of cleaning with an effective amount of at least one polypeptide having serine protease activity, wherein said polypepetide comprises a protease catalytic region comprising an amino acid sequence with at least 96% identity with the amino acid sequence of SEQ ID NO:18, or an amino acid sequence of SEQ ID NO:20; and, optionally, further comprising the step of rinsing said surface or item after contacting said surface or item with said polypeptide. Another embodiment is directed to a method of cleaning comprising contacting a surface or an item in need of cleaning with an effective amount of at least one polypeptide having serine protease activity, wherein said polypepetide comprises an amino acid sequence with at least 91% identity with the amino acid sequence of SEQ ID NO:22, or at least 94% identity with the amino acid sequence of SEQ ID NO:23; and, optionally, further comprising the step of rinsing said surface or item after contacting said surface or item with said polypeptide. A yet further embodiment is directed to a method of cleaning comprising contacting a surface or an item in need of cleaning with an effective amount of at least one polypeptide having serine protease activity, wherein said polypepetide comprises (i) an amino acid sequence with at least 91% identity with the amino acid sequence of SEQ ID NO:22, or (ii) a protease catalytic region comprising an amino acid sequence with at least 96% identity with the amino acid sequence of SEQ ID NO:18; and, optionally, further comprising the step of rinsing said surface or item after contacting said surface or item with said polypeptide. A yet further embodiment is directed to a method of cleaning comprising contacting a surface or an item in need of cleaning with an effective amount of at least one polypeptide having serine protease activity, wherein said polypepetide comprises (i) an amino acid sequence with at least 94% identity with the amino acid sequence of SEQ ID NO:23, or (ii) a protease catalytic region comprising an amino acid sequence of SEQ ID NO:20; and, optionally, further comprising the step of rinsing said surface or item after contacting said surface or item with said polypeptide. In some embodiments, the item is dishware or fabric.

BRIEF DESCRIPTION OF THE DRAWINGS AND SEQUENCES

FIG. 1. Plasmid AprE-SspCPro29 for expression of AprE-SspCPro29 protease.

Figure 2:
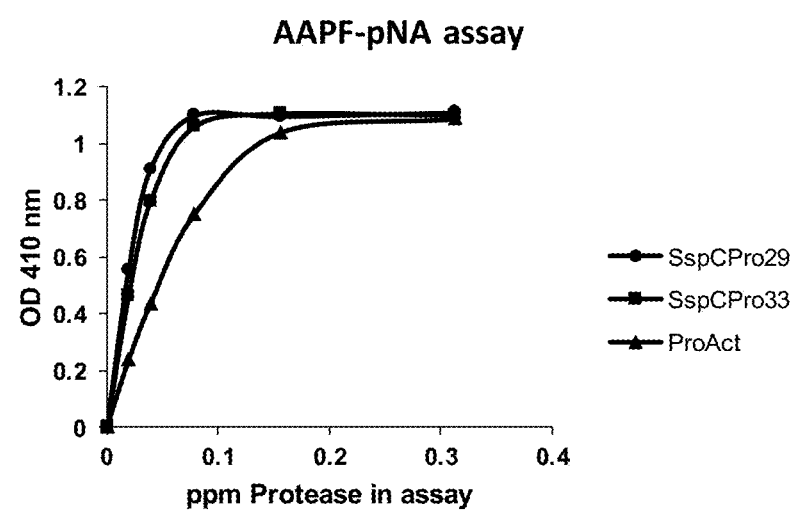

FIG. 2. Enzyme activity dose responses of serine proteases SspCPro29, SspCPro33 and ProAct on on AAPF-pNA substrate.

Figure 3:
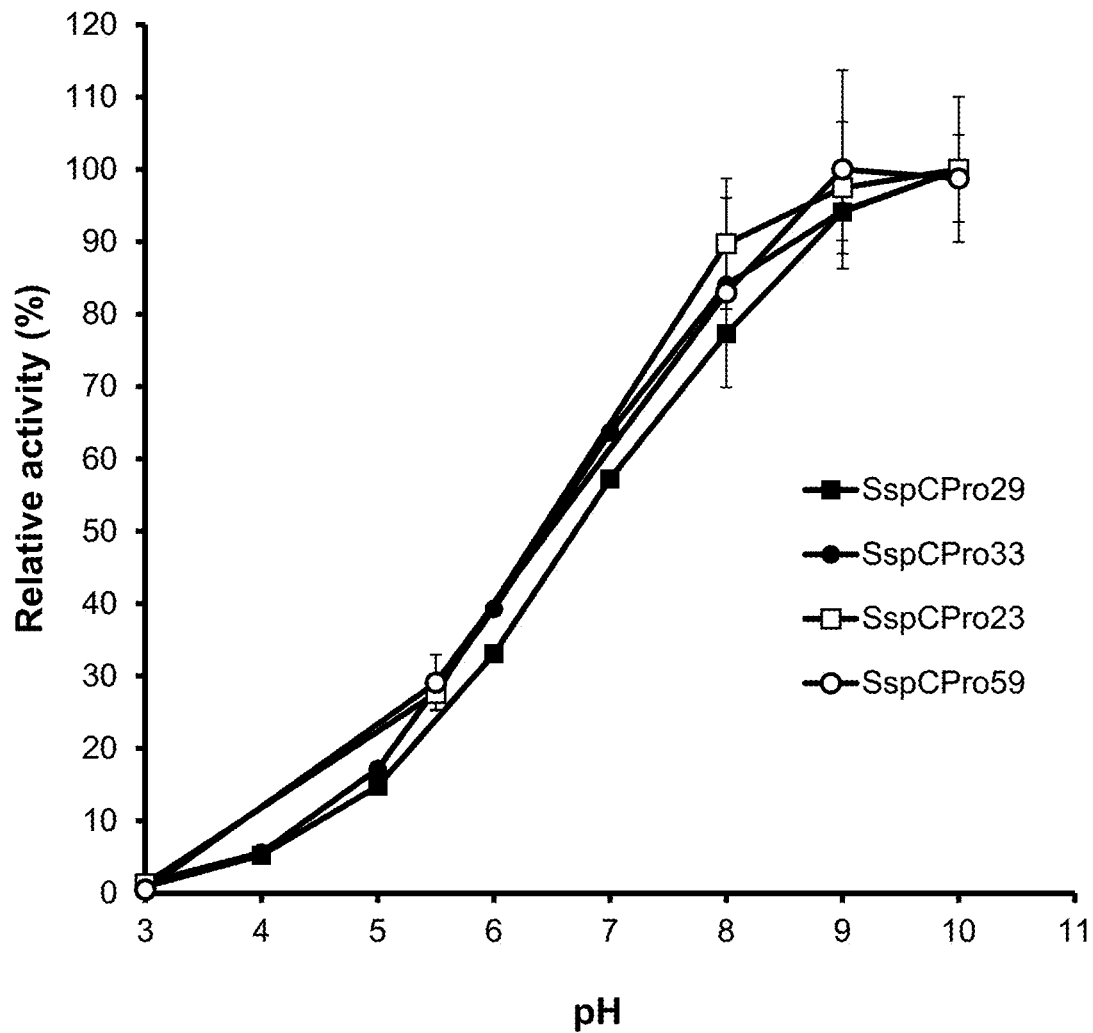

FIG. 3. pH profile of serine proteases SspCPro23, SspCPro29. SspCPro33 and SspCPro59.

Figure 4:
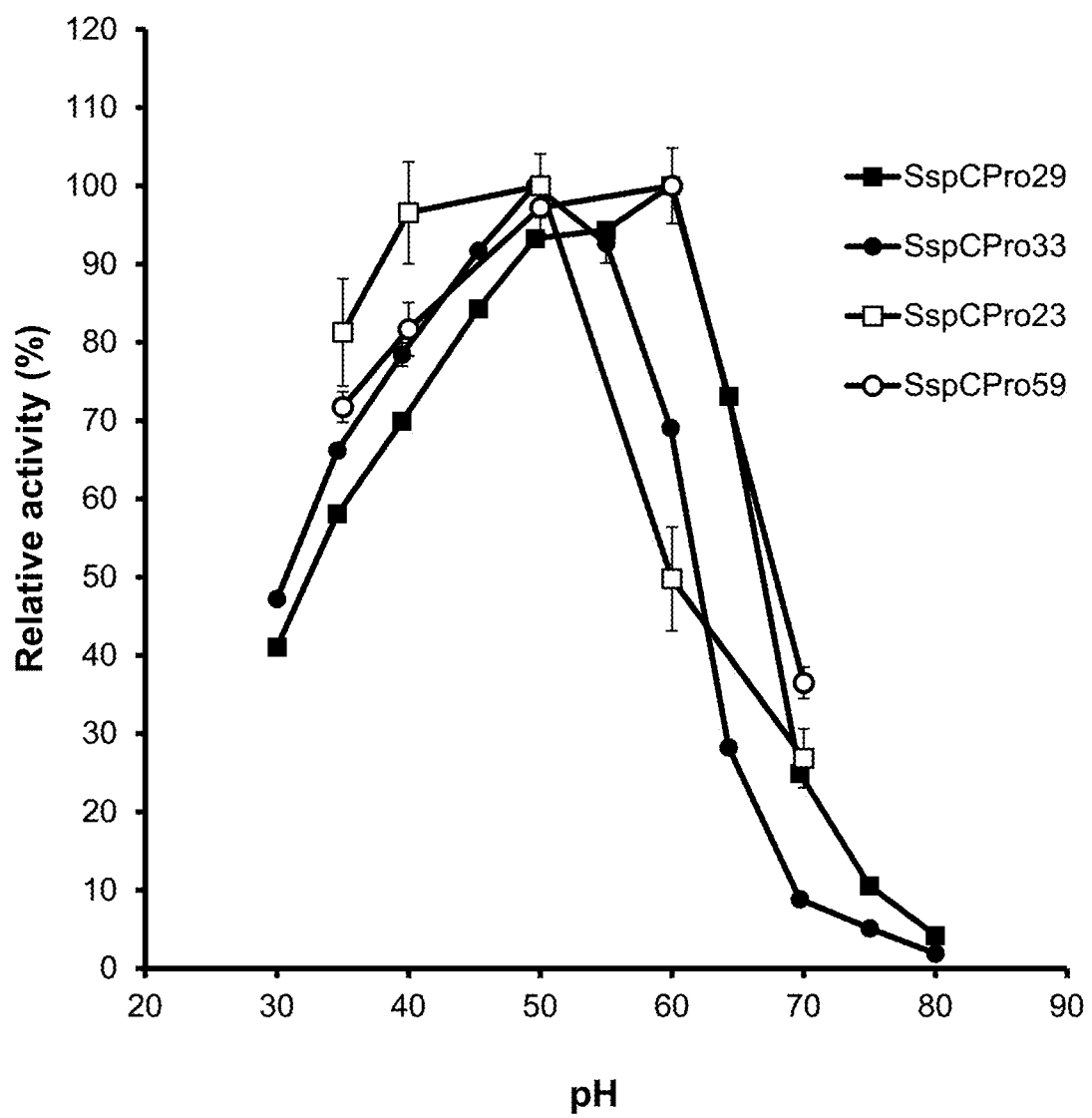

FIG. 4. Temperature profile of serine proteases SspCPro23, SspCPro29. SspCPro33 and SspCPro59.

Figure 5A:
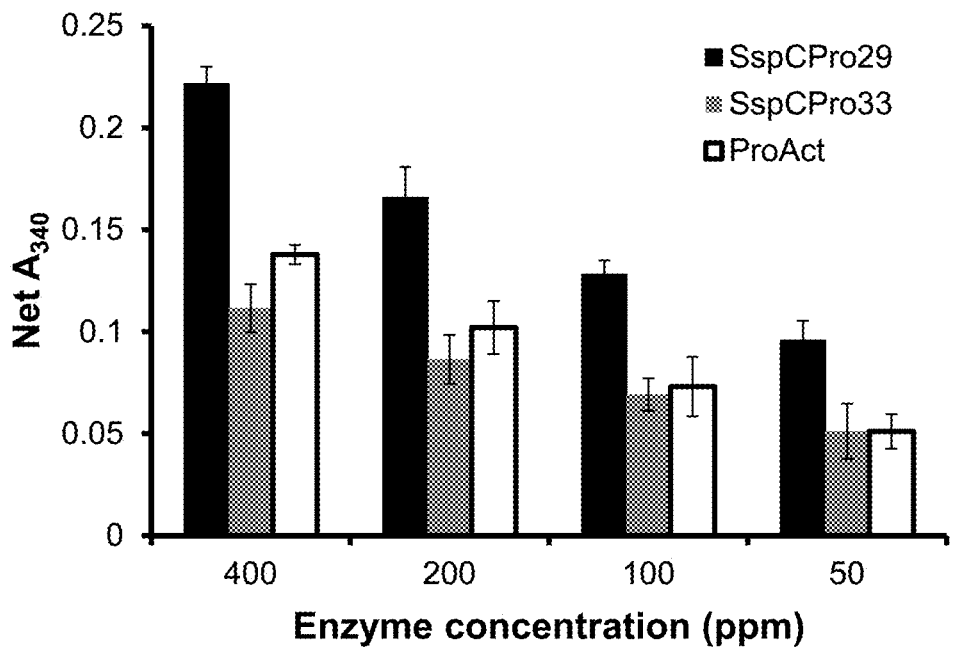

FIG. 5A. Hydrolysis of corn soy meal detected by OPA for serine proteases SspCPro29 and SspCPro33 at pH 6.

Figure 5B:
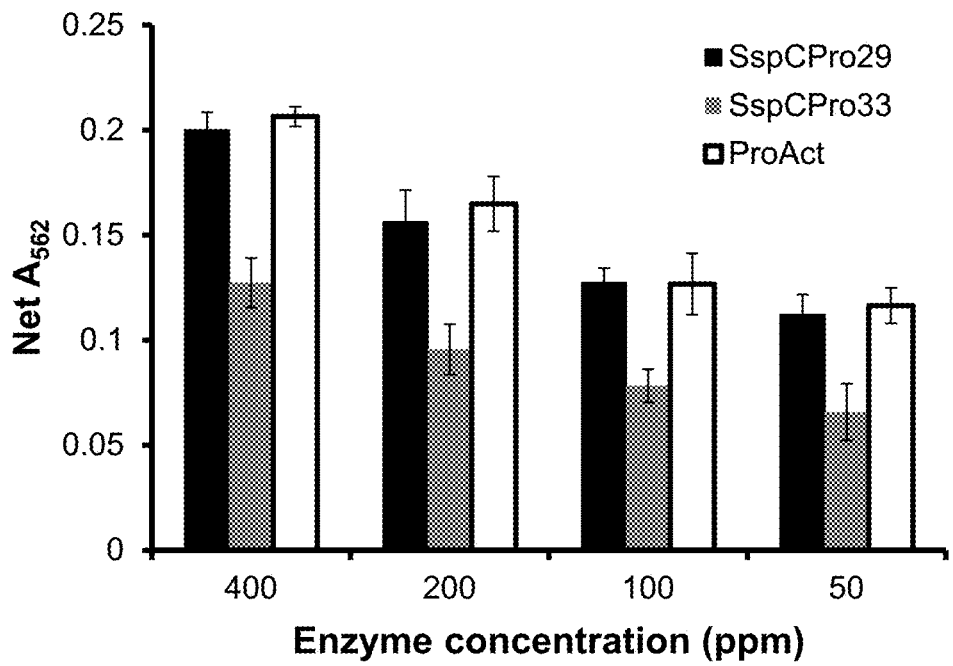

FIG. 5B. Hydrolysis of corn soy meal detected by BCA for serine proteases SspCPro29 and SspCPro33 at pH 6.

Figure 6:
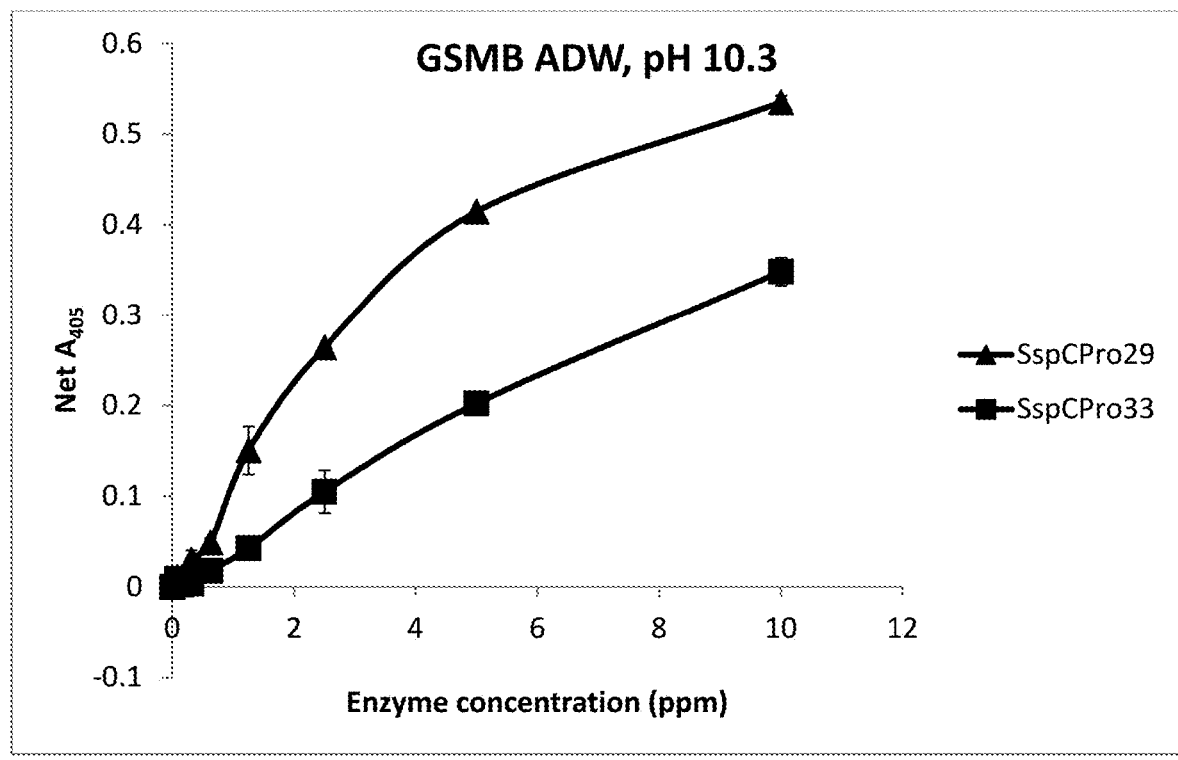

FIG. 6. Cleaning performance of SspCPro29 and SspCPro33 proteases in GSM-B ADW detergent at pH 10.3.

Figure 7:
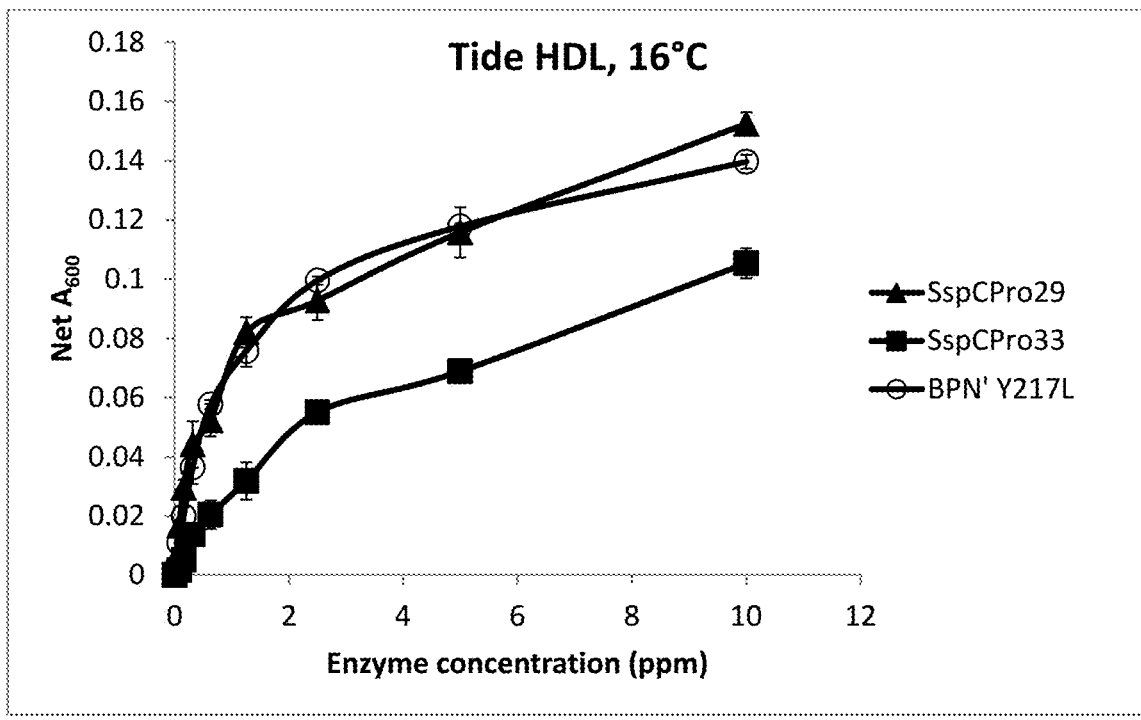

FIG. 7. Cleaning performance of SspCPro29, SspCPro33 and BPN'Y217L proteases in liquid laundry detergent at 16° C.

Figure 8:
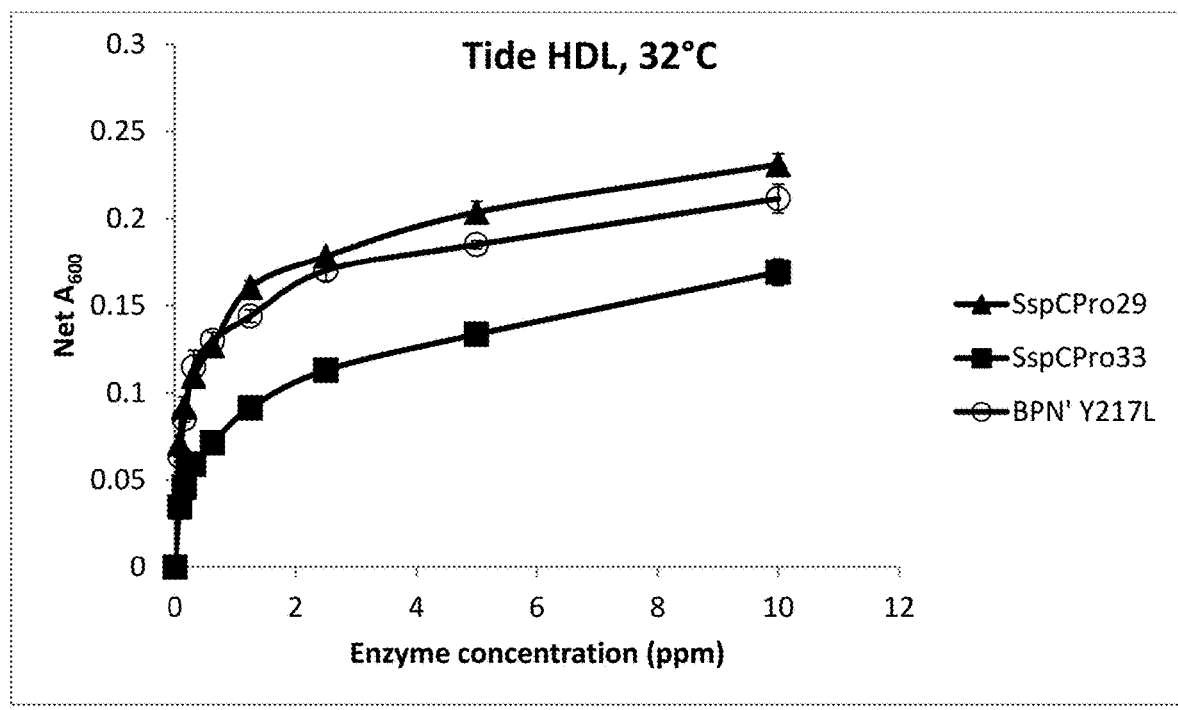

FIG. 8. Cleaning performance of SspCPro29, SspCPro33 and BPN'Y217L proteases in liquid laundry detergent at 32° C.

Figure 9:
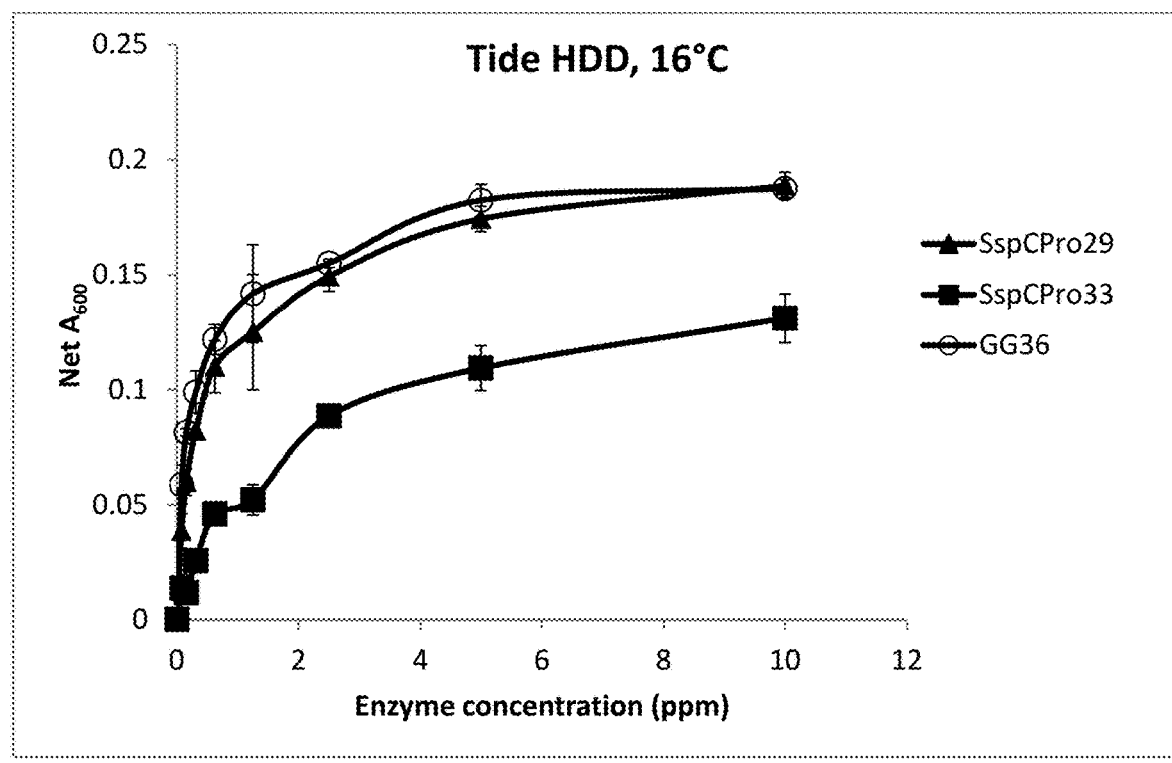

FIG. 9. Cleaning performance of SspCPro29, SspCPro33 and GG36 proteases in powder laundry detergent at 16° C.

Figure 10:
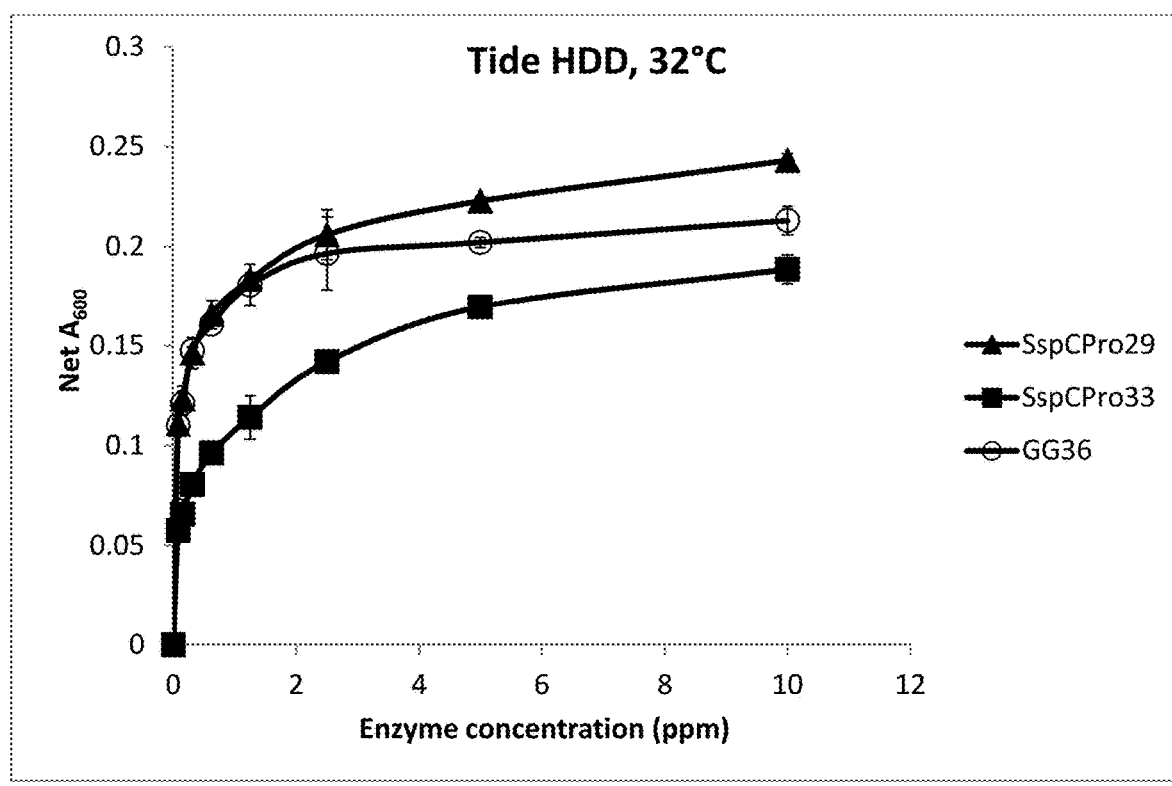

FIG. 10. Cleaning performance of SspCPro29, SspCPro33 and GG36 proteases in powder laundry detergent at 32° C.

FIGS. 11A-11D. Multiple sequence alignment of full length sequence of various *Streptomyces* sp trypsin-like serine proteases.

Figure 12A:
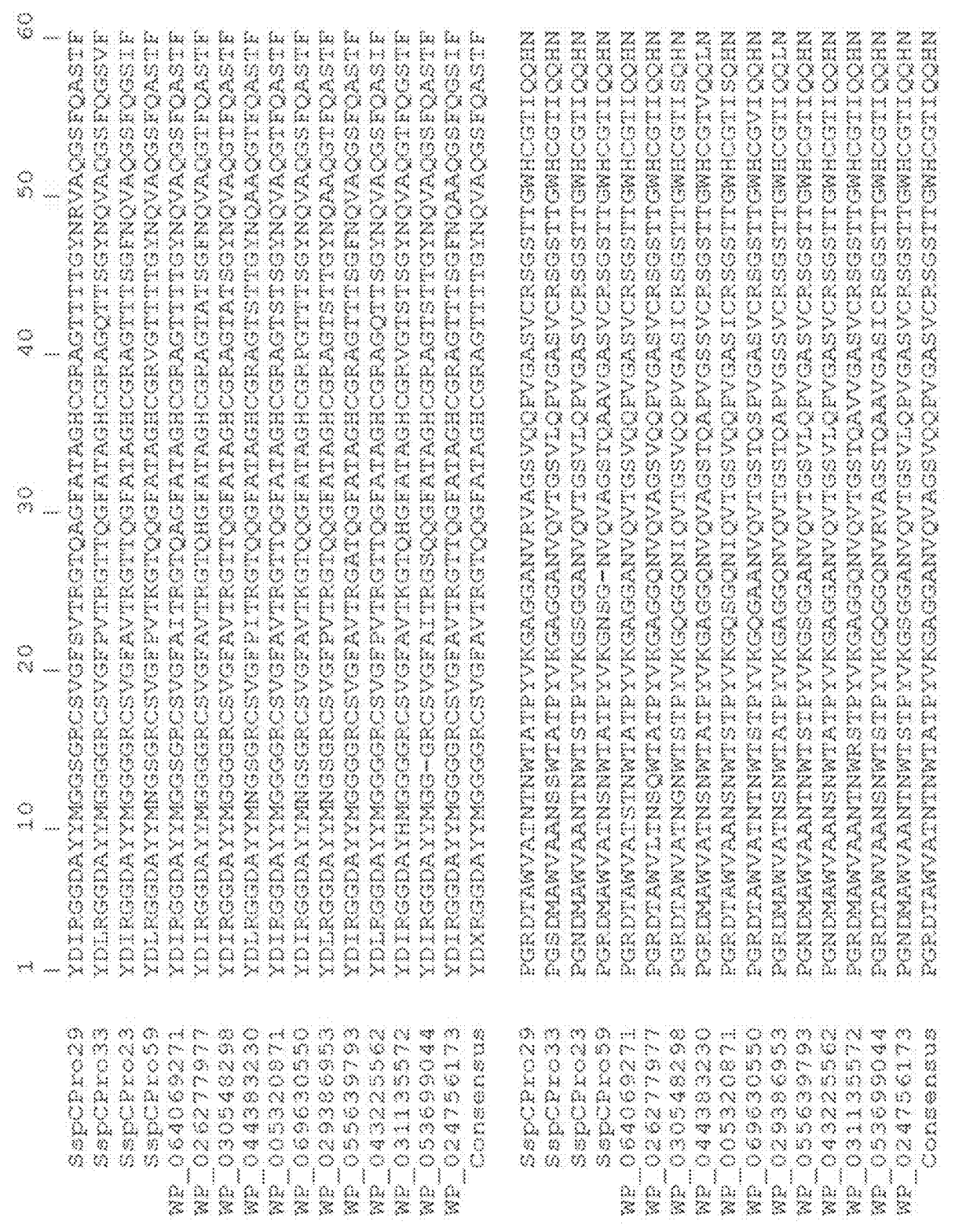

FIGS. 12A-12B. Multiple sequence alignment of predicted catalytic core sequences of *Streptomyces* sp trypsin-like serine proteases.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO:1 sets forth the nucleotide sequence of the SspCPro29 gene isolated from *Streptomyces* sp. C009 is set forth as. SEQ ID NO:2 sets forth the predicted signal sequence of the SspCPro29 precursor protein. SEQ ID NO:3 sets forth the amino acid sequence of the SspCPro29 precursor protein. SEQ ID NO:4 sets forth the nucleotide sequence of the SspCPro33 gene isolated from *Streptomyces* sp. C001. SEQ ID NO:5 sets forth the predicted signal sequence of the SspCPro33 precursor protein. SEQ ID NO:6 sets forth the amino acid sequence of the SspCPro33 precursor protein. SEQ ID NO:7 sets forth the nucleotide sequence of the SspCPro23 gene isolated from *Streptomyces* sp. C003. SEQ ID NO:8 sets forth the predicted signal sequence of the SspCPro23 precursor protein. SEQ ID NO:9 sets forth the amino acid sequence of the SspCPro23 precursor protein. SEQ ID NO:10 sets forth the nucleotide sequence of the SspCPro59 gene isolated from *Streptomyces* sp. C055. SEQ ID NO:11 sets forth the predicted signal sequence of the SspCPro59 precursor protein. SEQ ID NO:12 sets forth the amino acid sequence of the SspCPro59 precursor protein. SEQ ID NO: 13 sets forth the nucleotide sequences of synthetic AprE-SspCPro23. SEQ ID NO: 14 sets forth the nucleotide sequences of AprE-SspCPro29. SEQ ID NO: 15 sets forth the nucleotide sequences of AprE-SspCPro33. SEQ ID NO: 16 sets forth the nucleotide sequences of AprE-SspCPro59 genes. SEQ ID NO: 17 sets forth the AprE signal sequence that was used to direct the recombinant proteins for secretion in *B. subtilis*. SEQ ID NO: 18 sets forth the predicted catalytic domain for SspCPro29. SEQ ID NO: 19 sets forth the predicted catalytic domain for SspCPro 23. SEQ ID NO: 20 sets forth the predicted catalytic domain for SspCPro 33. SEQ ID NO: 21 sets forth the predicted catalytic domain for SspCPro 59. SEQ ID NO:22 sets forth the predicted full length amino acid sequence for SspCPro29. SEQ ID NO:23 sets forth the predicted full length amino acid sequence for SspCPro33. SEQ ID NO:24 sets forth the predicted full length amino acid sequence for SspCPro23. SEQ ID NO:25 sets forth the predicted full length amino acid sequence for SspCPro59. SEQ ID NO:26 sets forth the sequence of *Streptomyces* sp serine protease WP_064069271. SEQ ID NO:27 sets forth the sequence of *Streptomyces* sp serine protease WP_043225562. SEQ ID NO:28 sets forth the sequence of *Streptomyces* sp serine protease WP_024756173. SEQ ID NO:29 sets forth the sequence of *Streptomyces* sp serine protease WP_030548298. SEQ ID NO:30 sets forth the sequence of *Streptomyces* sp serine protease WP_005320871. SEQ ID NO:31 sets forth the sequence of *Streptomyces* sp serine protease WP_055639793. SEQ ID NO:32 sets forth the sequence of *Streptomyces* sp serine protease WO2015048332-44360. SEQ ID NO:33 sets forth the sequence of *Streptomyces* sp serine protease WO2015048332-44127. SEQ ID NO:34 sets forth the sequence of *Streptomyces* sp serine protease WP_030313004. SEQ ID NO:35 sets forth the sequence of *Streptomyces* sp serine protease WP_030212164. SEQ ID NO:36 sets forth the sequence of *Streptomyces* sp serine protease WP_030749137. SEQ ID NO:37 sets forth the sequence of *Streptomyces* sp serine protease WP_031004112. SEQ ID NO:38 sets forth the sequence of *Streptomyces* sp serine protease WP_026277977. SEQ ID NO:39 sets forth the amino acid sequence of the catalytic domain of Streptgrisin C. SEQ ID NO:40 sets forth the amino acid sequence of BPN'-Y217L protein. SEQ ID NO:41 sets forth the amino acid sequence of GG36 protein. SEQ ID NO:42 sets forth the amino acid sequence of residues 204-394 pf S_albulus WP_064069271. SEQ ID NO:43 sets forth the amino acid sequence of residues 204-394 of S_sp_NRRL_F-5193 WP_043225562 protein. SEQ ID NO:44 sets forth the amino acid sequence of residues 201-391 of S_exfoliatus WP_024756173. SEQ ID NO:45 sets forth the amino acid sequence of residues 207-397 of S_albus WP_030548298. SEQ ID NO:46 sets forth the amino acid sequence of residues 204-394 of S_pristinaespiralis_WP_005320871. SEQ ID NO:47 sets forth the amino acid sequence of residues 138-328 of S_leeuwenhoekii_WP_029386953. SEQ ID NO:48 sets forth the amino acid sequence of residues 207-397 of *Streptomyces* sp. CNT372_WP_026277977. SEQ ID NO:49 sets forth the amino acid sequence residues 208-398 of *Streptomyces cyaneogriseus*_P_044383230. SEQ ID NO:50 sets forth the amino acid sequence of residues 193-383 of *Streptomyces niveus* WP_069630550. SEQ ID NO:51 sets forth the amino acid sequence of residues 201-391 of *Streptomyces venezuelae* WP_055639793. SEQ ID NO:52 sets forth the amino acid sequence of residues 211-401 of *Streptomyces* sp. NRRL F-5755_WP_053699044. SEQ ID NO:53 sets forth the amino acid sequence of residues 205-395 of *Streptomyces fradiae*_WP_031135572. SEQ ID NO 54 sets forth the predicted catalytic domain consensus sequence from FIG. 12.

DETAILED DESCRIPTION

In this disclosure, a number of terms and abbreviations are used. The following definitions apply unless specifically stated otherwise.

The articles "a", "an", and "the" preceding an element or component are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

The term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

The term "protease" means a protein or polypeptide domain derived from a microorganism, e.g., a fungus, bacterium, or from a plant or animal, and that has the ability to catalyze cleavage of peptide bonds at one or more of various positions of a protein backbone (e.g., E.C. 3.4). The terms "protease", "peptidase" and "proteinase" can be used interchangeably. Proteases can be found in animals, plants, fungi, bacteria, archaea and viruses. Proteolysis can be achieved by enzymes currently classified into six broad groups based on their catalytic mechanisms: aspartyl proteases, cysteine proteases, trypsin-like serine proteases, threonine proteases, glutamic proteases, and metalloproteases.

The term "serine protease" refers to enzymes that cleave peptide bonds in proteins, in which serine serves as the nucleophilic amino acid at the active site of the enzyme. Serine proteases fall into two broad categories based on their structure: the chymotrypsin-like (trypsin-like) and the subtilisins. In the MEROPS protease classification system, proteases are distributed among 16 superfamilies and numerous families. The family S8 includes the subtilisins and the family S1 includes the chymotrypsin-like (trypsin-like) enzymes. The subfamily S1E includes the trypsin-like serine proteases from Strepmocyces organisms, such as Streptogricins A, B and C. The terms "serine protease", "trypsin-like serine protease" and "chymotrypsin-like protease" are used interchangeably herein.

The terms "animal" and "subject" are used interchangeably herein. An animal includes all non-ruminant (including humans) and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

A "feed" and a "food," respectively, means any natural or artificial diet, meal or the like or components of such meals intended or suitable for being eaten, taken in, digested, by a non-human animal and a human being, respectively.

As used herein, the term "food" is used in a broad sense and covers food and food products for humans as well as food for non-human animals (i.e. a feed).

The term "feed" is used with reference to products that are fed to animals in the rearing of livestock. The terms "feed" and "animal feed" are used interchangeably.

The term "direct-fed microbial" ("DFM") as used herein is source of live (viable) naturally occurring microorganisms. A DFM can comprise one or more of such naturally occurring microorganisms such as bacterial strains. Categories of DFMs include Bacillus, Lactic Acid Bacteria and Yeasts. Thus, the term DFM encompasses one or more of the following: direct fed bacteria, direct fed yeast, direct fed yeast and combinations thereof.

Bacilli are unique, gram-positive rods that form spores. These spores are very stable and can withstand environmental conditions such as heat, moisture and a range of pH. These spores germinate into active vegetative cells when ingested by an animal and can be used in meal and pelleted diets. Lactic Acid Bacteria are gram-positive cocci that produce lactic acid which are antagonistic to pathogens. Since Lactic Acid Bacteria appear to be somewhat heat-sensitive, they are not used in pelleted diets. Types of Lactic Acid Bacteria include Bifidobacterium, Lactobacillus and Streptococcus.

The term "prebiotic" means a non-digestible food ingredient that beneficially affects the host by selectively stimulating the growth and/or the activity of one or a limited number of beneficial bacteria.

The term "probiotic culture" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut. Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a subject.

The term "CFU" as used herein means "colony forming units" and is a measure of viable cells in which a colony represents an aggregate of cells derived from a single progenitor cell.

The term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated. The terms "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The terms "peptides", "proteins" and "polypeptides are used interchangeably herein and refer to a polymer of amino acids joined together by peptide bonds. A "protein" or "polypeptide" comprises a polymeric sequence of amino acid residues. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". When describing modifications, a position followed by amino acids listed in parentheses indicates a list of substitutions at that position by any of the listed amino acids. For example, 6(L,I) means position 6 can be substituted with a leucine or isoleucine. At times, in a sequence, a slash (/) is used to define substitutions, e.g. F/V, indicates that the particular position may have a phenylalanine or valine at that position.

A "prosequence" or "propeptide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Proteases are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or enzyme without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question.

The term "reference", with respect to a polypeptide described herein, refers to a naturally-occurring polypeptide that does not include a man-made substitution, insertion, or deletion at one or more amino acid positions, as well as a naturally-occurring or synthetic polypeptide that includes one or more man-made substitutions, insertions, or deletions at one or more amino acid positions. Similarly, the term "reference", with respect to a polynucleotide, refers to a naturally-occurring polynucleotide that does not include a man-made substitution, insertion, or deletion of one or more nucleosides, as well as a naturally-occurring or synthetic polynucleotide that includes one or more man-made substitutions, insertions, or deletions at one or more nucleosides. For example, a polynucleotide encoding a wild-type or parental polypeptide is not limited to a naturally-occurring polynucleotide, and encompasses any polynucleotide encoding the wild-type or parental polypeptide.

The term "amino acid" refers to the basic chemical structural unit of a protein or polypeptide. The following abbreviations used herein to identify specific amino acids can be found in Table 2.

TABLE 2

One and Three Letter Amino Acid Abbreviations

| Amino Acid | Three-Letter Abbreviation | One-Letter Abbreviation |
|---|---|---|
| Alanine | Ala | A |
| Arginine | Arg | R |
| Asparagine | Asn | N |
| Thermostable serine acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

It would be recognized by one of ordinary skill in the art that modifications of amino acid sequences disclosed herein can be made while retaining the function associated with the disclosed amino acid sequences. For example, it is well known in the art that alterations in a gene which result in the production of a chemically equivalent amino acid at a given site, but do not affect the functional properties of the encoded protein are common. For example, any particular amino acid in an amino acid sequence disclosed herein may be substituted for another functionally equivalent amino acid. For the purposes of this disclosure, substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as thermostable serine acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

The term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

The term "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "coding sequence" refers to a nucleotide sequence which codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding sites, and stem-loop structures.

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The terms "regulatory sequence" or "control sequence" are used interchangeably herein and refer to a segment of a nucleotide sequence which is capable of increasing or decreasing expression of specific genes within an organism. Examples of regulatory sequences include, but are not limited to, promoters, signal sequence, operators and the like. As noted above, regulatory sequences can be operably linked in sense or antisense orientation to the coding sequence/gene of interest.

"Promoter" or "promoter sequences" refer to DNA sequences that define where transcription of a gene by RNA polymerase begins. Promoter sequences are typically located directly upstream or at the 5' end of the transcription initiation site. Promoters may be derived in their entirety from a native or naturally occurring sequence, or be composed of different elements derived from different promoters found in nature, or even comprise synthetic DNA segments. It is understood by those skilled in the art that different promoters may direct the expression of a gene in different tissues or cell type or at different stages of development, or in response to different environmental or physiological conditions ("inducible promoters").

The "3' non-coding sequences" refer to DNA sequences located downstream of a coding sequence and include sequences encoding regulatory signals capable of affecting mRNA processing or gene expression, such as termination of transcription.

The term "transformation" as used herein refers to the transfer or introduction of a nucleic acid molecule into a host organism. The nucleic acid molecule may be introduced as a linear or circular form of DNA. The nucleic acid molecule may be a plasmid that replicates autonomously, or it may integrate into the genome of a production host. Production hosts containing the transformed nucleic acid are referred to as "transformed" or "recombinant" or "transgenic" organisms or "transformants".

The term "recombinant" as used herein refers to an artificial combination of two otherwise separated segments of nucleic acid sequences, e.g., by chemical synthesis or by the manipulation of isolated segments of nucleic acids by genetic engineering techniques. For example, DNA in which one or more segments or genes have been inserted, either naturally or by laboratory manipulation, from a different molecule, from another part of the same molecule, or an artificial sequence, resulting in the introduction of a new sequence in a gene and subsequently in an organism. The terms "recombinant", "transgenic", "transformed", "engineered" or "modified for exogenous gene expression" are used interchangeably herein.

The terms "recombinant construct", "expression construct", "recombinant expression construct" and "expression cassette" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The terms "production host", "host" and "host cell" are used interchangeably herein and refer to any organism, or cell thereof, whether human or non-human into which a recombinant construct can be stably or transiently introduced in order to express a gene. This term encompasses any progeny of a parent cell, which is not identical to the parent cell due to mutations that occur during propagation.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, N Y (1988); *Biocomputing: Informatics and Genome Projects* (Smith, D. W., ed.) Academic Press, N Y (1993); *Computer Analysis of Sequence Data, Part I* (Griffin, A. M., and Griffin, H. G., eds.) Humana Press, N J (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence. As used herein, "homologous proteins" or "homologous proteases" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences.

The phrase "substantially-free of boron" refers to a composition or formulation that contains trace amounts of boron, for example, less than about 1000 ppm (1 mg/kg or liter equals 1 ppm), less than about 100 ppm, less than about 50 ppm, less than about 10 ppm, or less than about 5 ppm, or less than about 1 ppm. The trace amounts of boron may be present in the composition or formulation through, for example, the addition of other components containing trace amounts of boron and not by virtue of intentional addition to the detergent or formulation.

The term "cleaning activity" refers to cleaning performance achieved by a reference protease or one or more polypeptide described herein under conditions prevailing during the proteolytic, hydrolyzing, cleaning, or other process described herein. In some embodiments, cleaning performance of a reference protease or one or more polypeptide described herein may be determined by using one or more assay directed to cleaning one or more enzyme sensitive stain on an item or surface (e.g., a stain resulting from food, grass, blood, ink, milk, oil, and/or egg protein). Cleaning performance of a reference protease or one or more polypeptide described herein can be determined by subjecting the stain on an item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, as well as those cleaning assays and methods included in the Examples provided below.

The term "cleaning effective amount" of a reference protease or one or more polypeptide described herein refers to the amount of protease or one or more polypeptide described herein that achieves the desired level of enzymatic activity in the cleaning composition. Such effective amounts are readily ascertained by one of ordinary skill in the art and are based on many factors, such as the particular protease used, the cleaning application, the formulation of the cleaning composition, and whether a liquid or dry (e.g., granular, tablet, bar) composition is required, etc.

The term "cleaning adjunct material" refers to any liquid, solid, or gaseous material included in cleaning composition other than the one or more polypeptide described herein. In some embodiments, one or more cleaning composition described herein includes one or more cleaning adjunct material. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the one or more polypeptide described herein.

Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., Trends in Genetics 16, (6):276-277 (2000)). Multiple alignment of the sequences can be performed using the CLUSTAL method (such as CLUSTALW; for example version 1.83) of alignment (Higgins and Sharp, CABIOS, 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein END-GAP=-1, protein GAPDIST=4, and KTUPLE=1. In one embodiment, a fast or slow alignment is used with the default settings where a slow alignment. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=S, and TOP DIAGONALS SAVED=5. The MUSCLE program (Robert C. Edgar. MUSCLE: multiple sequence alignment with high accuracy and high throughput Nucl. Acids Res. (2004) 32 (5): 1792-1797) is yet another example of a multiple sequence alignment algorithm.

Various polypeptide amino acid sequences and polynucleotide sequences are disclosed herein. Variants of these sequences that are at least about 70-85%, 85-90%, or 90%-95% identical to the sequences disclosed herein may be used in certain embodiments. Alternatively, a variant polypeptide sequence or polynucleotide sequence in certain embodiments can have at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function of the disclosed sequence, or at least about 85%, 86%, 87%, 88%, 89%, 90%, 91%, 92%, 93%, 94%, 95%, 96%, 97%, 98%, or 99% of the function of the disclosed sequence.

The term "variant", with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. The terms "expression cassette" and "expression vector are used interchangeably herein and refer to a specific vector containing a gene and having elements in addition to the gene that allow for expression of that gene in a host.

The term "expression", as used herein, refers to the production of a functional end-product (e.g., an mRNA or a protein) in either precursor or mature form. Expression may also refer to translation of mRNA into a polypeptide.

Expression of a gene involves transcription of the gene and translation of the mRNA into a precursor or mature protein. "Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals. "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms The expression vector can be one of any number of vectors or cassettes useful for the transformation of suitable production hosts known in the art. Typically, the vector or cassette will include sequences directing transcription and translation of the relevant gene, a selectable marker, and sequences allowing autonomous replication or chromosomal integration. Suitable vectors generally include a region 5' of the gene which harbors transcriptional initiation controls and a region 3' of the DNA fragment which controls transcriptional termination. Both control regions can be derived from homologous genes to genes of a transformed production host cell and/or genes native to the production host, although such control regions need not be so derived.

Possible initiation control regions or promoters that can be included in the expression vector are numerous and familiar to those skilled in the art. Virtually any promoter capable of driving these genes is suitable, including but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus*. In some embodiments, the promoter is a constitutive or inducible promoter. A "constitutive promoter" is a promoter that is active under most environmental and developmental conditions. An "inducible" or "repressible" promoter is a promoter that is active under environmental or developmental regulation. In some embodiments, promoters are inducible or repressible due to changes in environmental factors including but not limited to, carbon, nitrogen or other nutrient availability, temperature, pH, osmolarity, the presence of heavy metal(s), the concentration of inhibitor(s), stress, or a combination of the foregoing, as is known in the art. In some embodiments, the inducible or repressible promoters are inducible or repressible by metabolic factors, such as the level of certain carbon sources, the level of certain energy sources, the level of certain catabolites, or a combination of the foregoing as is known in the art. In one embodiment, the promoter is one that is native to the host cell. For example, when *T. reesei* is the host, the promoter is a native *T. reesei* promoter such as the cbh1 promoter which is deposited in GenBank under Accession Number D86235.

Suitable non-limiting examples of promoters include cbh1, cbh2, egl1, egl2, egl3, egl4, egl5, xyn1, and xyn2, repressible acid phosphatase gene (phoA) promoter of *P. chrysogenus* (see e.g., Graessle et al., (1997) *Appl. Environ. Microbiol.*, 63:753-756), glucose repressible PCK1 promoter (see e.g., Leuker et al., (1997), *Gene*, 192:235-240), maltose inducible, glucose-repressible MET3 promoter (see Liu et al., (2006), *Eukary. Cell*, 5:638-649), pKi promoter and cpcl promoter. Other examples of useful promoters include promoters from *A. awamori* and *A. niger* glucoamylase genes (see e.g., Nunberg et al., (1984) *Mol. Cell Biol.* 15 4:2306-2315 and Boel et al., (1984) *EMBO J* 3:1581-1585). Also, the promoters of the *T. reesei* xln1 gene may be useful (see e.g., EPA 137280A1).

DNA fragments which control transcriptional termination may also be derived from various genes native to a preferred production host cell. In certain embodiments, the inclusion of a termination control region is optional. In certain embodiments, the expression vector includes a termination control region derived from the preferred host cell.

The expression vector can be included in the production host, particularly in the cells of microbial production hosts. The production host cells can be microbial hosts found within the fungal or bacterial families and which grow over a wide range of temperature, pH values, and solvent tolerances. For example, it is contemplated that any of bacteria, algae, and fungi such as filamentous fungi and yeast may suitably host the expression vector.

Inclusion of the expression vector in the production host cell may be used to express the protein of interest so that it may reside intracellularly, extracellularly, or a combination of both inside and outside the cell, Extracellular expression renders recovery of the desired protein from a fermentation product more facile than methods for recovery of protein produced by intracellular expression.

Certain embodiments relate to an isolated polypeptide having serine protease activity, selected from: a) a polypeptide comprising an amino acid sequence with at least 91% identity with the amino acid sequence of SEQ ID NO:22; b) a polypeptide comprising an amino acid sequence with at least 94% identity with the amino acid sequence of SEQ ID NO:23; c) a polypeptide comprising an amino acid sequence with at least 98% identity with the amino acid sequence of SEQ ID NO:24; and d) a polypeptide comprising an amino acid sequence with at least 80% identity with the amino acid sequence of SEQ ID NO:25.

In another embodiment, there is disclosed an isolated polypeptide having serine protease activity and comprising a predicted precursor amino acid sequence selected from: SEQ ID NO:3; SEQ ID NO:6; SEQ ID NO:9; and SEQ ID NO:12.

In still another embodiment, there is disclosed an isolated polypeptide having serine protease activity and comprising a protease catalytic region selected from: a) an amino acid sequence with at least 96% identity with the amino acid sequence of SEQ ID NO:18; b) an amino acid sequence with at least 98% identity with the amino acid sequence of SEQ ID NO:19; c) an amino acid sequence of SEQ ID NO:20; and d) an amino acid sequence with at least 91% identity with the amino acid sequence of SEQ ID NO:21.

Other embodiments include a recombinant construct comprising a regulatory sequence functional in a production host operably linked to a nucleotide sequence encoding at least one polypeptide selected from: a) a polypeptide comprising an amino acid sequence with at least 91% identity with the amino acid sequence of SEQ ID NO:22; b) a polypeptide comprising an amino acid sequence with at least 94% identity with the amino acid sequence of SEQ ID NO:23; c) a polypeptide comprising an amino acid sequence with at least 98% identity with the amino acid sequence of SEQ ID NO:24; d) a polypeptide comprising an amino acid sequence with at least 80% identity with the amino acid sequence of SEQ ID NO:25. In some embodiments, the production host is selected from the group consisting of fungi, bacteria, and algae. In other embodiments, the production host is used to produce at least one polypeptide described herein comprising: (a) transforming a production host with the recombinant construct described herein; and (b) culturing the production host of step (a) under conditions whereby at least one polypeptide described herein is produced. According to this method, at least one polypeptide described herein is optionally recovered from the production host. In another aspect, a serine protease-containing culture supernatant is obtained by using any of the methods described herein.

Also described herein is a recombinant microbial production host for expressing at least one polypeptide described herein, said recombinant microbial production host comprising a recombinant construct described herein. In another embodiment, this recombinant microbial production host is selected from the group consisting of bacteria, fungi and algae.

Expression will be understood to include any step involved in producing at least one polypeptide described herein including, but not limited to, transcription, post-transcriptional modification, translation, post-translation modification and secretion.

Techniques for modifying nucleic acid sequences utilizing cloning methods are well known in the art.

A polynucleotide encoding a trypsin-like serine protease can be manipulated in a variety of ways to provide for expression of the polynucleotide in a *Bacillus* host cell. Manipulation of the polynucleotide sequence prior to its insertion into a nucleic acid construct or vector may be desirable or necessary depending on the nucleic acid construct or vector or the *Bacillus* host cell. The techniques for modifying nucleotide sequences utilizing cloning methods are well known in the art.

Regulatory sequences are defined above. They include all components, which are necessary or advantageous for the expression of a trypsin-like serine protease. Each control sequence may be native or foreign to the nucleotide sequence encoding the trypsin-like serine protease. Such regulatory sequences include, but are not limited to, a leader, a polyadenylation sequence, a propeptide sequence, a promoter, a signal sequence and a transcription terminator. Regulatory sequences may be provided with linkers for the purpose of introducing specific restriction sites facilitating ligation or the regulatory sequences with the coding region of the nucleotide sequence encoding a trypsin-like serine protease.

A nucleic acid construct comprising a polynucleotide encoding a trypsin-like serine protease may be operably linked to one or more control sequences capable of directing the expression of the coding sequence in a *Bacillus* host cell under conditions compatible with the control sequences.

Each control sequence may be native or foreign to the polynucleotide encoding a trypsin-like serine protease. Such control sequences include, but are not limited to, a leader, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a trypsin-like serine protease.

The control sequence may be an appropriate promoter region, a nucleotide sequence that is recognized by a *Bacillus* host cell for expression of the polynucleotide encoding a a trypsin-like serine protease. The promoter region contains transcription control sequences that mediate the expression of a trypsin-like serine protease. The promoter region may be any nucleotide sequence that shows transcriptional activity in the *Bacillus* host cell of choice and may be obtained from genes directing synthesis of extracellular or intracellular polypeptides having biological activity either homologous or heterologous to the *Bacillus* host cell.

The promoter region may comprise a single promoter or a combination of promoters. Where the promoter region comprises a combination of promoters, the promoters are preferably in tandem. A promoter of the promoter region can be any promoter that can initiate transcription of a polynucleotide encoding a polypeptide having biological activity in a *Bacillus* host cell of interest. The promoter may be native, foreign, or a combination thereof, to the nucleotide sequence encoding a polypeptide having biological activity. Such a promoter can be obtained from genes directing synthesis of extracellular or intracellular polypeptides having biological activity either homologous or heterologous to the *Bacillus* host cell.

Thus, in certain embodiments, the promoter region comprises a promoter obtained from a bacterial source. In other embodiments, the promoter region comprises a promoter obtained from a Gram positive or Gram negative bacterium. Gram positive bacteria include, but are not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but are not limited to, *E. coli, Pseudomonas, Salmonella, Campylobacter, Helicobacter, Flavobacterium, Fusobacterium, Ilyobacter, Neisseria*, and *Ureaplasma*.

The promoter region may comprise a promoter obtained from a *Bacillus* strain (e.g., *Bacillus agaradherens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*; or from a *Streptomyces* strain (e.g., *Streptomyces lividans* or *Streptomyces murinus*).

Examples of suitable promoters for directing transcription of a polynucleotide encoding a polypeptide having biological activity in the methods of the present disclosure are the promoters obtained from the *E. coli* lac operon, *Streptomyces coelicolor* agarase gene (dagA), *Bacillus lentus* or *Bacillus clausii* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. tenebfionis CryIIIA gene (crylliA) or portions thereof, prokaryotic beta-lactamase gene (Villa-Kamaroff et al., 1978, Proceedings of the National Academy of Sciences USA 75:3727-3731), and *Bacillus megaterium* xylA gene (Rygus and Hillen, 1992, J. Bacteriol. 174: 3049-3055; Kim et al., 1996, Gene 181: 71-76). Other examples are the promoter of the spo1 bacterial phage promoter and the tac promoter (DeBoer et al., 1983, Proceedings of the National Academy of Sciences USA 80:21-25). Further promoters are described in "Useful proteins from recombinant bacteria" in Scientific American, 1980, 242:74-94; and in Sambrook, Fritsch, and Maniatis, 1989, Molecular Cloning, A Laboratory Manual, 2d edition, Cold Spring Harbor, N.Y.

The promoter region may comprise a promoter that is a "consensus" promoter having the sequence TTGACA for the "−35" region and TATAAT for the "−10" region. The consensus promoter may be obtained from any promoter that can function in a *Bacillus* host cell. The construction of a "consensus" promoter may be accomplished by site-directed mutagenesis using methods well known in the art to create a promoter that conforms more perfectly to the established consensus sequences for the "−10" and "−35" regions of the vegetative "sigma A-type" promoters for *Bacillus subtilis* (Voskuil et al., 1995, Molecular Microbiology 17: 271-279).

A control sequence may also be a suitable transcription terminator sequence, such as a sequence recognized by a *Bacillus* host cell to terminate transcription. The terminator sequence is operably linked to the 3' terminus of the nucleotide sequence encoding a trypsin-like serine protease. Any terminator that is functional in the *Bacillus* host cell may be used.

The control sequence may also be a suitable leader sequence, a non-translated region of a mRNA that is important for translation by a *Bacillus* host cell. The leader sequence is operably linked to the 5' terminus of the nucleotide sequence directing synthesis of the polypeptide having biological activity. Any leader sequence that is functional in a *Bacillus* host cell of choice may be used in the present invention.

The control sequence may also be a mRNA stabilizing sequence. The term "mRNA stabilizing sequence" is defined herein as a sequence located downstream of a promoter region and upstream of a coding sequence of a polynucleotide encoding a trypsin-like serine protease to which the promoter region is operably linked, such that all mRNAs synthesized from the promoter region may be processed to generate mRNA transcripts with a stabilizer sequence at the 5' end of the transcripts. For example, the presence of such a stabilizer sequence at the 5' end of the mRNA transcripts increases their half-life (Agaisse and Lereclus, 1994, supra, Hue et al., 1995, Journal of Bacteriology 177: 3465-3471). The mRNA processing/stabilizing sequence is complementary to the 3' extremity of bacterial 16S ribosomal RNA. In certain embodiments, the mRNA processing/stabilizing sequence generates essentially single-size transcripts with a stabilizing sequence at the 5' end of the transcripts. The mRNA processing/stabilizing sequence is preferably one, which is complementary to the 3' extremity of a bacterial 16S ribosomal RNA. See, U.S. Pat. Nos. 6,255,076 and 5,955,310.

The nucleic acid construct can then be introduced into a *Bacillus* host cell using methods known in the art or those methods described herein for introducing and expressing a trypsin-like serine protease.

A nucleic acid construct comprising a DNA of interest encoding a protein of interest can also be constructed similarly as described above.

For obtaining secretion of the protein of interest of the introduced DNA, the control sequence may also comprise a signal peptide coding region, which codes for an amino acid sequence linked to the amino terminus of a polypeptide that can direct the expressed polypeptide into the cell's secretory pathway. The signal peptide coding region may be native to the polypeptide or may be obtained from foreign sources. The 5' end of the coding sequence of the nucleotide sequence may inherently contain a signal peptide coding region naturally linked in translation reading frame with the segment of the coding region that encodes the secreted polypeptide. Alternatively, the 5' end of the coding sequence may contain a signal peptide coding region that is foreign to that portion of the coding sequence that encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a *Bacillus* species. However, any signal peptide coding region capable of directing the expressed polypeptide into the secretory pathway of a *Bacillus* host cell of choice may be used in the present invention.

An effective signal peptide coding region for a *Bacillus* host cell, is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene.

Thus, a polynucleotide construct comprising a nucleic acid encoding a trypsin-like serine protease construct comprising a nucleic acid encoding a polypeptide of interest (POI) can be constructed such that it is expressed by a host cell. Because of the known degeneracies in the genetic code, different polynucleotides encoding an identical amino acid sequence can be designed and made with routine skills in the art. For example, codon optimizations can be applied to optimize production in a particular host cell.

Nucleic acids encoding proteins of interest can be incorporated into a vector, wherein the vector can be transferred into a host cell using well-known transformation techniques, such as those disclosed herein.

The vector may be any vector that can be transformed into and replicated within a host cell. For example, a vector comprising a nucleic acid encoding a POI can be transformed and replicated in a bacterial host cell as a means of propagating and amplifying the vector. The vector also may be transformed into a *Bacillus* expression host of the disclosure, so that the protein encoding nucleic acid (e.g., an ORF) can be expressed as a functional protein.

A representative vector which can be modified with routine skill to comprise and express a nucleic acid encoding a POI is vector p2JM103BBI.

A polynucleotide encoding a trypsin-like serine protease or a POI can be operably linked to a suitable promoter, which allows transcription in the host cell. The promoter may be any nucleic acid sequence that shows transcriptional activity in the host cell of choice and may be derived from genes encoding proteins either homologous or heterologous to the host cell. Means of assessing promoter activity/strength are routine for the skilled artisan.

Examples of suitable promoters for directing the transcription of a polynucleotide sequence encoding comS1 polypeptide or a POI of the disclosure, especially in a bacterial host, include the promoter of the lac operon of *E. coli*, the *Streptomyces coelicolor* agarase gene dagA or celA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes, and the like.

A promoter for directing the transcription of a polynucleotide sequence encoding a POI can be a wild-type aprE promoter, a mutant aprE promoter or a consensus aprE promoter set forth in PCT International Publication No. WO2001/51643. In certain other embodiments, a promoter for directing the transcription of a polynucleotide sequence encoding a POI is a wild-type spoVG promoter, a mutant spoVG promoter, or a consensus spoVG promoter (Frisby and Zuber, 1991).

A promoter for directing the transcription of the polynucleotide sequence encoding a trypsin-like serine protease or a POI is a ribosomal promoter such as a ribosomal RNA promoter or a ribosomal protein promoter. The ribosomal RNA promoter can be a rrn promoter derived from *B. subtilis*, more particularly, the rrn promoter can be a rrnB, rrnI or rrnE ribosomal promoter from *B. subtilis*. In certain embodiments, the ribosomal RNA promoter is a P2 rrnI promoter from *B. subtilis* set forth in PCT International Publication No. WO2013/086219.

A suitable vector may further comprise a nucleic acid sequence enabling the vector to replicate in the host cell. Examples of such enabling sequences include the origins of replication of plasmids pUC19, pACYC177, pUB110, pE194, pAMB1, 0.1702, and the like.

A suitable vector may also comprise a selectable marker, e.g., a gene the product of which complements a defect in the isolated host cell, such as the dal genes from *B. subtilis* or *B. licheniformis*; or a gene that confers antibiotic resistance such as, e.g., ampicillin resistance, kanamycin resistance, chloramphenicol resistance, tetracycline resistance and the like.

A suitable expression vector typically includes components of a cloning vector, such as, for example, an element that permits autonomous replication of the vector in the selected host organism and one or more phenotypically detectable markers for selection purposes. Expression vectors typically also comprise control nucleotide sequences such as, for example, promoter, operator, ribosome binding site, translation initiation signal and optionally, a repressor gene, one or more activator genes sequences, or the like.

Additionally, a suitable expression vector may further comprise a sequence coding for an amino acid sequence capable of targeting the protein of interest to a host cell organelle such as a peroxisome, or to a particular host cell compartment. Such a targeting sequence may be, for example, the amino acid sequence "SKL". For expression under the direction of control sequences, the nucleic acid sequence of the protein of interest can be operably linked to the control sequences in a suitable manner such that the expression takes place.

Protocols, such as described herein, used to ligate the DNA construct encoding a protein of interest, promoters, terminators and/or other elements, and to insert them into suitable vectors containing the information necessary for replication, are well known to persons skilled in the art.

An isolated cell, either comprising a polynucleotide construct or an expression vector, is advantageously used as a host cell in the recombinant production of a POI. The cell may be transformed with the DNA construct encoding the POI, conveniently by integrating the construct (in one or more copies) into the host chromosome. Integration is generally deemed an advantage, as the DNA sequence thus introduced is more likely to be stably maintained in the cell. Integration of the DNA constructs into the host chromosome may be performed applying conventional methods, for example, by homologous or heterologous recombination. For example, PCT International Publication No. WO2002/14490 describes methods of *Bacillus* transformation, transformants thereof and libraries thereof. Alternatively, the cell may be transformed with an expression vector as described above in connection with the different types of host cells.

It is, in other embodiments, advantageous to delete genes from expression hosts, where the gene deficiency can be cured by an expression vector. Known methods may be used to obtain a bacterial host cell having one or more inactivated genes. Gene inactivation may be accomplished by complete or partial deletion, by insertional inactivation or by any other means that renders a gene nonfunctional for its intended purpose, such that the gene is prevented from expression of a functional protein.

Techniques for transformation of bacteria and culturing the bacteria are standard and well known in the art. They can be used to transform the improved hosts of the present invention for the production of recombinant proteins of interest. Introduction of a DNA construct or vector into a host cell includes techniques such as transformation, electroporation, nuclear microinjection, transduction, transfection (e.g., lipofection mediated and DEAE-Dextrin mediated transfection), incubation with calcium phosphate DNA precipitate, high velocity bombardment with DNA-coated microprojectiles, gene gun or biolistic transformation and protoplast fusion, and the like. Transformation and expression methods for bacteria are also disclosed in Brigidi et al. (1990). A general transformation and expression protocol for protease deleted *Bacillus* strains is described in Ferrari et al. (U.S. Pat. No. 5,264,366).

Methods for transforming nucleic acids into filamentous fungi such as *Aspergillus* spp., e.g., *A. oryzae* or *A. niger, H. grisea, H. insolens*, and *T. reesei*. are well known in the art. A suitable procedure for transformation of *Aspergillus* host cells is described, for example, in EP238023. A suitable procedure for transformation of *Trichoderma* host cells is described, for example, in Steiger et al 2011, *Appl. Environ. Microbiol.* 77:114-121.

The choice of a production host can be any suitable microorganism such as bacteria, fungi and algae.

Typically, the choice will depend upon the gene encoding the trypsin-like serine protease and its source.

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. Basic texts disclosing the general methods that can be used include Sambrook et al., Molecular Cloning, A Laboratory Manual (2nd ed. 1989); Kriegler, Gene Transfer and Expression: A Laboratory Manual (1990); and Ausubel et al., eds., Current Protocols in Molecular Biology (1994)). The methods of transformation of the present invention may result in the stable integration of all or part of the transformation vector into the genome of a host cell, such as a filamentous fungal host cell. However, transformation resulting in the maintenance of a self-replicating extra-chromosomal transformation vector is also contemplated.

Many standard transfection methods can be used to produce bacterial and filamentous fungal (e.g. *Aspergillus* or *Trichoderma*) cell lines that express large quantities of the protease. Some of the published methods for the introduction of DNA constructs into cellulase-producing strains of *Trichoderma* include Lorito, Hayes, DiPietro and Harman, (1993) Curr. Genet. 24: 349-356; Goldman, VanMontagu and Herrera-Estrella, (1990) Curr. Genet. 17:169-174; and Penttila, Nevalainen, Ratto, Salminen and Knowles, (1987) Gene 6: 155-164, also see U.S. Pat. Nos. 6,022,725; 6,268,328 and Nevalainen et al., "The Molecular Biology of *Trichoderma* and its Application to the Expression of Both Homologous and Heterologous Genes" in Molecular Industrial Mycology, Eds, Leong and Berka, Marcel Dekker Inc., NY (1992) pp 129-148; for *Aspergillus* include Yelton, Hamer and Timberlake, (1984) Proc. Natl. Acad. Sci. USA 81: 1470-1474, for *Fusarium* include Bajar, Podila and Kolattukudy, (1991) Proc. Natl. Acad. Sci. USA 88: 8202-

8212, for *Streptomyces* include Hopwood et al., 1985, Genetic Manipulation of *Streptomyces*: Laboratory Manual, The John Innes Foundation, Norwich, UK and Fernandez-Abalos et al., Microbiol 149:1623-1632 (2003) and for *Bacillus* include Brigidi, DeRossi, Bertarini, Riccardi and Matteuzzi, (1990) FEMS Microbiol. Lett. 55: 135-138). However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well-known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the gene.

After the expression vector is introduced into the cells, the transfected or transformed cells are cultured under conditions favoring expression of genes under control of the promoter sequences.

The medium used to cultivate the cells may be any conventional medium suitable for growing the host cell and obtaining expression of an alpha-glucosidase polypeptide. Suitable media and media components are available from commercial suppliers or may be prepared according to published recipes (e.g., as described in catalogues of the American Type Culture Collection).

A thermostable serine polypeptide secreted from the host cells can be used, with minimal post-production processing, as a whole broth preparation.

Depending upon the host cell used post-transcriptional and/or post-translational modifications may be made. One non-limiting example of a post-transcriptional and/or post-translational modification is "clipping" or "truncation" of a polypeptide. For example, this may result in taking an trypsin-like serine protease from an inactive or substantially inactive state to an active state as in the case of a pro-peptide undergoing further post-translational processing to a mature peptide having the enzymatic activity. In another instance, this clipping may result in taking a mature thermostable serine protease polypeptide and further removing N or C-terminal amino acids to generate truncated forms of the thermostable serine protease that retain enzymatic activity.

Other examples of post-transcriptional or post-translational modifications include, but are not limited to, myristoylation, glycosylation, truncation, lipidation and tyrosine, serine or threonine phosphorylation. The skilled person will appreciate that the type of post-transcriptional or post-translational modifications that a protein may undergo may depend on the host organism in which the protein is expressed.

In some embodiments, the preparation of a spent whole fermentation broth of a recombinant microorganism can be achieved using any cultivation method known in the art resulting in the expression of a trypsin-like serine protease.

Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the alpha-glucosidase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

Host cells may be cultured under suitable conditions that allow expression of a trypsin-like serine protease. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or sophorose.

Any of the fermentation methods well known in the art can suitably be used to ferment the transformed or the derivative fungal strain as described above. In some embodiments, fungal cells are grown under batch or continuous fermentation conditions.

A classical batch fermentation is a closed system, where the composition of the medium is set at the beginning of the fermentation, and the composition is not altered during the fermentation. At the beginning of the fermentation, the medium is inoculated with the desired organism(s). In other words, the entire fermentation process takes place without addition of any components to the fermentation system throughout.

Alternatively, a batch fermentation qualifies as a "batch" with respect to the addition of the carbon source. Moreover, attempts are often made to control factors such as pH and oxygen concentration throughout the fermentation process. Typically the metabolite and biomass compositions of the batch system change constantly up to the time the fermentation is stopped. Within batch cultures, cells progress through a static lag phase to a high growth log phase and finally to a stationary phase, where growth rate is diminished or halted. Left untreated, cells in the stationary phase would eventually die. In general, cells in log phase are responsible for the bulk of production of product. A suitable variation on the standard batch system is the "fed-batch fermentation" system. In this variation of a typical batch system, the substrate is added in increments as the fermentation progresses. Fed-batch systems are useful when it is known that catabolite repression would inhibit the metabolism of the cells, and/or where it is desirable to have limited amounts of substrates in the fermentation medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are well known in the art.

Continuous fermentation is another known method of fermentation. It is an open system where a defined fermentation medium is added continuously to a bioreactor, and an equal amount of conditioned medium is removed simultaneously for processing. Continuous fermentation generally maintains the cultures at a constant density, where cells are maintained primarily in log phase growth. Continuous fermentation allows for the modulation of one or more factors that affect cell growth and/or product concentration. For example, a limiting nutrient, such as the carbon source or nitrogen source, can be maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Separation and concentration techniques are known in the art and conventional methods can be used to prepare a concentrated solution or broth comprising a trypsin-like serine protease polypeptide of the invention.

After fermentation, a fermentation broth is obtained, the microbial cells and various suspended solids, including residual raw fermentation materials, are removed by conventional separation techniques in order to obtain a trypsin-like serine protease solution. Filtration, centrifugation, microfiltration, rotary vacuum drum filtration, ultrafiltration, centrifugation followed by ultra-filtration, extraction, or chromatography, or the like, are generally used.

It may at times be desirable to concentrate a solution or broth comprising an alpha-glucosidase polypeptide to optimize recovery. Use of un-concentrated solutions or broth would typically increase incubation time in order to collect the enriched or purified enzyme precipitate.

The enzyme-containing solution can be concentrated using conventional concentration techniques until the desired enzyme level is obtained. Concentration of the enzyme containing solution may be achieved by any of the techniques discussed herein. Examples of methods of enrichment and purification include but are not limited to rotary vacuum filtration and/or ultrafiltration.

The trypsin-like serine protease-containing solution or broth may be concentrated until such time the enzyme activity of the concentrated a trypsin-like serine protease polypeptide-containing solution or broth is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides.

Exemplary metal halides include sodium chloride, potassium chloride, sodium bromide, potassium bromide and blends of two or more of these metal halides. The metal halide precipitation agent, sodium chloride, can also be used as a preservative. For production scale recovery, trypsin-like serine protease polypeptides can be enriched or partially purified as generally described above by removing cells via flocculation with polymers. Alternatively, the enzyme can be enriched or purified by microfiltration followed by concentration by ultrafiltration using available membranes and equipment. However, for some applications, the enzyme does not need to be enriched or purified, and whole broth culture can be lysed and used without further treatment. The enzyme can then be processed, for example, into granules.

Trypsin-like serine proteases may be isolated or purified in a variety of ways known to those skilled in the art depending on what other components are present in the sample. Standard purification methods include, but are not limited to, chromatography (e.g., ion exchange, affinity, hydrophobic, chromatofocusing, immunological and size exclusion), electrophoretic procedures (e.g., preparative isoelectric focusing), differential solubility (e.g., ammonium sulfate precipitation), extraction microfiltration, two phase separation. For example, the protein of interest may be purified using a standard anti-protein of interest antibody column. Ultrafiltration and diafiltration techniques, in conjunction with protein concentration, are also useful. For general guidance in suitable purification techniques, see Scopes, Protein Purification (1982). The degree of purification necessary will vary depending on the use of the protein of interest. In some instances, no purification will be necessary.

Assays for detecting and measuring the enzymatic activity of an enzyme, such as a trypsin-like serine protease polypeptide, are well known. Various assays for detecting and measuring activity of proteases (e.g., thermostable serine protease polypeptides), are also known to those of ordinary skill in the art. In particular, assays are available for measuring protease activity that are based on the release of acid-soluble peptides from casein or hemoglobin, measured as absorbance at 280 nm or colorimetrically using the Folin method, and hydrolysis of the dye-labeled azocasein, measured as absorbance at 440-450 nm.

Other exemplary assays involve the solubilization of chromogenic substrates (See e.g., Ward, "Proteinases," in Fogarty (ed.). Microbial Enzymes and Biotechnology, Applied Science, London, [1983], pp. 251-317). A protease detection assay method using highly labeled fluorescein isothiocyanate (FITC) casein as the substrate, a modified version of the procedure described by Twining [Twining, S. S., (1984) "Fluorescein Isothiocyanate-Labeled Casein Assay for Proteolytic Enzymes" Anal. Biochem. 143:30-34] may also be used.

Other exemplary assays include, but are not limited to: cleavage of casein into trichloroacetic acid-soluble peptides containing tyrosine and tryptophan residues, followed by reaction with Folin-Ciocalteu reagent and colorimetric detection of products at 660 nm, cleavage of internally quenched FRET (Fluorescence Resonance Energy Transfer) peptide substrates followed by detection of product using a fluorometer.

Fluorescence Resonance Energy Transfer (FRET) is the non-radiative transfer of energy from an excited fluorophore (or donor) to a suitable quencher (or acceptor) molecule. FRET is used in a variety of applications including the measurement of protease activity with substrates, in which the fluorophore is separated from the quencher by a short peptide sequence containing the enzyme cleavage site. Proteolysis of the peptide results in fluorescence as the fluorophore and quencher are separated. Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

In still another aspect, there is disclosed a feed, feedstuff, feed additive composition, premix, food or grain product comprising at least one polypeptide described herein either alone or in combination with at least one direct fed microbial, at least one other enzyme, or at least one direct fed microbial and at least one other enzyme.

The at least one enzyme can be selected from, but is not limited to, enzymes such as, e.g., alpha-amylase, amyloglucosidase, phytase, pullulanase, beta-glucanase, cellulase, xylanase, etc.

Any of these enzymes can be used in an amount ranging from 0.5 to 500 micrograms/g feed or feedstock.

Alpha-amylases (alpha-1,4-glucan-4-glucanohydrolase, EC 3.2.1.1.) hydrolyze internal alpha-1,4-glucosidic linkages in starch, largely at random to produce smaller molecular weight dextrans. These polypeptides are used, inter alia, in starch processing and in alcohol production. Any alpha-amylases can be used, e.g., those described in U.S. Pat. Nos. 8,927,250 and 7,354,752.

Amyloglucosidase catalyzes the hydrolysis of termina 1,4-linked alpha-D-glucose residues successively from the non-reducing ends of maltooligo- and polysaccharides with release of beta-D-glucose. Any amyloglucosidase can be used.

Phytase refers to a protein or polypeptide which is capable of catalyzing the hydrolysis of phytate to (1) myo-inositol and/or (2) mono-, di-, tri-, tetra-, and/or penta-phosphatess thereof and (3) inorganic phosphate. For example, enzymes having catalytic activity as defined in Enzyme Commission EC number 3.1.3.8 or EC number 3.1.3.26. Any phytase can be used such as described in U.S. Pat. Nos. 8,144,046, 8,673,609, and 8,053,221.

Pullulanase (EC 3.2.1.41) is a specific kind of glucanase, an amylolytic exoenzyme that degrades pullan (a polysaccharide polymer consisting of maltotriose units, also known as alpha-1,4-; alpha-1,6-glucan. Thus, it is an example of a debranching enzyme. Pullulanase is also known as pullulan-6-glucanohydrolase.

Pullulanases are generally secreted by a *Bacillus* species. For example, *Bacillus* deramificans (U.S. Pat. No. 5,817, 498; 1998), *Bacillus* acidopullulyticus (European Patent No. 0 063 909) and *Bacillus* naganoensis (U.S. Pat. No. 5,055, 403). Enzymes having pullulanase activity used commercially are produced, for example, from *Bacillus* species (trade name OPITMAX® 1-100 from DuPont-Genencor and Promozyme® D2 fro Novozymes). Other examples of debranching enzymes include, but are not limited to, iso-amylase from *Sulfolobus solfataricus*, *Pseudomonas* sp. and thermostable pullulanase from *Fervidobacterium nodosum* (e.f, WO2010/76113). The iso-amylase from *Pseudomonas* sp. is available as purified enzyme from Megazyme International. Any pullulanase can be used.

Glucanases are enzymes that break down a glucan, a polysaccharide made several glucose sub-units. As they perform hydrolysis of the glucosidic bond, they are hydrolases.

Beta-glucanase enzymes (EC 3.2.1.4) digests fiber. It helps in the breakdown of plant walls (cellulose).

Cellulases are any of several enzymes produced by fungi, bacteria and protozoans that catalyze cellulolysis, the decomposition of cellulose and of some related polysaccharides. The name is also used for any naturally-occurring mixture or complex of various such enzymes, that act serially or synergistically to decompose cellulosic material. Any cellulases can be used.

Xylanase (EC 3.2.1.8) is the name given to a class of enzymes which degrade the linear polysaccharide beta-1,4-xylan into xylose, those breaking down hemicellulose, one of the major components of plant cell walls. Any xylanases can be used.

At least one DFM may comprise at least one viable microorganism such as a viable bacterial strain or a viable yeast or a viable fungi. Preferably, the DFM comprises at least one viable bacteria.

It is possible that the DFM may be a spore forming bacterial strain and hence the term DFM may be comprised of or contain spores, e.g. bacterial spores. Thus, the term "viable microorganism" as used herein may include microbial spores, such as endospores or conidia. Alternatively, the DFM in the feed additive composition described herein may not comprise of or may not contain microbial spores, e.g. endospores or conidia.

The microorganism may be a naturally-occurring microorganism or it may be a transformed microorganism.

A DFM as described herein may comprise microorganims from one or more of the following genera: *Lactobacillus*, *Lactococcus*, *Streptococcus*, *Bacillus*, *Pediococcus*, *Enterococcus*, *Leuconostoc*, *Carnobacterium*, *Propionibacterium*, *Bifidobacterium*, *Clostridium* and *Megasphaera* and combinations thereof.

Preferably, the DFM comprises one or more bacterial strains selected from the following *Bacillus* spp: *Bacillus subtilis*, *Bacillus cereus*, *Bacillus licheniformis*, *Bacillus pumilis* and *Bacillus amyloliquefaciens*.

The genus "*Bacillus*", as used herein, includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. gibsonii*, *B. pumilis* and *B. thuringiensis*. It is recognized that the genus *Bacillus* continues to undergo taxonomical reorganization. Thus, it is intended that the genus include species that have been reclassified, including but not limited to such organisms as *Bacillus stearothermophilus*, which is now named "*Geobacillus stearothermophilus*", or *Bacillus polymyxa*, which is now "*Paenibacillus polymyxa*" The production of resistant endospores under stressful environmental conditions is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

In another aspect, the DFM may be further combined with the following *Lactococcus* spp: *Lactococcus cremoris* and *Lactococcus lactis* and combinations thereof.

The DFM may be further combined with the following *Lactobacillus* spp: *Lactobacillus buchneri*, *Lactobacillus acidophilus*, *Lactobacillus casei*, *Lactobacillus kefiri*, *Lactobacillus bifidus*, *Lactobacillus brevis*, *Lactobacillus helveticus*, *Lactobacillus paracasei*, *Lactobacillus rhamnosus*, *Lactobacillus salivarius*, *Lactobacillus curvatus*, *Lactobacillus bulgaricus*, *Lactobacillus sakei*, *Lactobacillus reuteri*, *Lactobacillus fermentum*, *Lactobacillus farciminis*, *Lactobacillus lactis*, *Lactobacillus delbreuckii*, *Lactobacillus plantarum*, *Lactobacillus paraplantarum*, *Lactobacillus farciminis*, *Lactobacillus rhamnosus*, *Lactobacillus crispatus*, *Lactobacillus gasseri*, *Lactobacillus johnsonii* and *Lactobacillus jensenii*, and combinations of any thereof.

In still another aspect, the DFM may be further combined with the following *Bifidobacteria* spp: *Bifidobacterium lactis*, *Bifidobacterium bifidium*, *Bifidobacterium longum*, *Bifidobacterium animalis*, *Bifidobacterium breve*, *Bifidobacterium infantis*, *Bifidobacterium catenulatum*, *Bifidobacterium pseudocatenulatum*, *Bifidobacterium adolescentis*, and *Bifidobacterium angulatum*, and combinations of any thereof.

There can be mentioned bacteria of the following species: *Bacillus subtilis*, *Bacillus licheniformis*, *Bacillus amyloliquefaciens*, *Bacillus pumilis*, *Enterococcus*, *Enterococcus* spp, and *Pediococcus* spp, *Lactobacillus* spp, *Bifidobacterium* spp, *Lactobacillus acidophilus*, *Pediococsus acidilactici*, *Lactococcus lactis*, *Bifidobacterium bifidum*, *Bacillus subtilis*, *Propionibacterium thoenii*, *Lactobacillus farciminis*, *Lactobacillus rhamnosus*, *Megasphaera elsdenii*, *Clostridium butyricum*, *Bifidobacterium animalis* ssp. *animalis*, *Lactobacillus reuteri*, *Bacillus cereus*, *Lactobacillus salivarius* ssp. *Salivarius*, *Propionibacteria* sp and combinations thereof.

A direct-fed microbial described herein comprising one or more bacterial strains may be of the same type (genus, species and strain) or may comprise a mixture of genera, species and/or strains.

Alternatively, a DFM may be combined with one or more of the products or the microorganisms contained in those products disclosed in WO2012110778, and summarized as follows:

*Bacillus subtilis* strain 2084 Accession No. NRR1 B-50013, *Bacillus subtilis* strain LSSAO1 Accession No. NRRL B-50104, and *Bacillus subtilis* strain 15A-P4 ATCC Accession No. PTA-6507 (from Enviva Pro®. (formerly known as Avicorr®); *Bacillus subtilis* Strain C3102 (from Calsporin®); *Bacillus subtilis* Strain PB6 (from Clostat®); *Bacillus pumilis* (8G-134); *Enterococcus* NCIMB 10415 (SF68) (from Cylactin®); *Bacillus subtilis* Strain C3102 (from Gallipro® & GalliproMax®); *Bacillus licheniformis* (from Gallipro®Tect®); *Enterococcus* and *Pediococcus* (from Poultry Star®); *Lactobacillus, Bifidobacterium* and/or *Enterococcus* from Protexin®); *Bacillus subtilis* strain QST 713 (from Proflora®); *Bacillus amyloliquefaciens* CECT-5940 (from Ecobiol® & Ecobiol® Plus); *Enterococcus faecium* SF68 (from Fortiflora®); *Bacillus subtilis* and *Bacillus licheniformis* (from BioPlus2B®); Lactic acid bacteria 7 *Enterococcus faecium* (from Lactiferm®); *Bacillus* strain (from CSI®); *Saccharomyces cerevisiae* (from Yea-Sacc®); *Enterococcus* (from Biomin IMB52®); *Pediococcus acidilactici, Enterococcus, Bifidobacterium animalis* ssp. *animalis, Lactobacillus reuteri, Lactobacillus salivarius* ssp. *salivarius* (from Biomin C5®); *Lactobacillus farciminis* (from Biacton®); *Enterococcus* (from Oralin E1707®); *Enterococcus* (2 strains), *Lactococcus lactis* DSM 1103 (from Probios-pioneer PDFM®); *Lactobacillus rhamnosus* and *Lactobacillus* farciminis (from Sorbiflore®); *Bacillus subtilis* (from Animavit®); *Enterococcus* (from Bonvital®); *Saccharomyces cerevisiae* (from Levucell SB 20®); *Saccharomyces cerevisiae* (from Levucell SC 0 & SC10® ME); *Pediococcus* acidilacti (from Bactocell); *Saccharomyces cerevisiae* (from ActiSaf® (formerly BioSaf®)); *Saccharomyces cerevisiae* NCYC Sc47 (from Actisaf® SC47); *Clostridium butyricum* (from Miya-Gold®); *Enterococcus* (from Fecinor and Fecinor Plus®); *Saccharomyces cerevisiae* NCYC R-625 (from InteSwine®); *Saccharomyces cerevisia* (from BioSprint®); *Enterococcus* and *Lactobacillus rhamnosus* (from Provita®); *Bacillus subtilis* and *Aspergillus oryzae* (from PepSoyGen-C®); *Bacillus cereus* (from Toyocerin®); *Bacillus cereus* var. toyoi NCIMB 40112/CNCM I-1012 (from TOYOCERIN®), or other DFMs such as *Bacillus licheniformis* and *Bacillus subtilis* (from BioPlus® YC) and *Bacillus subtilis* (from GalliPro®).

The DFM may be combined with Enviva® PRO which is commercially available from Danisco A/S. Enviva Pro® is a combination of *Bacillus* strain 2084 Accession No. NRR1 B-50013, *Bacillus* strain LSSAO1 Accession No. NRRL B-50104 and *Bacillus* strain 15A-P4 ATCC Accession No. PTA-6507 (as taught in U.S. Pat. No. 7,754,469 B—incorporated herein by reference).

It is also possible to combine the DFM described herein with a yeast from the genera: *Saccharomyces* spp.

Preferably, the DFM described herein comprisies microorganisms which are generally recognised as safe (GRAS) and, preferably are GRAS-approved.

A person of ordinary skill in the art will readily be aware of specific species and/or strains of microorganisms from within the genera described herein which are used in the food and/or agricultural industries and which are generally considered suitable for animal consumption.

In some embodiments, it is important that the DFM be heat tolerant, i.e. is thermotolerant. This is particularly the case when the feed is pelleted. Therefore, in another embodiment, the DFM may be a thermotolerant microorganism, such as a thermotolerant bacteria, for example *Bacillus* spp.

In other aspects, it may be desirable that the DFM comprises a spore producing bacteria, such as Bacilli, e.g. *Bacillus* spp. Bacilli are able to form stable endospores when conditions for growth are unfavorable and are very resistant to heat, pH, moisture and disinfectants.

The DFM described herein may decrease or prevent intestinal establishment of pathogenic microorganism (such as *Clostridium perfringens* and/or *E. coli* and/or *Salmonella* spp and/or *Campylobacter* spp.). In other words, the DFM may be antipathogenic. The term "antipathogenic" as used herein means the DFM counters an effect (negative effect) of a pathogen.

As described above, the DFM may be any suitable DFM. For example, the following assay "DFM ASSAY" may be used to determine the suitability of a microorganism to be a DFM. The DFM assay as used herein is explained in more detail in US2009/0280090. For avoidance of doubt, the DFM selected as an inhibitory strain (or an antipathogenic DFM) in accordance with the "DFM ASSAY" taught herein is a suitable DFM for use in accordance with the present disclosure, i.e. in the feed additive composition according to the present disclosure.

Tubes were seeded each with a representative pathogen (e.g., bacteria) from a representative cluster.

Supernatant from a potential DFM, grown aerobically or anaerobically, is added to the seeded tubes (except for the control to which no supernatant is added) and incubated. After incubation, the optical density (OD) of the control and supernatant treated tubes was measured for each pathogen.

Colonies of (potential DFM) strains that produced a lowered OD compared with the control (which did not contain any supernatant) can then be classified as an inhibitory strain (or an antipathogenic DFM). Thus, The DFM assay as used herein is explained in more detail in US2009/0280090.

Preferably, a representative pathogen used in this DFM assay can be one (or more) of the following: *Clostridium*, such as *Clostridium perfringens* and/or *Clostridium difficile*, and/or *E. coli* and/or *Salmonella* spp and/or *Campylobacter* spp. In one preferred embodiment the assay is conducted with one or more of *Clostridium perfringens* and/or *Clostridium difficile* and/or *E. coli*, preferably *Clostridium perfringens* and/or *Clostridium difficile*, more preferably *Clostridium perfringens*.

Antipathogenic DFMs include one or more of the following bacteria and are described in WO2013029013: *Bacillus subtilis* strain 3BP5 Accession No. NRRL B-50510, *Bacillus subtilis* strain 918 ATCC Accession No. NRRL B-50508, and *Bacillus subtilis* strain 1013 ATCC Accession No. NRRL B-50509.

DFMs may be prepared as culture(s) and carrier(s) (where used) and can be added to a ribbon or paddle mixer and mixed for about 15 minutes, although the timing can be increased or decreased. The components are blended such that a uniform mixture of the cultures and carriers result. The final product is preferably a dry, flowable powder. The DFM(s) comprising one or more bacterial strains can then be added to animal feed or a feed premix, added to an animal's water, or administered in other ways known in the art (preferably simultaneously with the enzymes described herein).

Inclusion of the individual strains in the DFM mixture can be in proportions varying from 1% to 99% and, preferably, from 25% to 75%

Suitable dosages of the DFM in animal feed may range from about $1\times10^3$ CFU/g feed to about $1\times10^{10}$ CFU/g feed, suitably between about $1\times10^4$ CFU/g feed to about $1\times10^8$ CFU/g feed, suitably between about $7.5\times10^4$ CFU/g feed to about $1\times10^7$ CFU/g feed.

In another aspect, the DFM may be dosed in feedstuff at more than about $1\times10^3$ CFU/g feed, suitably more than about $1\times10^4$ CFU/g feed, suitably more than about $5\times10^4$ CFU/g feed, or suitably more than about $1\times10^5$ CFU/g feed.

The DFM may be dosed in a feed additive composition from about $1\times10^3$ CFU/g composition to about $1\times10^{13}$ CFU/g composition, preferably $1\times10^5$ CFU/g composition to about $1\times10^{13}$ CFU/g composition, more preferably between about $1\times10^6$ CFU/g composition to about $1\times10^{12}$ CFU/g composition, and most preferably between about $3.75\times10^7$ CFU/g composition to about $1\times10^{11}$ CFU/g composition. In another aspect, the DFM may be dosed in a feed additive composition at more than about $1\times10^5$ CFU/g composition, preferably more than about $1\times10^6$ CFU/g composition, and most preferably more than about $3.75\times10^7$ CFU/g composition. In one embodiment the DFM is dosed in the feed additive composition at more than about $2\times10^5$ CFU/g composition, suitably more than about $2\times10^6$ CFU/g composition, suitably more than about $3.75\times10^7$ CFU/g composition.

A feed additive composition for use in animal feed may comprise at least one polypeptide described herein, either alone or in combination with (i) at least one direct fed microbial, at least one other enzyme, or at least one direct fed microbial and at least one other enzyme, and (ii) at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben, and propyl paraben.

In still another aspect, there is disclosed a granulated feed additive composition for use in animal feed comprising at least one polypeptide described herein, either alone or in combination with at least one direct fed microbial, at least one other enzyme, at least one direct fed microbial and at least one other enzyme, wherein the granulated feed additive composition comprises particles produced by a process selected from the group consisting of high shear granulation, drum granulation, extrusion, spheronization, fluidized bed agglomeration, fluidized bed spray coating, spray drying, freeze drying, prilling, spray chilling, spinning disk atomization, coacervation, tableting, and a combination thereof.

Furthermore, the particles of the granulated feed additive composition can have a mean diameter of greater than 50 microns and less than 2000 microns.

The feed additive composition can be a liquid form and the liquid form can also be suitable for spray-drying on a feed pellet.

Animal feeds may include plant material such as corn, wheat, sorghum, soybean, canola, sunflower or mixtures of any of these plant materials or plant protein sources for poultry, pigs, ruminants, aquaculture and pets. It is contemplated that animal performance parameters, such as growth, feed intake and feed efficiency, but also improved uniformity, reduced ammonia concentration in the animal house and consequently improved welfare and health status of the animals will be improved. More specifically, as used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention and/or by improved ability to avoid the negative effects of necrotic enteritis and/or by an improved immune response in the subject resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio. As used herein, the term "feed efficiency" refers to the amount of weight gain in an animal that occurs when the animal is fed ad-libitum or a specified amount of food during a period of time.

By "increased feed efficiency" it is meant that the use of a feed additive composition according the present invention in feed results in an increased weight gain per unit of feed intake compared with an animal fed without said feed additive composition being present.

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

In some embodiments, the compositions described herein can improve the digestibility or utilization of dietary hemicellulose or fibre in a subject. In some embodiments, the subject is a pig.

Nitrogen retention as used herein means as subject's ability to retain nitrogen from the diet as body mass. A negative nitrogen balance occurs when the excretion of nitrogen exceeds the daily intake and is often seen when the muscle is being lost. A positive nitrogen balance is often associated with muscle growth, particularly in growing animals.

Nitrogen retention may be measured as the difference between the intake of nitrogen and the excreted nitrogen by means of the total collection of excreta and urine during a period of time. It is understood that excreted nitrogen includes undigested protein from the feed, endogenous proteinaceous secretions, microbial protein, and urinary nitrogen.

The term survival as used herein means the number of subject remaining alive. The term "improved survival" may be another way of saying "reduced mortality".

The term carcass yield as used herein means the amount of carcass as a proportion of the live body weight, after a commercial or experimental process of slaughter. The term carcass means the body of an animal that has been slaughtered for food, with the head, entrails, part of the limbs, and feathers or skin removed. The term meat yield as used herein means the amount of edible meat as a proportion of the live body weight, or the amount of a specified meat cut as a proportion of the live body weight.

An "increased weight gain" refers to an animal having increased body weight on being fed feed comprising a feed additive composition compared with an animal being fed a feed without said feed additive composition being present.

The term "animal" as used herein includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feed", "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

Trypsin-like serine proteases described herein or a feed additive composition may be used as, or in the preparation of, a feed. The terms "feed additive composition" and "enzyme composition" are used interchangeably herein.

The feed may be in the form of a solution or as a solid or as a semi-solid depending on the use and/or the mode of application and/or the mode of administration.

When used as, or in the preparation of, a feed, such as functional feed, the enzyme or feed additive composition described herein may be used in conjunction with one or more of: a nutritionally acceptable carrier, a nutritionally acceptable diluent, a nutritionally acceptable excipient, a nutritionally acceptable adjuvant, a nutritionally active ingredient. For example, there be mentioned at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

In a preferred embodiment the enzyme or feed additive composition of the present invention is admixed with a feed component to form a feedstuff. The term "feed component" as used herein means all or part of the feedstuff. Part of the feedstuff may mean one constituent of the feedstuff or more than one constituent of the feedstuff, e.g. 2 or 3 or 4 or more. In one embodiment the term "feed component" encompasses a premix or premix constituents. Preferably, the feed may be a fodder, or a premix thereof, a compound feed, or a premix thereof. A feed additive composition may be admixed with a compound feed, a compound feed component or to a premix of a compound feed or to a fodder, a fodder component, or a premix of a fodder.

Any feedstuff described herein may comprise one or more feed materials selected from the group comprising a) cereals, such as small grains (e.g., wheat, barley, rye, oats, triticale and combinations thereof) and/or large grains such as maize or sorghum; b) by products from cereals, such as corn gluten meal, wet-cake (particularly corn based wet-cake), Distillers Dried Grains (DDG) (particularly corn based Distillers Dried Grains (cDDG)), Distillers Dried Grains with Solubles (DDGS) (particularly corn based Distillers Dried Grains with Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

The term "fodder" as used herein means any food which is provided to an animal (rather than the animal having to forage for it themselves). Fodder encompasses plants that have been cut. Furthermore, fodder includes silage, compressed and pelleted feeds, oils and mixed rations, and also sprouted grains and legumes.

Fodder may be obtained from one or more of the plants selected from: corn (maize), alfalfa (Lucerne), barley, birdsfoot trefoil, brassicas, Chau moellier, kale, rapeseed (canola), rutabaga (swede), turnip, clover, alsike clover, red clover, subterranean clover, white clover, fescue, brome, millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, canola meal, rapeseed meal, lupin, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

In one embodiment the feedstuff comprises or consists of corn, DDGS (such as cDDGS), wheat, wheat bran or any combination thereof.

In one embodiment the feed component may be corn, DDGS (e.g. cDDGS), wheat, wheat bran or a combination thereof. In one embodiment the feedstuff comprises or consists of corn, DDGS (such as cDDGS) or a combination thereof.

A feedstuff described herein may contain at least 30%, at least 40%, at least 50% or at least 60% by weight corn and soybean meal or corn and full fat soy, or wheat meal or sunflower meal.

For example, a feedstuff may contain between about 5 to about 40% corn DDGS. For poultry, the feedstuff on average may contain between about 7 to 15% corn DDGS. For swine (pigs), the feedstuff may contain on average 5 to 40% corn DDGS. It may also contain corn as a single grain, in which case the feedstuff may comprise between about 35% to about 80% corn.

In feedstuffs comprising mixed grains, e.g. comprising corn and wheat for example, the feedstuff may comprise at least 10% corn.

In addition or in the alternative, a feedstuff also may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, corn gluten feed, wetcake, Distillers Dried Grains (DDG), Distillers Dried Grains with Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton. In one aspect, the feedstuff as described herein comprises at least one high fibre material and/or at least one by-product of the at least one high fibre feed material selected from the group consisting of Distillers Dried Grains with Solubles (DDGS), particularly cDDGS, wet-cake, Distillers Dried Grains (DDG), particularly cDDG, wheat bran, and wheat for example. In one embodiment the feedstuff of the present invention comprises at least one high fibre material and/or at least one by-product of the at least one high fibre feed material selected from the group consisting of Distillers Dried Grains with Solubles (DDGS), particularly cDDGS, wheat bran, and wheat for example.

The feed may be one or more of the following: a compound feed and premix, including pellets, nuts or (cattle) cake; a crop or crop residue: corn, soybeans, sorghum, oats, barley copra, straw, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term "feed" as used herein encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

Animal feed can also include a fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

In still another aspect, animal feed encompasses bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of a trypsin-like serine protease enzyme (or composition comprising the thermostable serine protease) to a product (e.g. the feed). Examples of application methods which may be used, include, but are not limited to, treating the product in a material comprising the feed additive composition, direct application by mixing the feed additive composition with the product, spraying the feed additive composition onto the product surface or dipping the product into a preparation of the feed additive composition. In one embodiment the feed additive composition of the present invention is preferably admixed with the product (e.g. feedstuff). Alternatively, the feed additive composition may be included in the emulsion or raw ingredients of a feedstuff. For some applications, it is important that the composition is made available on or to the surface of a product to be affected/treated. This allows the composition to impart a performance benefit.

In some aspects, the thermostable serine proteases described are used for the pretreatment of food or feed. For example, the feed having 10-300% moisture is mixed and incubated with the proteases at 5-80° C., preferably at 25-50° C., more preferably between 30-45° C. for 1 min to 72 hours under aerobic conditions or 1 day to 2 months under anaerobic conditions. The pre-treated material can be fed directly to the animals (so called liquid feeding). The pre-treated material can also be steam pelleted at elevated temperatures of 60-120° C. The proteases can be impregnated to feed or food material by a vacuum coater.

Trypsin-like serine proteases (or composition comprising the thermostable serine proteases) may be applied to intersperse, coat and/or impregnate a product (e.g. feedstuff or raw ingredients of a feedstuff) with a controlled amount of said enzyme.

Preferably, the feed additive composition will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the enzyme components and/or DFM that were present/active in the additive before heating to the specified temperature are still present/active after it cools to room temperature. Preferably, at least about 80% of the protease component and/or DFM comprising one or more bacterial strains that were present and active in the additive before heating to the specified temperature are still present and active after it cools to room temperature. In a particularly preferred embodiment the feed additive composition is homogenized to produce a powder.

Alternatively, the feed additive composition is formulated to granules as described in WO2007/044968 (referred to as TPT granules) incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the at least one protease and/or DFM comprising one or more bacterial strains. Preferably, the salt used for the salt coating has a water activity greater than 0.25 or constant humidity greater than 60% at 20° C. Preferably, the salt coating comprises a $Na_2SO_4$.

The method of preparing a feed additive composition may also comprise the further step of pelleting the powder. The powder may be mixed with other components known in the art. The powder, or mixture comprising the powder, may be forced through a die and the resulting strands are cut into suitable pellets of variable length.

A method of preparing trypsin-like serine proteases (or composition comprising the thermostable serine proteases) may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour. It will be understood that the thermostable serine proteases (or composition comprising the thermostable serine proteases) described herein are suitable for addition to any appropriate feed material.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins. In some embodiments, the feedstuff is a corn soybean meal mix.

Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting, in particular by suitable techniques that may include at least the use of steam.

The feedstuff may be a feedstuff for a monogastric animal, such as poultry (for example, broiler, layer, broiler breeders, turkey, duck, geese, water fowl), and swine (all age categories), a ruminant such as cattle (e.g. cows or bulls (including calves)), horses, sheep, a pet (for example dogs, cats) or fish (for example agastric fish, gastric fish, freshwater fish such as salmon, cod, trout and carp, e.g. koi carp, marine fish such as sea bass, and crustaceans such as shrimps, mussels and scallops). Preferably the feedstuff is for poultry.

The feed additive composition and/or the feedstuff comprising same may be used in any suitable form. The feed additive composition may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions may be mixed with feed or administered in the drinking water.

A feed additive composition, comprising admixing a protease as taught herein with a feed acceptable carrier, diluent or excipient, and (optionally) packaging.

The feedstuff and/or feed additive composition may be combined with at least one mineral and/or at least one vitamin. The compositions thus derived may be referred to herein as a premix.

In some embodiments, trypsin-like serine protease can be present in the feedstuff in the range of 1 ppb (parts per billion) to 10% (w/w) based on pure enzyme protein. In some embodiments, the protease is present in the feedstuff is in the range of 1-100 ppm (parts per million). A preferred dose can be 1-20 g of trypsin-like serine protease per ton of feed product or feed composition or a final dose of 1-20 ppm trypsin-like serine protease in final product.

Preferably, a trypsin-like serine protease is present in the feedstuff should be at least about 200 PU/kg or at least about 300 PU/kg feed or at least about 400 PU/kg feed or at least about 500 PU/kg feed or at least about 600 PU/kg feed, at least about 700 PU/kg feed, at least about 800 PU/kg feed, at least about 900 PU/kg feed or at least about 1000 PU/kg feed, or at least about 1500 PU/kg feed, or at least about 2000 PU/kg feed or at least about 2500 PU/kg feed, or at least about 3000 PU/kg feed, or at least about 3500 PU/kg feed, or at least about 4000 PU/kg feed, or at least about 4500 PU/kg feed, or at least about 5000 PU/kg feed.

In another aspect, a trypsin-like serine protease can be present in the feedstuff at less than about 60,000 PU/kg feed, or at less than about 70,000 PU/kg feed, or at less than about 80,000 PU/kg feed, or at less than about 90,000 PU/kg feed, or at less than about 100,000 PU/kg feed, or at less than about 200,000 PU/kg feed, or at less than about 60000 PU/kg feed, or at less than about 70000 PU/kg feed.

Ranges can include, but are not limited to, any combination of the lower and upper ranges discussed above.

It will be understood that one protease unit (PU) is the amount of enzyme that liberates 2.3 micrograms of phenolic compound (expressed as tyrosine equivalents) from a casein substrate per minute at pH 10.0 at 50° C. This may be referred to as the assay for determining 1 PU.

Formulations comprising any of trypsin-like serine protease and compositions described herein may be made in any suitable way to ensure that the formulation comprises active enzymes. Such formulations may be as a liquid, a dry powder or a granule. Preferably, the feed additive composition is in a liquid form and, the liquid form may be suitable for spray-drying on a feed pellet.

Dry powder or granules may be prepared by means known to those skilled in the art, such as, high shear granulation, drum granulation, extrusion, spheronization, fluidized bed agglomeration, fluidized bed spray Trypsin-like serine proteases and compositions described herein may be coated, for example encapsulated. In one embodiment, the coating protects the enzymes from heat and may be considered a thermo-protectant.

Feed additive composition described herein can be formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

The feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

The granule may be produced using a steam-heated pelleting process which may be conducted between 85° C. and 95° C. for up to several minutes.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g. spraying, the enzyme(s) onto a carrier substrate, such as ground wheat for example.

In one embodiment the feed additive composition may be formulated as a premix. By way of example only the premix may comprise one or more feed components, such as one or more minerals and/or one or more vitamins.

In one embodiment a direct fed microbial ("DFM") and/or thermostable serine proteases are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbate, glycerol, sucrose, propylene glycol, 1,3-propane diol, glucose, parabens, sodium chloride, citrate, acetate, phosphate, calcium, metabisulfite, formate and mixtures thereof.

Some embodiments are directed to a method of cleaning, comprising contacting a surface or an item in need of cleaning with an effective amount of at least one polypeptide described herein or at least one composition described herein; and optionally further comprising the step of rinsing said surface or item after contacting said surface or item with said polypeptide or composition. In other embodiments, the item is dishware or fabric.

Further embodiments are directed to a method of cleaning comprising contacting a surface or an item in need of cleaning with an effective amount of at least one polypeptide having serine protease activity, wherein said polypepetide comprises a protease catalytic region comprising an amino acid sequence with at least 96% identity with the amino acid sequence of SEQ ID NO:18, or an amino acid sequence of SEQ ID NO:20; and, optionally, further comprising the step of rinsing said surface or item after contacting said surface or item with said polypeptide. Another embodiment is directed to a method of cleaning comprising contacting a surface or an item in need of cleaning with an effective amount of at least one polypeptide having serine protease activity, wherein said polypepetide comprises an amino acid sequence with at least 91% identity with the amino acid sequence of SEQ ID NO:22, or at least 94% identity with the amino acid sequence of SEQ ID NO:23; and, optionally, further comprising the step of rinsing said surface or item after contacting said surface or item with said polypeptide. A yet further embodiment is directed to a method of cleaning comprising contacting a surface or an item in need of cleaning with an effective amount of at least one polypeptide having serine protease activity, wherein said polypepetide comprises (i) an amino acid sequence with at least 91% identity with the amino acid sequence of SEQ ID NO:22, or (ii) a protease catalytic region comprising an amino acid sequence with at least 96% identity with the amino acid sequence of SEQ ID NO:18; and, optionally, further comprising the step of rinsing said surface or item after contacting said surface or item with said polypeptide. A yet further embodiment is directed to a method of cleaning comprising contacting a surface or an item in need of cleaning with an effective amount of at least one polypeptide having serine protease activity, wherein said polypepetide comprises (i) an amino acid sequence with at least 94% identity with the amino acid sequence of SEQ ID NO:23, or (ii) a protease catalytic region comprising an amino acid sequence of SEQ ID NO:20; and, optionally, further comprising the step of rinsing said surface or item after contacting said surface or item with said polypeptide.

Still further embodiments are directed to a method of cleaning comprising contacting a surface or an item in need of cleaning with a composition comprising an effective amount of at least one polypeptide having serine protease activity, wherein said polypepetide comprises a protease catalytic region comprising an amino acid sequence with at least 96% identity with the amino acid sequence of SEQ ID NO:18, or an amino acid sequence of SEQ ID NO:20; and, optionally, further comprising the step of rinsing said surface or item after contacting said surface or item with said polypeptide. Another embodiment is directed to a method of cleaning comprising contacting a surface or an item in need of cleaning with a composition comprising an effective amount of at least one polypeptide having serine protease activity, wherein said polypepetide comprises an amino acid sequence with at least 91% identity with the amino acid sequence of SEQ ID NO:22, or at least 94% identity with the amino acid sequence of SEQ ID NO:23; and, optionally, further comprising the step of rinsing said surface or item after contacting said surface or item with said polypeptide. A yet further embodiment is directed to a method of cleaning comprising contacting a surface or an item in need of cleaning with a composition comprising an effective amount of at least one polypeptide having serine protease activity, wherein said polypepetide comprises (i) an amino acid sequence with at least 91% identity with the amino acid sequence of SEQ ID NO:22, or (ii) a protease catalytic region comprising an amino acid sequence with at least 96% identity with the amino acid sequence of SEQ ID NO:18; and, optionally, further comprising the step of rinsing said surface or item after contacting said surface or item with said polypeptide. A yet further embodiment is directed to a method of cleaning comprising contacting a surface or an item in need of cleaning with a composition comprising an effective amount of at least one polypeptide having serine protease activity, wherein said polypepetide comprises (i) an amino acid sequence with at least 94% identity with the amino acid sequence of SEQ ID NO:23, or (ii) a protease catalytic region comprising an amino acid sequence of SEQ ID NO:20; and, optionally, further comprising the step of rinsing said surface or item after contacting said surface or item with said polypeptide.

In still another embodiment, at least one polypeptide described herein has enzymatic activity (e.g., protease activity) and thus is useful in cleaning applications, including but not limited to, methods for cleaning dishware items, tableware items, fabrics, and items having hard surfaces (e.g., the hard surface of a table, table top, wall, furniture item, floor, ceiling, etc.). Some embodiments are directed to at least cleaning composition comprising at least one polypeptide described herein. The enzymatic activity (e.g., protease enzyme activity) of at least one polypeptide described herein can be readily determined through procedures well known to those of ordinary skill in the art. The Examples presented infra describe methods for evaluating cleaning performance. In some embodiments, at least one polypeptide described herein has protease activity in the presence of a surfactant. In other embodiments, the surfactant is selected from the group consisting of a non-ionic surfactant, an anionic surfactant, a cationic surfactant, a zwitterionic surfactant, an ampholytic surfactant, a semi-polar non-ionic surfactant, and a combination thereof. In some embodiments, the protease activity comprises suc-AAPF-pNA activity.

In some embodiments, at least one polypeptide described herein demonstrates cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, one or more serine protease described herein demonstrates cleaning performance in ADW detergent compositions. In some embodiments, the cleaning performance in ADW detergent compositions includes cleaning of egg yolk stains. In some embodiments, one or more serine protease described herein demonstrates cleaning performance in laundry detergent compositions. In some embodiments, the cleaning performance in laundry detergent compositions includes cleaning of blood/milk/ink stains. In one or more cleaning composition described herein, one or more serine protease described herein demonstrates cleaning performance with or without a bleach component.

Assays for detecting and measuring the enzymatic activity of an enzyme, such as, e.g., at least one polypeptide described herein are well known. Various assays for detecting and measuring activity of proteases (e.g., at least one polypeptide described herein) are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.), Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

Unless otherwise noted, all component or composition levels provided herein are made in reference to the active level of that component or composition, and are exclusive of impurities, for example, residual solvents or by-products, which may be present in commercially available sources. Enzyme component weights are based on total active protein. All percentages and ratios are calculated by weight unless otherwise indicated. All percentages and ratios are calculated based on the total composition unless otherwise indicated. Compositions of the invention include detergent compositions. In the exemplified detergent compositions, the enzymes levels are expressed as pure enzyme by weight of the total composition and unless otherwise specified, the detergent ingredients are expressed by weight of the total compositions.

One embodiment is directed to a composition comprising at least one polypeptide having serine protease activity described herein. In some embodiments, the composition is a cleaning composition. In other embodiments, the composition is a detergent composition. In yet other embodiments, the composition is selected from a laundry detergent composition, an ADW detergent composition, a (hand or manual) dishwashing detergent composition, a hard surface cleaning composition, an eyeglass cleaning composition, a medical instrument cleaning composition, a disinfectant (e.g., malodor or microbial) composition, and a personal care cleaning composition. In still other embodiments, the composition is a laundry detergent composition, an ADW deteregent composition, or a (hand or manual) dishwashing detergent composition. Even still further embodiments are directed to a fabric cleaning composition, while other embodiments are directed to a non-fabric cleaning composition.

Some embodiments are directed to a composition described herein, wherein said composition comprises at least one polypeptide having serine protease activity described herein. In other embodiments, the composition described herein comprises at least one polypeptide having serine protease activity, wherein said polypeptide comprises a protease catalytic region comprising an amino acid sequence with at least 96% identity with the amino acid sequence of SEQ ID NO:18, or an amino acid sequence of SEQ ID NO:20. In an even further embodiment, the composition descrned herein comprises at least one polypeptide having serine protease activity, wherein said polypeptide comprises an amino acid sequence with at least 91% identity with the amino acid sequence of SEQ ID NO:22, or at least 94% identity with the amino acid sequence of SEQ ID NO:23. In a still further embodiment, the composition described herein comprises at least one polypeptide having serine protease activity, wherein said polypeptide comprises (i) an amino acid sequence with at least 91% identity with the amino acid sequence of SEQ ID NO:22, or (ii) a protease catalytic region comprising an amino acid sequence with at least 96% identity with the amino acid sequence of SEQ ID NO:18. In an even still further embodiment, the composition described herein comprises at least one polypeptide having serine protease activity, wherein said polypeptide comprises (i) an amino acid sequence with at least 94% identity with the amino acid sequence of SEQ ID NO:23, or (ii) a protease catalytic region comprising an amino acid sequence of SEQ ID NO:20. In some embodiments, the composition described herein further comprises one or more surfactant. In yet other embodiments, the at least one polypeptide having serine protease activity described herein has cleaning activity in one or more composition described herein. In still other embodiments, the at least one polypeptide having serine protease activity described herein has cleaning activity at about 16° C. and/or about 32° C. in one or more composition described herein. In still other embodiments, the composition described herein is selected from a laundry detergent, a fabric softening detergent, a dishwashing detergent, and a hard-surface cleaning detergent.

In some embodiments, a composition described herein further comprises: (i) one or more other enzymes selected from acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, oxidoreductases, pectate lyases, pectin acetyl esterases, pectinases, pentosanases, perhydrolases, peroxidases, phenoloxidases, phosphatases, phospholipases, phytases, polyesterases, polygalacturonases, additional proteases, pullulanases, reductases, rhamnogalacturonases, cellulases, beta-glucanases, tannases, transglutaminases, xylan acetyl-esterases, xylanases, and xylosidases; (ii) one or more ions selected from calcium and zinc; (iii) one or more adjunct materials; (iv) one or more stabilizers; (v) from about 0.001% to about 1.0 weight % of said polypeptide; (vi) one or more bleaching agents; and (vii) combinations thereof.

Another embodiment is directed to a composition comprising one or more adjunct materials and at least one polypeptide described herein. The nature of the adjunct materials employed in any particular composition, and levels of incorporation thereof, will depend on the physical form of the composition and the cleaning application for which such composition will be used.

Exemplary adjunct materials include, but are not limited to, bleach catalysts, an additional enzyme, enzyme stabilizers (including, for example, an enzyme stabilizing system), chelants, optical brighteners, soil release polymers, dye transfer agents, dispersants, suds suppressors, dyes, perfumes, colorants, filler salts, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. Suitable examples of other adjunct materials and levels of use can be found in U.S. Pat. Nos. 5,576,282; 6,306,812; 6,326,348; 6,610,642; 6,605,458; 5,705,464; 5,710,115; 5,698,504; 5,695,679; 5,686,014; and 5,646,101. In embodiments in which one or more adjunct material is not compatible with one or more serine protease described herein suitable methods of keeping the adjunct material(s) and protease(s) separated (i.e., not in contact with each other) can be employed until combination of the two components is appropriate. Such separation methods include any suitable method known in the art (e.g., gelcaps, encapsulation, tablets, physical separation, etc.). The aforementioned adjunct materials may constitute the balance of the cleaning compositions described herein.

In yet another embodiment, at least one composition described herein is advantageously employed for example, in laundry applications, hard surface cleaning applications, dishwashing applications, including automatic dishwashing and hand dishwashing, as well as cosmetic applications such as dentures, teeth, hair and skin cleaning and disinfecting applications, such as, for example, but not limited to, disinfecting an automatic dishwashing or laundry machine. The at least one polypeptide described herein is also suited for use in contact lens cleaning and wound debridement applications.

In yet still a further embodiment, at least one composition described herein contains phosphate, is phosphate-free, contains boron, is boron-free, or combinations thereof. In other embodiments, the at least one composition described herein is a boron-free composition. In some embodiments, a boron-free composition is a composition to which a borate stabilizer has not been added. In another embodiment, a boron-free composition is a composition that contains less than 5.5% boron. In a still further embodiment, a boron-free composition is a composition that contains less than 4.5% boron. In yet still another embodiment, a boron-free composition is a composition that contains less than 3.5% boron. In yet still a further embodiment, a boron-free composition is a composition that contains less than 2.5% boron. In even further embodiments, a boron-free composition is a composition that contains less than 1.5% boron. In another embodiment, a boron-free composition is a composition that contains less than 1.0% boron. In still further embodiments, a boron-free composition is a composition that contains less than 0.5% boron. In still further embodiments, at least one composition described herein is substantially-free of boron. In some embodiments, at least one composition described herein is phosphate-free. In still other embodiments, at least one composition described herein contains phosphate. In even still other embodiments, at least one composition described herein comprises at least one polypeptide described herein and one or more of an excipient, adjunct material, and/or additional enzyme.

At least one polypeptide described herein also finds use in cleaning additive products. In some embodiments, one or more cleaning additive finds use at low temperatures. Some embodiments provide cleaning additive products comprising at least one polypeptide described herein, which additive is ideally suited for inclusion in a wash process when additional bleaching effectiveness is desired. Such instances include, but are not limited to low temperature cleaning applications. In some embodiments, the additive product is in its simplest form, o at least one polypeptide described herein. In some embodiments, the additive is packaged in dosage form for addition to a cleaning process. In some embodiments, the additive is packaged in dosage form for addition to a cleaning process where a source of peroxygen is employed and increased bleaching effectiveness is desired.

Exemplary fillers or carriers for granular compositions include, but are not limited to, for example, various salts of sulfate, carbonate and silicate; talc; and clay. Exemplary fillers or carriers for liquid compositions include, but are not limited to, for example, water or low molecular weight primary and secondary alcohols including polyols and diols (e.g., methanol, ethanol, propanol and isopropanol). In some embodiments, the compositions contain from about 5% to about 90% of such filler or carrier. Acidic fillers may be included in such compositions to reduce the pH of the resulting solution in the cleaning method or application.

In another embodiment, at least one composition described herein is in a form selected from gel, tablet, powder, granular, solid, liquid, unit dose, and combinations thereof. In yet another embodiment, at least one composition described herein is in a form selected from a low water compact formula, low water HDL or UD, or high water formula or HDL. In some embodiments, the cleaning composition describe herein is in a unit dose form. In other embodiments, the unit does form is selected from pills, tablets, capsules, gelcaps, sachets, pouches, multi-compartment pouches, and pre-measured powders, and liquids. In some embodiments, the unit dose format is designed to provide a controlled release of the ingredients from a multi-compartment pouch (or other unit dose format). Suitable unit dose and controlled release formats are described, for example, in EP2100949; WO 02/102955; U.S. Pat. Nos. 4,765,916; 4,972,017; and WO 04/111178. In some embodiments, the unit dose form is a tablet or powder contained in a water-soluble film or pouch.

The present cleaning compositions or cleaning additives comprise an effective amount of at least one polypeptide described herein, alone or in combination with one or more additional enzyme. Typically, the present cleaning compositions comprise at least about 0.0001 weight percent, from about 0.0001 to about 10, from about 0.001 to about 1, or from about 0.01 to about 0.1 weight percent of at least one polypeptide described herein. In another embodiment, at least one composition described herein comprises from about 0.01 to about 10 mg, about 0.01 to about 5 mg, about 0.01 to about 2 mg, about 0.01 to about 1 mg, about 0.05 to about 1 mg, about 0.5 to about 10 mg, about 0.5 to about 5 mg, about 0.5 to about 4 mg, about 0.5 to about 4 mg, about 0.5 to about 3 mg, about 0.5 to about 2 mg, about 0.5 to about 1 mg, about 0.1 to about 10 mg, about 0.1 to about 5 mg, about 0.1 to about 4 mg, about 0.1 to about 3 mg, about 0.1 to about 2 mg, about 0.1 to about 1 mg, or about 0.1 to about 0.5 mg of at least one polypeptide described herein per gram of composition.

In some embodiments, at least one polypeptide described herein cleans at low temperatures. In other embodiments, at least one composition described herein cleans at low temperatures. In other embodiments, at least one composition described herein comprises an effective amount of at least one polypeptide described herein as useful or effective for cleaning a surface in need of proteinaceous stain removal.

The compositions described herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. Some embodiments provide a composition formulated to have an alkaline pH under wash conditions, such as a pH of from about 8.0 to about 12.0, or from about 8.5 to about 11.0, or from about 9.0 to about 11.0. In some embodiments, the composition described herein is formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the composition is dissolved 1:100 (wt:wt) in de-ionised water at 20° C. and measured using a conventional pH meter. Techniques for controlling pH include the use of buffers, alkalis, acids, etc., and are well known to those skilled in the art.

In some embodiments, when the at least one polypeptide described herein is employed in a granular composition or liquid, it is desirable for the polypeptide to be in the form of an encapsulated particle to protect it from other components in the composition during storage. In addition, encapsulation is also a means of controlling the availability of the polypeptide during the cleaning process. In some embodiments, encapsulation enhances the performance of polypeptide and/or additional enzymes. In this regard, at least one polypeptide described herein is encapsulated with any suitable encapsulating material known in the art. In some embodiments, the encapsulating material typically encapsulates at least part of the polypeptide. Typically, the encapsulating material is water-soluble and/or water-dispersible. In some embodiments, the encapsulating material has a glass transition temperature (Tg) of 0° C. or higher. Tg is described in more detail in WO97/11151. The encapsulating material is typically selected from carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP0922499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Akzo Nobel Chemicals International, B.V.), and PM6545, PM6550, PM7220, PM7228, EXTENDOSPHERES® (Sphere One Inc.), LUXSIL® (Potters Industries LLC), Q-CEL® (Potters Industries LLC), and SPHERICEL® (Potters Industries LLC).

There are a variety of wash conditions including varying detergent formulations, wash water volumes, wash water temperatures, and lengths of wash time, to which proteases involved in washing are exposed. A low detergent concentration system includes detergents where less than about 800 ppm of the detergent components are present in the wash water. A medium detergent concentration includes detergents where between about 800 ppm and about 2000 ppm of the detergent components are present in the wash water. A high detergent concentration system includes detergents where greater than about 2000 ppm of the detergent components are present in the wash water. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

Different geographies typically have different water hardness. Water hardness is usually described in terms of the grains per gallon mixed $Ca^{2+}/Mg^{2+}$. Hardness is a measure of the amount of calcium (Ca') and magnesium (Mg') in the water. Most water in the United States is hard, but the degree of hardness varies. Moderately hard (60-120 ppm) to hard (121-181 ppm) water has 60 to 181 parts per million.

| Water | Grains per gallon | Parts per million |
| --- | --- | --- |
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Other embodiments are directed to at least one composition comprising from about 0.00001% to about 10% by weight composition of at least one polypeptide described herein and from about 99.999% to about 90.0% by weight composition of one or more adjunct material. In another embodiment, the composition comprises from about 0.0001% to about 10%, about 0.001% to about 5%, about 0.001% to about 2%, or about 0.005% to about 0.5% by weight composition of at least one polypeptide described herein and from about 99.9999% to about 90.0%, about 99.999% to about 98%, about 99.995% to about 99.5% by weight composition of one or more adjunct material.

In other embodiments, the composition described herein comprises at least one polypeptide described herein and one or more additional enzymes. The one or more additional enzyme is selected from acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, malanases, mannanases, metalloproteases, oxidases, pectate lyases, pectin acetyl esterases, pectinases, pentosanases, peroxidases, phenoloxidases, phosphatases, phospholipases, phytases, polygalacturonases, additional proteases, pullulanases, reductases, rhamnogalacturonases, beta-glucanases, tannases, transglutaminases, xylan acetyl-esterases, xylanases, xyloglucanases, xylosidases, and any combination or mixture thereof. Some embodiments are directed to a combination of enzymes (i.e., a "cocktail") comprising conventional enzymes like amylase, lipase, cutinase and/or cellulase in conjunction with at least one polypeptide described herein and/or one or more additional protease.

In another embodiment, at least one composition described herein comprises at least one polypeptide described herein and one or more additional protease. In one embodiment, the additional protease is a serine protease. Suitable additional proteases include those of animal, vegetable or microbial origin. In some embodiments, the additional protease is a microbial protease. In other embodiments, the additional protease is a chemically or genetically modified mutant. In another embodiment, the additional protease is an alkaline microbial protease or a trypsin-like protease. Exemplary alkaline proteases include subtilisins derived from, for example, *Bacillus* (e.g., subtilisin, *lentus, amyloliquefaciens*, subtilisin Carlsberg, subtilisin 309, subtilisin 147 and subtilisin 168). Exemplary additional proteases include but are not limited to those described in WO92/21760, WO95/23221, WO2008010925, WO09/149200, WO09/149144, WO09/149145, WO 10/056640, WO10/056653, WO2010 0566356, WO11/072099, WO2011013022, WO11/140364, WO12/151534, WO2015038792, WO2015089447, WO2015089441, WO2015143360, WO2016061438, WO2016069548, WO 2016069544, WO2016069557, WO2016069563, WO2016069569, WO2016069552, WO2016 145428, WO2016183509, WO2016205755, US 2008/0090747, U.S. Pat. Nos. 5,801,039, 5,340,735, 5,500,364, 5,855,625, RE34606, U.S. Pat. Nos. 5,955,340, 5,700,676, 6,312,936, 6,482,628, 8,530,219, U.S. Provisional Appl Nos. 62/331,282, 62/332,417, 62/343,618, 62/351,649, 62/437,174, 62/437,171, 62/437,509, as well as metalloproteases described in WO1999014341, WO1999033960, WO1999014342, WO1999034003, WO2007044993, WO2009058303, WO 2009 058661, WO2014071410, WO2014194032, WO2014194034, WO2014194054, and WO2014194117. Exemplary additional proteases include, but are not limited to trypsin (e.g., of porcine or bovine origin) and the *Fusarium* protease described in WO89/06270.

Exemplary commercial proteases include, but are not limited to MAXATASE, MAXACAL, MAXAPEM, OPTICLEAN®, OPTIMASE®, PROPERASE®, PURAFECT®, PURAFECT® OXP, PURAMAX®, EXCELLASE®, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST (Danisco US); ALCALASE®, ALCALASE® ULTRA, BLAZE®, BLAZE® EVITY®, BLAZE® EVITY® 16L, CORONASE®, SAVINASE®, SAVINASE® ULTRA, SAVINASE® EVITY®, SAVINASE® EVERTS®, PRIMASE, DURAZYM, POLARZYME®, OVOZYME®, KANNASE®, LIQUANASE®, LIQUANASE® EVERTS®, NEUTRASE®, PROGRESS UNO®, RELASE® and ESPERASE® (Novozymes); BLAP™ and BLAP™ variants (Henkel); LAVERGY™ PRO 104 L (BASF), and KAP® (*B. alkalophilus* subtilisin (Kao)).

Another embodiment is directed to a composition comprising at least one polypeptide described herein and one or more lipase. In some embodiments, the composition comprises from about 0.00001% to about 10%, about 0.0001% to about 10%, about 0.001% to about 5%, about 0.001% to about 2%, or about 0.005% to about 0.5% lipase by weight composition. An exemplary lipase can be a chemically or genetically modified mutant. Exemplary lipases include, but are not limited to, e.g., those of bacterial or fungal origin, such as, e.g., *H. lanuginosa* lipase (see, e.g., EP 258068 and EP 305216), T *lanuginosus* lipase (see, e.g., WO 2014/059360 and WO2015/010009), *Rhizomucor miehei* lipase (see, e.g., EP 238023), *Candida* lipase, such as *C. antarctica* lipase (e.g., *C. antarctica* lipase A or B) (see, e.g., EP 214761), *Pseudomonas* lipases such as *P. alcaligenes* and *P. pseudoalcaligenes* lipase (see, e.g., EP 218272), *P. cepacia* lipase (see, e.g., EP 331376), *P. stutzeri* lipase (see, e.g., GB 1,372,034), *P. fluorescens* lipase, *Bacillus* lipase (e.g., *B. subtilis* lipase (Dartois et al., Biochem. Biophys. Acta 1131: 253-260 (1993)), *B. stearothermophilus* lipase (see, e.g., JP 64/744992), and *B. pumilus* lipase (see, e.g., WO 91/16422)). Exemplary cloned lipases include, but not limited to *Penicillium camembertii* lipase (See, Yamaguchi et al., Gene 103:61-67 (1991)), *Geotricum candidum* lipase (See, Schimada et al., J. Biochem., 106:383-388 (1989)), and various *Rhizopus* lipases, such as, *R. delemar* lipase (See, Hass et al., Gene 109:117-113 (1991)), *R. niveus* lipase (Kugimiya et al., Biosci. Biotech. Biochem. 56:716-719 (1992)) and *R. oryzae* lipase. Other lipolytic enzymes, such as cutinases, may also find use in one or more composition describe herein, including, but not limited to, e.g., cutinase derived from *Pseudomonas mendocina* (see, WO 88/09367) and/or *Fusarium solani pisi* (see, WO90/09446). Exemplary commercial lipases include, but are not limited to M1 LIPASE, LUMA FAST, and LIPOMAX (Genecor); LIPEX®, LIPOCLEAN®, LIPOLASE and LIPOLASE® ULTRA (Novozymes); and LIPASE PS (Amano Pharmaceutical Co. Ltd).

A still further embodiment is directed to a composition comprising at least one polypeptide described herein and one or more amylase. In one embodiment, the composition comprises from about 0.00001% to about 10%, about 0.0001% to about 10%, about 0.001% to about 5%, about 0.001% to about 2%, or about 0.005% to about 0.5% amylase by weight composition. Any amylase (e.g., alpha and/or beta) suitable for use in alkaline solutions may be useful to include in such composition. An exemplary amylase can be a chemically or genetically modified mutant. Exemplary amylases include, but are not limited to those of bacterial or fungal origin, such as, for example, amylases described in GB 1,296,839, WO9100353, WO9402597, WO94183314, WO9510603, WO9526397, WO9535382, WO9605295, WO9623873, WO9623874, WO 9630481, WO9710342, WO9741213, WO9743424, WO9813481, WO 9826078, WO9902702, WO 9909183, WO9919467, WO9923211, WO9929876, WO9942567, WO 9943793, WO9943794, WO 9946399, WO0029560, WO0060058, WO0060059, WO0060060, WO 0114532, WO0134784, WO 0164852, WO0166712, WO0188107, WO0196537, WO02092797, WO 0210355, WO0231124, WO 2004055178, WO2004113551, WO2005001064, WO2005003311, WO 2005018336, WO2005019443, WO2005066338, WO2006002643, WO2006012899, WO2006012902, WO2006031554, WO 2006063594, WO2006066594, WO2006066596, WO2006136161, WO 2008000825, WO2008088493, WO2008092919, WO2008101894, WO2008/112459, WO2009061380, WO2009061381, WO 2009100102, WO2009140504, WO2009149419, WO 2010/059413, WO 2010088447, WO2010091221, WO2010104675, WO2010115021, WO10115028, WO2010117511, WO 2011076123, WO2011076897, WO2011080352, WO2011080353, WO 2011080354, WO2011082425, WO2011082429, WO 2011087836, WO2011098531, WO2013063460, WO2013184577, WO 2014099523, WO2014164777, and WO2015077126. Exemplary commercial amylases include, but are not limited to AMPLIFY®, AMPLIFY PRIME®, BAN, DURAMYL®, TERMAMYL®, TERMAMYL® ULTRA, FUNGAMYL®, STAINZYME®, STAINZYME® PLUS, STAINZYME® ULTRA, and STAINZYME® EVITY® (Novozymes); EFFECTENZ™ S 1000, POWERASE®, PREFERENZ™ S 100, PREFERENZ™ S 110, EXCELLENZ™ S 2000, RAPIDASE and MAXAMYL® P (Danisco US).

Yet a still further embodiment is directed to a composition comprising at least one polypeptide described herein and one or more cellulase. In one embodiment, the composition comprises from about 0.00001% to about 10%, 0.0001% to about 10%, about 0.001% to about 5%, about 0.001% to about 2%, or about 0.005% to about 0.5% cellulase by weight of composition. Any suitable cellulase may find used in a composition described herein. An exemplary cellulase can be a chemically or genetically modified mutant. Exemplary cellulases include but are not limited, to those of bacterial or fungal origin, such as, for example, is described in WO2005054475, WO2005056787, U.S. Pat. Nos. 7,449, 318, 7,833,773, 4,435,307; EP 0495257; and U.S. Provisional Appl. No. 62/296,678. Exemplary commercial cellulases include, but are not limited to, CELLUCLEAN®, CELLUZYME®, CAREZYME®, ENDOLASE®, RENOZYME®, and CAREZYME® PREMIUM (Novozymes); REVITALENZ® 100, REVITALENZ® 200/220, and REVITALENZ® 2000 (Danisco US); and KAC-500(B) (Kao Corporation). In some embodiments, cellulases are incorporated as portions or fragments of mature wild-type or variant cellulases, wherein a portion of the N-terminus is deleted (see, e.g., U.S. Pat. No. 5,874,276).

An even still further embodiment is directed to a composition comprising at least one polypeptide described herein and one or more mannanase. In one embodiment, the composition comprises from about 0.00001% to about 10%, about 0.0001% to about 10%, about 0.001% to about 5%, about 0.001% to about 2%, or about 0.005% to about 0.5% mannanase by weight composition. An exemplary mannanase can be a chemically or genetically modified mutant. Exemplary mannanases include, but are not limited to, those of bacterial or fungal origin, such as, for example, as is described in WO2016007929, USPNs 6566114, 6602842, and 6440991, and International Appl Nos. PCT/US2016/060850 and PCT/US2016/060844. Exemplary commercial mannanases include, but are not limited to MANNAWAY® (Novozymes) and EFFECTENZ™ M 1000, PREFERENZ® M 100, MANNASTAR®, and PURABRITE (Danisco US).

A yet even still further embodiment is directed to a composition comprising at least one polypeptide described herein and one or more peroxidase and/or oxidase enzyme. In one embodiment, the composition comprises from about 0.00001% to about 10%, about 0.0001% to about 10%, about 0.001% to about 5%, about 0.001% to about 2%, or about 0.005% to about 0.5% peroxidase or oxidase by weight composition. A peroxidase may be used in combination with hydrogen peroxide or a source thereof (e.g., a percarbonate, perborate or persulfate) and an oxidase may be used in combination with oxygen. Peroxidases and oxidases are used for "solution bleaching" (i.e., to prevent transfer of a textile dye from a dyed fabric to another fabric when the fabrics are washed together in a wash liquor), alone or in combination with an enhancing agent (see, e.g., WO9412621 and WO9501426). An exemplary peroxidase and/or oxidase can be a chemically or genetically modified mutant. Exemplary peroxidases/oxidases include, but are not limited to those of plant, bacterial, or fungal origin.

Another embodiment is directed to a composition comprising at least one polypeptide described herein and one or more perhydrolase, such as, for example, is described in WO2005056782, WO2007106293, WO2008063400, WO2008106214, and WO2008106215.

In yet another embodiment, at least one polypeptide described herein and one or more additional enzyme contained in at least one composition described herein may each independently range to about 10%, wherein the balance of the cleaning composition is one or more adjunct material.

In some embodiments, at least one composition described herein finds use as a detergent additive, wherein said additive is in a solid or liquid form. Such additive products are intended to supplement and/or boost the performance of conventional detergent compositions and can be added at any stage of the cleaning process. In some embodiments, the density of the laundry detergent composition ranges from about 400 to about 1200 g/liter, while in other embodiments it ranges from about 500 to about 950 g/liter of composition measured at 20° C.

Some embodiments are directed to a laundry detergent composition comprising at least one polypeptide described herein and one or more adjunct materials selected from surfactants, enzyme stabilizers, builder compounds, polymeric compounds, bleaching agents, additional enzymes, suds suppressors, dispersants, lime-soap dispersants, soil suspension agents, anti-redeposition agents, corrosion inhibitors, and combinations thereof. In some embodiments, the laundry compositions also contain softening agents.

Further embodiments are directed to manual dishwashing compositions comprising at least one polypeptide described herein and one or more adjunct material selected from surfactants, organic polymeric compounds, suds enhancing agents, group II metal ions, solvents, hydrotropes, and additional enzymes.

Other embodiments are directed to at least one composition described herein, wherein said composition is a compact granular fabric cleaning composition that finds use in laundering colored fabrics or provides softening through the wash capacity, or is a heavy duty liquid (HDL) fabric cleaning composition. Exemplary fabric cleaning compositions and/or processes for making are described in U.S. Pat. Nos. 6,610,642 and 6,376,450. Other exemplary cleaning compositions are described, for example, in U.S. Pat. Nos. 6,605,458; 6,294,514; 5,929,022; 5,879,584; 5,691,297; 5,565,145; 5,574,005; 5,569,645; 5,565,422; 5,516,448; 5,489,392; and 5,486,303; 4,968,451; 4,597,898; 4,561,998; 4,550,862; 4,537,706; 4,515,707; and 4,515,705.

In some embodiments, the cleaning compositions comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N(CH$_2$COOM)$_2$ where R is C$_{1-12}$alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl)aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400µ to about 1200µ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle is a highly active particle comprising a high level of amino carboxylic builder. Sulphuric acid has also been found to further contribute to the stability of the final particle.

Additional embodiments are directed to a cleaning composition comprising at least one polypeptide described herein and one or more surfactant and/or surfactant system, wherein the surfactant is selected from nonionic surfactants, anionic surfactants, cationic surfactants, ampholytic surfactants, zwitterionic surfactants, semi-polar nonionic surfactants, and mixtures thereof. In some embodiments, the surfactant is present at a level of from about 0.1 to about 60%, while in alternative embodiments the level is from about 1 to about 50%, while in still further embodiments the level is from about 5 to about 40%, by weight of the composition.

In some embodiments, at least one composition described herein comprises one or more detergent builders or builder systems. In one embodiment, the composition comprises from about 1%, from about 0.1% to about 80%, from about 3% to about 60%, from about 5% to about 40%, or from about 10% to about 50% builder by weight composition. Exemplary builders include, but are not limited to alkali metal; ammonium and alkanolammonium salts of polyphosphates; alkali metal silicates; alkaline earth and alkali metal carbonates; aluminosilicates; polycarboxylate compounds; ether hydroxypolycarboxylates; copolymers of maleic anhydride with ethylene or vinyl methyl ether, 1, 3, 5-trihydroxy benzene-2, 4, 6-trisulphonic acid, and carboxymethyloxysuccinic acid; ammonium and substituted ammonium salts of polyacetic acids such as ethylenediamine tetraacetic acid and nitrilotriacetic acid; polycarboxylates such as mellitic acid, succinic acid, citric acid, oxydisuccinic acid, polymaleic acid, benzene 1,3,5-tricarboxylic acid, carboxymethyloxysuccinic acid; and soluble salts thereof.

In some such compositions, the builders form water-soluble hardness ion complexes (e.g., sequestering builders), such as citrates and polyphosphates, e.g., sodium tripolyphosphate, sodium tripolyphospate hexahydrate, potassium tripolyphosphate, and mixed sodium and potassium tripolyphosphate. Exemplary builders are described in, e.g., EP 2100949. In some embodiments, the builders include phosphate builders and non-phosphate builders. In some embodiments, the builder is a phosphate builder. In some embodiments, the builder is a non-phosphate builder. In some embodiments, the builder comprises a mixture of phosphate and non-phosphate builders. Exemplary phosphate builders include, but are not limited to mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, at least one composition described herein comprises one or more chelating agent. In one embodiment, the composition comprises from about 0.1% to about 15% or about 3% to about 10% chelating agent by weight composition. Exemplary chelating agents include, but are not limited to, e.g., copper, iron, manganese, and mixtures thereof.

In some embodiments, at least one composition described herein comprises one or more deposition aid. Exemplary deposition aids include, but are not limited to, e.g., polyethylene glycol; polypropylene glycol; polycarboxylate; soil release polymers, such as, e.g., polytelephthalic acid; clays such as, e.g., kaolinite, montmorillonite, atapulgite, illite, bentonite, and halloysite; and mixtures thereof.

In other embodiments, at least one composition described herein comprises one or more anti-redeposition agent or non-ionic surfactant (which can prevent the re-deposition of soils) (see, e.g., EP 2100949). For example, in ADW compositions, non-ionic surfactants find use for surface modification purposes, in particular for sheeting, to avoid filming and spotting and to improve shine. These non-ionic surfactants also find use in preventing the re-deposition of soils. In some embodiments, the non-ionic surfactant can be ethoxylated nonionic surfactants, epoxy-capped poly(oxyalkylated) alcohols and amine oxides surfactants.

In some embodiments, at least one composition described herein comprises one or more dye transfer inhibiting agent. Exemplary polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, polyvinylimidazoles, and mixtures thereof. In one embodiment, the composition comprises from about 0.0001% to about 10%, about 0.01% to about 5%, or about 0.1% to about 3% dye transfer inhibiting agent by weight composition.

In some embodiments, at least one composition described herein comprises one or more silicate. Exemplary silicates include, but are not limited to, sodium silicates, e.g., sodium disilicate, sodium metasilicate, and crystalline phyllosilicates. In some embodiments, silicates are present at a level of from about 1% to about 20% or about 5% to about 15% by weight of the composition.

In some additional embodiments, at least one composition described herein comprises one or more dispersant. Exemplary water-soluble organic materials include, but are not limited to, e.g., homo- or co-polymeric acids or their salts, in which the polycarboxylic acid comprises at least two carboxyl radicals separated from each other by not more than two carbon atoms.

In some further embodiments, at least one composition described herein comprises one or more enzyme stabilizer. In some embodiments, the enzyme stabilizer is water-soluble sources of calcium and/or magnesium ions. In some embodiments, the enzyme stabilizers include oligosaccharides, polysaccharides, and inorganic divalent metal salts, including alkaline earth metals, such as calcium salts. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). Chlorides and sulfates also find use in some embodiments. Exemplary oligosaccharides and polysaccharides (e.g., dextrins) are described, for example, in WO 07/145964. In some embodiments, reversible protease inhibitors also find use, such as boron-containing compounds (e.g., borate, 4-formyl phenyl boronic acid, and phenyl-boronic acid derivatives (such for example, thos described in WO96/41859) and/or a peptide aldehyde, such as, for example, is further described in WO2009/118375 and WO2013004636.

In some embodiments, at least one composition described herein comprises one or more bleach, bleach activator, and/or bleach catalyst. In some embodiments, at least one composition described herein comprises one or more inorganic and/or organic bleaching compound. Exemplary inorganic bleaches include, but are not limited to perhydrate salts, e.g., perborate, percarbonate, perphosphate, persulfate, and persilicate salts. In some embodiments, inorganic perhydrate salts are alkali metal salts. In some embodiments, inorganic perhydrate salts are included as the crystalline solid, without additional protection, although in some other embodiments, the salt is coated. Bleach activators are typically organic peracid precursors that enhance the bleaching action in the course of cleaning at temperatures of 60° C. and below. Exemplary bleach activators include compounds which, under perhydrolysis conditions, give aliphatic peroxoycarboxylic acids having from about 1 to about 10 carbon atoms or about 2 to about 4 carbon atoms, and/or optionally substituted perbenzoic acid. Exemplary bleach activators ae described, for example, in EP 2100949. Exemplary bleach catalysts include, but are not limited to, manganese triazacyclononane and related complexes, as well as cobalt, copper, manganese, and iron complexes. Additional exemplary bleach catalysts are described, for example, in U.S. Pat. Nos. 4,246,612; 5,227,084; 4,810,410; WO 99/06521; and EP 2100949.

In some embodiments, at least one composition described herein comprises one or more catalytic metal complexes. In some embodiments, a metal-containing bleach catalyst finds use. In some embodiments, the metal bleach catalyst comprises a catalyst system comprising a transition metal cation of defined bleach catalytic activity (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof (see, e.g., U.S. Pat. No. 4,430,243). In some embodiments, one or more composition described herein is catalyzed by means of a manganese compound. Such compounds and levels of use are described, for example, in U.S. Pat. No. 5,576,282. In additional embodiments, cobalt bleach catalysts find use and are included in one or more composition described herein. Various cobalt bleach catalysts are described, for example, in U.S. Pat. Nos. 5,597,936 and 5,595,967.

In some additional embodiments, at least one described herein includes a transition metal complex of a macropolycyclic rigid ligand (MRL). As a practical matter, and not by way of limitation, in some embodiments, the compositions and cleaning processes described herein are adjusted to provide on the order of at least one part per hundred million, from about 0.005 ppm to about 25 ppm, about 0.05 ppm to about 10 ppm, or about 0.1 ppm to about 5 ppm of active MRL in the wash liquor. Exemplary MRLs include, but are not limited to special ultra-rigid ligands that are cross-bridged, such as, e.g., 5,12-diethyl-1,5,8,12-tetraazabicyclo (6.6.2) hexadecane. Exemplary metal MRLs are described, for example, in WO 2000/32601 and U.S. Pat. No. 6,225,464.

In another embodiment, at least one composition described herein comprises one or more metal care agent. In some embodiments, the composition comprises from about 0.1% to about 5% metal care agent by weight composition. Exemplary metal care agents include, for example, aluminum, stainless steel, and non-ferrous metals (e.g., silver and copper). Additional exemplary metal care agents are described, for example, in EP 2100949, WO 94/26860, and WO 94/26859. In some compositions, the metal care agent is a zinc salt.

In some embodiments, the cleaning composition is a high density liquid (HDL) composition comprising at least one polypeptide described herein. The HDL liquid laundry detergent can comprise a detersive surfactant (10-40%) comprising anionic detersive surfactant selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof; and optionally non-ionic surfactant selected from a group of linear or branched or random chain, substituted or unsubstituted alkyl alkoxylated alcohol, for example, a $C_8$-$C_{18}$alkyl ethoxylated alcohol and/or $C_6$-$C_{12}$alkyl phenol alkoxylates, optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from alkanolamine sulpho-betaines); ampholytic surfactants; semi-polar non-ionic surfactants; and mixtures thereof.

The composition can comprise optionally, a surfactancy boosting polymer consisting of amphiphilic alkoxylated grease cleaning polymers selected from a group of alkoxylated polymers having branched hydrophilic and hydrophobic properties, such as alkoxylated polyalkylenimines in the range of 0.05 wt %-10 wt % and/or random graft polymers typically comprising a hydrophilic backbone comprising monomers selected from the group consisting of: unsaturated $C_1$-$C_6$carboxylic acids, ethers, alcohols, aldehydes, ketones, esters, sugar units, alkoxy units, maleic anhydride, saturated polyalcohols such as glycerol, and mixtures thereof and hydrophobic side chain(s) selected from the group consisting of: $C_4$-$C_{25}$alkyl group, polypropylene, polybutylene, vinyl ester of a saturated $C_2$-$C_6$mono-carboxylic acid, $C_1$-$C_6$alkyl ester of acrylic or methacrylic acid, and mixtures thereof.

The composition can comprise additional polymers such as soil release polymers including, for example, anionically end-capped polyesters, for example SRP1; polymers comprising at least one monomer unit selected from saccharide, dicarboxylic acid, polyol and combinations thereof, in random or block configuration; ethylene terephthalate-based polymers and co-polymers thereof in random or block configuration, for example, Repel-o-tex SF, SF-2 and SRP6, Texcare SRA100, SRA300, SRN100, SRN170, SRN240, SRN300 and SRN325, Marloquest SL; anti-redeposition polymers (0.1 wt % to10 wt %, including, for example, carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof; vinylpyrrolidone homopolymer; and/or polyethylene glycol with a molecular weight in the range of from 500 to 100,000 Da); cellulosic polymer (including, for example, alkyl cellulose; alkyl alkoxyalkyl cellulose; carboxyalkyl cellulose; alkyl carboxyalkyl cellulose, examples of which include carboxymethyl cellulose, methyl cellulose, methyl hydroxyethyl cellulose, methyl carboxymethyl cellulose; and mixtures thereof); and polymeric carboxylate (such as, for example, maleate/acrylate random copolymer or polyacrylate homopolymer).

The composition can further comprise saturated or unsaturated fatty acid, preferably saturated or unsaturated $C_{12}$-$C_{24}$ fatty acid (0-10 wt %); deposition aids (including, for example, polysaccharides, cellulosic polymers, polydiallyl dimethyl ammonium halides (DADMAC), and co-polymers of DADMAC with vinyl pyrrolidone, acrylamides, imidazoles, imidazolinium halides, and mixtures thereof, in random or block configuration; cationic guar gum; cationic cellulose such as cationic hydoxyethyl cellulose; cationic starch; cationic polyacylamides; and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition can further comprise silicone or fatty-acid based suds suppressors; an enzyme stabilizer; hueing dyes, calcium and magnesium cations, visual signaling ingredients, anti-foam (0.001 to about 4.0 wt %), and/or structurant/thickener (0.01-5 wt %) selected from the group consisting of diglycerides, triglycerides, ethylene glycol distearate, microcrystalline cellulose, cellulose based materials, microfiber cellulose, biopolymers, xanthan gum, gellan gum, and mixtures thereof.

In some embodiments, the composition is a high density powder (HDD) composition comprising at least one polypeptide described herein. The HDD powder laundry detergent can comprise a detersive surfactant including anionic detersive surfactants (selected from linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from 1 linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from alkyl pyridinium compounds, alkyl quaternary ammonium compounds, alkyl quaternary phosphonium compounds, alkyl ternary sulphonium compounds, and mixtures thereof); zwitterionic and/or amphoteric detersive surfactants (selected from alkanolamine sulpho-betaines); ampholytic surfactants; semi-polar non-ionic surfactants and mixtures thereof; builders (phosphate free builders, e.g., zeolite builders examples of which include zeolite A, zeolite X, zeolite P and zeolite MAP in the range of 0 to less than 10 wt %); phosphate builders, e.g., sodium tri-polyphosphate in the range of 0 to less than 10 wt %; citric acid, citrate salts and nitrilotriacetic acid or salt thereof in the range of less than 15 wt %; silicate salt (sodium or potassium silicate or sodium meta-silicate in the range of 0 to less than 10 wt % or layered silicate (SKS-6)); carbonate salt (sodium carbonate and/or sodium bicarbonate in the range of 0 to less than 10 wt %); and bleaching agents (photobleaches, e.g., sulfonated zinc phthalocyanines, sulfonated aluminum phthalocyanines, xanthenes dyes, and mixtures thereof); hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOB S, nitrile quats, and mixtures thereof); hydrogen peroxide; sources of hydrogen peroxide (inorganic perhydrate salts, e.g., mono or tetra hydrate sodium salt of perborate, percarbonate, persulfate, perphosphate, or persilicate); preformed hydrophilic and/or hydrophobic peracids (selected from percarboxylic acids and salts, percarbonic acids and salts, perimidic acids and salts, peroxymonosulfuric acids and salts, and mixtures thereof); and/or bleach catalyst (e.g., imine bleach boosters, such as iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof), metal-containing bleach catalyst (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further comprise additional detergent ingredients including perfume microcapsules, starch encapsulated perfume accord, an enzyme stabilizer, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the composition is an ADW detergent composition comprising at least one polypeptide described herein. The ADW detergent composition can comprise two or more non-ionic surfactants selected from ethoxylated non-ionic surfactants, alcohol alkoxylated surfactants, epoxy-capped poly(oxyalkylated) alcohols, and amine oxide surfactants present in amounts from 0-10% by wt; builders in the range of 5-60% by wt. comprising either phosphate (mono-phosphates, di-phosphates, tri-polyphosphates or oligomeric-poylphosphates), sodium tripolyphosphate-STPP or phosphate-free builders (amino acid based compounds, e.g., MGDA (methyl-glycine-diacetic acid) and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), and B-alaninediacetic acid (B-ADA) and their salts), homopolymers and copolymers of poly-carboxylic acids and their partially or completely neutralized salts, monomeric polycarboxylic acids and hydroxycarboxylic acids and their salts in the range of 0.5-50% by wt; sulfonated/carboxylated polymers (provide dimensional stability to the product) in the range of about 0.1 to about 50% by wt; drying aids in the range of about 0.1 to about 10% by wt (selected from polyesters, especially anionic polyesters optionally together with further monomers with 3-6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1 to about 20% by wt (sodium or potassium silicates, e.g., sodium disilicate, sodium meta-silicate and crystalline phyllosilicates); bleach-inorganic (e.g., perhydrate salts such as perborate, percarbonate, perphosphate, persulfate and persilicate salts) and organic (e.g., organic peroxyacids including diacyl and tetraacylperoxides, especially diperoxydodecanedioc acid, diperoxytetradecanedioc acid, and diperoxyhexadecanedioc acid); bleach activator-organic peracid precursors in the range from about 0.1 to about 10% by wt; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1-5% by wt (selected from benzatriazoles, metal salts and complexes, and silicates); enzymes in the range from about 0.01-5.0 mg of active enzyme per gram of ADW detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, and mixtures thereof); and enzyme stabilizer components (selected from oligosaccharides, polysaccharides and inorganic divalent metal salts).

More embodiments are directed to compositions and methods of treating fabrics (e.g., to desize a textile) using at least one polypeptide described herein. Fabric-treating methods are well known in the art (see, e.g., U.S. Pat. No. 6,077,316). For example, the feel and appearance of a fabric can be improved by a method comprising contacting the fabric with a polypeptide described herein in a solution. The fabric can be treated with the solution under pressure.

At least one polypeptide described herein can be applied during or after weaving a textile, during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. At least one polypeptide described herein can be applied during or after weaving to remove the sizing starch or starch derivatives. After weaving, the polypeptide can be used to remove the size coating before further processing the fabric to ensure a homogeneous and wash-proof result. At least one polypeptide described herein can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. At least one polypeptide described herein can be used in methods of finishing denim garments (e.g., a "bio-stoning process"), enzymatic desizing and providing softness to fabrics, and/or finishing process.

Non-limiting examples of compositions and methods disclosed herein include the following embodiments:

1. An isolated polypeptide having serine protease activity, selected from:
    a) a polypeptide comprising an amino acid sequence with at least 91% identity with the amino acid sequence of SEQ ID NO:22;
    b) a polypeptide comprising an amino acid sequence with at least 94% identity with the amino acid sequence of SEQ ID NO:23;
    c) a polypeptide comprising an amino acid sequence with at least 98% identity with the amino acid sequence of SEQ ID NO:24; and
    d) a polypeptide comprising an amino acid sequence with at least 80% identity with the amino acid sequence of SEQ ID NO:25.

2. An isolated polypeptide having serine protease activity and comprising a predicted precursor amino acid sequence selected from: SEQ ID NO:3; SEQ ID NO:6; SEQ ID NO:9; and SEQ ID NO:12.

3. An isolated polypeptide having serine protease activity and comprising a protease catalytic region selected from:
    a) an amino acid sequence with at least 96% identity with the amino acid sequence of SEQ ID NO:18;
    b) an amino acid sequence with at least 98% identity with the amino acid sequence of SEQ ID NO:19;
    c) an amino acid sequence of SEQ ID NO:20; and
    d) an amino acid sequence with at least 91% identity with the amino acid sequence of SEQ ID NO:21.

4. A recombinant construct comprising a regulatory sequence functional in a production host operably linked to a nucleotide sequence encoding at least one polypeptide of any of embodiments 1-3.

5. The recombinant construct of embodiment 4, wherein said host is selected from the group consisting of fungi, bacteria, and algae.

6. A method for producing at least one polypeptide comprising:
    (a) transforming a production host with the recombinant construct of embodiment 4; and
    (b) culturing the production host of step (a) under conditions whereby at least one polypeptide is produced.

7. A method according to embodiment 6, wherein the polypeptideis optionally recovered from the production host.

8. A serine protease-containing culture supernatant obtained by the method of embodiment 6 or 7.

9. A recombinant microbial production host for expressing at least one polypeptide, said recombinant microbial production host comprising the recombinant construct of embodiment 4.

10. A production host according to embodiment 9, wherein said host is selected from the group consisting of bacteria, fungi and algae.

11. Animal feed comprising at least one polypeptide of any one of embodiments 1-3, wherein said polypeptide is present in an amount from 1-20 g/ton feed.

12. The animal feed of embodiment 11, further comprising: a) at least one direct fed microbial or b) at least one other enzyme or c) at least one direct fed microbial and at least one other enzyme.

13. A feed, feedstuff, a feed additive composition or premix comprising at least one polypeptide of any one of embodiments 1-3.

14. The feed, feedstuff, feed additive composition or premix of embodiment 13, further comprising: a) at least one direct fed microbial or b) at least one other enzyme or c) at least one direct fed microbial and at least one other enzyme.

15. The feed additive composition of embodiments 13 or 14, wherein said composition further comprises at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben, and propyl paraben.

16. A granulated feed additive composition for use in animal feed comprising at least one polypeptide of any one of embodiments 1-3, wherein the granulated feed additive composition comprises particles produced by a process selected from the group consisting of high shear granulation, drum granulation, extrusion, spheronization, fluidized bed agglomeration, fluidized bed spray coating, spray drying, freeze drying, prilling, spray chilling, spinning disk atomization, coacervation, tableting, and combination thereof.

17. The granulated feed additive composition of embodiment 16, wherein the mean diameter of the particles is greater than 50 microns and less than 2000 microns.

18. The feed additive composition of embodiment 17, wherein said composition is in a liquid form.

19. The feed additive composition of embodiment 18, wherein said composition is in a liquid form suitable for spray-drying on a feed pellet.

20. A cleaning or detergent composition comprising at least one polypeptide of embodiment 1 or 3.

21. The composition of embodiment 20, wherein said polypeptide comprises a protease catalytic region comprising an amino acid sequence of SEQ ID NO:20, or an amino acid sequence with at least 96% identity with the amino acid sequence of SEQ ID NO:18.

22. The composition of embodiment 20, wherein said polypeptide comprises an amino acid sequence with at least 91% identity with the amino acid sequence of SEQ ID NO:22, or at least 94% identity with the amino acid sequence of SEQ ID NO:23.

23. The composition of embodiment 20, wherein said polypeptide comprises (i) an amino acid sequence with at least 91% identity with the amino acid sequence of SEQ ID NO:22, or (ii) a protease catalytic region comprising an amino acid sequence with at least 96% identity with the amino acid sequence of SEQ ID NO:18.

24. The composition of embodiment 20, wherein said polypeptide comprises (i) an amino acid sequence with at least 94% identity with the amino acid sequence of SEQ ID NO:23, or (ii) a protease catalytic region comprising an amino acid sequence of SEQ ID NO:20.

25. The composition of any one of embodiments 20-24, wherein said composition further comprises one or more surfactant.

26. The composition of any one of embodiments 20-25, wherein said polypeptide has cleaning activity in said composition.

27. The composition of any one of embodiments 20-26, wherein said polypeptide has cleaning activity in said composition at about 16° C. and/or about 32° C.

28. The composition of any one of embodiments 20-27, wherein said composition is selected from a laundry detergent, a fabric softening detergent, a dishwashing detergent, and a hard-surface cleaning detergent.

29. The composition of any one of embodiments 20-28, further comprising (i) one or more other enzymes selected from acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, oxidoreductases, pectate lyases, pectin acetyl esterases, pectinases, pentosanases, perhydrolases, peroxidases, phenoloxidases, phosphatases, phospholipases, phytases, polyesterases, polygalacturonases, additional proteases, pullulanases, reductases, rhamnogalacturonases, cellulases, beta-glucanases, tannases, transglutaminases, xylan acetyl-esterases, xylanases, and xylosidases; (ii) one or more ions selected from calcium and zinc; (iii) one or more adjunct materials; (iv) one or more stabilizers; (v) from about 0.001% to about 1.0 weight % of said polypeptide; (vi) one or more bleaching agents; and (vii) combinations thereof.

30. The composition of any one of embodiments 20-29, wherein said composition is phosphate-free.

31. The composition of any one of embodiments 20-29, wherein said composition contains phosphate.

32. The composition of any one of embodiments 20-31, wherein said composition is boron free.

33. The composition of any one of embodiments 20-31, wherein said composition contains boron.

34. The composition of any one of embodiments 20-33, wherein said composition is a granular, powder, solid, bar, liquid, tablet, gel, paste and/or unit dose composition.

35. A method of cleaning, comprising contacting a surface or an item in need of cleaning with an effective amount of at least one polypeptide of embodiment 1 or 3; and optionally further comprising the step of rinsing said surface or item after contacting said surface or item with said polypeptide.

36. The method of embodiment 35, wherein said polypeptide comprises a protease catalytic region comprising an amino acid sequence of SEQ ID NO:20, or an amino acid sequence with at least 96% identity with the amino acid sequence of SEQ ID NO:18.

37. The method of embodiment 35, wherein said polypeptide comprises an amino acid sequence with at least 91% identity with the amino acid sequence of SEQ ID NO:22, or at least 94% identity with the amino acid sequence of SEQ ID NO:23.

38. The method of embodiment 35, wherein said polypeptide comprises (i) an amino acid sequence with at least 91% identity with the amino acid sequence of SEQ ID NO:22, or (ii) a protease catalytic region comprising an amino acid sequence with at least 96% identity with the amino acid sequence of SEQ ID NO:18.

39. The method of embodiment 35, wherein said polypeptide comprises (i) an amino acid sequence with at least 94% identity with the amino acid sequence of SEQ ID NO:23, or (ii) a protease catalytic region comprising an amino acid sequence of SEQ ID NO:20.

40. A method of cleaning, comprising contacting a surface or an item in need of cleaning with the composition of any one of embodiments 20-34; and optionally further comprising the step of rinsing said surface or item after contacting said surface or item with said composition.

41. The method of any one of embodiments 35-40, wherein said item is dishware or fabric.

EXAMPLES

Unless defined otherwise herein, all technical and scientific terms used herein have the same meaning as commonly understood by one of ordinary skill in the art to which this disclosure belongs. Singleton, et al., *DICTIONARY OF MICROBIOLOGY AND MOLECULAR BIOLOGY*, 2D ED., John Wiley and Sons, New York (1994), and Hale & Marham, *THE HARPER COLLINS DICTIONARY OF BIOLOGY*, Harper Perennial, N.Y. (1991) provide one of skill with a general dictionary of many of the terms used with this disclosure.

The disclosure is further defined in the following Examples. It should be understood that the Examples, while indicating certain embodiments, is given by way of illustration only. From the above discussion and the Examples, one skilled in the art can ascertain essential characteristics of this disclosure, and without departing from the spirit and scope thereof, can make various changes and modifications to adapt to various uses and conditions.

Example 1

Cloning of *Streptomyces* sp Trypsin-Type Serine Proteases

Four bacterial strains (*Streptomyces* sp. C004, *Streptomyces* sp. C009, *Streptomyces* sp. C001 and *Streptomyces* sp. S055) were selected as potential sources of enzymes which may be useful in various industrial applications. Chromosomal DNA was isolated from the four strains and sequenced using Illumina's next generation sequencing technology. Genes encoding trypsin-like serine proteases were identified after annotation in the four aforementioned *Streptomyces* species; and their nucleotide or amino acid sequence identified.

The genes for all 4 proteins have an N-terminal signal peptide as predicted by SignalP software version 4.0 (Nordahl Petersen et al. (2011) Nature Methods, 8:785-786), suggesting that they are all secreted enzymes.

The nucleotide sequence of the SspCPro29 gene isolated from *Streptomyces* sp. C009 is set forth as SEQ ID NO:1. The predicted signal sequence of the SspCPro29 precursor protein is set forth as SEQ ID NO:2. The amino acid sequence of the SspCPro29 precursor protein is set forth as SEQ ID NO:3.

The nucleotide sequence of the SspCPro33 gene isolated from *Streptomyces* sp. C001 is set forth as SEQ ID NO:4: The predicted signal sequence of the SspCPro33 precursor protein is set forth as SEQ ID NO:5. The amino acid sequence of the SspCPro33 precursor protein is set forth as SEQ ID NO:6. The nucleotide sequence of the SspCPro23 gene isolated from *Streptomyces* sp. C003 is set forth as SEQ ID NO:7.

The predicted signal sequence of the SspCPro23 precursor protein is set forth as SEQ ID NO:8. The amino acid sequence of the SspCPro23 precursor protein is set forth as SEQ ID NO:9. The nucleotide sequence of the SspCPro59 gene isolated from *Streptomyces* sp. C055 is set forth as SEQ ID NO:10.

The predicted signal sequence of the SspCPro59 precursor protein is set forth as SEQ ID NO:11. The amino acid sequence of the SspCPro59 precursor protein is set forth as SEQ ID NO:12.

Based on signal sequence prediction the full length amino acid sequences are predicted as follows: SspCPro29 (SEQ ID NO:22); SspCPro33 (SEQ ID NO: 23); SspCPro23 (SEQ ID NO:24); and SspCPro59 (SEQ ID NO:25).

Example 2

Expression of *Streptomyces* sp Trypsin-Type Serine Proteases

The DNA sequences encoding the propeptide-mature form (precursor protein minus signal sequence) of *Streptomyces* sp trypsin homologs SspCPro23, SspC29, SspC33 and SspC59 were synthesized and were each inserted into the *Bacillus subtilis* expression vector p2JM103BBI (Vogtentanz, *Protein Expr Purif,* 55:40-52, 2007) by Generay (Shanghai, China). The resulting plasmids were designated pGX384(AprE-SspCPro23), pGX390(AprE-SspCPro29), pGX394(AprE-SspCPro33) and pGX738 (AprE-SspCPro59). The synthetic genes have an alternative start codon (GTG).

The plasmid map of pGX390(AprE-SspCPro29) is provided in FIG. 1 and the other three plasmids have similar composition with the exception of the inserted gene encoding each serine protease gene of interest (GOI). The nucleotide sequences of synthetic AprE-SspCPro23, AprE-SspCPro29, AprE-SspCPro33, and AprE-SspCPro59 genes are set forth as SEQ ID NO: 13, 14, 15 and 16, respectively. Ligation of the gene encoding each GOI into the linearized expression vector resulted in the addition of three codons (encoding residues Ala-Gly-Lys) between the 3' end of the sequence encoding the *B. subtilis* AprE signal and the 5' end of the sequence encoding the propeptide-mature sequence. The AprE signal sequence (SEQ ID NO: 17) was used to direct the recombinant proteins for secretion in *B. subtilis*.

The expression plasmids were then transformed into suitable *B. subtilis* cells and the transformed cells were cultured on Luria Agar plates supplemented with 5 ppm Chloramphenicol and 1.2% skim milk (Cat #232100, Difco). Colonies forming largest clear halos were picked and used to inoculated liquid cultures. The fermentation was carried out in 250 mL shake flasks using a MOPS-based defined medium, supplemented with 5 mM $CaCl_2$).

For purification of SspCPro29 and SspCPro33 proteases, clarified supernatant from shake flask cultures was subjected to column chromatography using hydrophophic interaction and ion exchange resins. The resulting active protein fractions were then pooled and concentrated via the 10K Amicon Ultra devices, and stored in 40% glycerol at −20° C. until usage.

Utilizing the protein sequence annotations for the *Streptomyces griseus* serine protease Streptogrisin C (Uniprot accession number P52320), the various sequence regions of the SspCPro29, SspCPro 23, SspCPro 33 and SspCPro 59 were further analyzed to identify the putative amino acid residues comprising the catalytic domains of these proteases. Streptogrisin C is expressed as a 457 residue polypeptide that comprises a signal sequence (residues 1-34), a propeptide region (residues 35-202), and a mature chain (residues 203 to 457).

The mature chain is further comprised of a catalytic domain (residues 203 to 393, SEQ ID NO:39), a linker (residues 394-413) and a chitin binding region (residues 415-457). Based on this information, the catalytic domains for SspCPro29, SspCPro 23, SspCPro 33 and SspCPro 59 were predicted as: SEQ ID NO: 18, SEQ ID NO: 19, SEQ ID NO: 20, and SEQ ID NO: 21, respectively.

Example 3

Proteolytic Activity of *Streptomyces* sp Trypsin-Type Serine Proteases

The proteolytic activities of purified SspCPro29 and SspCPro33 were measured in 50 mM HEPES buffer (pH 8), using Suc-Ala-Ala-Pro-Phe-pNA (AAPF-pNA, Cat #L-1400.0250, BACHEM) as a substrate. A sample of the commercial product RONOZYME® ProAct protease (DSM) was used as a reference. Prior to the reaction, the enzymes were diluted with Purified water (Millipore) to specific concentrations. The AAPF-pNA was dissolved in Dimethyl sulfoxide (DMSO, Cat #STBD2470V, Sigma) to a final concentration of 10 mM.

To initiate the reaction, firstly 5 µL of AAPF-pNA was mixed with 85 µL of HEPES buffer in a non-binding 96-well microtiter plate (96-MTP) (Corning Life Sciences, #3641) and incubated at 40° C. for 5 min at 600 rpm in a Thermomixer (Eppendorf), then 10 µL of the diluted enzyme (or Purified $H_2O$ alone as the blank control) was added. After 10 min incubation in a Thermomixer at 40° C. and 600 rpm, the reaction plate was directly read at 410 nm using a SpectraMax 190. Net $A_{410}$ was calculated by subtracting the $A_{410}$ of the blank control from that of enzyme, and then plotted against different protein concentrations (from 0.02 ppm to 0.3125 ppm). Each value was the mean of triplicate assays.

The proteolytic activity on AAPF-pNA substrate is shown on FIG. 2 as Net $A_{410}$. The proteolytic activities of SspCPro23 and SsCPro59 were measured using clarified supernatant from shake flask cultures. The clarified culture supernatant of *B. subtilis* cells transformed with p2JM103BBI (lacking a protease gene) was used as the vector control. Prior to the reaction, the supernatants were diluted 200 fold with purified water. The assay procedure was carried out as described above, and the Net $A_{410}$ was calculated by subtracting the $A_{410}$ of the vector control from that of enzyme sample. Each value was the mean of triplicate assays. The proteolytic activity is shown as Net $A_{410}$ on Table 1, indicating that SspCPro23 and SspCPro59 are active proteases.

TABLE 1

| Enzyme activity of SspCPro59 and SspCPro23 on pNA-AAPF substrate | |
|---|---|
| Protein ID | Net absorbance 410 nm |
| SspCPro23 | 0.24 |
| SspCPro59 | 0.27 |

Example 4 pH Profile of *Streptomyces* sp Trypsin-Type Serine Proteases

With AAPF-pNA as the substrate, the pH profile of trypsin homologs was studied in 25 mM glycine/sodium acetate/HEPES buffer with different pH values (ranging from pH 3 to 10). Prior to the assay, 85 µL of 25 mM glycine/sodium acetate/HEPES buffer with a specific pH value was first mixed with 5 µL of 10 mM AAPF-pNA in a 96-MTP, and then 10 µL of purified water. Diluted enzyme (0.2 ppm for purified SspCPro29 and SspCPro33, or clarified supernatant of SspCPro23 and SspCPro59 diluted 200 fold) was then added to initiate the reaction. Water, or supernatant from vector control (200 fold diluted) were used as the blank control for purified or unpurified enzymes, respectively. The reaction was performed and analyzed as described in Example 3. Enzyme activity at each pH was reported as relative activity where the activity at the optimal pH was set to be 100%. The pH values tested for purified enzymes (SspCPro29 and SspCPro33) were 3, 4, 5, 6, 7, 8, 9 and 10; and for the unpurified (SspCPro23 and SspCPro59) were 3, 5.5, 8, 9, 10. Each value was the mean of triplicate assays.

As shown in FIG. 3, all the trypsin homologs were alkaline proteases.

Example 5

Temperature Profile of *Streptomyces* sp Trypsin-Type Serine Proteases

The temperature profile of trypsin homologs was analyzed in 50 mM HEPES buffer (pH 8) using the AAPF-pNA assay. Prior to the reaction, 85 µL of 50 mM pH 8.0 HEPES buffer and 5 µL of 10 mM AAPF-pNA were added in a 200 µL PCR tube, which was then subsequently incubated in a Peltier Thermal Cycler (BioRad) at desired temperatures (between 30-80° C.) for 5 min. After the incubation, 10 µL of enzyme sample (0.2 ppm for purified SspCPro29 and SspCPro33, and clarified supernatant (200 fold diluted) for SspCPro23 and SspCPro59) was added to the substrate to initiate the reaction. Water alone or supernatant from vector control (200 fold diluted) was added as the blank control for purified or unpurified enzymes, respectively. Following 10 min incubation in the Peltier Thermal Cycler at different temperatures, 80 µL of the reaction mixture was transferred to a new 96-MTP and the absorbance was read at 410 nm. The activity was reported as relative activity where the activity at the optimal temperature was set to be 100%. The tested temperatures for purified enzymes (SspCPro29 and SspCPro33) were 30, 35, 40, 45, 50, 55, 60, 65, 70, 75 and 80° C.; and for unpurified proteins SspCPro23 and SspCPro59 were tested at 35, 40, 50, 60 and 70° C. Each value reported is the mean of triplicate assays. Results are shown in FIG. 4.

Example 6

Corn Soy Meal Hydrolysis by *Streptomyces* sp Trypsin-Type Serine Proteases

The extent of corn soy meal hydrolysis (60% corn flour and 40% soybean meal) by the trypsin homologs was evaluated using the OPA (o-phthalaldehyde) or the BCA (bicinchoninic acid) detection assays described below, to measure the amount of newly produced N-terminal amine groups or soluble peptides, respectively, released into the supernatant after the enzymatic reactions. To conduct the assays, 140 µL of the corn soy meal substrate (10% (w/w) corn soy meal slurry suspended in MES pH 6 buffer) was mixed with 20 µL of a diluted purified enzyme sample (SspCPro29 and SspCPro33) or with 60 µL of the clarified supernatant (SspCPro23 and SspCPro59)-in a 96-MTP. After incubation for 2 hrs at 40° C. in an incubator, the plates were centrifuged at 3700 rpm for 15 min at 4° C. The resulting supernatant was diluted 10 times in water to prepare for subsequent reaction product detection using the OPA and BCA assays. For purified proteases, a sample of RONOZYME® ProAct protease (DSM) was included as the commercial benchmark protease and water was used as the (no enzyme) blank control. For the unpurified, the supernatant from vector control was applied as the blank control.

The OPA reagent was prepared by mixing 30 mL of 2% tri-sodium phosphate buffer (pH 11), 800 µL of 4% OPA (Cat #P1378, Sigma, dissolved in 96% ethanol), 1 mL of 3.52% dithiothreitol (Cat #D0632, Sigma), and 8.2 mL of $H_2O$. The reaction was initiated by adding 10 µL of the 10× diluted protease reaction to 175 µL OPA reagent in a 96-MTP (Cat #3635, Corning Life Sciences). After 2 min incubation at 20° C., the absorbance of the resulting solution was measured at 340 nm ($A_{340}$) using a spectrophotometer. The net $A_{340}$ was calculated by subtracting the $A_{340}$ of the blank (water for SspCPro29 and SspCPro33; supernatant from vector control for SspCPro23 and SspCPro59) control from that of each protease reaction, to measure the extent of corn soy meal hydrolysis achieved by each protease sample. The results are shown on FIG. 5A and Table 2.

The BCA reaction was conducted by mixing 10 µL diluted supernatant with 200 BCA reagent following manufacturer guidelines The incubation was conducted in a thermomixer at 37° C. for 30 min and the product of the reactions were measured in a spectrophotometer as an endpoint absorbance reading at 562 nm. The net $A_{562}$ was calculated by subtracting the $A_{562}$ of the blank (water for SspCPro29 and SspCPro33; supernatant from vector control for SspCPro23 and SspCPro59) control from that of each protease reaction, to measure the extent of corn soy meal hydrolysis achieved by each protease sample. The results are shown on FIG. 5B and Table 2.

TABLE 2

OPA and BCA corn soy meal hydrolysis by SspCPro23 and SspCPro59 proteases at pH 6

| | OPA ($Net_{340}$) | BCA ($Net_{562}$) |
|---|---|---|
| SspCPro23 | 0.04 | 0.04 |
| SspCPro59 | 0.06 | 0.06 |

Example 7

Pepsin Stability of *Streptomyces* sp Trypsin-Type Serine Proteases

Pepsin stability of trypsin homologs was analyzed by incubating them with pepsin (Sigma, Cat. No. P7000) in 50 mM sodium acetate buffer (pH 3.0) and using AAPF-pNA as the substrate for remaining activity measurement. Trypsin homologs and pepsin were first mixed in ratios (w/w) of 1:0, 1:25, 1:250 or 1:2500, where the trypsin homologs were dosed at 20 ppm; and the resulting mixture was subsequently incubated at 37° C. for 30 min. Meanwhile, 20 ppm aliquots of each trypsin homolog were kept on ice as untreated controls. For remaining activity measurement, 5 µL of 10 mM AAPF-pNA was mixed with 85 µL of HEPES buffer (50 mM, pH 8.0) in a 96-MTP, then 10 µL of the purified water diluted mixture (0.2 ppm or $H_2O$ alone as the blank control) was added. The reaction was performed and analyzed as described in Example 3.

Table 3 shows the residual enzyme activity following pepsin treatment, where the activity of the untreated samples kept on ice was set to 100%.

TABLE 3

Pepsin stability of serine proteases SspCPro29 and SspCPro33

| | trypsin | | trypsin:pepsin (ratios) | |
|---|---|---|---|---|
| Sample | untreated | only | 1:25 | 1:250 | 1:2500 |
| SspCPro29 | 100 | 82 | 87 | 97 | 104 |
| SspCPro33 | 100 | 97 | 95 | 98 | 106 |
| ProAct | 100 | 101 | 102 | 100 | 94 |

Example 8

Stability of SspCPro29 Protease Under Feed Pelleting Conditions

The pelleting conditions were as follows: 62.5 g of a concentrated solution of SspCPro29 protease consisting of 38.37 g protein was diluted in tap water to 600 mL, and mixed with 120 kg of corn soy feed (60% Corn, 31.5% Soybean meal, 4.0% Soy oil, 0.4% Salt, 0.2% DL-Methionine, 1.16% Limestone, 1.46% calcium phosphate, and 1.25% vitamin and mineral mixture, by weight). This mixture was pelleted at 90° C., or 95° C. for 30 seconds. A similarly prepared mixture of enzyme sample and corn soy feed (mash feed) that did not undergo pelleting serves as control. The extraction conditions were as follows: 1g pelleted feed or mash feed was grinded, mixed with 10 mL buffer (100 mM Tris buffer with 1% SDS pH 10), in 10 mL beaker with a magnetic stir bar at room temperature (22° C.) for 10 min, then centrifuged at 4000 rpm using a bench top centrifuge for 10 min. The supernatant was filtered through a glass fiber filter. The filtrate was directly used in the enzyme activity assay. The enzyme activity assay conditions were as follows: 0.18 mL 0.1M Tricine buffer (pH 9.75 with 1% SDS), 1 µL enzyme feed extract, and 20 µL AAPF-pNA substrate (10 mg/ml in DMSO) were mixed at 900 rpm for 1min. Samples were incubated at 30° C. for 120 min with constant shaking.

The extent of the reaction was determined by measuring absorbance at 410 nm in a spectrophotometer. Results are shown on Table 4.

TABLE 4

Pelleting stability of SspCPro29 measured as recovery of enzyme activity from pellets versus untreated mash

| Sample | % recovery | cv |
|---|---|---|
| no pelleting | 100 | 3.6 |
| 90° C. pelleting | 78.7 | 3.6 |
| 95° C. pelleting | 62.0 | 4.1 |

Example 9

Hydrolysis and Solubilization Protein in Corn Soy Feed with SspCPro29 Protease and SspCPro33 Protease The reaction contained in 96 well MTP 1404, 10% (w/w) corn soy feed slurry (Yu S, Cowieson A, Gilbert C, Plumstead P, Dalsgaard S., Interactions of phytate and myo-inositol phosphate esters (IP1-5) including IP5 isomers with dietary protein and iron and inhibition of pepsin. J. Anim. Sci. 2012, 90:1824-1832) with pH adjusted to pH 3.0, 204, the protease in 50 mM Na-acetate pH3.0 giving a final concentration to the corn soy feed at 0, 250, 500, 750, 1000 and 1250 ppm, and 10 μL pepsin (Sigma P7000 dissolved in water at 1.69 mg/ml). The plate was incubated at 40° C. for 45 min in an iEMS Incubator/Shaker (Thermo Scientific) at 1150 rpm. At the end of the incubation porcine pancreatin (Sigma P7545, 0.4636 mg/mL in 1M sodium bicarbonate) 34 μL, was added and the plate was further incubated at 40° C. for 60 mi in the iEMS shaking at 1150 rpm. After the incubation, the plate was centrifuged at 5° C., 4000 rpm for 15 min. The supernatant 10 μL, supernatant was transferred to new 96 well MTP containing 90 μL, water (10× dilution). The 10 time diluted supernatant was determined for OPA (protein hydrolysis) and BCA (protein solubilization) values at 340 nm and 562 nm, respectively.

Protein hydrolysis using o-phthaldialdehyde (OPA) reagent was done basically as described before with minor modifications (P. M. NIELSEN, D. PETERSEN, and C. DAMBMANN, Improved method for determining food protein degree of hydrolysis, J. Food Sci. 66:642-646, 2001). The OPA reagent was prepared freshly by mixing 30 mL tri-sodium phosphate (Na3PO4.12H2O, 2% w/v in water with pH adjusted pH11), 0.8 mL OPA (0.4 g o-phthaldialdehyde 97% (OPA) in 10 mL 96% ethanol, saved at −20° C.), 1 ml DTT solution (0.352 g DL-dithiothreitol (DTT) 99% in 10 mL water and water to a final volume of 40 mL. The reagent was kept in the dark and used right after the preparation. The 10× diluted supernatant 20 μL, was mixed with 175 μL, of the OPA reagent for 5 seconds and read at 340 nm exactly after 2 min.

Protein solubilization was measured by using the Pierce BCA Protein Assay Kit (Cat no. 23225 from Thermo Fisher Scientific). The supernatant 20 μL, was mixed with 200 μL, of the BCA reagent (prepared before use by mixing 50 mL BCA reagent A with 1 mL BCA regent B according to the manufacturer's instruction). The mixture was incubated at 37° C. for 30 min before absorbance at 562 nm was measured.

Tables 5.1 and 5.2 show that protein hydrolysis and protein solubilization in the corn soy feed increased with the increase of the SspCPro29 and SspCPro33 (respectively) protease dose from 0 to 1250 ppm in the presence of both pepsin and pancreatin. The respective correlation coefficient ($R^2$) for hydrolysis and solubilization was 0.90 and 0.97.

TABLE 5.1

Hydrolysis and protein solubilization of corn soy feed with SspCPro29 protease

| | Enzyme concentration(ppm) | | | | | | Correlation coefficient ($R^2$) |
|---|---|---|---|---|---|---|---|
| | 0 | 250 | 500 | 750 | 1000 | 1250 | |
| Protein hydrolysis (OD340 OPA assay) | 0.529 | 0.689 | 0.761 | 0.806 | 0.835 | 0.884 | 0.900 |
| Protein solubilization (OD 562 BCA assay) | 0.818 | 0.856 | 0.897 | 0.911 | 0.936 | 0.992 | 0.970 |

TABLE 5.2

Hydrolysis and protein solubilization of corn soy feed with SspCPro33 protease

| | Enzyme concentration(ppm) | | | | | | Correlation coefficient ($R^2$) |
|---|---|---|---|---|---|---|---|
| | 0 | 250 | 500 | 750 | 1000 | 1250 | |
| Protein hydrolysis (OD340 OPA assay) | 0.513 | 0.634 | 0.682 | 0.698 | 0.717 | 0.753 | 0.854 |
| Protein solubilization (OD 562 BCA assay) | 0.806 | 0.807 | 0.844 | 0.839 | 0.844 | 0.895 | 0.818 |

Example 10

Cleaning Performance of SspCPro29 and SspCPro33 in ADW Conditions

The cleaning performance of SspCPro29 and SspCPro33 proteases was tested using PA-S-38 (egg yolk, with pigment, aged by heating) microswatches (CFT-Vlaardingen, The Netherlands) at pH 10.3 using a model automatic dishwashing (ADW) detergent. To prepare rinsed PAS38 swatches, 180 μL 10 mM CAPS buffer (pH 11) was added to 96-MTPs containing PAS38 swatches. The plates were sealed and incubated in an iEMs incubator for 30 min at 60° C., 1100 rpm. After incubation the buffer was removed and the swatches were rinsed with purified $H_2O$. The plates were air dried prior to use in the performance assay.

Purified protease samples were diluted to 200 ppm in 10 mM NaCl containing 0.1 mM $CaCl_2$ and 0.005% TWEEN® 80. The tests were performed in 3 g/L GSM-B detergent. The composition of GSM-B detergent (in weight percent) is as follows: 30% sodium citrate dehydrate, 25% sodium disilicate (Protil A, Cognis), 12% maleic acid/acrylic acid copolymer sodium Salt (SOKALAN® CP5 BASF), 5% sodium perborate monohydrate, 2% TAED, 2% linear fatty alcohol ethoxylate, and sodium carbonate anhydrous added to 100%. A 190 μL aliquot of the GSM-B detergent was added to a 96-MTP containing 1 rinsed PAS38 microswatch per well, and the reaction was initiated by the addition of 10 μL of diluted enzymes (or the dilution solution alone as the blank control). The 96-MTP was sealed and placed in an incubator/shaker for 30 min at 40° C. and 1150 rpm. After incubation, 100 μL of wash liquid from each well was transferred to a new 96-MTP, and its absorbance was measured at 405 nm using a spectrophotometer. The protease activity on the PAS38 model stain is reported as Net $A_{405}$, by subtracting the $A_{405}$ of the blank control from that of enzyme treated sample.

Dose responses in the PAS38 microswatches using GSM-B detergent at pH 10.3 for SspCPro29 and SspCPro33 are shown in FIG. 6.

Example 11

Cleaning Performance of SspCPro29 and SspCPro33 in Laundry Conditions

The cleaning performance of SspCPro29 and SspCPro33 proteases in liquid and powder laundry detergent was tested using EMPA-116 (cotton soiled with blood/milk/ink) microswatches (obtained from CFT Vlaardingen, The Netherlands) at pH 8.0 or pH 10.0. Prior to the tests, commercial liquid detergent (Tide® Clean Breeze™, Proctor & Gamble, USA) was incubated at 95° C. for 1 hour to inactivate the enzymes present in the detergent. The heat treated detergent was further diluted with 5 mM HEPES (pH 8.0) to a final concentration of 0.788 g/L. The water hardness of this buffered liquid detergent was adjusted to 100 ppm $Ca^{2+}$: $Mg^{2+}$ (3:1 ratio). For buffered powder detergent preparation, the commercial detergent (Tide®, Proctor & Gamble, China) was dissolved to 2 g/L in water with 100 ppm water hardness and heated in a microwave to mere boiling to inactivate enzymes. Proteolytic assays were subsequently performed to confirm the inactivation of proteases in the commercial detergents.

Prior to the tests, the EMPA-116 microswatches were rinsed with water and air dried. To initiate the reactions, 190 µL of buffered detergent was added to 96-MTP wells containing the rinsed EMPA-116 microswatches, followed by the addition of 10 µL of diluted enzyme (or Hao as blank control). The 96-MTPs were sealed and incubated for 20 min in iEMs at 32° C. and in Thermomixer at 16° C., respectively. After incubation, 100 µL of wash liquid from each well was transferred to a new 96-MTP, and the absorbance was measured at 600 nm using a spectrophotometer. The Net $A_{600}$ was calculated by subtracting the $A_{600}$ of the blank control from that of the enzyme treated samples. Dose response curves for SspCPro29 and SspCPro33 on EMPA-116 microswatches in liquid and powder laundry detergent at 16° C. and 32° C. were obtained. The BPN' Y217L protease (SEQ ID NO:40) was used as reference for HDL evaluation, and the GG36 protease (SEQ ID NO:41) was used as reference for HDD evaluation.

The cleaning performance results are shown in FIGS. 7 and 8 using the HDL detergent at 16 and 32° C., and in FIGS. 9 and 10 using the HDD detergent at 16 and 32° C.

Example 12

Protein Sequence Analyses of Predicted Full Length *Streptomyces* sp. Trypsin-Type Serine Proteases Related proteins were identified by a BLAST search (Altschul et al., Nucleic Acids Res, 25:3389-402, 1997) using the predicted full length amino acid sequences for SspCPro29 (SEQ ID NO:22); SspCPro33 (SEQ ID NO: 23); SspCPro23 (SEQ ID NO:24); and SspCPro59 (SEQ ID NO:25) against Public and Genome Quest Patent databases with search parameters set to default values and a subset are shown on Tables 6A and 6B (SspCPro29); Tables 7A and 7B (SspCPro33); Tables 8A and 8B (SspCPro23); and Tables 9A and 9B (SspCPro59), respectively. Percent identity (PID) for both search sets is defined as the number of identical residues divided by the number of aligned residues in the pairwise alignment. Value labeled "Sequence length" on tables corresponds to the length (in amino acids) for the proteins referenced with the listed Accession numbers, while "Aligned length" refers to sequence used for alignment and PID calculation.

TABLE 6A

List of sequences with percent identity to SspCPro29 full length protein identified from the NCBI non-redundant protein database

| Accession # | PID | Organism | Sequence Length | Alignment Length |
|---|---|---|---|---|
| WP_064069271 | 90.8 | Streptomyces albulus | 453 | 426 |
| WP_030548298 | 80.7 | Streptomyces albus | 459 | 424 |
| WP_005320871 | 79.3 | Streptomyces pristinaespiralis | 453 | 430 |
| WP_026277977 | 79.0 | Streptomyces sp. CNT372 | 458 | 428 |
| WP_019886521 | 75.7 | Streptomyces purpureus | 463 | 432 |
| WP_029386953 | 75.3 | Streptomyces leeuwenhoekii | 394 | 393 |
| WP_030027622 | 75.1 | Streptomyces flavotricini | 348 | 353 |
| WP_030212164 | 74.8 | Streptomyces bikiniensis | 454 | 421 |
| WP_055639793 | 74.8 | Streptomyces venezuelae | 451 | 428 |

TABLE 6B

List of sequences with percent identity to SspCPro29 full length protein identified from Genome Quest database

| GQ Identifier | PID | Organism | Sequence Length | Alignment length |
|---|---|---|---|---|
| US8076468-0024 | 79.5 | Streptomyces griseus | 255 | 253 |
| WO2015048332-44022 | 79.3 | Streptomyces pristinaespiralis ATCC 25486 | 453 | 463 |
| EP2205730-0009 | 77.7 | Streptomyces sp. | 256 | 255 |

TABLE 7A

List of sequences with percent identity to SspCPro33 full length protein identified from the NCBI non-redundant protein database

| Accession # | PID | Organism | Sequence Length | Alignment Length |
|---|---|---|---|---|
| WP_043225562 | 93.7 | Streptomyces sp. NRRL F-5193 | 456 | 426 |
| WP_031004112 | 92.7 | Streptomyces sp. NRRL F-5727 | 454 | 426 |
| WP_030498660 | 91.8 | Microtetraspora glauca | 455 | 426 |
| WP_030749137 | 87.3 | Streptomyces griseus | 456 | 426 |

TABLE 7A-continued

List of sequences with percent identity to SspCPro33 full length protein identified from the NCBI non-redundant protein database

| Accession # | PID | Organism | Sequence Length | Alignment Length |
|---|---|---|---|---|
| WP_030212164 | 86.2 | *Streptomyces bikiniensis* | 454 | 419 |
| WP_062759972 | 85.2 | *Streptomyces* sp. WAC04657 | 454 | 419 |
| WP_030027622 | 84.5 | *Streptomyces flavotricini* | 348 | 349 |
| WP_053644256 | 83.8 | *Streptomyces* sp. NRRL F-6492 | 455 | 419 |
| WP_030313004 | 83.2 | *Streptomyces flavochromogenes* | 456 | 422 |
| WP_015038204 | 82.9 | *Streptomyces venezuelae* ATCC 10712 | 456 | 422 |
| WP_055639793 | 82.8 | *Streptomyces venezuelae* | 451 | 425 |
| WP_030016658 | 82.7 | *Streptomyces lavendulae* | 369 | 369 |
| WP_055599201 | 82.6 | *Streptomyces aureus* | 456 | 420 |
| WP_053685358 | 82.6 | *Streptomyces* sp. XY 593 | 451 | 419 |
| WP_024756173 | 82.4 | *Streptomyces exfoliatus* | 451 | 425 |
| WP_030658602 | 82.3 | *Streptomyces* sp. H036 | 451 | 419 |
| WP_053627230 | 82.1 | *Streptomyces* sp. XY 511 | 451 | 419 |
| WP_030965679 | 81.9 | *Streptomyces* sp. NRRL S-378 | 449 | 419 |
| WP_030208917 | 81.8 | *Streptomyces griseoluteus* | 456 | 424 |
| WP_017236541 | 81.8 | *Streptomyces* sp. SS | 456 | 424 |
| WP_056557852 | 81.8 | *Streptomyces* sp. Root66D1 | 454 | 418 |
| WP_030545445 | 81.6 | *Streptomyces exfoliatus* | 456 | 424 |
| WP_033200913 | 81.6 | *Streptomyces viridochromogenes* | 456 | 424 |
| WP_046779091 | 81.5 | *Streptomyces yangpuensis* | 451 | 426 |
| WP_033218333 | 81.4 | *Streptomyces virginiae* | 449 | 420 |
| WP_031153386 | 81.4 | *Streptomyces erythrochromogenes* | 448 | 419 |
| WP_030850543 | 81.2 | *Streptomyces* | 450 | 426 |
| WP_053171320 | 81.1 | *Streptomyces virginiae* | 449 | 419 |
| WP_030896075 | 81.0 | *Streptomyces virginiae* | 451 | 426 |
| BAU88265 | 81.0 | *Streptomyces laurentii* | 445 | 426 |
| WP_053705101 | 81.0 | *Streptomyces* sp. WM6368 | 449 | 420 |
| WP_030385747 | 81.0 | *Streptomyces* sp. NRRL S-241 | 449 | 420 |
| WP_045323790 | 80.9 | *Streptomyces* sp. NRRL F-4428 | 449 | 425 |
| WP_053634074 | 80.8 | *Streptomyces* sp. MMG1064 | 451 | 426 |
| WP_053679192 | 80.8 | *Streptomyces* sp. XY66 | 451 | 426 |
| WP_030829885 | 80.8 | *Streptomyces* sp. NRRL S-104 | 451 | 426 |
| WP_030712260 | 80.7 | *Streptomyces* sp. NRRL S-237 | 449 | 420 |
| WP_037919299 | 80.6 | *Streptomyces* sp. PCS3-D2 | 454 | 428 |
| WP_053632580 | 80.5 | *Streptomyces* sp. H021 | 451 | 426 |
| WP_052876505 | 80.1 | *Streptomyces* sp. NRRL F-4335 | 451 | 422 |
| WP_030774478 | 80.0 | *Streptomyces* sp. NRRL F-2664 | 450 | 426 |
| WP_031144485 | 80.0 | *Streptomyces xanthophaeus* | 447 | 419 |
| WP_007266194 | 77.8 | *Streptomyces* sp. C | 455 | 427 |
| WP_005320871 | 76.8 | *Streptomyces pristinaespiralis* | 453 | 431 |
| WP_030548298 | 75.9 | *Streptomyces albus* | 459 | 428 |
| WP_026277977 | 75.1 | *Streptomyces* sp. CNT372 | 458 | 430 |
| WP_019886521 | 74.7 | *Streptomyces purpureus* | 463 | 430 |
| WP_029386953 | 74.6 | *Streptomyces leeuwenhoekii* | 394 | 393 |

TABLE 7B

List of sequences with percent identity to SspCPro33 full length protein identified from Genome Quest database

| GQ Identifier | PID | Organism | Sequence Length | Alignment length |
|---|---|---|---|---|
| WO2015048332-44360 | 82.9 | *Streptomyces venezuelae* | 456 | 422 |
| WO2015048332-44127 | 77.8 | *Streptomyces* sp. C | 455 | 427 |
| WO2015048332-44022 | 76.8 | *Streptomyces pristinaespiralis* ATCC 25486 | 453 | 431 |
| US8076468-0024 | 76.0 | *Streptomyces griseus* | 255 | 254 |
| US8076468-0009 | 75.0 | *Streptomyces* sp.; Strain 1AG3 | 256 | 256 |

TABLE 8A

List of sequences with percent identity to SspCPro23 full length protein identified from the NCBI non-redundant protein database

| Accession # | PID | Organism | Sequence Length | Alignment Length |
|---|---|---|---|---|
| WP_024756173 | 97.1 | *Streptomyces exfoliatus* | 451 | 421 |
| WP_055639793 | 94.8 | *Streptomyces venezuelae* | 451 | 421 |
| WP_030313004 | 89.4 | *Streptomyces flavochromogenes* | 456 | 425 |
| WP_033200913 | 89.3 | *Streptomyces viridochromogenes* | 456 | 422 |
| WP_017236541 | 89.1 | *Streptomyces* sp. SS | 456 | 422 |
| WP_055599201 | 89.0 | *Streptomyces aureus* | 456 | 418 |
| WP_030545445 | 88.5 | *Streptomyces exfoliatus* | 456 | 419 |
| WP_030208917 | 88.5 | *Streptomyces griseoluteus* | 456 | 419 |
| WP_015038204 | 88.3 | *Streptomyces venezuelae* ATCC 10712 | 456 | 419 |
| WP_056557852 | 87.7 | *Streptomyces* sp. Root66D1 | 454 | 423 |
| WP_053644256 | 85.7 | *Streptomyces* sp. NRRL F-6492 | 455 | 419 |
| WP_062759972 | 85.4 | *Streptomyces* sp. WAC04657 | 454 | 419 |
| WP_030212164 | 85.4 | *Streptomyces bikiniensis* | 454 | 419 |
| BAU88265 | 85.0 | *Streptomyces laurentii* | 445 | 419 |
| WP_030749137 | 84.6 | *Streptomyces griseus* | 456 | 422 |
| WP_043225562 | 84.6 | *Streptomyces* sp. NRRL F-5193 | 456 | 422 |
| WP_031004112 | 84.5 | *Streptomyces* sp. NRRL F-5727 | 454 | 420 |
| WP_030498660 | 83.6 | *Microtetraspora glauca* | 455 | 421 |
| WP_030027622 | 83.3 | *Streptomyces flavotricini* | 348 | 347 |
| WP_053685358 | 81.8 | *Streptomyces* sp. XY593 | 451 | 417 |
| WP_030658602 | 81.5 | *Streptomyces* sp. H036 | 451 | 417 |
| WP_037919299 | 81.5 | *Streptomyces* sp. PCS3-D2 | 454 | 416 |
| WP_053627230 | 81.3 | *Streptomyces* sp. XY511 | 451 | 417 |
| WP_030016658 | 81.0 | *Streptomyces lavendulae* | 369 | 368 |
| WP_045323790 | 80.9 | *Streptomyces* sp. NRRL F-4428 | 449 | 419 |
| WP_030965679 | 80.7 | *Streptomyces* sp. NRRL S-378 | 449 | 420 |
| WP_007266194 | 80.4 | *Streptomyces* sp. C | 455 | 424 |
| WP_030896075 | 80.3 | *Streptomyces virginiae* | 451 | 421 |
| WP_053634074 | 80.3 | *Streptomyces* sp. MMG1064 | 451 | 421 |
| WP_053679192 | 80.3 | *Streptomyces* sp. XY66 | 451 | 421 |
| WP_053705101 | 80.2 | *Streptomyces* sp. WM6368 | 449 | 420 |
| WP_031153386 | 80.2 | *Streptomyces erythrochromogenes* | 448 | 419 |
| WP_031144485 | 80.1 | *Streptomyces xanthophaeus* | 447 | 418 |
| WP_046779091 | 80.0 | *Streptomyces yangpuensis* | 451 | 421 |
| WP_030829885 | 80.0 | *Streptomyces* sp. NRRL S-104 | 451 | 421 |
| WP_053632580 | 80.0 | *Streptomyces* sp. H021 | 451 | 421 |
| WP_030385747 | 80.0 | *Streptomyces* sp. NRRL S-241 | 449 | 420 |
| WP_053171320 | 79.8 | *Streptomyces virginiae* | 449 | 420 |
| WP_030712260 | 79.8 | *Streptomyces* sp. NRRL S-237 | 449 | 420 |
| WP_033218333 | 79.5 | *Streptomyces virginiae* | 449 | 420 |
| WP_030850543 | 79.5 | *Streptomyces* | 450 | 420 |
| WP_030774478 | 79.3 | *Streptomyces* sp. NRRL F-2664 | 450 | 421 |
| WP_052876505 | 78.9 | *Streptomyces* sp. NRRL F-4335 | 451 | 422 |
| WP_019886521 | 78.9 | *Streptomyces purpureus* | 463 | 426 |
| WP_005320871 | 78.0 | *Streptomyces pristinaespiralis* | 453 | 419 |
| WP_030548298 | 76.6 | *Streptomyces albus* | 459 | 427 |
| WP_064069271 | 75.5 | *Streptomyces albulus* | 453 | 421 |
| WP_026277977 | 75.3 | *Streptomyces* sp. CNT372 | 458 | 417 |

TABLE 8B

List of sequences with percent identity to SspCPro23 full length protein identified from Genome Quest database

| GQ Identifier | PID | Organism | Sequence Length | Alignment length |
|---|---|---|---|---|
| WO2015048332-44360 | 88.3 | *Streptomyces venezuelae* | 456 | 419 |
| WO2015048332-44127 | 80.4 | *Streptomyces* sp. C | 455 | 424 |
| WO2015048332-44022 | 78.0 | *Streptomyces pristinaespiralis* ATCC 25486 | 453 | 419 |
| US8076468-0024 | 77.1 | *Streptomyces griseus* | 255 | 253 |
| EP2205730-0009 | 76.5 | *Streptomyces* sp.; Strain 1AG3 | 256 | 255 |

TABLE 9A

List of sequences with percent identity to SspCPro59 full length protein identified from the NCBI non-redundant protein database

| Accession # | PID | Organism | Sequence Length | Alignment Length |
|---|---|---|---|---|
| WP_029386953 | 78.1 | Streptomyces leeuwenhoekii | 394 | 392 |
| WP_046250145 | 77.3 | Streptomyces sp. MBT28 | 357 | 357 |
| WP_069630550 | 76.9 | Streptomyces niveus | 444 | 429 |
| WP_031232554 | 76.5 | Streptomyces niveus | 444 | 429 |
| EST18641 | 76.5 | Streptomyces niveus NCIMB 11891 | 459 | 429 |
| WP_064729342 | 76.3 | Streptomyces parvulus | 457 | 427 |
| WP_047121827 | 75.8 | Streptomyces leeuwenhoekii | 464 | 434 |
| WP_063482838 | 75.7 | Streptomyces ambofaciens | 454 | 419 |
| WP_044383230 | 75.6 | Streptomyces cyaneogriseus | 464 | 434 |
| AJP05780 | 75.6 | Streptomyces cyaneogriseus subsp. noncyanogenus | 452 | 434 |
| WP_055418378 | 75.5 | Streptomyces pactum | 457 | 429 |
| WP_069979026 | 75.4 | Streptomyces rubrolavendulae | 454 | 427 |
| WP_030027622 | 75.3 | Streptomyces flavotricini | 348 | 352 |
| WP_031135572 | 75.2 | Streptomyces fradiae | 454 | 427 |
| WP_030970235 | 75.1 | Streptomyces sp. NRRL F-4835 | 437 | 426 |
| CAH04620 | 74.9 | Streptomyces fradiae | 454 | 427 |
| WP_019329665 | 74.9 | Streptomyces sp. T0R3209 | 457 | 426 |
| WP_031022018 | 74.9 | Streptomyces sp. NRRL WC-3795 | 457 | 426 |
| WP_053135598 | 74.6 | Streptomyces ambofaciens ATCC 23877 | 454 | 426 |
| WP_023590970 | 74.5 | Streptomyces thermolilacinus SPC6 | 455 | 428 |
| WP_059300010 | 74.5 | Streptomyces canus | 455 | 427 |

TABLE 9B

List of sequences with percent identity to SspCPro59 full length protein identified from Genome Quest database

| GQ Identifier | PID | Organism | Sequence Length | Alignment length |
|---|---|---|---|---|
| US8076468-0024 | 79.8 | Streptomyces griseus | 255 | 253 |
| EP2205730-0009 | 76.9 | Streptomyces sp.; Strain lAG3 | 256 | 255 |
| WO2015048332-43724 | 75.2 | Streptomyces fradiae | 454 | 427 |
| WO2015048332-43726 | 74.9 | Streptomyces fradiae | 454 | 427 |

The amino acid sequences for SspCPro29 (SEQ ID NO:22); SspCPro33 (SEQ ID NO:23); SspCPro23 (SEQ ID NO:24); and SspCPro59 (SEQ ID NO:25) and the sequences of other Streptomyces sp serine proteases: WP_064069271 (SEQ ID NO:26); WP_043225562 (SEQ ID NO:27); WP_024756173 (SEQ ID NO:28); WP_030548298 (SEQ ID NO:29); WP_005320871 (SEQ ID NO:30); WP_055639793 (SEQ ID NO:31); WO2015048332-44360 (SEQ ID NO:32); WO2015048332-44127 (SEQ ID NO:33); WP_030313004 (SEQ ID NO:34); WP_030212164 (SEQ ID NO:35); WP_030749137 (SEQ ID NO:36); WP_031004112 (SEQ ID NO:37); and WP_026277977 (SEQ ID NO:38) were aligned with default parameters using the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797). The multiple sequence alignment for the overlapping regions is shown on FIG. 11.

Example 13

Protein Sequence Analysis of Predicted Catalytic Domains of Streptomyces sp Trypsin-Type Serine Proteases Related proteins were identified by a BLAST search (Altschul et al., Nucleic Acids Res, 25:3389-402, 1997) using the predicted catalytic domain sequences for SspCPro29 (SEQ ID NO:18); SspCPro33 (SEQ ID NO:19); SspCPro23 (SEQ ID NO:20); and SspCPro59 (SEQ ID NO:21) against Public and Genome Quest Patent databases with search parameters set to default values and a subset are shown on Tables 10A and 10B (SspCPro29); Tables 11A and 11B (SspCPro33); Tables 12A and 12B (SspCPro23); and Tables 13A and 13B (SspCPro59) respectively.

TABLE 10A

List of sequences with percent identity to SspCPro29 predicted catalytic domain identified from the NCBI non-redundant protein database

| Accession # | PID | Organism | Sequence Length | Alignment Length |
|---|---|---|---|---|
| WP_064069271 | 95.3 | Streptomyces albulus | 453 | 191 |
| WP_026277977 | 91.6 | Streptomyces sp. CNT372 | 458 | 191 |

TABLE 10A-continued

List of sequences with percent identity to SspCPro29 predicted catalytic domain identified from the NCBI non-redundant protein database

| Accession # | PID | Organism | Sequence Length | Alignment Length |
|---|---|---|---|---|
| WP_030548298 | 88.5 | *Streptomyces albus* | 459 | 191 |
| WP_044383230 | 88.4 | *Streptomyces cyaneogriseus* | 464 | 190 |
| AJP05780 | 88.4 | *Streptomyces cyaneogriseus* subsp. noncyanogenus | 452 | 190 |
| WP_005320871 | 88.0 | *Streptomyces pristinaespiralis* | 453 | 191 |
| WP_047121827 | 87.9 | *Streptomyces leeuwenhoekii* | 464 | 190 |
| WP_029386953 | 87.9 | *Streptomyces leeuwenhoekii* | 394 | 190 |
| WP_069630550 | 87.4 | *Streptomyces niveus* | 444 | 191 |
| WP_069979026 | 86.9 | *Streptomyces rubrolavendulae* | 454 | 191 |
| WP_055639793 | 86.9 | *Streptomyces venezuelae* | 451 | 191 |
| WP_031003261 | 86.8 | *Streptomyces* sp. NRRL WC-3773 | 461 | 190 |
| WP_053699044 | 86.8 | *Streptomyces* sp. NRRL F-5755 | 460 | 190 |
| WP_060732661 | 86.8 | *Streptomyces albus* subsp. albus | 460 | 190 |
| WP_030590236 | 86.8 | *Streptomyces griseoflavus* | 460 | 190 |
| WP_045323790 | 86.7 | *Streptomyces* sp. NRRL F-4428 | 449 | 188 |
| WP_030027622 | 86.7 | *Streptomyces flavotricini* | 348 | 188 |
| WP_031135572 | 86.4 | *Streptomyces fradiae* | 454 | 191 |
| WP_031232554 | 86.4 | *Streptomyces niveus* | 444 | 191 |
| EST18641 | 86.4 | *Streptomyces niveus* NCIMB 11891 | 459 | 191 |
| WP_043225562 | 86.4 | *Streptomyces* sp. NRRL F-5193 | 456 | 191 |
| WP_053800418 | 86.3 | *Streptomyces rimosus* subsp. pseudoverticillatus | 460 | 190 |
| WP_033032149 | 86.3 | *Streptomyces rimosus* | 460 | 190 |
| WP_031188739 | 86.3 | *Streptomyces rimosus* subsp. rimosus | 460 | 190 |
| WP_030639316 | 86.3 | *Streptomyces rimosus* | 460 | 190 |
| WP_030633274 | 86.3 | *Streptomyces rimosus* | 460 | 190 |
| WP_030372610 | 86.3 | *Streptomyces rimosus* | 460 | 190 |
| WP_030659657 | 86.3 | *Streptomyces rimosus* | 460 | 190 |
| WP_053685358 | 86.2 | *Streptomyces* sp. XY 593 | 451 | 188 |
| CAH04620 | 85.9 | *Streptomyces fradiae* | 454 | 191 |
| WP_046779091 | 85.9 | *Streptomyces yangpuensis* | 451 | 191 |
| WP_019886521 | 85.9 | *Streptomyces purpureus* | 463 | 191 |
| WP_030022977 | 85.8 | *Streptomyces monomycini* | 461 | 190 |
| WP_003983795 | 85.8 | *Streptomyces rimosus* subsp. rimosus | 460 | 190 |
| WP_053632580 | 85.6 | *Streptomyces* sp. H021 | 451 | 188 |
| WP_053627230 | 85.6 | *Streptomyces* sp. XY 511 | 451 | 188 |
| WP_053634074 | 85.6 | *Streptomyces* sp. MMG1064 | 451 | 188 |
| WP_053679192 | 85.6 | *Streptomyces* sp. XY66 | 451 | 188 |
| WP_030896075 | 85.6 | *Streptomyces virginiae* | 451 | 188 |
| WP_030829885 | 85.6 | *Streptomyces* sp. NRRL S-104 | 451 | 188 |
| WP_030658602 | 85.6 | *Streptomyces* sp. H036 | 451 | 188 |
| WP_037919299 | 85.6 | *Streptomyces* sp. PCS3-D2 | 454 | 188 |
| WP_030850543 | 85.6 | *Streptomyces* | 450 | 188 |
| WP_055599201 | 85.3 | *Streptomyces aureus* | 456 | 191 |
| WP_030313004 | 85.3 | *Streptomyces flavochromogenes* | 456 | 191 |
| WP_030965679 | 85.3 | *Streptomyces* sp. NRRL S-378 | 449 | 191 |
| WP_024756173 | 85.3 | *Streptomyces exfoliatus* | 451 | 191 |
| WP_030774478 | 85.1 | *Streptomyces* sp. NRRL F-2664 | 450 | 188 |
| WP_031153386 | 85.1 | *Streptomyces erythrochromogenes* | 448 | 188 |
| WP_053705101 | 85.1 | *Streptomyces* sp. WM6368 | 449 | 188 |
| WP_053171320 | 85.1 | *Streptomyces virginiae* | 449 | 188 |
| WP_030385747 | 85.1 | *Streptomyces* sp. NRRL S-241 | 449 | 188 |

TABLE 10B

List of sequences with percent identity to SspCPro29 predicted catalytic domain identified from Genome Quest database

| GQ Identifier | PID | Organism | Sequence Length | Alignment length |
|---|---|---|---|---|
| WO2015048332-44022 | 88.0 | *Streptomyces pristinaespiralis* ATCC 25486 | 453 | 191 |
| WO2015048332-43724 | 86.4 | *Streptomyces fradiae* | 454 | 191 |
| WO2015048332-43726 | 85.9 | *Streptomyces fradiae* | 454 | 191 |

TABLE 11A

List of sequences with percent identity to SspCPro33 predicted catalytic domain identified from the NCBI non-redundant protein database

| Accession # | PID | Organism | Sequence Length | Alignment Length |
|---|---|---|---|---|
| WP_043225562 | 97.4 | Streptomyces sp. NRRL F-5193 | 456 | 191 |
| WP_031004112 | 96.3 | Streptomyces sp. NRRL F-5727 | 454 | 190 |
| WP_030498660 | 95.3 | Microtetraspora glauca | 455 | 191 |
| WP_015038204 | 93.2 | Streptomyces venezuelae ATCC 10712 | 456 | 191 |
| WP_030212164 | 92.7 | Streptomyces bikiniensis | 454 | 191 |
| WP_007266194 | 92.7 | Streptomyces sp. C | 455 | 191 |
| WP_030712260 | 92.6 | Streptomyces sp. NRRL S-237 | 449 | 188 |
| WP_055599201 | 92.1 | Streptomyces aureus | 456 | 191 |
| WP_030749137 | 92.1 | Streptomyces griseus | 456 | 191 |
| WP_030313004 | 92.1 | Streptomyces flavochromogenes | 456 | 191 |
| WP_053705101 | 92.1 | Streptomyces sp. WM6368 | 449 | 191 |
| WP_053171320 | 92.1 | Streptomyces virginiae | 449 | 191 |
| WP_030385747 | 92.1 | Streptomyces sp. NRRL S-241 | 449 | 191 |
| WP_053685358 | 92.1 | Streptomyces sp. XY593 | 451 | 189 |
| WP_024756173 | 91.6 | Streptomyces exfoliatus | 451 | 191 |
| WP_055639793 | 91.6 | Streptomyces venezuelae | 451 | 191 |
| WP_030965679 | 91.6 | Streptomyces sp. NRRL S-378 | 449 | 191 |
| WP_053632580 | 91.5 | Streptomyces sp. H021 | 451 | 189 |
| WP_053627230 | 91.5 | Streptomyces sp. XY511 | 451 | 189 |
| WP_053634074 | 91.5 | Streptomyces sp. MMG1064 | 451 | 189 |
| WP_053679192 | 91.5 | Streptomyces sp. XY66 | 451 | 189 |
| WP_030896075 | 91.5 | Streptomyces virginiae | 451 | 189 |
| WP_030829885 | 91.5 | Streptomyces sp. NRRL S-104 | 451 | 189 |
| WP_030658602 | 91.5 | Streptomyces sp. H036 | 451 | 189 |
| WP_062759972 | 91.1 | Streptomyces sp. WAC04657 | 454 | 191 |
| WP_033218333 | 91.1 | Streptomyces virginiae | 449 | 191 |
| WP_037919299 | 91.1 | Streptomyces sp. PCS3-D2 | 454 | 191 |
| WP_046779091 | 91.1 | Streptomyces yangpuensis | 451 | 191 |
| WP_045323790 | 91.1 | Streptomyces sp. NRRL F-4428 | 449 | 191 |
| WP_030027622 | 91.1 | Streptomyces flavotricini | 348 | 191 |
| WP_030016658 | 91.1 | Streptomyces lavendulae | 369 | 191 |
| WP_030850543 | 91.0 | Streptomyces | 450 | 189 |
| WP_030545445 | 90.6 | Streptomyces exfoliatus | 456 | 191 |
| WP_030208917 | 90.6 | Streptomyces griseoluteus | 456 | 191 |
| WP_033200913 | 90.6 | Streptomyces viridochromogenes | 456 | 191 |
| WP_017236541 | 90.6 | Streptomyces sp. SS | 456 | 191 |
| WP_019886521 | 90.6 | Streptomyces purpureus | 463 | 191 |
| WP_031144485 | 90.6 | Streptomyces xanthophaeus | 447 | 191 |
| WP_052876505 | 90.6 | Streptomyces sp. NRRL F-4335 | 451 | 191 |
| WP_056557852 | 90.1 | Streptomyces sp. Root66D1 | 454 | 191 |
| WP_053644256 | 90.1 | Streptomyces sp. NRRL F-6492 | 455 | 191 |
| WP_031153386 | 89.5 | Streptomyces erythrochromogenes | 448 | 191 |
| WP_030774478 | 89.0 | Streptomyces sp. NRRL F-2664 | 450 | 191 |
| BAU88265 | 88.0 | Streptomyces laurentii | 445 | 191 |
| WP_030548298 | 86.4 | Streptomyces albus | 459 | 191 |
| WP_064069271 | 86.4 | Streptomyces albulus | 453 | 191 |
| WP_047121827 | 86.3 | Streptomyces leeuwenhoekii | 464 | 190 |
| WP_029386953 | 86.3 | Streptomyces leeuwenhoekii | 394 | 190 |
| WP_005320871 | 85.9 | Streptomyces pristinaespiralis | 453 | 191 |
| WP_026277977 | 85.9 | Streptomyces sp. CNT372 | 458 | 191 |
| WP_069630550 | 85.3 | Streptomyces niveus | 444 | 191 |
| WP_064729342 | 85.3 | Streptomyces parvulus | 457 | 191 |
| WP_069979026 | 85.3 | Streptomyces rubrolavendulae | 454 | 191 |
| WP_031135572 | 84.8 | Streptomyces fradiae | 454 | 191 |

TABLE 11B

List of sequences with percent identity to SspCPro33 predicted catalytic domain identified from Genome Quest database

| GQ Identifier | PID | Organism | Sequence Length | Alignment length |
|---|---|---|---|---|
| WO2015048332-44360 | 93.2 | Streptomyces venezuelae | 456 | 191 |
| WO2015048332-44127 | 92.7 | Streptomyces sp. C | 455 | 191 |
| WO2015048332-44022 | 85.9 | Streptomyces pristinaespiralis ATCC 25486 | 453 | 191 |
| WO2015048332-43724 | 84.8 | Streptomyces fradiae | 454 | 191 |

TABLE 12A

List of sequences with percent identity to SspCPro23 predicted catalytic domain identified from the NCBI non-redundant protein database

| Accession # | PID | Organism | Sequence Length | Alignment Length |
|---|---|---|---|---|
| WP_024756173 | 99.0 | *Streptomyces exfoliatus* | 451 | 191 |
| WP_055599201 | 98.4 | *Streptomyces aureus* | 456 | 191 |
| WP_030313004 | 98.4 | *Streptomyces flavochromogenes* | 456 | 191 |
| WP_055639793 | 98.4 | *Streptomyces venezuelae* | 451 | 191 |
| WP_015038204 | 96.9 | *Streptomyces venezuelae* ATCC 10712 | 456 | 191 |
| WP_030545445 | 95.8 | *Streptomyces exfoliatus* | 456 | 191 |
| WP_030208917 | 95.3 | *Streptomyces griseoluteus* | 456 | 191 |
| WP_019886521 | 95.3 | *Streptomyces purpureus* | 463 | 191 |
| WP_033200913 | 94.8 | *Streptomyces viridochromogenes* | 456 | 191 |
| WP_017236541 | 94.2 | *Streptomyces* sp. SS | 456 | 191 |
| WP_043225562 | 94.2 | *Streptomyces* sp. NRRL F-5193 | 456 | 191 |
| WP_056557852 | 93.2 | *Streptomyces* sp. Root66D1 | 454 | 191 |
| WP_053685358 | 93.1 | *Streptomyces* sp. XY593 | 451 | 189 |
| WP_053632580 | 92.6 | *Streptomyces* sp. H021 | 451 | 189 |
| WP_053627230 | 92.6 | *Streptomyces* sp. XY511 | 451 | 189 |
| WP_053634074 | 92.6 | *Streptomyces* sp. MMG1064 | 451 | 189 |
| WP_053679192 | 92.6 | *Streptomyces* sp. XY66 | 451 | 189 |
| WP_030896075 | 92.6 | *Streptomyces virginiae* | 451 | 189 |
| WP_030829885 | 92.6 | *Streptomyces* sp. NRRL S-104 | 451 | 189 |
| WP_030658602 | 92.6 | *Streptomyces* sp. H036 | 451 | 189 |
| WP_031004112 | 92.1 | *Streptomyces* sp. NRRL F-5727 | 454 | 190 |
| WP_030712260 | 92.0 | *Streptomyces* sp. NRRL S-237 | 449 | 188 |
| WP_053644256 | 91.6 | *Streptomyces* sp. NRRL F-6492 | 455 | 191 |
| WP_030749137 | 91.6 | *Streptomyces griseus* | 456 | 191 |
| WP_007266194 | 91.6 | *Streptomyces* sp. C | 455 | 191 |
| WP_053705101 | 91.6 | *Streptomyces* sp. WM6368 | 449 | 191 |
| WP_053171320 | 91.6 | *Streptomyces virginiae* | 449 | 191 |
| WP_030965679 | 91.6 | *Streptomyces* sp. NRRL S-378 | 449 | 191 |
| WP_030385747 | 91.6 | *Streptomyces* sp. NRRL S-241 | 449 | 191 |
| WP_037919299 | 91.6 | *Streptomyces* sp. PCS3-D2 | 454 | 191 |
| WP_030498660 | 91.1 | *Microtetraspora glauca* | 455 | 191 |
| WP_030212164 | 90.6 | *Streptomyces bikiniensis* | 454 | 191 |
| WP_033218333 | 90.6 | *Streptomyces virginiae* | 449 | 191 |
| WP_046779091 | 90.6 | *Streptomyces yangpuensis* | 451 | 191 |
| WP_030850543 | 90.5 | *Streptomyces* | 450 | 189 |
| WP_062759972 | 90.1 | *Streptomyces* sp. WAC04657 | 454 | 191 |
| WP_052876505 | 90.1 | *Streptomyces* sp. NRRL F-4335 | 451 | 191 |
| WP_045323790 | 90.1 | *Streptomyces* sp. NRRL F-4428 | 449 | 191 |
| WP_031153386 | 90.1 | *Streptomyces erythrochromogenes* | 448 | 191 |
| WP_030027622 | 90.1 | *Streptomyces flavotricini* | 348 | 191 |
| WP_030016658 | 90.1 | *Streptomyces lavendulae* | 369 | 191 |
| WP_031144485 | 89.5 | *Streptomyces xanthophaeus* | 447 | 191 |
| BAU88265 | 89.5 | *Streptomyces laurentii* | 445 | 191 |
| WP_030774478 | 89.0 | *Streptomyces* sp. NRRL F-2664 | 450 | 191 |
| WP_005320871 | 89.0 | *Streptomyces pristinaespiralis* | 453 | 191 |
| WP_030548298 | 89.0 | *Streptomyces albus* | 459 | 191 |
| WP_069630550 | 89.0 | *Streptomyces niveus* | 444 | 191 |
| WP_031232554 | 88.0 | *Streptomyces niveus* | 444 | 191 |
| EST18641 | 88.0 | *Streptomyces niveus* NCIMB 11891 | 459 | 191 |
| WP_064069271 | 87.4 | *Streptomyces albulus* | 453 | 191 |
| WP_069979026 | 87.4 | *Streptomyces rubrolavendulae* | 454 | 191 |
| WP_031135572 | 86.9 | *Streptomyces fradiae* | 454 | 191 |
| WP_026277977 | 86.4 | *Streptomyces* sp. CNT372 | 458 | 191 |
| CAH04620 | 86.4 | *Streptomyces fradiae* | 454 | 191 |
| WP_030659657 | 85.3 | *Streptomyces rimosus* | 460 | 190 |
| WP_047121827 | 84.7 | *Streptomyces leeuwenhoekii* | 464 | 190 |
| WP_029386953 | 84.7 | *Streptomyces leeuwenhoekii* | 394 | 190 |
| WP_053699044 | 84.7 | *Streptomyces* sp. NRRL F-5755 | 460 | 190 |
| WP_060732661 | 84.7 | *Streptomyces albus* subsp. albus | 460 | 190 |
| WP_030590236 | 84.7 | *Streptomyces griseoflavus* | 460 | 190 |

TABLE 12B

List of sequences with percent identity to SspCPro23 predicted catalytic domain identified from Genome Quest database

| GQ Identifier | PID | Organism | Sequence Length | Alignment length |
|---|---|---|---|---|
| WO2015048332-44360 | 96.9 | *Streptomyces venezuelae* | 456 | 191 |
| WO2015048332-44127 | 91.6 | *Streptomyces* sp. C | 455 | 191 |
| WO2015048332-44022 | 89.0 | *Streptomyces pristinaespiralis* ATCC 25486 | 453 | 191 |
| WO2015048332-43724 | 86.9 | *Streptomyces fradiae* | 454 | 191 |
| WO2015048332-43726 | 86.4 | *Streptomyces fradiae* | 454 | 191 |

TABLE 13A

List of sequences with percent identity to SspCPro59 predicted catalytic domain identified from the NCBI non-redundant protein database

| Accession # | PID | Organism | Sequence Length | Alignment Length |
|---|---|---|---|---|
| WP_047121827 | 90.5 | *Streptomyces leeuwenhoekii* | 464 | 190 |
| WP_029386953 | 90.5 | *Streptomyces leeuwenhoekii* | 394 | 190 |
| WP_069630550 | 89.5 | *Streptomyces niveus* | 444 | 191 |
| WP_044383230 | 89.5 | *Streptomyces cyaneogriseus* | 464 | 190 |
| AJP05780 | 89.5 | *Streptomyces cyaneogriseus* subsp. noncyanogenus | 452 | 190 |
| WP_053800418 | 88.9 | *Streptomyces rimosus* subsp. pseudoverticillatus | 460 | 190 |
| WP_033032149 | 88.9 | *Streptomyces rimosus* | 460 | 190 |
| WP_031188739 | 88.9 | *Streptomyces rimosus* subsp. rimosus | 460 | 190 |
| WP_030639316 | 88.9 | *Streptomyces rimosus* | 460 | 190 |
| WP_030633274 | 88.9 | *Streptomyces rimosus* | 460 | 190 |
| WP_030212164 | 88.5 | *Streptomyces bikiniensis* | 454 | 191 |
| WP_031232554 | 88.5 | *Streptomyces niveus* | 444 | 191 |
| EST18641 | 88.5 | *Streptomyces niveus* NCIMB 11891 | 459 | 191 |
| WP_030372610 | 88.4 | *Streptomyces rimosus* | 460 | 190 |
| WP_063482838 | 88.0 | *Streptomyces ambofaciens* | 454 | 191 |
| WP_053135598 | 88.0 | *Streptomyces ambofaciens* ATCC 23877 | 454 | 191 |
| WP_064069271 | 88.0 | *Streptomyces albulus* | 453 | 191 |
| WP_043225562 | 88.0 | *Streptomyces* sp. NRRL F-5193 | 456 | 191 |
| WP_031003261 | 87.9 | *Streptomyces* sp. NRRL WC-3773 | 461 | 190 |
| WP_003983795 | 87.9 | *Streptomyces rimosus* subsp. rimosus | 460 | 190 |
| WP_053699044 | 87.9 | *Streptomyces* sp. NRRL F-5755 | 460 | 190 |
| WP_062759972 | 87.4 | *Streptomyces* sp. WAC04657 | 454 | 191 |
| WP_064729342 | 87.4 | *Streptomyces parvulus* | 457 | 191 |
| WP_060732661 | 87.4 | *Streptomyces albus* subsp. albus | 460 | 190 |
| WP_030590236 | 87.4 | *Streptomyces griseoflavus* | 460 | 190 |
| WP_053627230 | 87.3 | *Streptomyces* sp. XY511 | 451 | 189 |
| WP_053685358 | 87.3 | *Streptomyces* sp. XY593 | 451 | 189 |
| WP_030658602 | 87.3 | *Streptomyces* sp. H036 | 451 | 189 |
| WP_053644256 | 86.9 | *Streptomyces* sp. NRRL F-6492 | 455 | 191 |
| WP_046250145 | 86.9 | *Streptomyces* sp. MBT28 | 357 | 191 |
| WP_031022018 | 86.9 | *Streptomyces* sp. NRRL WC-3795 | 457 | 191 |
| WP_030970235 | 86.9 | *Streptomyces* sp. NRRL F-4835 | 437 | 191 |
| WP_055418378 | 86.9 | *Streptomyces pactum* | 457 | 191 |
| WP_069979026 | 86.9 | *Streptomyces rubrolavendulae* | 454 | 191 |
| WP_030965679 | 86.9 | *Streptomyces* sp. NRRL S-378 | 449 | 191 |
| WP_030022977 | 86.8 | *Streptomyces monomycini* | 461 | 190 |
| WP_030659657 | 86.8 | *Streptomyces rimosus* | 460 | 190 |
| WP_053632580 | 86.8 | *Streptomyces* sp. H021 | 451 | 189 |
| WP_053634074 | 86.8 | *Streptomyces* sp. MMG1064 | 451 | 189 |
| WP_053679192 | 86.8 | *Streptomyces* sp. XY66 | 451 | 189 |
| WP_030896075 | 86.8 | *Streptomyces virginiae* | 451 | 189 |
| WP_030829885 | 86.8 | *Streptomyces* sp. NRRL S-104 | 451 | 189 |
| WP_019329665 | 86.4 | *Streptomyces* sp. TOR3209 | 457 | 191 |
| WP_015038204 | 86.4 | *Streptomyces venezuelae* ATCC 10712 | 456 | 191 |
| WP_055639793 | 86.4 | *Streptomyces venezuelae* | 451 | 191 |
| WP_037919299 | 86.4 | *Streptomyces* sp. PCS3-D2 | 454 | 191 |
| WP_031135572 | 86.4 | *Streptomyces fradiae* | 454 | 191 |
| WP_046779091 | 86.4 | *Streptomyces yangpuensis* | 451 | 191 |
| WP_026277977 | 86.4 | *Streptomyces* sp. CNT372 | 458 | 191 |
| WP_043506163 | 85.9 | *Streptomyces glaucescens* | 442 | 191 |
| WP_037929773 | 85.9 | *Streptomyces toyocaensis* | 435 | 191 |
| AIR96443 | 85.9 | *Streptomyces glaucescens* | 457 | 191 |
| KES08095 | 85.9 | *Streptomyces toyocaensis* | 457 | 191 |
| WP_030548298 | 85.9 | *Streptomyces albus* | 459 | 191 |

TABLE 13A-continued

List of sequences with percent identity to SspCPro59 predicted catalytic domain identified from the NCBI non-redundant protein database

| Accession # | PID | Organism | Sequence Length | Alignment Length |
|---|---|---|---|---|
| WP_005320871 | 85.9 | *Streptomyces pristinaespiralis* | 453 | 191 |
| WP_031144485 | 85.9 | *Streptomyces xanthophaeus* | 447 | 191 |
| CAH04620 | 85.9 | *Streptomyces fradiae* | 454 | 191 |
| WP_031153386 | 85.9 | *Streptomyces erythrochromogenes* | 448 | 191 |
| WP_045323790 | 85.9 | *Streptomyces* sp. NRRL F-4428 | 449 | 191 |
| WP_030027622 | 85.9 | *Streptomyces flavotricini* | 348 | 191 |
| WP_023590970 | 85.9 | *Streptomyces thermolilacinus* SPC6 | 455 | 191 |
| WP_055569787 | 85.9 | *Streptomyces atriruber* | 455 | 191 |
| WP_069884582 | 85.9 | *Streptomyces luteocolor* | 456 | 191 |
| WP_055698079 | 85.9 | *Streptomyces sdaceus* | 456 | 191 |
| WP_059300010 | 85.9 | *Streptomyces canus* | 455 | 191 |
| WP_039831526 | 85.8 | *Streptomyces viridosporus* | 442 | 190 |
| WP_050793881 | 85.8 | *Streptomyces ghanaensis* | 439 | 190 |
| EFE67698 | 85.8 | *Streptomyces ghanaensis* ATCC 14672 | 461 | 190 |
| WP_018959758 | 85.7 | *Streptomyces* sp. CNB091 | 459 | 189 |
| WP_030712260 | 85.6 | *Streptomyces* sp. NRRL S-237 | 449 | 188 |
| WP_058941217 | 85.3 | *Streptomyces kanasensis* | 459 | 191 |
| WP_053705101 | 85.3 | *Streptomyces* sp. WM6368 | 449 | 191 |
| WP_053171320 | 85.3 | *Streptomyces virginiae* | 449 | 191 |
| WP_030385747 | 85.3 | *Streptomyces* sp. NRRL S-241 | 449 | 191 |
| WP_037835235 | 85.3 | *Streptomyces* sp. NRRL F-5650 | 447 | 191 |
| WP_030793011 | 85.3 | *Streptomyces* sp. NRRL S-920 | 459 | 191 |
| WP_031004112 | 85.3 | *Streptomyces* sp. NRRL F-5727 | 454 | 190 |
| WP_030850543 | 85.2 | *Streptomyces* | 450 | 189 |
| WP_055599201 | 84.8 | *Streptomyces aureus* | 456 | 191 |
| WP_030313004 | 84.8 | *Streptomyces flavochromogenes* | 456 | 191 |
| WP_019886521 | 84.8 | *Streptomyces purpureus* | 463 | 191 |
| WP_024756173 | 84.8 | *Streptomyces exfoliatus* | 451 | 191 |
| WP_033218333 | 84.8 | *Streptomyces virginiae* | 449 | 191 |
| WP_053913363 | 84.8 | *Streptomyces* sp. TP-A0875 | 457 | 191 |
| WP_051821392 | 84.8 | *Streptomyces* sp. NRRL F-5065 | 457 | 191 |
| WP_030016658 | 84.8 | *Streptomyces lavendulae* | 369 | 191 |

TABLE 13B

List of sequences with percent identity to SspCPro59 predicted catalytic domain identified from Genome Quest database

| GQ Identifier | PID | Organism | Sequence Length | Alignment length |
|---|---|---|---|---|
| WO2015048332-43724 | 86.4 | *Streptomyces fradiae* | 454 | 191 |
| WO2015048332-44360 | 86.4 | *Streptomyces venezuelae* | 456 | 191 |
| WO2015048332-43726 | 85.9 | *Streptomyces fradiae* | 454 | 191 |
| WO2015048332-44022 | 85.9 | *Streptomyces pristinaespiralis* ATCC 25486 | 453 | 191 |
| WO2015048332-43751 | 85.8 | *Streptomyces ghanaensis* ATCC 14672 | 461 | 190 |
| WO2015048332-44127 | 84.3 | *Streptomyces* sp. C | 455 | 191 |
| US8535927-0035 | 84.2 | *Streptomyces griseus* | 195 | 190 |
| US8076468-0024 | 84.2 | *Streptomyces griseus* | 255 | 190 |
| WO2015048332-44248 | 84.2 | *Streptomyces* sp. W007 | 457 | 190 |
| WO2015048332-43810 | 84.2 | *Streptomyces griseus* | 457 | 190 |
| WO2015048332-43844 | 84.2 | *Streptomyces griseus* | 457 | 190 |
| US8076468-0023 | 84.2 | *Streptomyces griseus* | 457 | 190 |
| WO2015048332-43602 | 83.3 | *Streptomyces coelicoflavus* ZG0656 | 355 | 191 |
| WO2015048332-44050 | 83.2 | *Streptomyces roseosporus* NRRL 15998 | 455 | 190 |
| WO2015048332-43682 | 82.1 | *Streptomyces davawensis* JCM 4913 | 450 | 190 |
| WO2015048332-43645 | 81.7 | *Streptomyces coelicolor* | 463 | 191 |
| WO2015048332-43956 | 81.7 | *Streptomyces lividans* TK24 | 358 | 191 |
| US8535927-0036 | 81.7 | *Streptomyces coelicolor* | 197 | 191 |
| WO2015048332-43953 | 81.2 | *Streptomyces lividans* | 458 | 191 |
| WO2015048332-44149 | 80.5 | *Streptomyces* sp. e14 | 457 | 190 |
| US8076468-0009 | 80.1 | *Streptomyces* sp. | 256 | 191 |
| US8076468-0003 | 80.1 | *Streptomyces* sp. | 453 | 191 |
| US8076468-0011 | 80.1 | *Streptomyces* sp. | 428 | 191 |
| WO2005052161-0649 | 79.9 | *Streptomyces* | 381 | 189 |

TABLE 13B-continued

List of sequences with percent identity to SspCPro59 predicted catalytic domain identified from Genome Quest database

| GQ Identifier | PID | Organism | Sequence Length | Alignment length |
|---|---|---|---|---|
| WO2015048332-44081 | 79.9 | *Streptomyces* sp. | 382 | 189 |
| WO2005052146-0038 | 79.9 | *Streptomyces* sp. | 187 | 189 |
| WO2015048332-43913 | 79.0 | *Streptomyces hygroscopicus* | 439 | 190 |
| WO2015048332-44186 | 78.4 | *Streptomyces* sp. SirexAA-E | 449 | 190 |
| WO2015048332-44289 | 77.0 | *Streptomyces sviceus* ATCC 29083 | 454 | 191 |
| WO2015048332-44213 | 76.8 | *Streptomyces* sp. SM8 | 453 | 190 |
| WO2015048332-43423 | 76.8 | *Streptomyces albus* J1074 | 453 | 190 |
| WO2015048332-43766 | 76.3 | *Streptomyces griseoaurantiacus* M045 | 449 | 190 |

An alignment of the predicted catalytic domain sequences of SspCPro29 (SEQ ID NO: 18; aa 213-403 of SEQ ID NO:3); SspCPro33 (SEQ ID NO: 19, aa 204-394 of SEQ ID NO:6); SspCPro23 (SEQ ID NO: 20, aa 201-391 of SEQ ID NO:9); SspCPro59 (SEQ ID NO: 21, aa 206-395 of SEQ ID NO:12); WP_064069271 (SEQ ID NO:42, aa 204-394 of SEQ ID NO:26); WP_043225562 (SEQ ID NO:43, aa 204-394 of SEQ ID NO:27); WP_024756173 (SEQ ID NO:44, aa 201-391 of SEQ ID NO:28); WP_030548298 (SEQ ID NO:45, aa 207-397 of SEQ ID NO:29); WP_005320871 (SEQ ID NO:46, aa 204-394 of SEQ ID NO:30); amino acid residues 138-328 of WP_029386953 (SEQ ID NO:47); WP_026277977 (SEQ ID NO:48, aa 207-397 of SEQ ID NO:38); amino acid residues 208-398 of WP_044383230 (SEQ ID NO:49); amino acid residues 193-383 of WP_069630550 (SEQ ID NO:50); WP_055639793 (SEQ ID NO:51, aa 201-391 of SEQ ID NO:31); amino acid residues of 211-401 of WP_053699044 (SEQ ID NO:52); amino acid residues 205-395 of WP_031135572 (SEQ ID NO:53) was performed as described above and is shown in FIG. 12. The predicted catalytic domain consensus sequence from FIG. 12 is set forth as SEQ ID NO:54. For positions in consensus sequences were multiple amino acids are considered, they are depicted using X=I or L and the IUPAC codes: B=D or N.

What is claimed is:

1. A method of cleaning, comprising contacting a surface or an item in need of cleaning with an effective amount of at least one polypeptide selected from the group consisting of;
   a) a polypeptide comprising an amino acid sequence with at least 91% identity with the amino acid sequence of SEQ ID NO:22;
   b) a polypeptide comprising an amino acid sequence with at least 94% identity with the amino acid sequence of SEQ ID NO:23;
   c) a polypeptide comprising an amino acid sequence with at least 98% identity with the amino acid sequence of SEQ ID NO:24; and
   d) a polypeptide comprising an amino acid sequence with at least 80% identity with the amino acid sequence of SEQ ID NO:25;

and optionally further comprising the step of rinsing said surface or item after contacting said surface or item with said polypeptide.

2. The method of claim 1, wherein said polypeptide comprises a protease catalytic region comprising an amino acid sequence of SEQ ID NO:20, or an amino acid sequence with at least 96% identity with the amino acid sequence of SEQ ID NO:18.

3. The method of claim 1, wherein said polypeptide comprises an amino acid sequence with at least 91% identity with the amino acid sequence of SEQ ID NO:22, or at least 94% identity with the amino acid sequence of SEQ ID NO:23.

4. The method of claim 1, wherein said polypeptide comprises (i) an amino acid sequence with at least 91% identity with the amino acid sequence of SEQ ID NO:22, or (ii) a protease catalytic region comprising an amino acid sequence with at least 96% identity with the amino acid sequence of SEQ ID NO:18.

5. The method of claim 1, wherein said polypeptide comprises (i) an amino acid sequence with at least 94% identity with the amino acid sequence of SEQ ID NO:23, or (ii) a protease catalytic region comprising an amino acid sequence of SEQ ID NO:20.

6. The method of claim 1, wherein said item is dishware or fabric.

* * * * *